United States Patent
Zadeh et al.

(10) Patent No.: US 12,006,552 B2
(45) Date of Patent: Jun. 11, 2024

(54) METHYLOME BASED ANALYSIS AND TREATMENT FOR MENINGIOMA

(71) Applicant: UNIVERSITY HEALTH NETWORK, Toronto (CA)

(72) Inventors: Gelareh Zadeh, Toronto (CA); Kenneth Aldape, Bethesda, MD (US); Farshad Nassiri, Toronto (CA); Yasheng Maimaitijiang, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 691 days.

(21) Appl. No.: 16/503,025

(22) Filed: Jul. 3, 2019

(65) Prior Publication Data

US 2020/0010908 A1 Jan. 9, 2020

Related U.S. Application Data

(60) Provisional application No. 62/693,928, filed on Jul. 4, 2018.

(51) Int. Cl.
*C12Q 1/6886* (2018.01)
*C12Q 1/6809* (2018.01)
*C12Q 1/6816* (2018.01)
*C12Q 1/6827* (2018.01)
*G06F 17/18* (2006.01)
*G16B 20/20* (2019.01)
*G16B 40/10* (2019.01)
*G16H 50/30* (2018.01)

(52) U.S. Cl.
CPC ......... *C12Q 1/6886* (2013.01); *C12Q 1/6809* (2013.01); *C12Q 1/6816* (2013.01); *C12Q 1/6827* (2013.01); *G06F 17/18* (2013.01); *G16B 20/20* (2019.02); *G16B 40/10* (2019.02); *G16H 50/30* (2018.01); *C12Q 2600/154* (2013.01); *C12Q 2600/158* (2013.01)

(58) Field of Classification Search
CPC ..................... C12Q 2600/154; C12Q 1/6886
See application file for complete search history.

(56) References Cited

PUBLICATIONS

Sahm et al. Lancet Oncol. 2017. 18:682-94. (Year: 2017).*
Ostrom, Quinn T. et al. CBTRUS statistical report: Primary brain and other central nervous system tumors diagnosed in the United States in 2009-2013. Neuro-Oncology 2016;18: v1-v75. DOI:10.1093/neuonc/now207.
Weber, Damien C. et al; Adjuvant postoperative high-dose radiotherapy for atypical and malignant meningioma: A phase-II parallel non-randomized and observation study (EORTC 22042-26042). Radiotherapy and Oncology 128 2018; pp. 260-265. DOI:10.1016/j.radonc.2018.06.018.
Rogers, Leland et al. Intermediate-risk meningioma: Initial outcomes from NRG Oncology RTOG 0539. J Neurosurg. Jul. 2018;129(1); pp. 35-47. DOI:10.3171/2016.11.JNS161170.
Rogers, Leland et al. Meningiomas: Knowledge base, treatment outcomes, and uncertainties. A RANO review. J Neurosurg. Jan. 2015;122(1); pp. 4-23. DOI:10.3171/2014.7.JNS131644.
Brastianos, Priscilla K. et al. Genomic sequencing of meningiomas identifies oncogenic SMO and AKT1 mutations Nat Genet. Mar. 2013;45(3); pp. 285-289. DOI:10.1038/ng.2526.
Clark, Victoria E. et al. Genomic analysis of non-NF2 meningiomas reveals mutations in TRAF7, KLF4, AKT1, and SMO. Science Mar. 2013; 339(6123):1077-1080. DOI:10.1126/science.1233009.
Clark, Victoria E. et al. Recurrent somatic mutations in POLR2A define a distinct subset of meningiomas. Nat Genet. Oct. 2016; 48(10); pp. 1253-1259. DOI:10.1038/ng.3651.
Sahm, Felix et al. TERT Promoter Mutations and Risk of Recurrence in Meningioma. JNCI J Natl Cancer Inst. 2016;108(5):djv377. doi: 10.1093/jnci/djv377.
Sahm, Felix et al. DNA methylation-based classification and grading system for meningioma: a multicentre, retrospective analysis. Lancet Oncol. Mar. 2017;18(5); pp. 682-694. DOI:10.1016/S1470-2045(17)30155-9.
Olar, Adriana et al. Global epigenetic profiling identifies methylation subgroups associated with recurrence-free survival in meningioma. Acta Neuropathol. Mar. 2017;133(3); pp. 431-444. DOI: 10.1007/s00401-017-1678-x.
Reuss, David E. et al. Secretory meningiomas are defined by combined KLF4 K409Q and TRAF7 mutations. Acta Neuropathol. 2013;125(3); pp. 351-358. DOI:10.1007/s00401-013-1093-x.
Lee, Yohan et al. Genomic landscape of meningiomas. Brain Pathol. Jul. 2010;20(4); pp. 751-762. doi:10.1111/.1750-3639.2009.00356.x.
Claus, Elizabeth B. et al. Specific genes expressed in association with progesterone receptors in meningioma. Cancer Res. Jan. 2008; 68(1): pp. 314-322. DOI:10.1158/0008-5472.CAN-07-1796.
Hovestadt, Volker et al. Enhanced copy-number variation analysis using Illumina 450k methylation arrays. R package version 0.99. R Packag. 2015.
Aizer, Ayal A. et al. A prognostic cytogenetic scoring system to guide the adjuvant management of patients with atypical meningioma. Neuro Oncology 2016;18(2); pp. 269-274. DOI:10.1093/neuonc/nov177.
Heagerty, Patrick J. et al. Time-dependent ROC curves for censored survival data and a diagnostic marker. Biometrics. Jun. 2000; 56(2); pp. 337-344. DOI:10.1111/j.0006-341X.2000.00337.x.

(Continued)

*Primary Examiner* — Joseph G. Dauner
(74) *Attorney, Agent, or Firm* — Norton Rose Fulbright Canada LLP

(57) ABSTRACT

There is described herein a method of predicting recurrence free survival in a patient with meningioma comprising: (a) determining a tumor DNA methylation profile from a tumor sample from the patient, the tumor DNA methylation profile comprising the methylation status of at least 200 loci represented by the probes set forth in Table 9; and (b) calculating a risk of meningioma recurrence based on comparing the tumor DNA methylation profile and a reference methylation profile comprising the extent to which the methylation status of the at least 200 loci is associated with a risk of recurrence.

8 Claims, 22 Drawing Sheets

(56) References Cited

PUBLICATIONS

Huang, Da Wei et al. The DAVID Gene Functional Classification Tool: A novel biological module-centric algorithm to functionally analyze large gene lists. Genome Biology. Sep. 2007;8(9); pp. R183.1-R183.16; DOI:10.1186/gb-2007-8-9-r183.

Chambless, Lloyd E. et al. Estimation of time-dependent area under the ROC curve for long-term risk prediction. Statis. Med. 2006;25(20); pp. 3474-3486. DOI:10.1002/sim.2299.

Grambsch, Patricia M. et al. Proportional Hazards Tests and Diagnostics Based on Weighted Residuals; Biometrika, Aug. 1994, vol. 81, No. 3; pp. 515-526; http://www.jstor.org/stable/2337123.

Harmancl, Akdes S. et al. Integrated genomic analyses of de novo pathways underlying atypical meningiomas. Nature Communications, Feb. 2017;8:14433. DOI:10.1038/ncomms14433.

Balachandran, Vinod P. et al. Nomograms in oncology: more than meets the eye. Lancet Oncol. 2015;16(4):e173-80. doi:10.1016/S1470-2045(14)71116-7.

McShane, Lisa M. et al. Criteria for the use of omics-based predictors in clinical trials. Nature. Oct. 2013;502(7471); pp. 317-320. DOI:10.1038/nature12564.

Sproul, Duncan et al. Genomic insights into cancer-associated aberrant CpG island hypermethylation. Briefings in Functional Genomics. Jan. 2013;12(3); pp. 174-190. DOI:10.1093/bfgp/els063.

Huang, Raymond Y. et al. Proposed Response Assessment and Endpoints for Meningioma Clinical Trials: Report from the Response Assessment in Neuro-Oncology (RANO) Working Group. Neuro-Oncology, Aug. 2018; 21(1); pp. 26-36. DOI:10.1093/neuonc/noy137.

Simpson, Donald. The recurrence of intracranial meningiomas after surgical treatment. J. Neurol. Neurosurg Psychiat. Feb. 1957;20; pp. 22-39.

Louis, David N. et al. The 2016 World Health Organization Classification of Tumors of the Central Nervous System: a summary. Acta Neuropathol. 2016;131; pp. 803-820. DOI: 10.1007/s00401-016-1545-1.

\* cited by examiner

METHYLOME BASED ANALYSIS AND TREATMENT FOR MENINGIOMA

RELATED APPLICATIONS

This application claims priority to U.S. Provisional Application No. 62/693,928, which is hereby incorporated by reference in its entirety.

FIELD OF THE INVENTION

The invention relates to compositions and methods for use in treating and predicting meningioma recurrence.

BACKGROUND OF THE INVENTION

Meningiomas are the most common primary intracranial tumor. They account for 37% of all central nervous system tumors, and are continuing to increase in incidence with the ageing population[1]. They result in significant neurological morbidity and loss of quality of life by exerting mass effect on critical adjacent brain regions[1]. The current standard-of-care for nearly all patients with symptomatic meningiomas includes gross total tumor resection with removal of involved dura and bone when possible[2]. However, despite radical surgical resection, approximately 20% of meningiomas display aggressive behaviour with early tumor recurrence resulting in a clinical course of repetitive disease- and treatment-related morbidity. Radiation therapy can be used to provide disease control as an adjunct to surgery for a subset of tumors[3,4]. However, radiotherapy can often result in adverse radiation effects that lead to considerable morbidity and neurological dysfunction long-term precluding universal use in all patients[5]. One of the greatest clinical challenges faced by clinicians is the inability to predict early tumor recurrence at an individual patient level which limits the appropriate selection of patients who would benefit from adjuvant radiation therapy.

To date, the most reliable clinical factors associated with recurrence in meningiomas have been the World Health Organization (WHO) grade of the tumor and extent of tumor resection at surgery[2,6]. Although both are crudely associated with recurrence rates on a population level, they are challenged with inter-rater variability of grading and considerable within-grade variation of recurrence risk for individual patients[2,6]. In the past decade, several studies have focused on molecular profiling of meningiomas to refine biological subgroups[7-13]. With the exception of mutations in BAP1 and TERT promoter, each of which occur rarely in these tumors, the mutations identified in meningioma have not been shown to be tightly correlated to patient outcome with current standard of care[7-10]. We and others have independently shown that global DNA methylation profiling reveals robust methylome-based meningioma subtypes, however, the clinical translation of this to predict recurrence risk for individual patients has not been demonstrated to date.

SUMMARY OF THE INVENTION

To examine whether methylation profiles can be defined and validated for clinical utility, we aimed to develop and validate a methylome-based predictor of early meningioma recurrence that could be combined with established prognostic clinical factors to individualize decisions regarding the need for post-operative therapeutic interventions, in particular, whether to treat patients with adjuvant radiation therapy versus observation alone. Our work is the first in neuro-oncology to demonstrate the transformative utility of integrating clinical and molecular factors for use beyond simple classification into the realm of individualized prognostication.

Our work is the first to demonstrate the transformative utility of integrating clinical and molecular factors for use beyond simple classification into the realm of individualized prognostication for any brain tumor. Using our developed and validated tools that are publicly available, clinicians will be able combine clinical and molecular factors to determine an individualized probability of recurrence for patients with meningiomas. This represents a major advance in the field of personalized medicine for neuro-oncology, and the use of this tool can help clinicians overcome one of the most challenging limitations we face when treating patients with meningiomas.

In an aspect, there is provided a method of predicting recurrence free survival in a patient with meningioma comprising:
 (a) determining a tumor DNA methylation profile from a tumor sample from the patient, the tumor DNA methylation profile comprising the methylation status of at least 200 loci represented by the probes set forth in Table 9;
 (b) calculating a risk of meningioma recurrence based on comparing the tumor DNA methylation profile and a reference methylation profile comprising the extent to which the methylation status of the at least 200 loci is associated with a risk of recurrence.

In an aspect, there is provided an array consisting of the 9529 probes set forth in Table 9.

In an aspect, there is provided a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer implemented product for predicting recurrence free survival in a patient with meningioma comprising:
 (a) a means for receiving values corresponding to a tumor DNA methylation profile from a tumor sample from the patient, the DNA methylation profile comprising the methylation status of at least 200 loci represented by the probes set forth in Table 9;
 (b) a database comprising a reference methylation profile representing the extent to which each said methylation status of the at least 200 loci is associated with a risk of recurrence; and
 (c) a means for calculating a risk of meningioma recurrence based on a comparison of the tumor DNA methylation profile and the reference methylation profile.

In an aspect, there is provided a computer readable medium having stored thereon a data structure for storing the computer implemented product described herein. In an aspect, there is provided a computer system comprising
 (a) a user interface capable of receiving values corresponding to a tumor DNA methylation profile from a tumor sample from the patient, the DNA methylation profile comprising the methylation status of at least 200 loci represented by the probes set forth in Table 9;
 (b) a database including records comprising a reference methylation profile comprising the extent to which each said methylation status of the at least 200 loci is associated with a risk of recurrence;

(c) an output that displays a prediction of recurrence free survival based on a comparison of the tumor DNA methylation profile and the reference methylation profile. In an aspect, there is provided a method of predicting recurrence free survival in a patient with meningioma comprising:
(a) determining a tumor DNA methylation profile from a tumor sample from the patient, the tumor DNA methylation profile comprising the methylation status of at least 200 genes set forth in Table 9;
(b) calculating a risk of meningioma recurrence based on comparing the tumor DNA methylation profile and a reference methylation profile setting forth the extent to which the methylation status of the at least 200 genes is associated with a risk of recurrence.

BRIEF DESCRIPTION OF FIGURES

These and other features of the preferred embodiments of the invention will become more apparent in the following detailed description in which reference is made to the appended drawings wherein.

DETAILED DESCRIPTION

Figure 1:
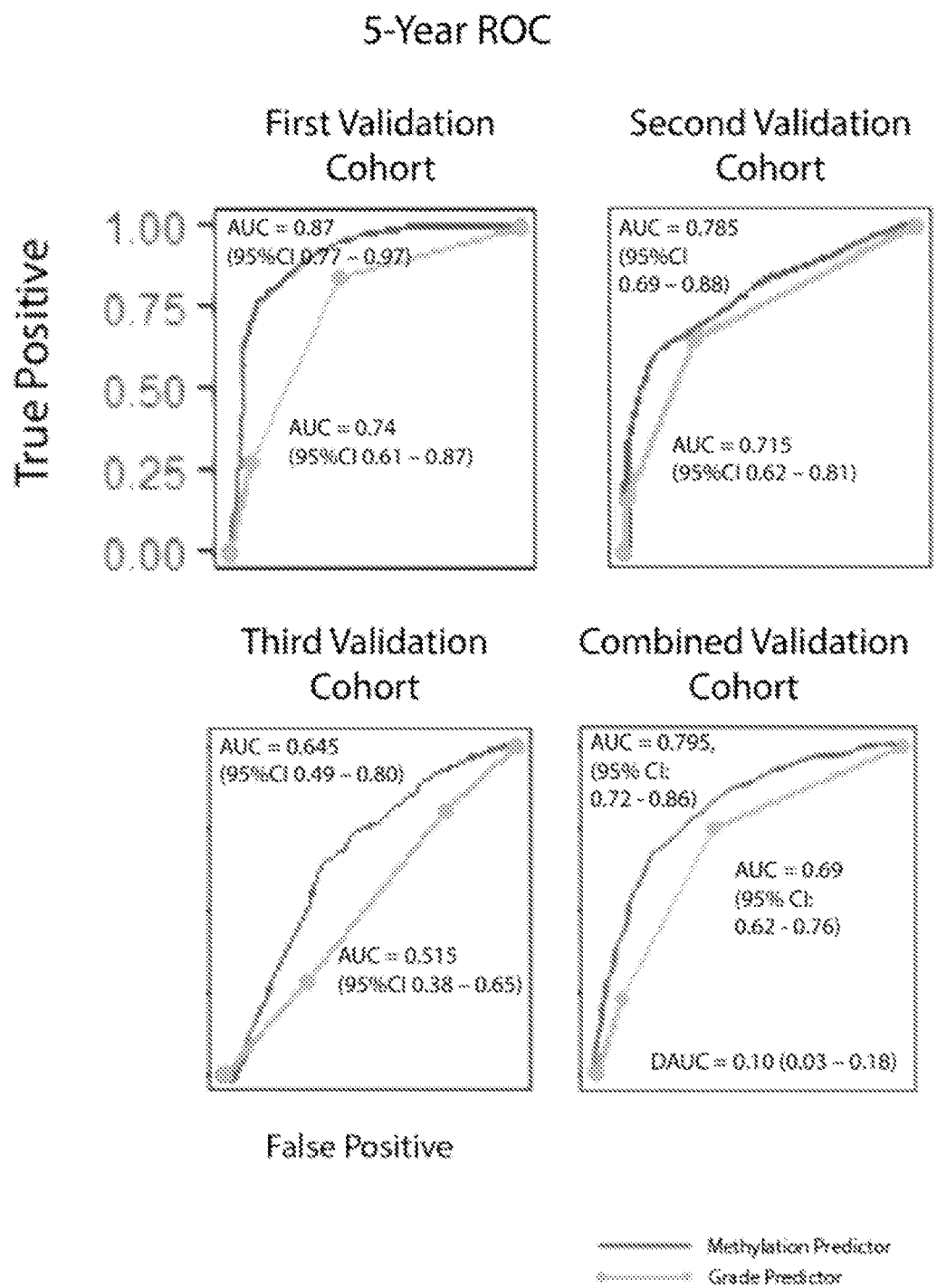
FIG. 1 shows comparison of grade-based and methylome-based recurrence-free survival predictor performance. Data presented are time-dependent receiver operating characteristic curve (ROC) and average area under the curve (AUC) as well as ΔAUC (DAUC) with 95% CI using 10,000 bootstrap resampling validation approach for methylome-based and grade-based predictors in the (A) first validation cohort and (B) second validation cohort (C) third validation cohort, (D) combined validation cohorts.

In the following description, numerous specific details are set forth to provide a thorough understanding of the invention. However, it is understood that the invention may be practiced without these specific details.

Variability in standard-of-care classifications preclude accurate predictions of early tumor recurrence for individual patients with meningioma limiting the appropriate selection of patients who would benefit from adjuvant radiotherapy to delay recurrence. We aimed to develop an individualized prediction model of early recurrence risk combining clinical and molecular factors in meningioma.

DNA methylation profiles of clinically-annotated tumor samples across multiple institutions were used to develop a methylome-model of 5-year recurrence-free-survival (RFS). Subsequently, a 5-year meningioma recurrence score was generated using a nomogram that integrated the methylome-model with established prognostic clinical factors. Performance of both models was evaluated and compared to standard-of-care models using multiple independent cohorts.

The methylome-based predictor of 5-year RFS performed favorably compared to a grade-based predictor when tested using the three validation cohorts ($\Delta$AUC=0.10, 95% CI 0.03-0.018) and was independently associated with RFS after adjusting for histopathological grade, extent of resection and burden of copy number alterations (HR 3.6, 95% CI 1.8-7.2, P<0.001). A nomogram combining the methylome-predictor with clinical factors demonstrated greater discrimination than a nomogram using clinical factors alone in two independent validation cohorts ($\Delta$AUC=0.25, 95% CI 0.22-0.27) and resulted in two groups with distinct recurrence patterns (HR 7.7, 95% CI 5.3-11.1, P<0.001) with clinical implications.

The models developed and validated in this study provide important prognostic information not captured by previously established clinical and molecular factors which could be used to individualize decisions regarding post-operative therapeutic interventions, in particular, whether to treat patients with adjuvant radiotherapy versus observation alone.

In an aspect, there is provided a method of predicting recurrence free survival in a patient with meningioma comprising:
(a) determining a tumor DNA methylation profile from a tumor sample from the patient, the tumor DNA methylation profile comprising the methylation status of at least 200 loci represented by the probes set forth in Table 9;
(b) calculating a risk of meningioma recurrence based on comparing the tumor DNA methylation profile and a reference methylation profile comprising the extent to which the methylation status of the at least 200 loci is associated with a risk of recurrence.

As used herein, "tumour DNA methylation profile" in a given genetic tumour sample is the extent of DNA methylation associated with the tumour DNA. In preferable embodiments, a tumour DNA methylation profile describes the extent of DNA methylation associated with specific loci in tumour DNA As used herein, "reference methylation profile" is the extent DNA methylation, preferably associated with specific loci, that is associated with a favourable or unfavourable outcomes as they relate to meningioma, for example, the risk of recurrence.

As used herein, "risk of recurrence" means the chance that a cancer that has been treated will recur. Risk recurrence may be stratified risk categories, i.e. low, intermediate, or high.

In some embodiments, the at least 200 loci is at least 500 loci.

In some embodiments, the at least 200 loci is at least 1000 loci.

In some embodiments, the at least 200 loci is at least 1500 loci.

In some embodiments, the at least 200 loci is at least 2000 loci.

In some embodiments, the at least 200 loci is at least 2500 loci.

In some embodiments, the at least 200 loci is at least 3500 loci.

In some embodiments, the at least 200 loci is at least 4000 loci.

In some embodiments, the at least 200 loci is at least 5000 loci.

In some embodiments, the at least 200 loci is at least 6000 loci.

In some embodiments, the at least 200 loci is at least 7000 loci.

In some embodiments, the at least 200 loci is at least 8000 loci.

In some embodiments, the at least 200 loci is at least 9000 loci.

In some embodiments, the at least 200 loci is at least 9500 loci.

In some embodiments, the at least 200 loci is at least 9529 loci.

In some embodiments, calculating the risk is based further on at least one of the WHO grading and Simpson grading of the tumor.

In some embodiments, the method further comprises calculating a predicted number of years of recurrence free survival (RFS Score).

In some embodiments, the method further comprises stratifying the patient into high, medium and low risk categories based on said RFS Score compared to known reference patients.

In some embodiments, the method further comprises treating the patient with adjuvant therapy if the patient is in the high or medium risk category.

In some embodiments, the adjuvant therapy comprises chemotherapy or radiotherapy.

In an aspect, there is provided an array consisting of the 9529 probes set forth in Table 9.

The present system and method may be practiced in various embodiments. A suitably configured computer device, and associated communications networks, devices, software and firmware may provide a platform for enabling one or more embodiments as described above. By way of example, FIG. 16 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 115, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 100 to communicate with other suitably configured data processing systems (not shown). One or more different types of sensors 135 may be used to receive input from various sources.

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present invention. In case of more than computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

In an aspect, there is provided a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer implemented product for predicting recurrence free survival in a patient with meningioma comprising:
(a) a means for receiving values corresponding to a tumor DNA methylation profile from a tumor sample from the patient, the DNA methylation profile comprising the methylation status of at least 200 loci represented by the probes set forth in Table 9;
(b) a database comprising a reference methylation profile representing the extent to which each said methylation status of the at least 200 loci is associated with a risk of recurrence; and
(c) a means for calculating a risk of meningioma recurrence based on a comparison of the tumor DNA methylation profile and the reference methylation profile.

In some embodiments, the computer implemented product described herein is for carrying out the method described herein.

In some embodiments, the computer implemented product further outputs a recommendation for adjuvant therapy if the patient has been classified into a medium or high risk group.

In an aspect, there is provided a computer readable medium having stored thereon a data structure for storing the computer implemented product described herein.

In an aspect, there is provided a computer system comprising
(a) a user interface capable of receiving values corresponding to a tumor DNA methylation profile from a tumor sample from the patient, the DNA methylation profile comprising the methylation status of at least 200 loci represented by the probes set forth in Table 9;
(b) a database including records comprising a reference methylation profile comprising the extent to which each said methylation status of the at least 200 loci is associated with a risk of recurrence;
(c) an output that displays a prediction of recurrence free survival based on a comparison of the tumor DNA methylation profile and the reference methylation profile. In an aspect, there is provided a method of predicting recurrence free survival in a patient with meningioma comprising:
(a) determining a tumor DNA methylation profile from a tumor sample from the patient, the tumor DNA methylation profile comprising the methylation status of at least 200 genes set forth in Table 9;
(b) calculating a risk of meningioma recurrence based on comparing the tumor DNA methylation profile and a reference methylation profile setting forth the extent to which the methylation status of the at least 200 genes is associated with a risk of recurrence.

In some embodiments, the at least 200 genes is at least 400, 600, 800, 1000, 1500, 2000, 2500, 3000, or 3237 genes.

As used herein, "processor" may be any type of processor, such as, for example, any type of general-purpose microprocessor or microcontroller (e.g., an Intel™ x86, PowerPC™, ARM™ processor, or the like), a digital signal processing (DSP) processor, an integrated circuit, a field programmable gate array (FPGA), or any combination thereof.

As used herein "memory" may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. Portions of memory 102 may be organized using a conventional filesystem, controlled and administered by an operating system governing overall operation of a device.

As used herein, "computer readable storage medium" (also referred to as a machine-readable medium, a processor-readable medium, or a computer usable medium having a computer-readable program code embodied therein) is a medium capable of storing data in a format readable by a computer or machine. The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The computer readable storage medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the computer readable storage medium. The instructions stored on the computer readable storage medium can be executed by a processor or other suitable processing device, and can interface with circuitry to perform the described tasks.

As used herein, "data structure" a particular way of organizing data in a computer so that it can be used efficiently. Data structures can implement one or more particular abstract data types (ADT), which specify the operations that can be performed on a data structure and the computational complexity of those operations. In comparison, a data structure is a concrete implementation of the specification provided by an ADT.

The advantages of the present invention are further illustrated by the following examples. The examples and their particular details set forth herein are presented for illustration only and should not be construed as a limitation on the claims of the present invention.

EXAMPLES

Methods and Materials
Study Design and Data Sources

This multicenter retrospective study was carried out in accordance with individual institutional ethics and review board guidelines and comprised a total of 486 patients with clinically annotated and available meningioma samples. Institutional waivers of informed consent were obtained due to minimal patient risk associated with this study. Two-hundred and eighty-two (N=282) fresh-frozen or formalin-fixed paraffin embedded (FFPE) meningioma tumor samples from multiple institutions (N=76 from Princess Margaret Cancer Research Centre, Toronto, Canada; N=206 from European centers including University of Heidelberg, Heidelberg, Germany and Goethe-University, Frankfurt, Germany and University of Tubingen, Tubingen, Germany, and University Hospital Zurich, Zurich, Switzerland and Medical University of Vienna, Vienna, Austria) comprised the discovery cohort, which was split into a training cohort (81%, N=228 samples) and first validation cohort (19%, N=54 samples) each balanced for tumor grade, tissue type, recurrence status and time to recurrence. One hundred and forty (N=140) FFPE meningioma tumor samples from a separate institution (MD Anderson Cancer Centre, Houston, USA) were used as a second validation cohort, and sixty-four (N=64) fresh frozen meningioma tumor samples from two other institutions were used as a third validation cohort (N=46 from Princess Margaret Cancer Research Centre; N=18 from The Chinese University of Hong Kong). The sample sets from Europe and MD Anderson comprised the subset of previously published samples for which clinical data (recurrence-free survival [RFS], WHO grade) were available[11,12]. Moreover, TERT promoter mutation status was available on a subset of previously published European samples[10,11]. Gene expression analysis was performed on publicly available microarray data on 98 patients with meningiomas of all grades (GSE16581[14] and GSE9438[15]). The outline for the overall study design is demonstrated in FIG. 7.

Definitions

Hematoxylin and eosin (H&E) slides for each patient were reviewed for meningioma diagnosis and WHO grading was performed according to the current WHO 2016 criteria at local institutions by experienced neuropathologists. Tumor recurrence and time to recurrence were the primary outcomes of interest and were collected locally for each sample as previously described[11,12]. Briefly, recurrence was defined as tumor growth following gross-total resection or tumor progression following subtotal resection. Time to recurrence was determined by reviewing post-operative imaging and calculating the duration from the date of surgery to first post-operative imaging documenting tumor recurrence in concordance with documentation in the medical charts. The extent of resection (Simpson grade[2]) was determined based on the surgeon's operative report in correlation with postoperative cranial imaging.

Generation of an Individualized Methylome-Predictor of 5-Year RFS

Figure 8:
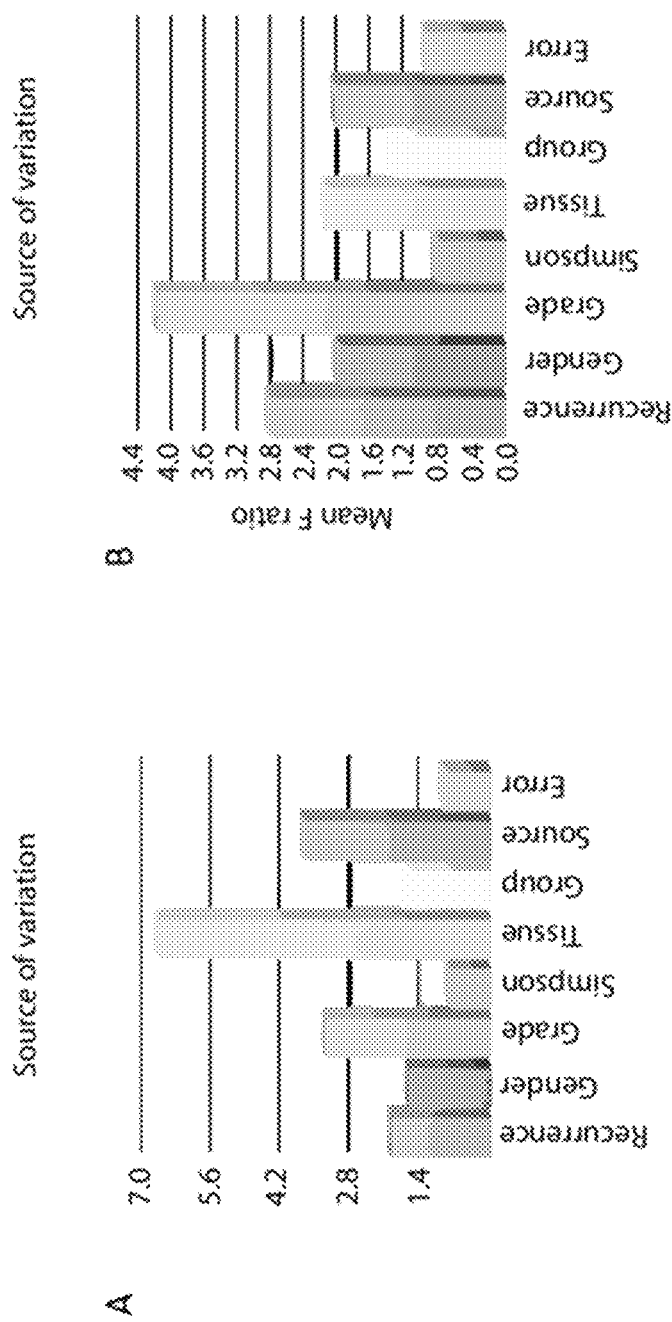
FIG. 8 shows sources of variability in feature selection from (A,C) 71538 probes that were highly correlated with RFS (P<0.01) in training set (B,D) 23571 probes common in samples from training set (University Health Network and University of Heidelberg FFPE and fresh frozen). Results demonstrate that with 23571 probes common in samples in the training set tissue source was not a major source of variation with convergence between the center of gravity and standard deviation on principal component analysis.
Figure 8:
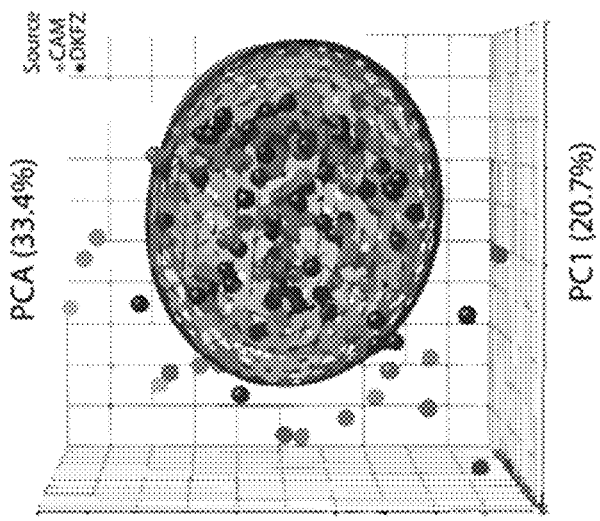
Figure 8:
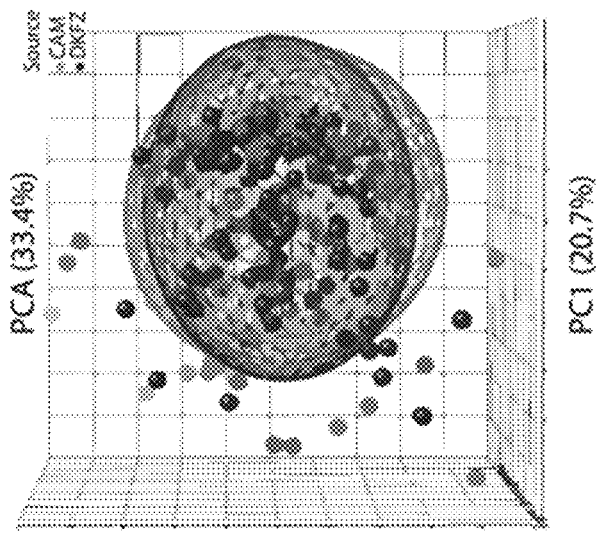

For DNA methylation and copy number analysis of the samples, DNA was extracted from each tumor and DNA methylation profiling was performed using Illumina™ 450 k HumanMethylation BeadChip or 850 k EPIC arrays as per manufacturer instructions at each institution. Raw data files (*.idat) were imported, processed, and normalized to integrate data from multiple generations of Infinium methylation arrays. Copy number aberrations were inferred from methylation array data[16] and burden of copy number alterations was computed per sample as previously described[17]. Probes that were common in both 450 k HumanMethylation Beadchip and 850 K EPIC arrays were selected as possible features for development of our predictor such that our predictor would be applicable to the landscape of available technologies. We used a multi-step strategy to select the probes to be used in the generation of our predictor (See FIG. 8).

To develop the methylome-based predictor of early meningioma recurrence, we performed generalized boosted regression modelling using the final selected probes in samples from the training cohort to predict 5-year RFS. Boosted regression modelling using WHO grade as a sole feature in the training cohort was also performed and tested in each validation cohort to compare methylation-based predictor performance to a standard-of-care model. Performance of both models was assessed by generating time-dependent receiver operating characteristic (ROC) curves and computing average areas under the ROC curves (AUC) for each validation cohort independently, along with their 95% confidence intervals using the bootstrap resampling method with 10,000 resamples[18].

Methylation probe annotation was performed using the UCSC Genome Browse (GRCh38/hg38 assembly). We used the Functional Annotation Clustering algorithm[19] of Database for Annotation, Visualization, and Integrated Discovery (DAVID)[19] Bioinformatics Resource 6.8 to identify redundant functional clusters represented by genes annotated with a minimum of 5 probes (See FIG. 9). Two publicly available microarray datasets (GSE16581[14] and GSE9438[15]) reporting on 22486 genes for 98 patients with meningiomas were pooled to correlate methylation data with gene expression data as an exploratory analysis.

Further details regarding the steps for generation, validation and characterization of the methylome-predictor of 5-year RFS is described below.

Generation of a Meningioma-Recurrence Score

Figure 10:
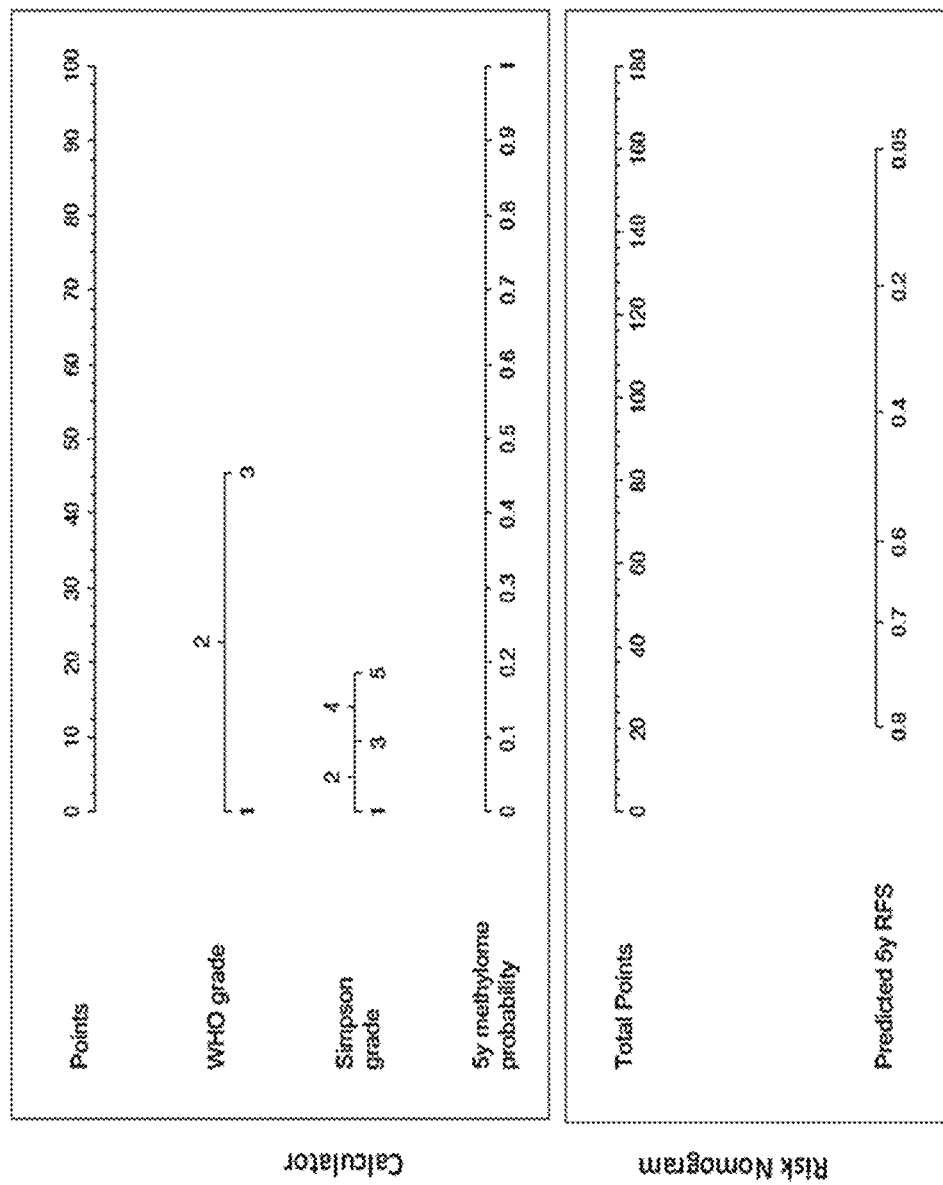
FIG. 10 shows nomogram calculator and risk nomogram. For a given patient, the cumulative points from each variable ("5y methylome probability", "WHO grade" and "Simpson grade") is calculated for a result of total points. The "risk nomogram" is then used to scale the total points to risk of 5-year RFS. A patient with a WHO grade 2 meningioma (23 points), simpson grade 3 resection (10 points), and 5-year methylome probability score of 0.6 (60 points) would have a cumulative 94 points, which would result in a 5-year predicted RFS probability of 40.5%. The 5-year methylome probability score would be generated via an online platform that utilizes the generated and validated predictor to create probability scores from methylation array-based analysis of a tumor sample (IDAT file).

To create a contemporary meningioma recurrence score that could be utilized by clinicians to predict early risk of recurrence for individual patients, we generated a nomogram based on a Cox model that incorporated the methylome-based predictor, WHO grade, and extent of resection using samples from the training cohort and second validation cohort to predict 5-year RFS. Both the training cohort and second validation cohort were used to train this nomogram in order to increase the number of samples available to capture the heterogeneity in the spectrum of data available. It is important to note that as none of the samples used to train this model were used to assess model performance on external validation. The global performance of the meningioma recurrence was assessed by generating time-dependent receiver operating characteristic (ROC) curves and computing average area under the ROC curves (AUC) for the first and third validation cohort independently, along with their 95% confidence intervals using the bootstrap resampling method with 10,000 resamples[18,20]. For comparison, a nomogram that incorporated only WHO grade and extent of resection as the sole features was also developed in similar fashion. Internal validation using bootstrap resampling using 10,000 resamples was also performed. Model calibration was assessed visually by plotting observed event rates against nomogram predicted probabilities for two risk groups. Detailed descriptions on nomogram calculations and use are described below and FIG. 10.

Statistical Analysis

Summary statistics are reported as counts (and proportions) for categorical variables and median (and range) for continuous variables, unless otherwise indicated. Cohort size was determined by availability of samples. Statistical analyses were performed in consultation with two expert biostatisticians (L.P and O.S).

To investigate the clinical relevance of the methylome-based predictor and meningioma recurrence score, distribution of survival times was performed using Kaplan-Meier methods and compared across groups using log-rank testing. The frequency of genome-wide copy number alterations across groups was computed and plotted using a custom algorithm. The performance of a methylome-based predictor was compared to grade-based predictor by computing an average $\Delta AUC$ ($AUC_{methylome}-AUC_{grade}$) and 95% CI from all bootstraps and the performance of the meningioma grade, recurrence score incorporating the methylome predictor was compared to a nomogram excluding the methylome predictor by computing average $\Delta AUC$ ($AUC_{combined\ nomogram}-AUC_{clinical\ only\ nomogram}$) and 95% CI in similar fashion.

Figure 11:
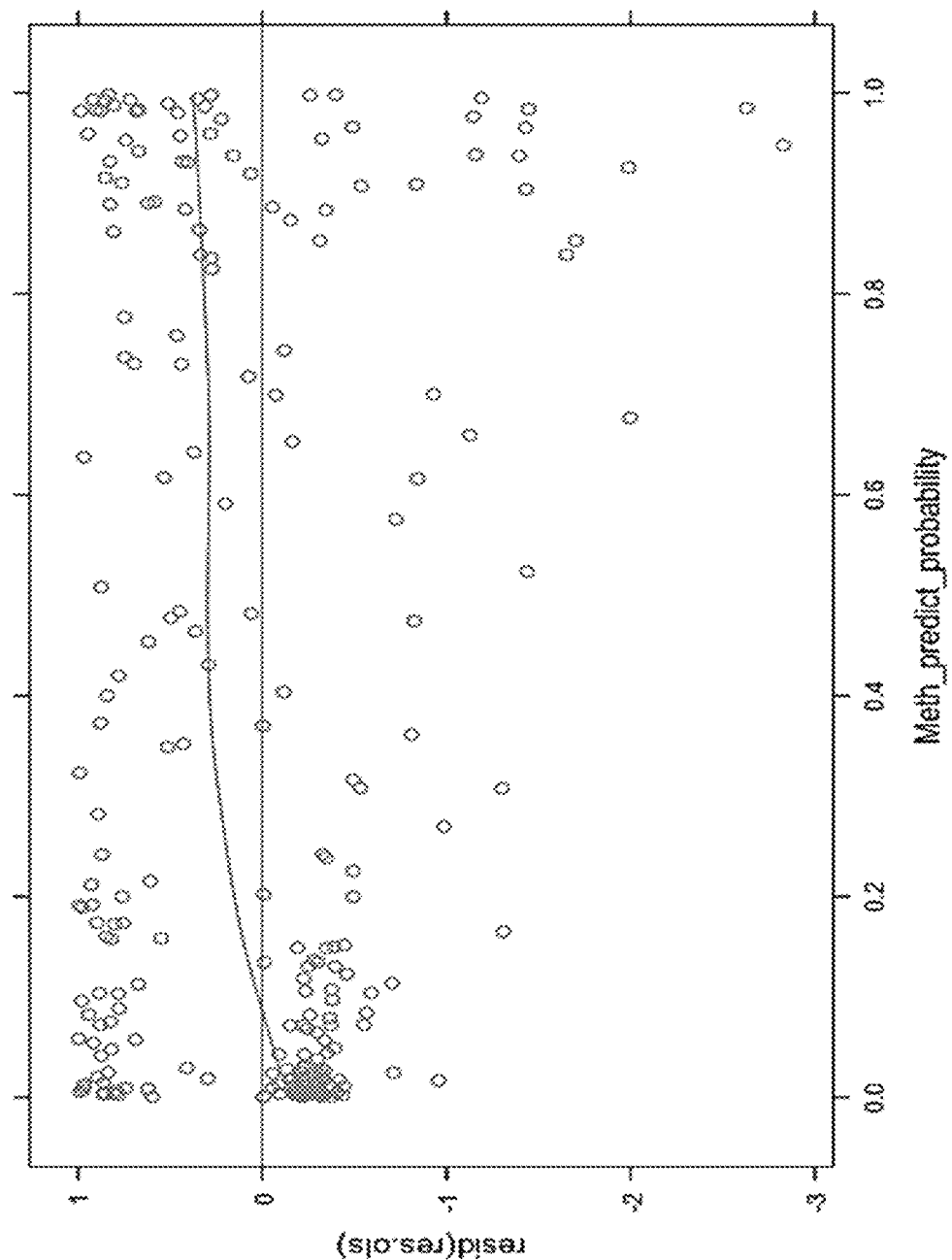
FIG. 11 shows plot of martingale residuals versus methylation-based predictor demonstrating appropriateness to model methylation-based predictor as a linear function in Cox model.
Figure 12:
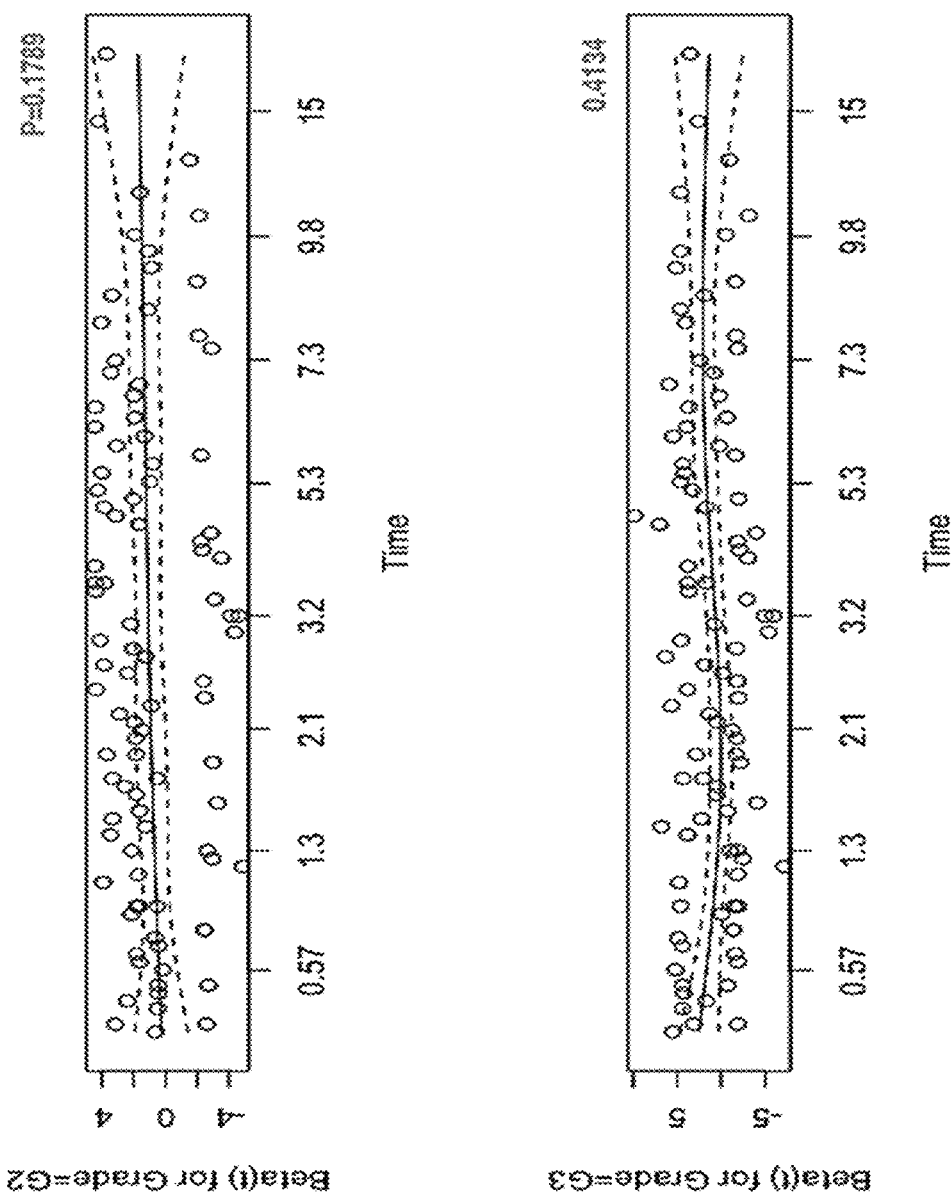
FIG. 12 shows plot of Schoenfeld residuals versus time for each covariate included in main Cox model demonstrating no violation of proportional hazard assumption.
Figure 12:
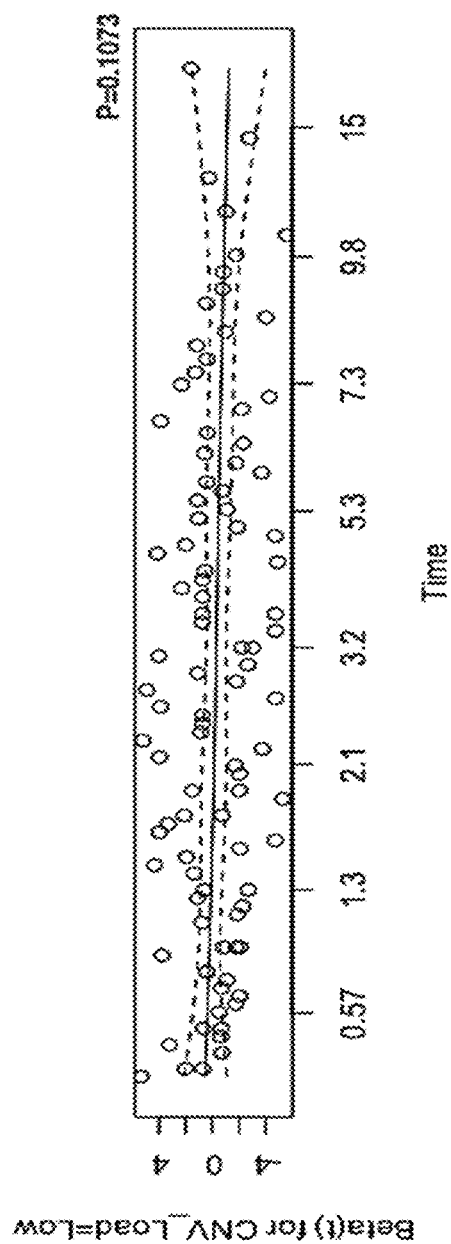
Figure 12:
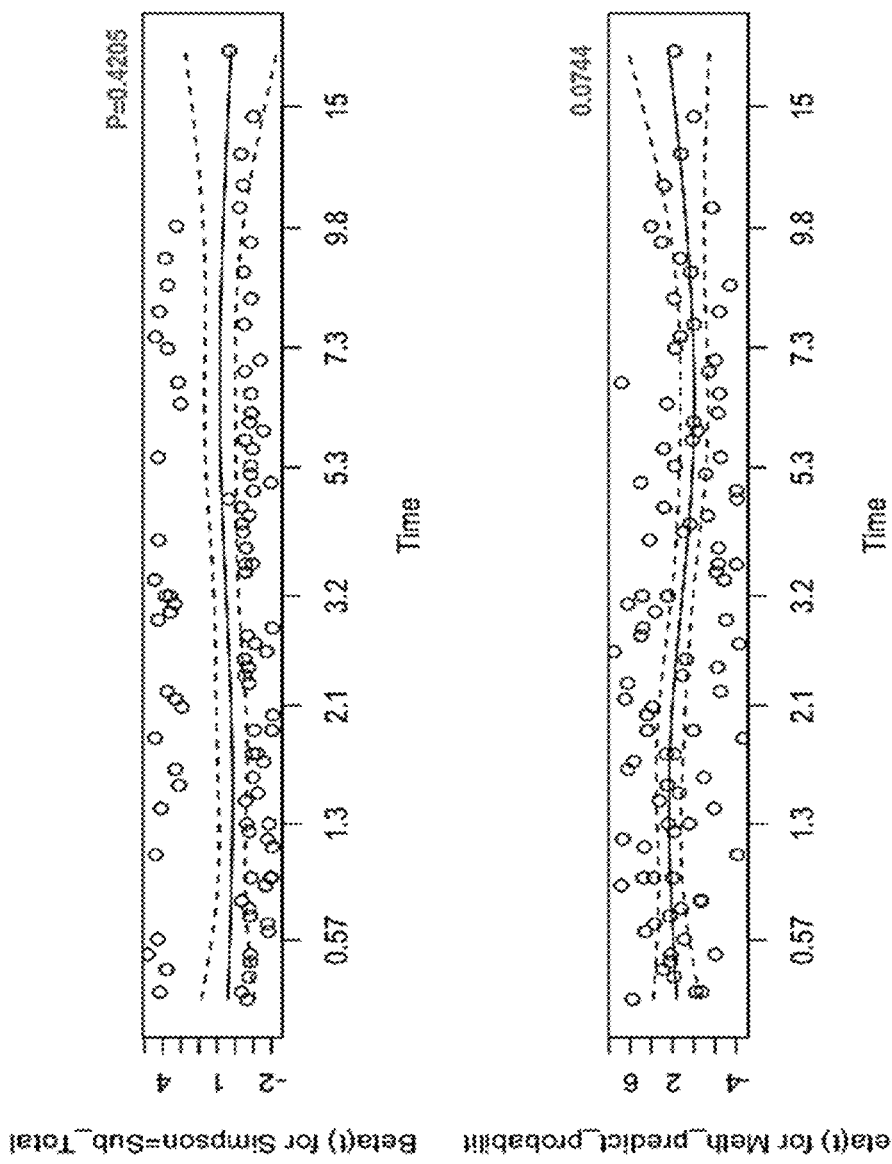

Hazard ratios, including 95% confidence intervals (CI), were calculated based on univariable and multivariable Cox regression modeling for the methylome-based predictor and other covariates including WHO grade, extent of resection, and burden of copy number alterations. Proportional hazards assumption was tested by computing Schoenfeld residuals for each covariate and testing was performed according to Grambsch and Therneau[21] (FIG. 11 and Table 1). Martingale residuals were plotted against methylation predictor probabilities to determine appropriateness of linear modeling (FIG. 12). Sensitivity analyses evaluating the possible confounding effects of TERT promoter mutations, receipt of adjuvant radiation therapy, and center-effects were performed using multivariable Cox regression in samples with available information. Comparison of proportions across groups was completed using $\chi^2$ test and Fisher Exact test, where appropriate.

Two-sided p-values are reported, and the threshold for statistical significance was set a priori at $\alpha=0.05$. We used R version 3.3.1 for all statistical analyses, model generation, and model validation.

Methylation Analysis

DNA was extracted from each tumor and DNA methylation profiling was performed using Illumina™ 450 k HumanMethylation BeadChip (Illumina, San Diego, CA, USA) or 850 k EPIC (Illumina, San Diego, CA, USA) arrays per manufacturer instructions at each institution. Raw data files (*.idat) were imported and processed using R 3.3.1 (The R foundation for Statistical Computing www.R-project.org) minfi package. We performed single-sample Noob (ssNoob) normalization to integrate data from multiple generations of Infinium methylation arrays[27]. Probes that failed to hybridize (detection p value >0.05) in one or more samples, probes that overlapped with single nucleotide polymorphisms, cross-reactive probes, and probes that localized on X and Y chromosomes were removed from analysis[28]. Samples with poor quality control were also removed (N=2). Missing values were imputed by boosted trees imputation using Imputation package (https://github.com/jeffwong/imputation). Differentially methylated probes were identified based on post-processed β-values.

Copy Number Analysis

DNA copy number alterations were inferred from DNA methylation data of tumor samples using the Bioconductor package conumee relative to normal cortex DNA methylation data[29]. Whole genome and chromosome-level plots were generated for each sample and manually inspected by two independent reviewers (F.N, S.S) for copy number alterations. Partial and complete losses or gains of the p and q arm of each chromosome was recorded at a threshold of |0.2|. Discrepancies between reviewers were resolved by consensus, and discussed with a third independent reviewer (M.Y) if necessary. The burden of copy number aberrations per sample was calculated as previously described[30]. In addition to this, the genome of each sample was split into bins of multiple probes and probe intensity values were combined for copy number annotation. A genome-wide copy number alteration plot demonstrating proportions of gains or losses per bin was produced according to a custom algorithm.

TERT Promoter Sequencing

A subset of samples had panel sequencing by applying a custom hybrid-capture approach (Agilent Technologies, CA, USA) as previously described[31].

Machine-Learning Algorithms and Statistical Analyses

Feature Selection

Probes that were common in both 450 k HumanMethylation Beadchip and 850 K EPIC arrays were selected as initial features for development in our algorithms. Feature selection was performed on samples in the training set only. First, univariable Cox regression analysis for survival using each initial feature was performed to create a rank list of discriminative probes. Probes that were highly correlated with RFS (P-value≤0.01) were selected for further analysis. To mitigate for batch differences in tissue source and center of tissue processing, Principal Component Analysis of the highest 50000, 40000, 30000, and 20000 variables probes of stratified by tissue source and institution in the training cohort (European Fresh frozen tissue, European FFPE tissue, Princess Margaret Cancer Center Fresh frozen tissue) was performed. Technical sources of variation were assessed by computing the F-ratio, and the set of highest variable probes that showed a reduction in the F-ratio for tissue source and tissue type with greatest convergence between the center of gravity and standard deviation was used to determine a common set of discriminatory probes. This approach was used strictly for feature selection without any transformation of data. Further feature refinement was performed using the minimum redundancy maximum relevance ensemble (mRMRe) package (https://cran.r-project.org/web/packages/mRMRe/index.html) that allows for parallelized ensemble features to select a set of relevant, complementary, and reliable features[6]. A minimal importance threshold of |2.5| was used for final feature selection.

Figure 7:
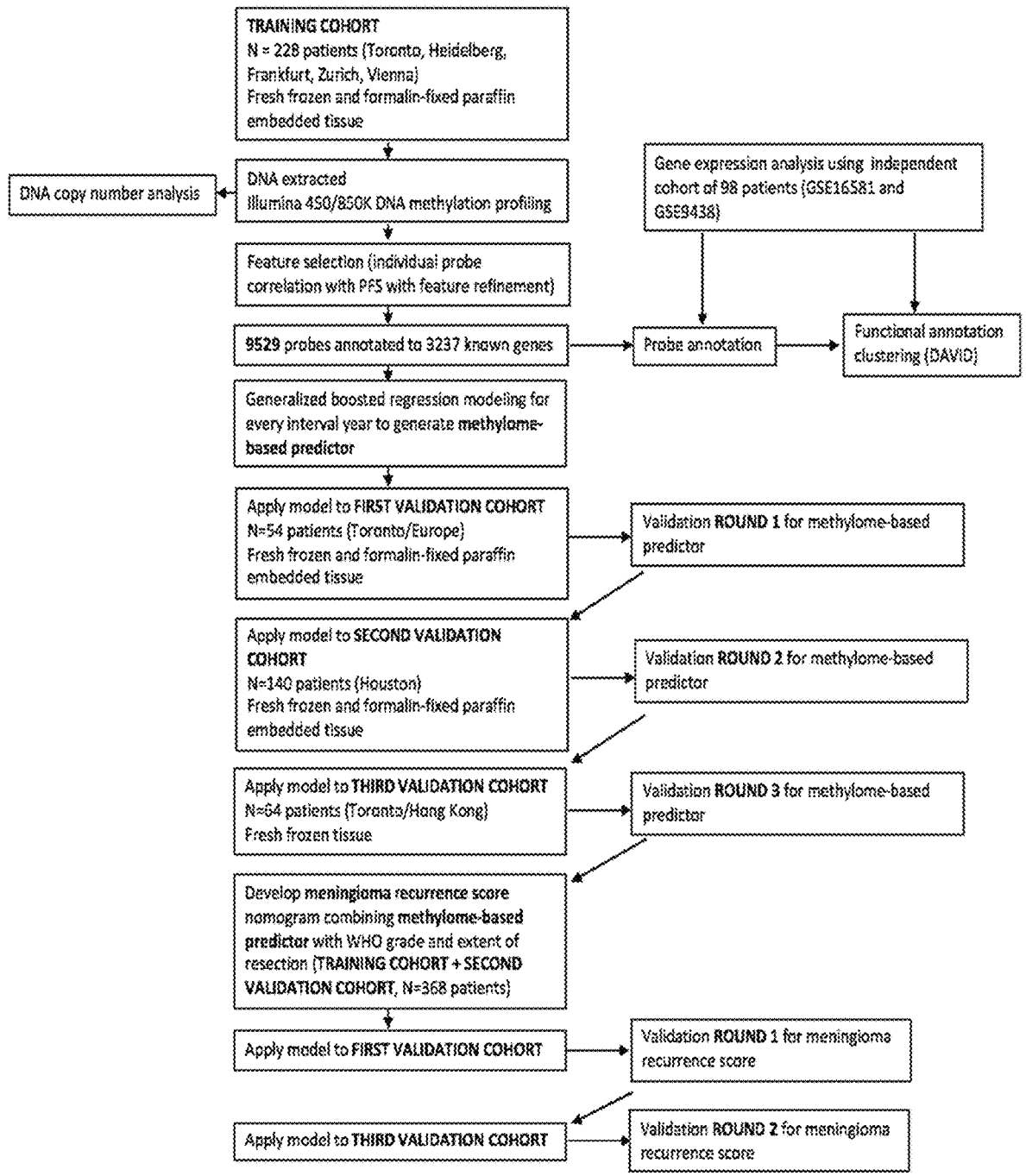
FIG. 7 shows outline of the overall study design. Illumina™ Infinium DNA methylation arrays were generated on meningioma samples (from Toronto), and additional methylation data from published work (Europe, Houston) were used to develop and validate the methylome-based predictor for recurrence-free survival (RFS). Cox modeling of individual probes was use for feature selection in a training set (N=228 patients) which was then applied to 3 independent validation sets (N=54, N=140, and N=64 patients). Genome-wide copy number alterations were inferred from DNA methylation data. Functional annotation of genes recurrently represented by the selected probes was performed and gene-expression analysis was correlated to DNA methylation profiles using two publicly available microarray datasets. Cox modeling was used to generate a 5-year meningioma recurrence score based on a nomogram that integrated the validated methylome-based predictor with established key clinical factors.

The distribution of patient and tumor characteristics in our discovery, first validation, and second validation cohorts are shown in Table 1. Our training dataset contained 228 samples with 341,172 overlapping probes from Illumina™ 450 k HumanMethylation BeadChips and 850 k EPIC arrays. Univariate Cox regression for survival using the training set revealed 71538 probes that were highly correlated with RFS (P<0.01). Principal Component Analysis based on the top 30000 variable probes form the 71538 available probes demonstrated the least batch related differences with convergence of centre of gravity and standard deviations between fresh frozen and FFPE samples from the Princess Margaret Cancer Center and samples from the University of Heidelberg (FIG. 7, appendix pp). Of the top 30000 variable probes, 23571 probes were in common in samples from Princess Margaret Cancer Center fresh frozen samples and European FFPE and fresh frozen samples and were selected for further refinement. Parallelized minimum redundancy maximum relevance ensemble revealed a final set of 9529 probes annotated to 3237 known genes that were selected as features for development of a methylome-based predictor of RFS.

Model Generation

To develop the predictor, we performed gradient boosted regression modeling using the final selected probes in samples from the training cohort to create and tune a tumor DNA methylome-based predictor of early (5-year). Gradient boosted modeling is an ensemble technique whereby weak individual tree-based prediction models are combined sequentially over ith number of iterations to produce a strong model for predicting outcome. In brief, at every iteration, a tree is grown, residuals are calculated for the tree, and a regression is run to minimize the residual and weights are updated accordingly. Our implementation is cox-proportion hazard model for right-censored data. Gradient boosted modeling using WHO grade (binarized) as a sole feature in the training cohort was also performed and tested in both validation cohorts for comparison of model performance.

Probe Annotation, Pathway, and Gene Expression Analysis

Probe annotation was performed using the UCSC Genome Browse (GRCh38/hg38 assembly). We used the Functional Annotation Clustering algorithm[33] of Database for Annotation, Visualization, and Integrated Discovery (DAVID)[33] Bioinformatics Resource 6.8 to identify functional clusters represented by genes annotated with a minimum of 5 probes. Functional clustering was performed using high classification stringency. The group enrichment score, which represents the geometric mean of the genes p-values in each cluster, was used to rank biological significance.

To correlate methylation data with gene expression, we pooled 2 publicly available microarray datasets (GSE16581[34] and GSE9438[35]) on 22486 genes for 98 patients with meningiomas. Affymetrix CEL files of each dataset were imported using Partek Genomics Suit Software (Partek, St. Louis, USA) and processed by quantile normalization, log 2 transformation, and Robust MultiArray Average background correction. Gene level integration was performed by averaging multiple probes mapped to each gene after inverse log 2 transformation for each dataset. Dataset integration was performed after batch effect correction, and fold changes and corresponding p-values of the genes of interest were obtained.

Nomogram Development

We used a Cox model to generate a nomogram combining methylome-based predictor scores, Simpson grade, and WHO grade as variables of interest using samples from the training cohort and validation cohort 2. Given that the development of the model is highly dependent on the input number of samples, we combined the training cohort and validation cohort 2 to generate this model. The tuning parameter $\lambda$ was trained using 10-fold cross-validation approach with 1 standard error selection rule. The model was externally validated using validation cohort 2 and validation cohort 3 (representing total of 2 rounds validation).

Nomogram Use

Figure 9:
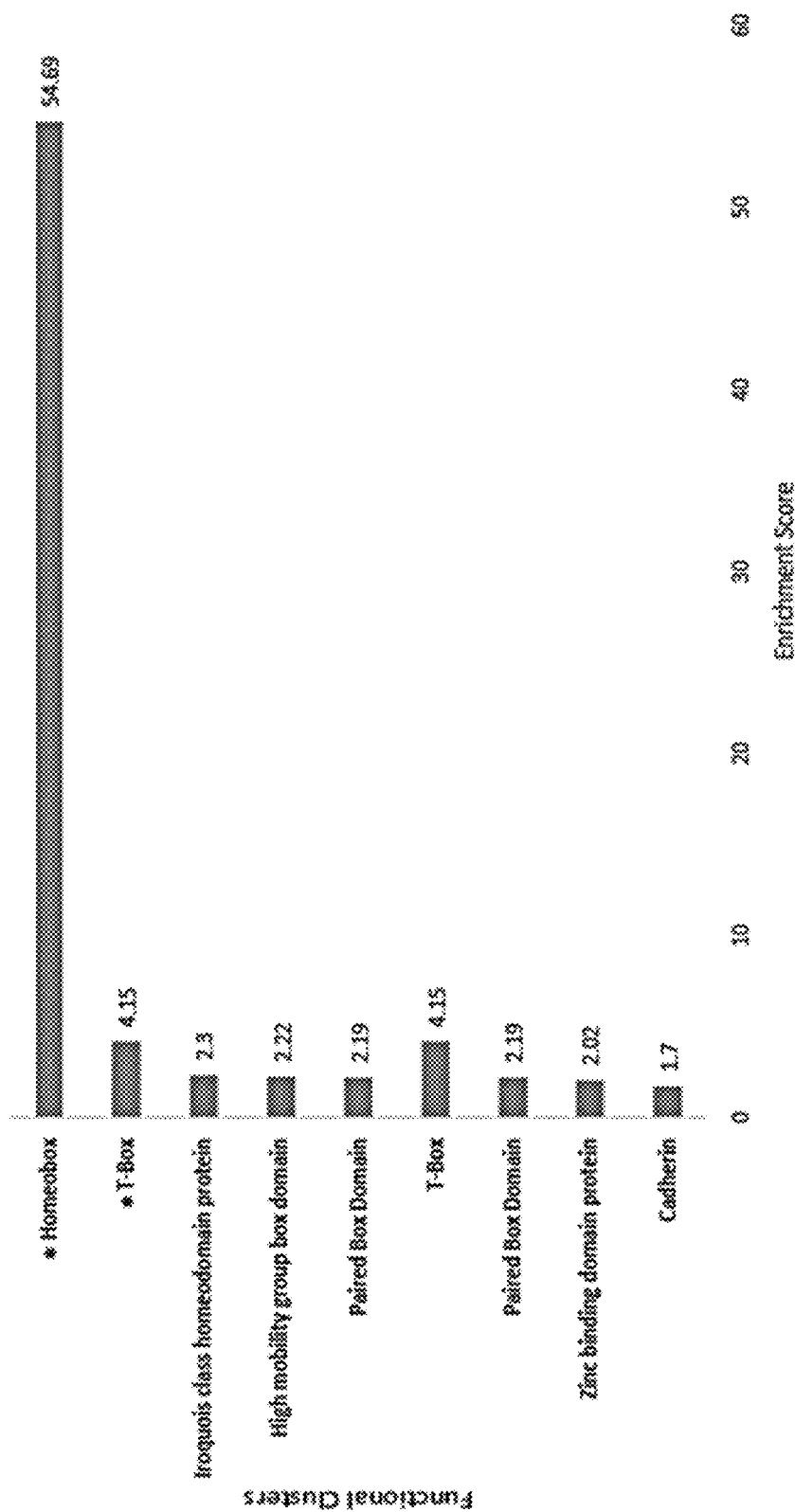
FIG. 9 shows enrichment scores from functional clustering of genes with minimum 5 annotated probes (* indicates Bonferonni adjusted p-values<0.05).

A nomogram is a two-dimensional diagram used to allow for approximate graphical calculation of mathematical function using scaled graphical devices. Each variable in the equation is scaled accordingly, and values for each variable are assigned points in the "calculator" (FIG. 9, appendix pp). The variables included into the nomogram are the "5y methylome probability", "WHO grade" and "Simpson grade". We are developing a publicly available platform where users can upload their raw IDAT files for their samples to receive the 5-year methylome based predictor probability. For a given patient, the cumulative points from each variable ("5y methylome probability", "WHO grade" and "Simpson grade") is calculated for a result of total points. The "risk nomogram" is then used to scale the total points to risk of 5-year RFS. To facilitate unrestricted global dissemination, we have created a freely available online calculator of the meningioma recurrence score (https://fnassiri.shinyapps.io/meningioma_recurrence_score_online_calculator/).

Statistical Analysis

Summary statistics are reported as counts (and proportions) for categorical variables and median (and range) for continuous variables, unless otherwise indicated. Cohort size was determined by availability of samples and not by a priori power calculations. Statistical analyses were performed in consultation with two expert biostatisticians (L.P and O.S).

To investigate the clinical relevance of the 5y methylome-based predictor distribution on survival times, we used Kaplan-Meier methods and comparisons across groups through log-rank testing. Performance of the predictor was assessed by independently computing probability of recurrence at 5 years in each of the 3 validation cohorts and in the combined validation cohorts using 10,000 bootstrap resampling approach. Receiver operator characteristic (ROC) curves were generated for each bootstrap using the Nearest Neighbour time-dependent ROC curve method of Heagerty, Lumley, and Pepe (2000)[36] and the area under the ROC curve (AUC) at 5-years was computed for each bootstrap and averaged to calculate the accuracy of our model to predict recurrence at 5 years in all validation cohorts. The performance of a methylome-based predictor was compared to grade-based predictor by computing $\Delta$AUC ($AUC_{methylome}-AUC_{grade}$) for each bootstrap and averaged to compute a mean $\Delta$AUC with 95% CI. To evaluate the prognostic utility of the methylome predictor in WHO grade I, II and WHO grade III tumors, we generated low and high risk groups by splitting from the median of probability results from the methylome predictor and performing Kaplan-Meier survival analyses.

The performance of the meningioma recurrence score incorporating the methylome predictor was compared to a nomogram excluding the methylome predictor by computing time-dependent AUC and $\Delta$AUC at 5-years in a similar fashion to above[36,37] Performance of the meningioma recurrence was assessed by independently computing probability of recurrence at 5 years in each of the 2 validation cohorts and in the combined validation cohorts using 10,000 bootstrap resampling approach. Receiver operator characteristic (ROC) curves were generated for each bootstrap and the area under the ROC curve (AUC)[37] at 5-years was computed for each bootstrap and averaged to calculate the accuracy of our model to predict recurrence at 5 years in all validation cohorts. The performance of the meningioma recurrence score was compared to a nomogram incorporating clinical factors only by computing ΔAUC (ΔAUC=AUC$_{combined\ nomogram}$−AUC$_{clinical\ only\ nomogram}$) for each bootstrap and averaged to compute a mean ΔAUC with 95% CI. Calibration of the meningioma recurrence score was assessed visually by plotting observed event rates against nomogram predicted probabilities for two risk groups (high and low risk). To investigate the clinical relevance of the meningioma-recurrence score, distribution of survival times was estimated using Kaplan-Meier methods and compared across high and low risk groups using log-rank testing.

Hazard ratios and their 95% confidence intervals (CI), were calculated based on univariable and multivariable Cox regression modeling for the methylome-based predictor and other covariates including WHO Grade, extent of resection, and burden of copy number alterations. In order to determine whether TERT promoter mutations, receipt of adjuvant radiation therapy, and treatment center were confounding the relationship between the methylome-based predictor and RFS, sensitivity analyses were reported including these factors as covariates where available. Plots of martingale residuals versus methylome-predictor values were generated to assess the appropriateness of the assumption of linear effect of the methylome-based predictor in the Cox regression model. The proportional hazards assumptions were evaluated by computing plots of Schoenfeld residuals for each covariate versus time. Weighted least-squares line were fitted to the residual plot, and proportional hazards testing was performed according to Grambsch and Therneau[12].

Results and Discussion

A set of 9529 probes were selected from an initial training cohort and generalized boosted regression modeling was performed to develop a DNA methylation-based predictor of 5-year recurrence risk in meningioma (FIG. 7). Three validation cohorts (Table 2) were used to test the performance of the methylation-based predictor compared to a grade-based predictor.

Validation of a Methylome-Predictor of Early Meningioma Recurrence

Figure 2:
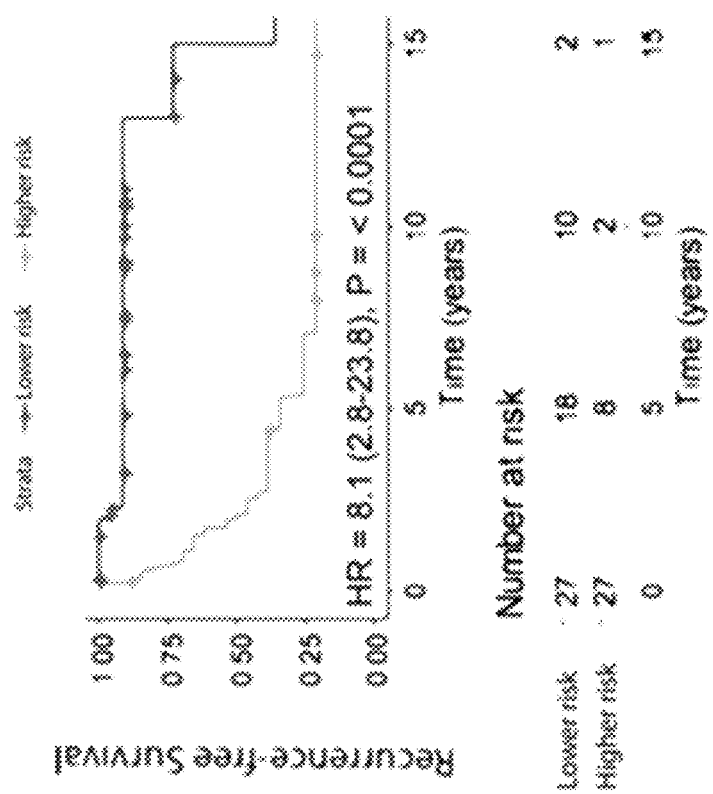
FIG. 2 shows recurrence-free survival (RFS) analysis of the first validation cohort (A), second validation cohort (B), and (C) third validation cohort using the 5y methylome-based RFS predictor, based on separation into distinct risk groups by median.
Figure 2:
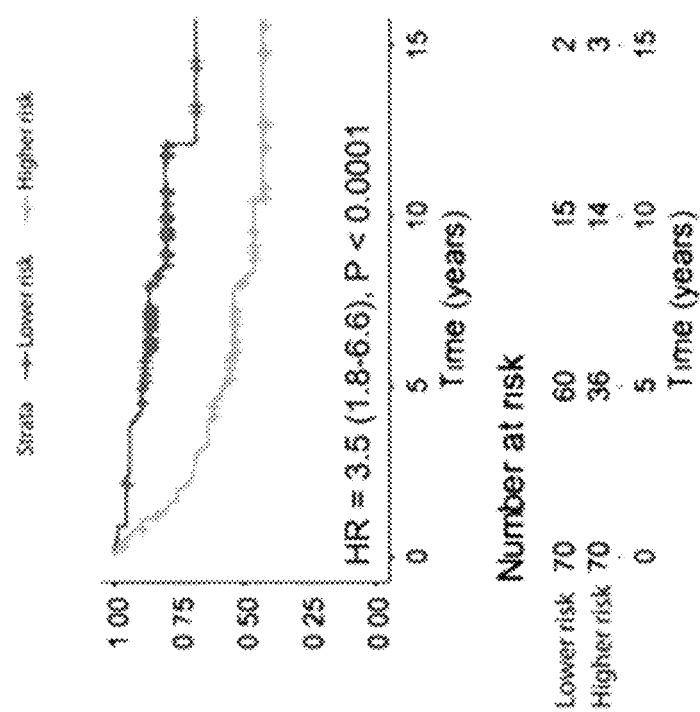
Figure 2:
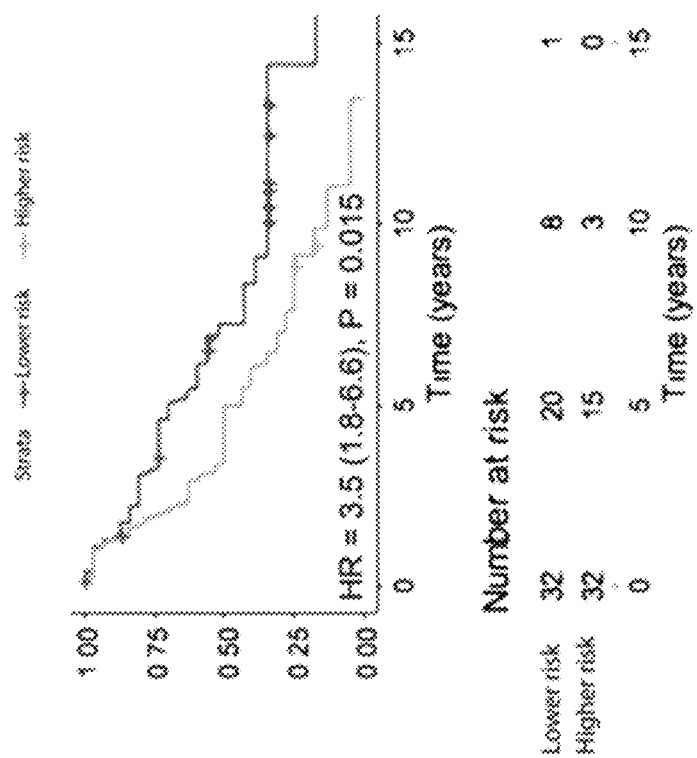

The methylome-based predictor performed favorably compared to the grade-based predictor at 5-years in each of the 3 validation cohorts (FIG. 1) with substantial statistical improvements in performance when tested in all combined validation cohorts (ΔAUC=0.10, 95% CI 0.03-0.18). When stratified by median, the 5-year methylome-predictor distinguished risk groups (lower and higher risk) in all 3 validation cohorts (FIG. 2). Patients in the higher risk group had a median RFS of 2.1 years, 8.1 years, and 4.2 years in the first, second, and third validation cohorts respectively compared to patients in the lower risk groups which had median RFS of "unreached" in the first and second validation cohorts and median RFS of 7.2 years in the third validation cohort (HR 8.1 95% CI 2.8-23.8, HR 3.5 95% CI 1.8-6.6, and HR 2.0, 95% CI 1.2-3.7, respectively).

Figure 3:
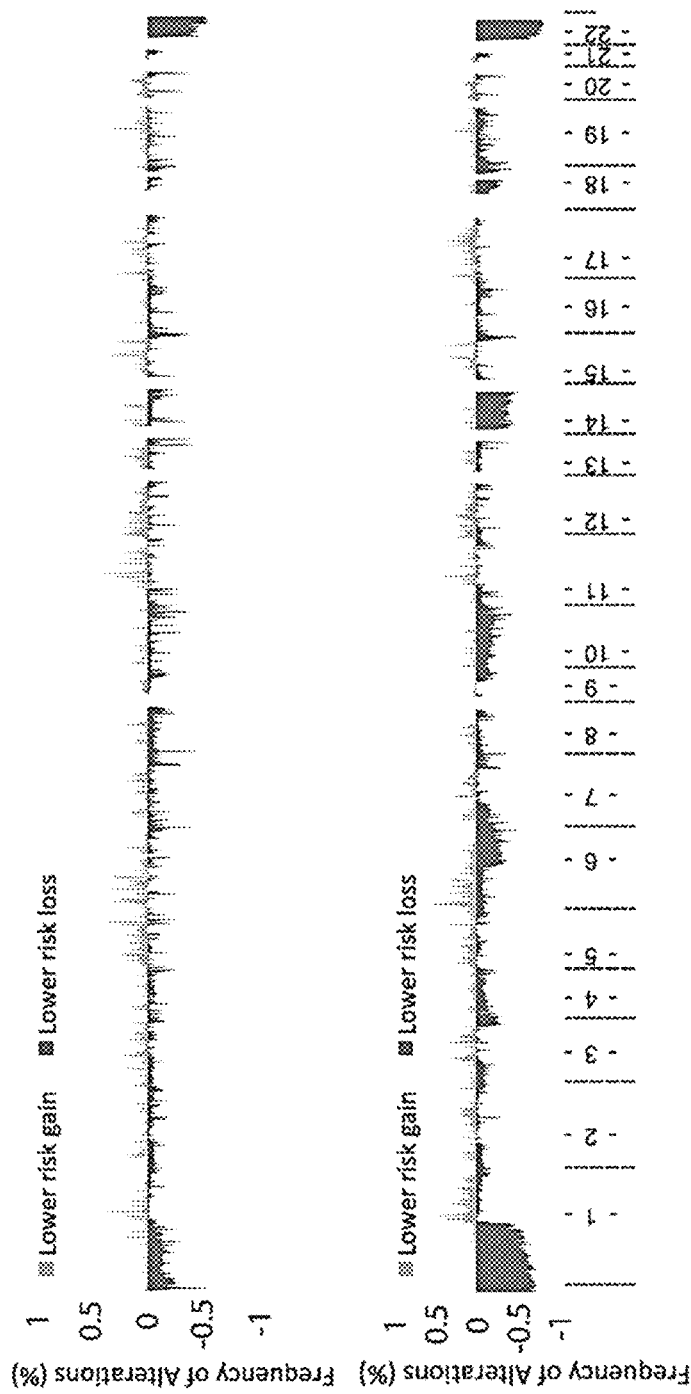
FIG. 3 shows frequency of copy number alterations across the genome stratified in risk groups according to the methylome-based predictor. Groups correspond to same groups seen in FIG. 2.

DNA copy number analysis demonstrated that increased frequency of copy number aberrations in the higher risk groups, as demonstrated by high proportion of chromosomal deletions in 1p, 4p, 6q, 10q, 14q, and 18q (FIG. 3). The total burden of copy number alterations was also correlated with risk groups, with greatest proportion of burden of copy number alterations found in the higher risk groups in all three validation cohorts (FIG. 9). It is noteworthy that of all patients with high burden of copy number aberrations from all three validation cohorts, only 12 patients (4.6%) were in the lower risk group.

Multivariable Cox regression analysis demonstrated that the 5-year methylome based predictor was independently associated with RFS in samples from all validation cohorts (HR 3.6, 95% CI 1.8-7.2, P<0.001) after controlling for tumor grade, extent of resection, burden of copy number alterations (Table S4). Sensitivity analyses including receipt of adjuvant therapy, TERT promoter mutations, and center of treatment as covariates did not alter this relationship and these covariates were not independently associated with RFS (Tables 5-7).

Figure 4:
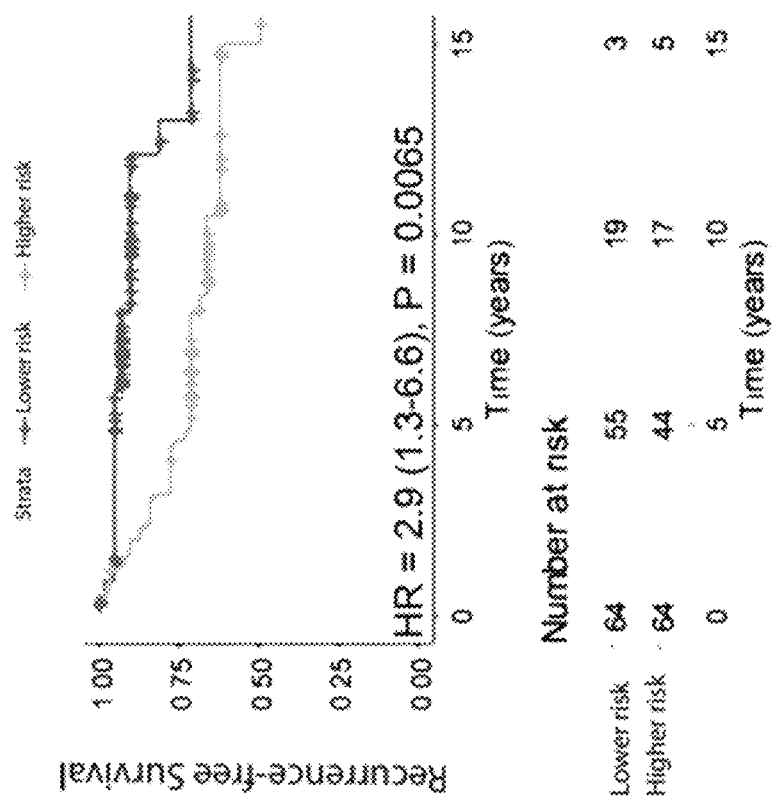
FIG. 4 shows recurrence-free survival (RFS) analysis of all WHO grade I (A), WHO grade II (B) and WHO grade III (C) tumors in all three validation cohorts.
Figure 4:
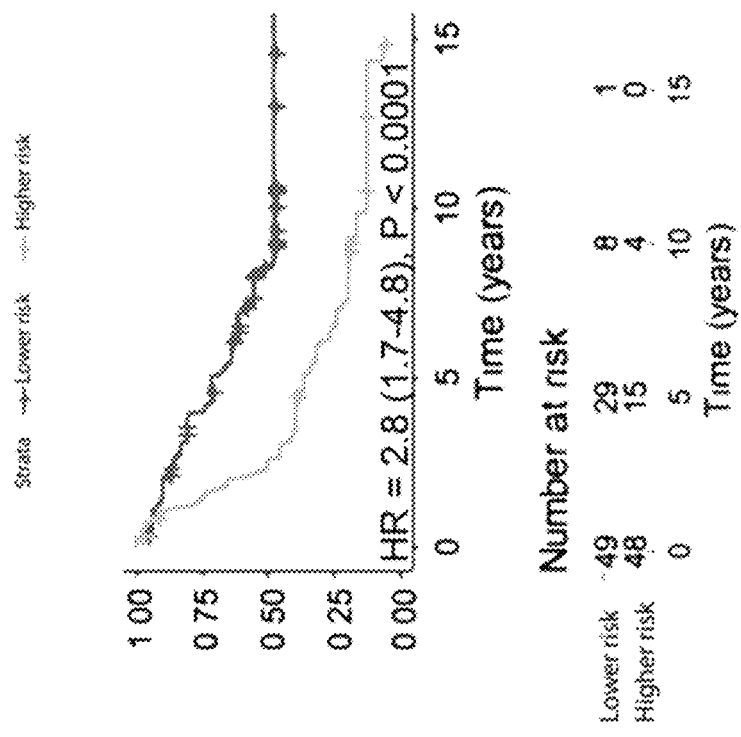
Figure 4:
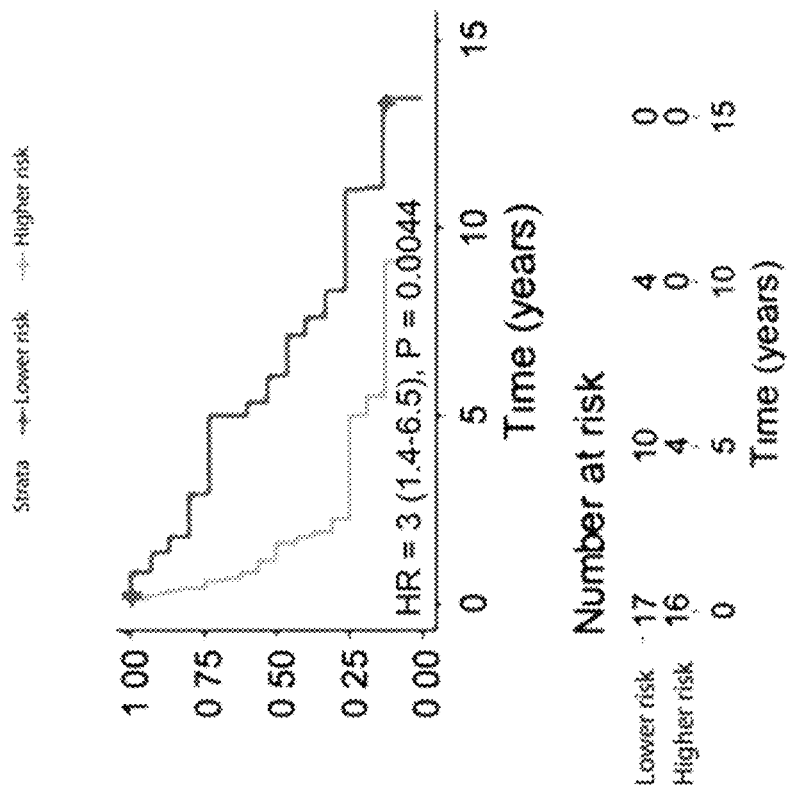

Current clinical practice relies on histopathologic grade to inform the decision of post-surgical management of meningioma. Patients with grade I tumors are most commonly monitored with serial imaging after surgery, while patients with grade II and III tumors are considered for adjuvant therapy, such as radiation, to prevent recurrence. There is, however, unexplained clinical variability in RFS within all grades of meningioma, and we examined the use of the 5-year methylome-predictor to address this issue. Among patients with WHO grade II tumors in all validation cohorts, the median RFS for the higher risk group was 2.6 years compared to a median RFS of 8.4 years in the lower risk group (HR 2.8, 95% CI 1.7-4.8, P<0.001, FIG. 4B). Patients with WHO Grade I tumors in all validation cohorts also had increased risk for recurrence in the higher risk group (HR 2.9, 95% CI 1.3-6.6, P=0.006, FIG. 4A) with only 3 patients in the lower risk group recurring within the first 5 years compared to 18 patients in the higher risk group. Lastly, patients with WHO Grade III tumors from all validation cohorts had poor median RFS in the higher risk group (1.3 years), compared to a median RFS of 6.0 years in the lower risk group (HR 3.0, 95% CI 1.4-6.5, P=0.004, FIG. 4C).

Characterization of Predictor CpG Sites

The selected 9529 probes used in our model comprise only 1% of all probes included on the 850K Illumina™ Array. These probes were enriched to be found in the promoter regions (N=3057, 32.1%) and located on CpG islands (N=4633, 48.6%) compared to all probes found on the 850K Illumina™ Array (29.6%, P<0.001 and 18.0%, P<0.001, respectively; Table 8) Of the 9529 probes, only 1261 (13.2%) were "favorable" probes associated with lower risk of recurrence when methylated (HR ranging from 0.002 to 0.38, on univariable Cox regression with associated P<0.001). The remaining 8237 (86.8%) probes were "unfavorable" probes associated with higher risk of recurrence when methylated (HR ranging from 2.45 to 517.82, on univariable Cox regression with associated P<0.001).

There were 2332 probes annotated to 294 genes with at least 5 probes represented per gene. Of these (Table 9), only 68 of 2332 probes (2.9%) were found to be "favorable" probes (associated with lower recurrence risk when methylated, HR ranging from 0.008 to 0.252 on univariable Cox regression with associated P<0.001). The remaining 2265 probes (97.1%) were found to be "unfavorable" probes associated with greater recurrence risk (associated with higher recurrence risk when methylated, HR ranging from 2.95 to 517.82 on univariable Cox regression with associated P<0.001). Functional annotation clustering of these 2265 "unfavorable" probes revealed that homeobox (enrichment score=54.33) and TBox (enrichment score=4.12) were highly significant redundant functional clusters (FIG. 9). Gene expression analysis of Homeobox family of genes and Tbox genes for which methylation data was also available, demonstrated that although these genes were relatively hypermethylated in recurrence-prone tumors, they were either upregulated or non-differentially expressed (Table 10).

Validation and Clinical Utility of a Meningioma Recurrence Score

Figure 5:
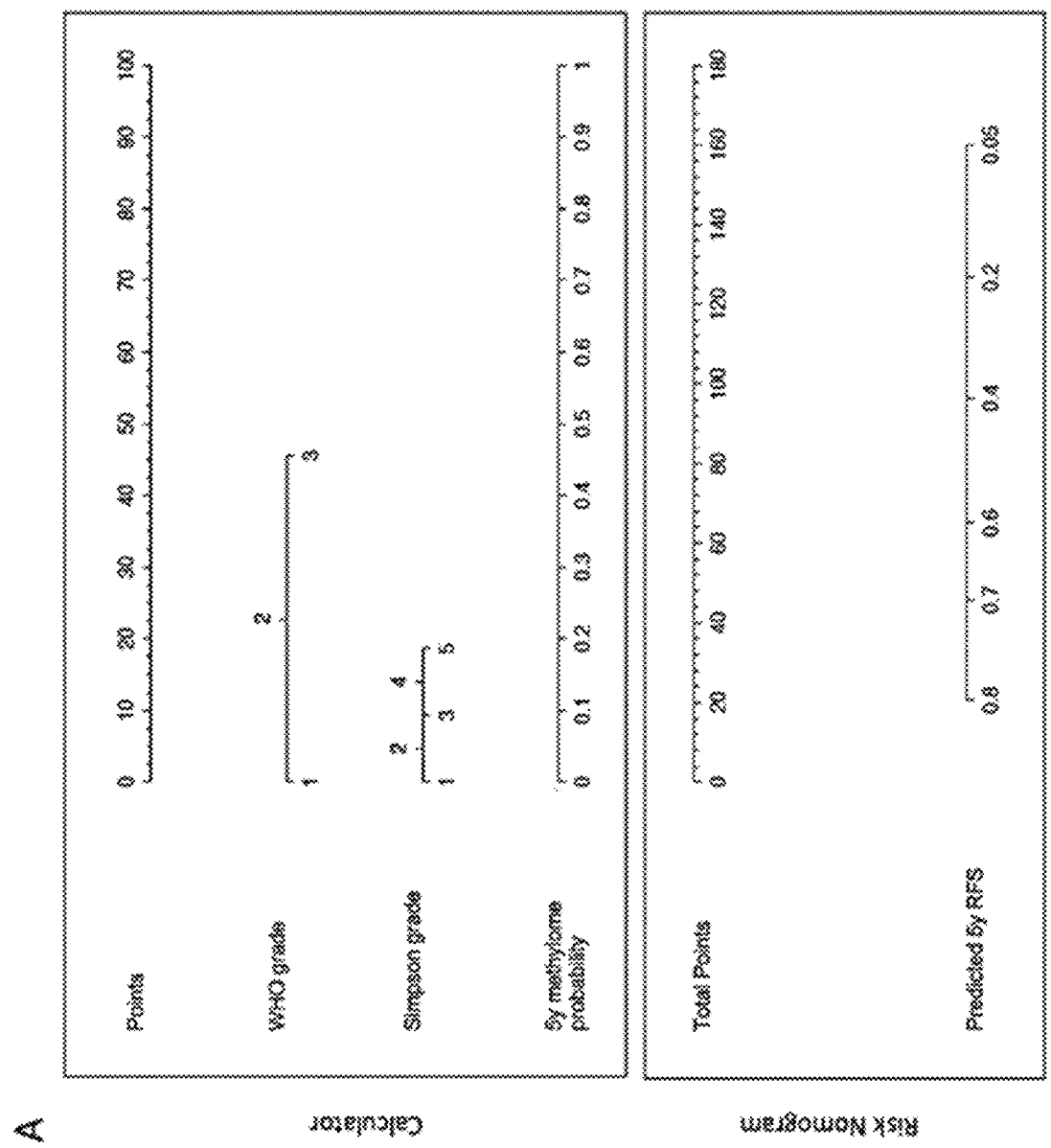
FIG. 5 shows a nomogram to predict 5-year recurrence risk in meningiomas (A) Total points generated from scoring of methylome-based RFS predictor, WHO grade, and Simpson grade are tallied in the calculator and correlated to 5-year RFS in the nomogram in the Risk Nomogram. (B) Time-dependent average AUC with 95% CI as well as ΔAUC (DAUC) with 95% CI using 10,000 bootstrap resampling validation approach generated for the meningioma recurrence score and a nomogram using clinical factors alone in the first and third validation cohorts as well as both combined validation cohorts. (C) Calibration curve of the nomogram to predict recurrence-free survival at 5 years in the combined validation cohort. The observed recurrence-free survival is plotted on the y-axis and nomogram predicted probability is plotted on the x-axis.
Figure 5:
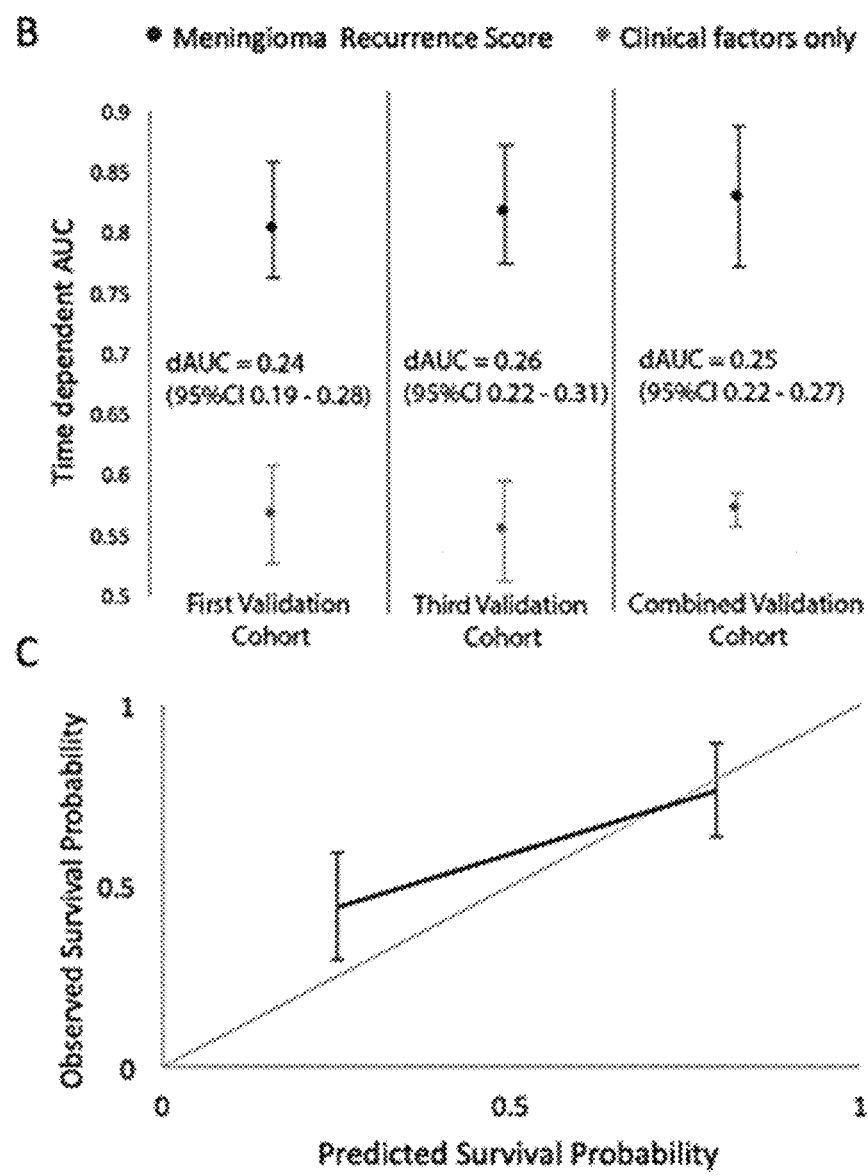
Figure 6:
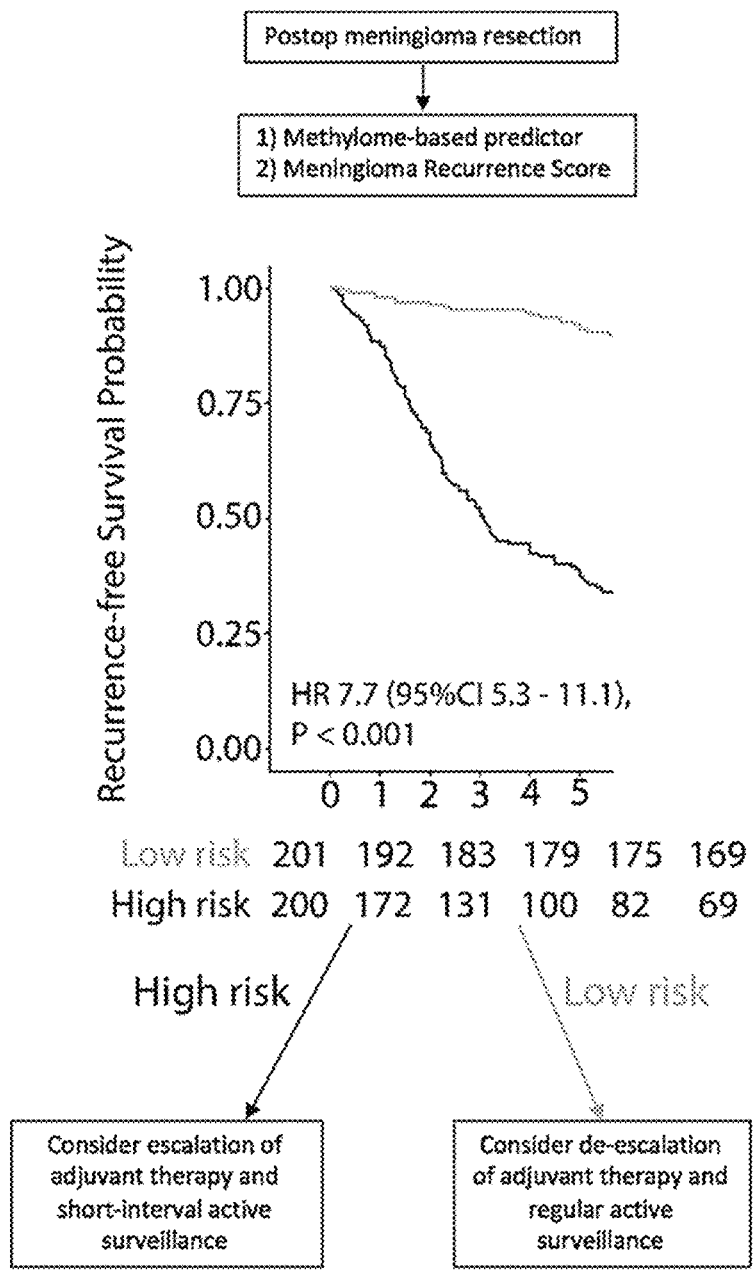
FIG. 6 shows the meningioma recurrence score identifies two risk groups (high risk versus low risk) that may help individualize adjuvant management decisions such as the need for radiation therapy in patients with meningiomas. Patient tumor samples can be interrogated for DNA methylation profile of selected 9529 probes and a 5-year methylome-based RFS predictor score is generated. This score is combined with tumor WHO grade and Simpson grade in the meningioma recurrence score to develop an individualized probability of 5-year recurrence-free survival.
Figure 13:
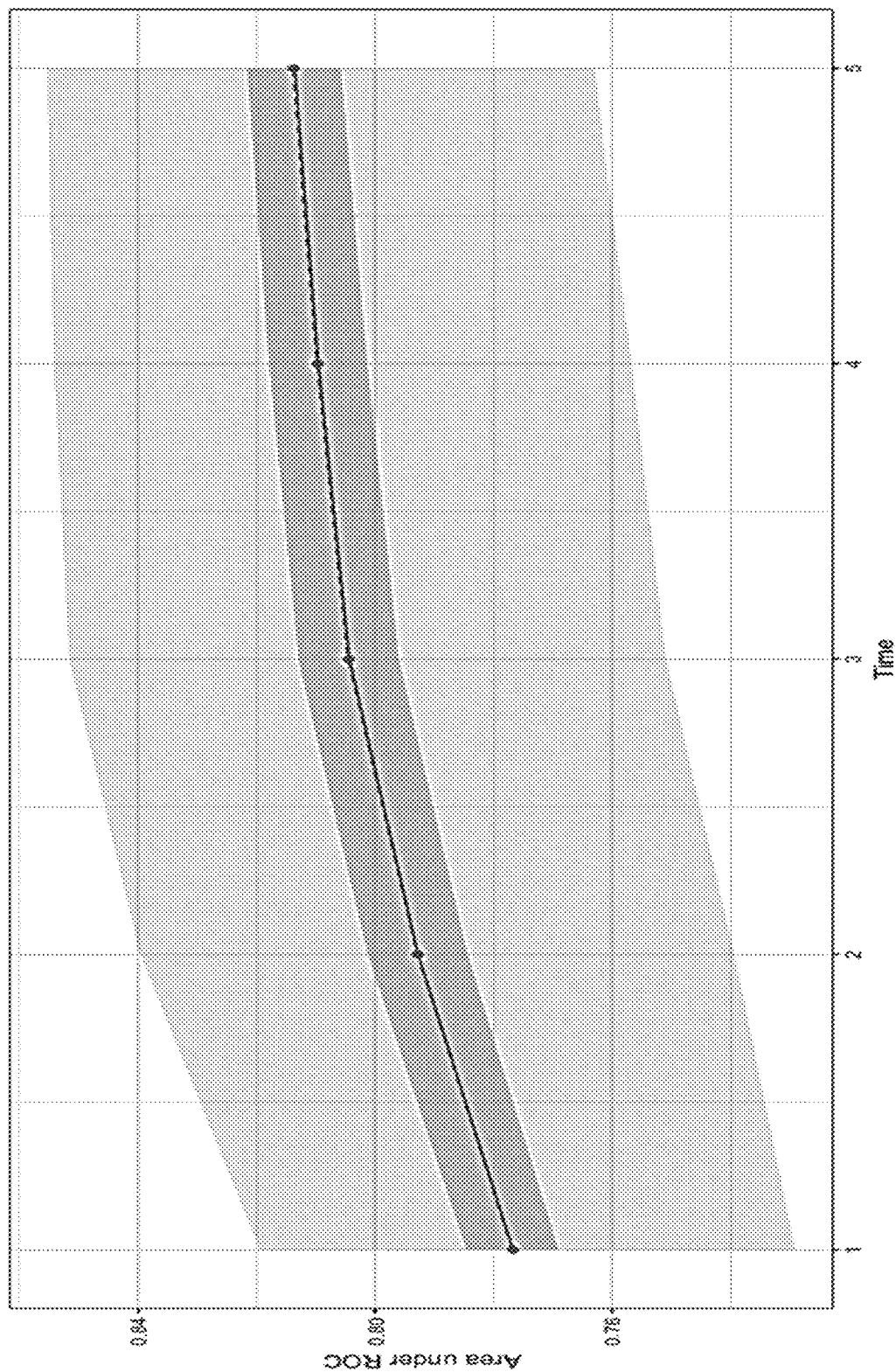
FIG. 13 shows internal validation using 10,000 bootstramp resampling method and and time-dependent AUC calculations of meningioma recurrence score. Solid lines represents the mean AUC, darkened grey area represents the interquartile range, and the light grey area represents the minimum and maximum.
Figure 14:
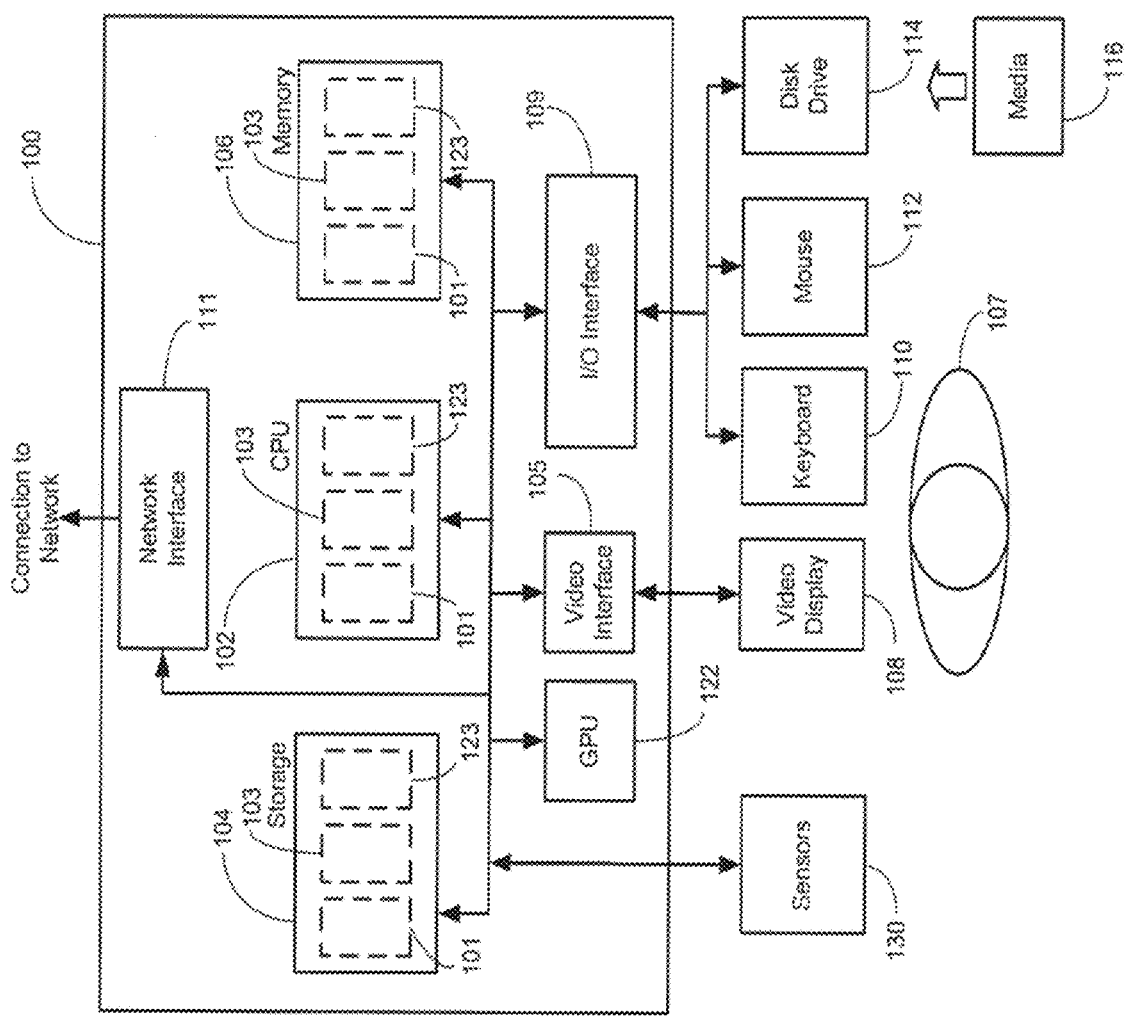
FIG. 14 shows suitable configured computer device, and associated communications networks, devices, software and firmware to provide a platform for enabling one or more embodiments as described herein.

To generate and validate a meningioma recurrence score that could be translated to the clinic, we developed a nomogram to predict 5-year RFS that incorporated the validated 5y methylome-based predictor with established prognostic covariates (WHO grade, and extent of resection) using samples from the training cohort and second validation cohort (FIG. 5). Validation of the nomogram using the first validation cohort and third validation cohort independently as well as both validation cohorts combined demonstrated greater predictive performance of the nomogram with methylome predictor included compared to a nomogram using clinical factors (WHO grade and extent of resection) alone ($\Delta AUC=0.24$, 95% CI 0.19-0.28; $\Delta AUC=0.26$, 95% CI 0.22-0.31; $\Delta AUC=0.25$, 95% CI 0.22-0.27 respectively, FIG. 5). The discriminative power of the meningioma recurrence score was approximately 82% in combined validation cohorts (AUC=0.82, 95% CI 0.76-0.87). The performance of the model using external validation and internal validation approaches were similar (FIG. 13). The highest proportion of allottable points given in the nomogram is based on probabilities from the methylome-based predictor, again suggesting that the methylome-predictor has greater importance in determining recurrence risk in meningiomas compared to established clinical factors. Calibration and Kaplan-Meier survival analysis of the meningioma recurrence score clearly stratifies patients with high risk and low risk for 5-year recurrence (HR 7.7, 95% CI 5.3-11.1, P<0.001, FIG. 6). Interestingly, while histologic grades II and III are meant to predict high recurrence risk, we find that the low-risk group in total contains 39 grade II tumors (34.5% of the grade II tumors) and 4 grade III tumors (8.3% of the grade III tumors).

Conversely, while a WHO grade I designation is meant to convey a low risk of recurrence, there were 35 (21.2%) patients with grade I tumors in the high-risk group. These results indicate refinement of risk estimate by the nomogram relative to current classification standards. To facilitate unrestricted global dissemination, we have created a freely available online calculator of the meningioma recurrence score https://meningiomas.shinyappsio/meningioma_recurrence_score_online_calculator/.

Details on imputations for the online calculator can be found in the methods above, and case examples demonstrating the power of personalized predictions are detailed below.

Case example #1 demonstrates the power of individualized prognostication. This is a case of a 58-year-old male with a right sided sphenoid wing meningioma that was resected completely (simpson grade 1). Histopathology demonstrated a WHO Grade I meningioma, 1 mitosis per 10HPF, no necrosis or other atypical features. Traditionally this patient would be considered cured of their disease (benign meningioma that is completely resected), however, in fact this patient experienced 30-months after initial resection. The methylation-based predictor score for this patient is 0.9785 (score ranges from 0 [lowest risk] to 1 [highest risk]). The meningioma recurrence score for this patient demonstrates a 71.75% risk of recurrence within 5-years making this patient high risk for recurrence. Copy number variation plot demonstrates a bland copy number landscape and does not demonstrate a high degree of burden of copy number alterations. Existing DNA methylation-classification systems deem this tumor to be of intermediate risk without clear predictions of 5-year recurrence risk.

Case example #2 further demonstrates the power of individualized prognostication. This is a case of a 45-year-old male with a right sided convexity meningioma that was resected completely (simpson grade 1). Histopathology demonstrated a meningothelial neoplasm with discohesive cells organized in sheets and a dominance of papillae with a vascular core: WHO Grade III papillary meningioma. Traditionally this patient would be considered high risk for recurrence and would be considered for adjuvant radiation therapy. However, this patient did not receive adjuvant radiation therapy (prolonged complicated post-operative course), and at 62-months after surgical resection the patient remains recurrence-free. The methylation-based predictor score for this patient is 0.9785 (score ranges from 0.004669 [lowest risk] to 1 [highest risk]). The meningioma recurrence score for this patient demonstrates a 19.07% risk of recurrence within 5-years making this patient low risk for recurrence. Copy number variation plot demonstrates gain in chromosome 10 and 22q loss. Existing DNA methylation-classification systems deem this tumor to be of intermediate risk without clear predictions of 5-year recurrence risk.

Discussion

In this multicenter study, we demonstrated the transformative utility of integrating clinical and molecular factors for use beyond simple classification into the realm of individualized prognostication in neuro-oncology. Our methylome-based predictor was more reliably able to predict early (5-year) recurrence-free survival in comparison with histologic grading and was associated with RFS independent of established clinical and molecular factors. Combining the methylome predictor with established prognostic clinical factors (WHO grade and extent of resection) in a meningioma recurrence score refined prognostication for individual patients with meningiomas beyond established prognostic clinical and molecular factors with therapeutic implications for individualizing decision-making regarding the need for adjuvant therapy after surgery in meningiomas.

Although WHO grade is associated with recurrence in populations of meningioma patients, and is currently used to guide therapy, the clear within-grade variation for risk of recurrence and inter-rater variability makes it challenging to rely on tumor grade alone to predict recurrence and guide postoperative management decisions for individual patients. As a manifestation of this imprecision, some patients with biologically aggressive tumors may be inappropriately subsumed in within the group of histologically benign tumors. With current standard of care, it is thought that up-front treatment with adjuvant radiation therapy after surgical resection offers the best chance to delay recurrence, and therefore some patients are not appropriately selected for adjuvant treatment with standard-of-care approaches[3,4]. Conversely, there are also some patients with histologically defined intermediate or higher-grade tumors that in fact harbor indolent tumor behavior. Such patients may be receiving adjuvant radiation therapy in the absence of a defined need. Radiation, even when optimized to minimize adverse effects, still carries the risk for adverse radiation effects such as reactive inflammation, vasculitis, and necrosis, all of which have sequelae on patient cognition and quality of life[5]. There is a clear need for a more refined predictor of recurrence patterns for individual patients with meningiomas beyond simple classifications, so that the decision for adjuvant therapy, radiotherapy or otherwise, can be appropriately selected and personalized for patients.

The burden of chromosomal alterations have repeatedly been shown to be one of the most important prognostic molecular alterations in meningioma[11,17,22]. Similar to others[11,22], we found recurrent alterations in 1p, 4p, 6q, 10q, 14q, and 18q in a subset of meningiomas that were enriched in higher risk group. However, using a previously published copy number score designed to identify meningiomas with high recurrence risk[17], we found that the burden of copy number alteration was not an independent predictor of recurrence once adjusted for methylation signature. Similarly, although TERT promoter mutations are known to be enriched in more aggressive meningiomas[10], our analysis demonstrated that TERT promoter mutation was not independently associated with RFS on multivariable analysis with the 5-year methylome predictor included in the model. Taken together, these results suggest that our 5-year methylome predictor can provide prognostic information beyond previously established molecular factors in meningioma.

Probes included in the predictor were selected based on correlations of either hypo- or hypermethylated status with respect to RFS. Interestingly, the distribution of these probes was not random, either with respect to methylation status nor with respect to association with known genes. The majority (over 86%) of our included probes were all associated with unfavorable RFS when hypermethylated. This suggests that in general, hypermethylation of a set of CpG sites in meningioma correlates with clinical aggressiveness. For example, hypermethylation of the homeobox and Tbox families of genes were found to be highly overrepresented in the set of relevant probes, suggesting possible involvement of this class of developmental factors in the clinical behavior of meningioma, which requires further validation.

To generate a tool that could be used by clinicians to capture the heterogeneity in recurrence risk in meningiomas, we established a 5-year meningioma recurrence score that combined our validated methylome-based predictor with well-established prognostic clinical factors (WHO grade and extent of resection). The performance of our meningioma recurrence score was improved with the methylome-based predictor included in the nomogram ($\Delta$AUC=0.25, 95% CI 0.22-0.27), and the overall discrimination of our nomogram was high (AUC approximately 82% in two independent cohorts). The construction, and evaluation, of our nomogram meets the standards of reporting on nomograms in oncology and is one of few to demonstrate robust evaluation using multiple independent validation cohorts[23]. Now that we have demonstrated that our tools are robustly validated, we are well positioned to prospectively validate the use of our tools to demonstrate efficacy with adjuvant therapy strategies in high-risk patients[24]. Our meningioma recurrence score informs both patients and clinicians about individualized risk of recurrence, can be used to guide clinicians regarding the need for adjuvant therapy and/or close clinical follow-up.

Our study has some limitations. First, although we have identified a group of probes with distinct epigenetic changes that in combination are predictive of recurrence risk in meningiomas for individual patients, it is unclear whether these changes may be conferring variant behavioural phenotypes or whether they are a surrogate for general cellular dysregulation. Nevertheless, the set of highly refined and selected probes in our predictor are enriched to be located on promotors of CpG islands where aberrant DNA methylation has clearly been linked to carcinogenesis[25]. The correlation of methylation with gene expression in our study was exploratory and would benefit from additional investigation with matched epigenetic and transcriptomic analysis in the same samples. Moreover, although each institution conformed to a common definition for tumour recurrence and time to recurrence, there is no universally standardized definition of recurrence in meningiomas. The Response Assessment in Neuro-Oncology guidelines may offer an avenue for standardized definition of recurrence to be collected on meningiomas in future clinical trials, which will help with communication across different centres and may also help with further model refinement[26].

Our predictor has been designed and validated such that it can be applied to data from fresh frozen or paraffin embedded tissues using the current commonly-used standard platform for genome-wide DNA methylation profiling, facilitating immediate adoption into clinical practice. Our newly developed and retrospectively validated meningioma recurrence score combines both methylome and clinical factors and can be freely used by clinicians to personalize decision making regarding post-operative management of the most common primary intracranial brain tumor via a web-based interface.

TABLE 1

Grambsch and Therneau Proportional Hazards Testing for Cox modeling

| Covariate | Rho | Chi-Sq | P-value |
|---|---|---|---|
| Grade = G2 | 0.1376 | 1.807 | 0.1789 |
| Grade = G3 | 0.0855 | 0.669 | 0.4134 |
| Simpson = Subtotal | 0.0832 | 0.649 | 0.4205 |
| Meth_predict_probability | −0.2036 | 3.184 | 0.0744 |
| CNV_Load = Low | −0.1574 | 2.593 | 0.1073 |
| GLOBAL | NA | 5.787 | 0.3275 |

TABLE 2

Distribution of patient and tumor characteristics used for training and validation.

| | Training Cohort (n = 228) | First Validation cohort (n = 54) | Second Validation Cohort (n = 140) | Third Validation Cohort (n = 64) |
|---|---|---|---|---|
| | | Source | | |
| Princess Margaret Cancer Centre | 62 (27%) | 14 (26%) | 0 (0%) | 46 (72%) |
| European Centres | 166 (73%) | 40 (74%) | 0 (0%) | 0 |

TABLE 2-continued

Distribution of patient and tumor characteristics used for training and validation.

|  | Training Cohort (n = 228) | First Validation cohort (n = 54) | Second Validation Cohort (n = 140) | Third Validation Cohort (n = 64) |
|---|---|---|---|---|
| M D Anderson Cancer Centre | 0 (0%) | 0 (0%) | 140 (100%) | 0 |
| Chinese University of Hong Kong | 0 | 0 | 0 | 18 (28%) |
| Tissue Type | | | | |
| FFPE | 118 (52%) | 31 (57%) | 140 (100%) | 0 (0%) |
| Fresh Frozen | 110 (48%) | 23 (43%) | 0 (0%) | 64 (100%) |
| WHO Grade | | | | |
| WHO I | 103 (45%) | 24 (44%) | 90 (64%) | 14 (22%) |
| WHO II | 91 (40%) | 22 (41%) | 43 (31%) | 32 (50%) |
| WHO III | 34 (15%) | 8 (15%) | 7 (5%) | 18 (28%) |
| Simpson Gradeφ | | | | |
| 1 | 86 (43%) | 18 (43%) | 69 (53%) | 8 (15%) |
| 2 | 71 (36%) | 14 (33%) | 36 (28%) | 18 (25%) |
| 3 | 2 (11%) | 4 (10%) | 9 (7%) | 6 (12%) |
| 4 | 19 (10%) | 6 (14%) | 15 (12%) | 19 (37%) |
| 5 | 1 (1%) | 0 (0%) | 0 (0%) | 0 (0%) |
| Recurrence | | | | |
| Yes | 92 (40%) | 21 (39%) | 93 (66%) | 50 (78%) |
| No | 136 (60%) | 33 (61%) | 47 (34%) | 14 (22%) |
| Time to recurrence or last follow-up | 4.8 (0.1-52) | 6.2 (0.25-22.9) | 7.0 (0.1-17.6) | 5.3 (0.1-18.5) |
| Genderφ | | | | |
| Female | 111 (66%) | 23 (62%) | 98 (70%) | 34 (53%) |
| Male | 57 (34%) | 14 (38%) | 42 (30%) | 30 (47%) |

φProportions are calculated based on available data (29 missing from training cohort, 12 missing from first validation cohort, 11 missing from second validation cohort, 13 missing from third validation cohort)

φProportions are calculated based on available data (60 missing from training cohort, 17 missing from first validation cohort)

TABLE 3

Distribution of burden of copy number alterations among risk groups defined by the 5-year methylome-based predictor.

| Cohort | Risk Group | High burden of copy number alterations | Low burden of copy number alterations | P-Value |
|---|---|---|---|---|
| First Validation Cohort | Low risk | 2 | 25 | <0.0001 |
|  | High risk | 16 | 11 |  |
| Second Validation Cohort | Low risk | 3 | 67 | 0.0099 |
|  | High risk | 32 | 38 |  |
| Third Validation Cohort | Low risk | 7 | 25 | 0.0097 |
|  | High risk | 18 | 14 |  |

TABLE 4

Results of univariable and multivariable cox proportional hazards model for 5 y methylation-based RFS predictor and associated covariates for all validation cohorts.

| Covariate | Univariable Cox HR (95% CI) | P | Multivariable Cox HR (95% CI) | P |
|---|---|---|---|---|
| 5 y methylation-based predictor | 8.5 (5.3-13.5) | <0.001 | 3.6 (1.8-7.2) | <0.001 |
| WHO Grade |  |  |  | <0.001 |
| Grade II vs I | 4.0 (2.6-6.2) | <0.001 | 2.6 (1.6-4.4) |  |
| Grade III vs I | 7.1 (4.2-11.8) | <0.001 | 3.1 (1.6-6.2) |  |
| Grade III vs II | 1.8 (1.1-2.7) | 0.010 | 1.2 (0.7-2.0) |  |
| Extent of Resection (subtotal vs gross total) | 2.2 (1.4-3.5) | <0.001 | 1.6 (1.0-2.5) | 0.050 |
| burden of copy number alterations (high vs low) | 2.9 (2.0-4.1) | <0.001 | 1.3 (0.8-2.1) | 0.36 |

HR, Hazard Ratio;
CI, Confidence Interval;
P, P-value;
WHO, World Health Organization

TABLE 5

Multivariable cox regression analysis including receipt of adjuvant radiation therapy as a covariate the third validation cohort.

| Covariates | Multivariable Cox | | | |
|---|---|---|---|---|
| | HR | lower .95 | upper .95 | P |
| Binary Methylome Classifier | 3.6 | 1.2 | 11.0 | 0.02 |
| WHO Grade II vs I | 2.4 | 0.8 | 6.7 | 0.10 |
| WHO Grade III vs I | 1.6 | 0.5 | 5.5 | 0.43 |
| Extent of Resection (subtotal vs gross total) | 1.0 | 0.5 | 2.2 | 0.93 |
| Copy number burden (high vs low) | 0.8 | 0.4 | 1.7 | 0.57 |
| Adjuvant radiotherapy (no vs yes) | 1.1 | 0.3 | 5.3 | 0.82 |

TABLE 6

Univariate and multivariable cox regression analysis including TERT promoter mutation status as a covariate in 103 samples.

| Covariates | Univariate Cox | | Multivariate Cox | |
|---|---|---|---|---|
| | HR (95% CI) | P | HR (95% CI) | P |
| Binary Methylome Classifier | 49.6 (17.3-142.3) | <0.001 | 40.2 (11.8-136.4) | <0.001 |
| WHO Grade II vs I | 10.3 (3.6-29) | <0.001 | 3.7 (1.2-12.1) | 0.02 |
| WHO Grade III vs I | 22.7 (7.4-69.8) | <0.001 | 3.1 (0.8-11.3) | 0.02 |
| Extent of Resection (subtotal vs gross total) | 2.1 (0.95-4.7) | 0.065 | 2.6 (1.0-6.4) | 0.05 |
| Copy number burden (high vs low) | 4 (2.2-7.3) | <0.001 | 0.8 (0.4-1.6) | 0.58 |
| Tert_Mutation (yes vs no) | 2.3 (0.56-9.5) | 0.25 | 1.7 (0.3-8.2) | 0.54 |
| Gender (male vs female) | 1.3 (0.57-3) | 0.52 | NA | NA |

TABLE 7

Multivariable cox regression analysis including center of treatment as covariate.

| Covariate | | HR (95% CI) | PVal |
|---|---|---|---|
| 5 y Methylome Predictor | | 3.15 (1.5-6.5) | 0.001 |
| Grade | Grade 2 vs 1 | 2.64 (1.5-4.5) | 0.001 |
| | Grade 3 vs 1 | 3.3 (1.5-7.2) | |
| Extent of resection (subtotal vs gross total) | | 1.38 (0.8-2.4) | 0.233 |
| CNV load (high vs low) | | 1.32 (0.8-2.2) | 0.289 |
| Center | Toronto vs Houston | 1.16 (0.67-1.99) | 0.736 |
| | Europe vs Houston | 1.43 (0.50-4.07) | |
| | Hong Kong vs Houston | 0.76 (0.28-2.03) | |

TABLE 8

Annotation of the location of 9529 probes selected in the methylome-predictor in comparison to all probes on 850K EPIC array relative to gene region and CpG island location

| | Annotation | | 9529 probes of methylome predictor | 867867 probes on 850K EPIC array | P-value |
|---|---|---|---|---|---|
| Relative to Gene Region | Body | | 3018 (31.7%) | 315159 (36.3%) | <0.001 |
| | Unknown | | 2470 (25.9%) | 233769 (26.9%) | 0.02 |
| | Promoter | 200-1500 BP upstream TSS | 1537 (16.1%) | 110079 (13.5%) | <0.001 |
| | | 5' Untranslated Region | 774 (8.1%) | 77468 (8.9%) | 0.006 |
| | | 0-200 BP upstream TSS | 746 (7.8%) | 62439 (7.2%) | 0.017 |
| | 1st Exon | | 643 (6.7%) | 28604 (3.3%) | <0.01 |
| | 3' Untranslated Region | | 247 (2.7%) | 22518 (2.6%) | 0.987 |
| | Exon Band | | 94 (1.0%) | 10831 (1.2%) | 0.022 |

TABLE 8-continued

Annotation of the location of 9529 probes selected in the methylome-predictor in comparison to all probes on 850K EPIC array relative to gene region and CpG island location

| | Annotation | 9529 probes of methylome predictor | 867867 probes on 850K EPIC array | P-value |
|---|---|---|---|---|
| Relative to CpG Island | Island | 4633 (48.6%) | 155862 (18.0%) | <0.001 |
| | Not annotated | 1470 (15.4%) | 488877 (56.3%) | <0.001 |
| | South Shore | 1318 (13.8%) | 71784 (8.3%) | <0.001 |
| | North Shore | 1172 (12.3%) | 74446 (8.6%) | <0.001 |
| | South Shelf | 471 (4.9%) | 38500 (4.4%) | 0.016 |
| | North Shelf | 465 (4.9%) | 38398 (4.4%) | 0.031 |

Bp, base-pairs;
TSS = Transcription Start Site

TABLE 9

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg00015770 | QRFPR | Island | 1stExon | 14.3473 | 9.95E−09 | 0.138082675 | 0.261372515 |
| cg00028128 | TBR1 | S_Shelf | Body | 11.0144 | 4.04E−10 | 0.238240155 | 0.420623714 |
| cg00025981 | RGCC | Island | TSS1500 | 13.4779 | 2.04E−07 | 0.278465393 | 0.400282216 |
| cg00028678 | ARHGEF4 | S_Shore | TSS1500 | 7.83729 | 1.72E−06 | 0.374075353 | 0.527289047 |
| cg00035316 | HOXD8 | Island | TSS1500 | 8.19499 | 1.75E−07 | 0.259222378 | 0.402969469 |
| cg00036347 | C2CD4D | S_Shore | 5URT | 6.32633 | 0.000335 | 0.529091437 | 0.640249798 |
| cg00048759 | GPC2 | Island | TSS1500 | 22.4346 | 5.62E−07 | 0.500048411 | 0.59538254 |
| cg00055679 | RNF219-AS1 | Island | Body | 7.3267 | 0.001505 | 0.263971124 | 0.319811879 |
| cg00060304 | DKFZp686K1684 | Island | TSS1500 | 6.85957 | 3.35E−07 | 0.145730157 | 0.279207375 |
| cg00063471 | TNFAIP8L3 | Island | Body | 4.61555 | 9.76E−06 | 0.173224235 | 0.322641626 |
| cg00073003 | SOX1 | N_Shore | 3UTR | 4.47482 | 0.001662 | 0.179921681 | 0.246076945 |
| cg00099393 | PTPRN2 | Island | Body | 5.48057 | 0.00105 | 0.128069916 | 0.192229567 |
| cg00117172 | RUNX3 | Island | Body | 3.27872 | 0.004437 | 0.208241782 | 0.307430286 |
| cg00123478 | ZNF518B | Island | 5URT | 7.47258 | 0.000952 | 0.598658535 | 0.682374916 |
| cg00130808 | LOC145845 | N_Shore | TSS200 | 6.13389 | 3.35E−05 | 0.550275743 | 0.667232657 |
| cg00143249 | MNX1 | Island | Body | 11.927 | 1.68E−07 | 0.120366053 | 0.221959892 |
| cg00155423 | WNT10A | S_Shore | 3UTR | 4.56435 | 1.20E−05 | 0.247210136 | 0.400766036 |
| cg00155526 | NPR3 | Island | Body | 9.51657 | 1.13E−10 | 0.128321035 | 0.317251422 |
| cg00158122 | LINC01475 | Island | Body | 8.44283 | 1.93E−05 | 0.211539824 | 0.290543888 |
| cg00168835 | BATF3 | S_Shore | TSS1500 | 10.9964 | 1.44E−08 | 0.157700387 | 0.327996862 |
| cg00182639 | TBX5 | S_Shore | 5URT | 9.07991 | 3.62E−05 | 0.267472135 | 0.358273393 |
| cg00184452 | DMRTA2 | Island | 5URT | 9.26715 | 9.20E−06 | 0.369912535 | 0.488499566 |
| cg00204465 | MYO15B | Island | TSS200 | 18.2843 | 1.65E−07 | 0.432291532 | 0.569108097 |
| cg00204782 | TBX1 | Island | Body | 7.11802 | 0.000168 | 0.277246944 | 0.352428077 |
| cg00222472 | PBX1 | Island | Body | 53.3916 | 7.01E−10 | 0.626374364 | 0.779958919 |
| cg00237475 | SKOR1 | Island | Body | 41.9155 | 1.70E−11 | 0.286564279 | 0.402228939 |
| cg00247571 | DLEU1 | S_Shelf | Body | 12.6755 | 9.44E−06 | 0.619350287 | 0.736634889 |
| cg00254681 | PRRT1 | Island | Body | 4.91582 | 0.000384 | 0.45187213 | 0.574644258 |
| cg00255368 | ESRRG | Island | 5URT | 24.9928 | 1.04E−09 | 0.201514705 | 0.301703141 |
| cg00262621 | MMP23B | Island | TSS1500 | 20.2182 | 2.11E−11 | 0.322781532 | 0.514607172 |
| cg00286125 | HSPB6 | Island | Body | 7.51548 | 0.0061 | 0.2262581 | 0.307019648 |
| cg00298065 | ZNF274 | Island | 5URT | 19.2971 | 2.29E−06 | 0.441851876 | 0.527302697 |
| cg00299047 | AMH | Island | 3UTR | 8.71985 | 5.28E−06 | 0.363207318 | 0.482147364 |
| cg00299972 | TLX1 | N_Shelf | Body | 5.5743 | 0.000114 | 0.222249019 | 0.311564492 |
| cg00306311 | FAM184B | S_Shore | TSS1500 | 15.1553 | 4.00E−07 | 0.467489628 | 0.608092889 |
| cg00323305 | THRB-AS1 | Island | Body | 3.66558 | 0.000772 | 0.306803767 | 0.410433175 |
| cg00337466 | ADAM8 | S_Shore | TSS200 | 9.14915 | 0.001243 | 0.483277667 | 0.566343525 |
| cg00360794 | LTK | Island | Body | 6.26784 | 9.08E−05 | 0.231788209 | 0.325944037 |
| cg00384539 | PRDM14 | Island | TSS200 | 9.99496 | 7.02E−08 | 0.279072411 | 0.449507265 |
| cg00407546 | GATA3-AS1 | Island | Body | 3.46913 | 0.000579 | 0.317624764 | 0.442800135 |
| cg00418216 | HOXA11-AS | N_Shelf | Body | 10.8013 | 1.89E−07 | 0.24663633 | 0.362670161 |
| cg00425918 | NKX2-6 | Island | Body | 9.38265 | 5.96E−07 | 0.204725219 | 0.31011622 |
| cg00431187 | HOXA3 | N_Shore | 5URT | 6.00991 | 0.000107 | 0.542800519 | 0.649365232 |
| cg00434010 | SIM1 | Island | Body | 3.48419 | 0.003568 | 0.305682189 | 0.394276621 |
| cg00435063 | PTPRN2 | Island | Body | 5.33199 | 0.001217 | 0.587097132 | 0.655655859 |
| cg00445405 | OTX1 | S_Shelf | Body | 8.33913 | 0.000345 | 0.61314032 | 0.699363943 |
| cg00463767 | OTX1 | N_Shelf | Body | 13.8807 | 9.82E−07 | 0.386075581 | 0.510870212 |
| cg00487737 | ACP5 | Island | 5URT | 7.60446 | 8.30E−05 | 0.283832876 | 0.389328057 |
| cg00490421 | CPM | N_Shore | Body | 8.80887 | 2.79E−05 | 0.121409683 | 0.197785945 |
| cg00495775 | HOXD11 | Island | TSS200 | 23.6619 | 4.66E−09 | 0.361394388 | 0.482595971 |
| cg00499700 | F2RL1 | Island | Body | 34.626 | 7.96E−07 | 0.580510938 | 0.702986657 |
| cg00503840 | DLX5 | S_Shelf | Body | 10.5934 | 8.43E−06 | 0.36137724 | 0.465306939 |
| cg00504902 | HLA-F | S_Shore | Body | 38.2707 | 3.47E−07 | 0.618025124 | 0.732500929 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg00505979 | BATF3 | Island | TSS1500 | 13.1933 | 4.36E−09 | 0.190875209 | 0.332468709 |
| cg00506343 | HOXC6 | N_Shelf | TSS1500 | 4.73712 | 0.002987 | 0.187823819 | 0.255529205 |
| cg00507727 | ICA1 | Island | TSS1500 | 6.64856 | 1.05E−06 | 0.132393885 | 0.281706708 |
| cg00513205 | NEUROG1 | S_Shore | TSS1500 | 5.27111 | 0.000329 | 0.39426914 | 0.490526892 |
| cg00553149 | GPC2 | Island | TSS1500 | 18.1344 | 9.34E−09 | 0.212716633 | 0.338965681 |
| cg00556112 | DRD4 | Island | TSS200 | 7.85766 | 1.58E−06 | 0.105448181 | 0.21671902 |
| cg00567703 | HOXC6 | Island | 5URT | 11.0544 | 0.001377 | 0.631858618 | 0.695643606 |
| cg00574563 | LHX1 | Island | Body | 13.5746 | 2.14E−06 | 0.178375121 | 0.279195108 |
| cg00585714 | GDF6 | Island | Body | 22.2416 | 1.59E−07 | 0.384686736 | 0.485336515 |
| cg00599564 | HCG9 | N_Shore | Body | 9.96976 | 3.16E−06 | 0.315296405 | 0.455941313 |
| cg00616687 | SIM2 | Island | 1stExon | 8.69529 | 1.99E−06 | 0.13890162 | 0.250153308 |
| cg00629427 | LOC101927248 | Island | Body | 7.72239 | 0.0027 | 0.256282319 | 0.315180947 |
| cg00663077 | ZFP42 | Island | TSS1500 | 16.3122 | 1.98E−11 | 0.255874873 | 0.442182767 |
| cg00667789 | TACSTD2 | Island | 1stExon | 8.87345 | 9.19E−09 | 0.15310286 | 0.314582388 |
| cg00673290 | APOB | Island | Body | 5.25098 | 0.000244 | 0.223405913 | 0.332389431 |
| cg00674304 | POMC | Island | TSS200 | 5.27037 | 6.75E−07 | 0.168430801 | 0.35566962 |
| cg00687252 | IER3 | Island | Body | 15.5542 | 1.52E−08 | 0.292954449 | 0.478726894 |
| cg00714725 | CYP26C1 | Island | Body | 5.42767 | 4.62E−06 | 0.321032609 | 0.4883889 |
| cg00716277 | PTPRN2 | Island | Body | 12.9091 | 0.000588 | 0.627002504 | 0.678445412 |
| cg00733728 | RNF219-AS1 | Island | Body | 12.7367 | 1.43E−09 | 0.147365766 | 0.281130976 |
| cg00756451 | TBX5 | N_Shelf | 5URT | 4.87224 | 0.001593 | 0.116043461 | 0.183096098 |
| cg00762160 | PAX9 | S_Shore | TSS1500 | 4.68286 | 0.000734 | 0.292460912 | 0.394197498 |
| cg00767496 | GATM | S_Shore | TSS1500 | 4.70187 | 0.002308 | 0.528059922 | 0.624643222 |
| cg00779924 | GATA3-AS1 | Island | Body | 3.25869 | 0.000528 | 0.259543895 | 0.403046957 |
| cg00790395 | CYP26C1 | Island | Body | 3.42408 | 0.009074 | 0.141589595 | 0.206579638 |
| cg00795248 | LHX9 | S_Shore | Body | 6.53616 | 0.001004 | 0.142651392 | 0.204692423 |
| cg00806704 | CDX2 | N_Shore | Body | 6.69678 | 4.09E−06 | 0.226390116 | 0.353402851 |
| cg00838969 | LHX4 | Island | Body | 4.37342 | 0.000467 | 0.210484062 | 0.311900389 |
| cg00840332 | LEP | Island | TSS200 | 19.4166 | 3.46E−08 | 0.110332463 | 0.199627364 |
| cg00864474 | NTN1 | Island | 3UTR | 8.22807 | 4.07E−05 | 0.416496222 | 0.553032606 |
| cg00867835 | SSPO | N_Shelf | Body | 4.84487 | 0.002995 | 0.520465853 | 0.59548602 |
| cg00877329 | HPSE2 | S_Shelf | TSS1500 | 3.80475 | 0.000822 | 0.390047555 | 0.508399569 |
| cg00882235 | LHX4 | Island | Body | 4.1817 | 0.000724 | 0.174457011 | 0.275198746 |
| cg00887814 | MGAT4D | Island | Body | 9.51895 | 3.00E−05 | 0.219418518 | 0.308325924 |
| cg00905524 | HOXA10-HOXA9 | N_Shore | Body | 17.5414 | 1.01E−06 | 0.23800934 | 0.334874145 |
| cg00913949 | ESRRG | Island | TSS1500 | 6.09855 | 3.51E−07 | 0.157221884 | 0.309361008 |
| cg00926215 | PAX3 | S_Shore | Body | 9.13898 | 1.99E−07 | 0.249208929 | 0.366095146 |
| cg00928397 | SP9 | N_Shore | TSS1500 | 12.9978 | 2.69E−06 | 0.292032191 | 0.386723358 |
| cg00947782 | RNF39 | Island | Body | 5.61442 | 1.19E−05 | 0.182835554 | 0.304016971 |
| cg00949753 | PROX1-AS1 | N_Shelf | Body | 7.39327 | 6.34E−05 | 0.306086752 | 0.41201897 |
| cg00963169 | ELAVL4 | Island | Body | 8.81412 | 6.00E−08 | 0.146744189 | 0.276138886 |
| cg00970313 | PAX9 | S_Shore | TSS1500 | 5.5904 | 2.00E−06 | 0.210648826 | 0.372550414 |
| cg00982919 | LHX2 | Island | Body | 6.85613 | 7.27E−05 | 0.242806392 | 0.340290604 |
| cg00982984 | SHF | S_Shelf | TSS200 | 40.0921 | 2.70E−07 | 0.518320116 | 0.649603374 |
| cg00983437 | TCF15 | S_Shore | TSS1500 | 20.8662 | 4.04E−07 | 0.253828081 | 0.37306729 |
| cg00985729 | IER3 | S_Shore | TSS1500 | 9.63816 | 1.55E−05 | 0.444252713 | 0.586434717 |
| cg00989858 | IRF6 | Island | 1stExon | 11.0236 | 1.18E−11 | 0.244929281 | 0.480542075 |
| cg01003803 | FGF20 | S_Shore | 1stExon | 7.92263 | 9.04E−07 | 0.163873199 | 0.289283328 |
| cg01031400 | TNFRSF10D | Island | 1stExon | 15.099 | 2.48E−07 | 0.353605187 | 0.504678649 |
| cg01040654 | NKX2-5 | S_Shelf | TSS1500 | 19.4478 | 1.52E−06 | 0.475049721 | 0.598085697 |
| cg01054755 | PROB1 | Island | 1stExon | 4.64664 | 3.28E−05 | 0.185086912 | 0.394057883 |
| cg01078824 | HOXA10-HOXA9 | S_Shore | TSS200 | 23.8284 | 7.79E−07 | 0.388179169 | 0.474411404 |
| cg01141459 | HORMAD2 | Island | 1stExon | 12.3408 | 5.29E−11 | 0.289014186 | 0.475438706 |
| cg01156550 | ASCL2 | Island | TSS1500 | 7.62818 | 0.000133 | 0.321988195 | 0.415341281 |
| cg01163842 | GSC | Island | Body | 6.00845 | 4.52E−08 | 0.16968596 | 0.357688175 |
| cg01172183 | STK3 | Island | 5URT | 6.86487 | 0.000136 | 0.210523216 | 0.297804929 |
| cg01174140 | SCGB3A1 | Island | TSS1500 | 61.2054 | 2.63E−09 | 0.38314558 | 0.51960802 |
| cg01177854 | ESRP2 | Island | TSS1500 | 7.29629 | 0.002198 | 0.340034271 | 0.403061717 |
| cg01182865 | GATA4 | S_Shore | 5URT | 4.34361 | 0.005784 | 0.3635323 | 0.430418091 |
| cg01229452 | CHRN81 | S_Shore | Body | 12.3569 | 0.00012 | 0.332403204 | 0.429466364 |
| cg01243879 | PRR18 | Island | TSS1500 | 4.35388 | 0.004791 | 0.556669002 | 0.644357909 |
| cg01258751 | SIM1 | N_Shelf | TSS1500 | 8.06674 | 4.45E−06 | 0.13555699 | 0.225022553 |
| cg01277331 | WNT10A | Island | Body | 42.1238 | 8.38E−08 | 0.462205953 | 0.585142222 |
| cg01277872 | MECOM | N_Shore | 5URT | 5.07848 | 0.001534 | 0.219323731 | 0.295871049 |
| cg01285501 | HOXA9 | Island | TSS1500 | 11.8904 | 8.64E−06 | 0.258052078 | 0.354405145 |
| cg01286685 | RNF39 | N_Shelf | Body | 9.47702 | 4.65E−06 | 0.53858096 | 0.668791707 |
| cg01287476 | M1AP | Island | TSS1500 | 5.89148 | 0.001394 | 0.493774202 | 0.583026212 |
| cg01295203 | PRDM14 | Island | TSS1500 | 8.30724 | 2.01E−06 | 0.296310646 | 0.422670067 |
| cg01323777 | KCNAB3 | N_Shelf | TSS200 | 5.12493 | 0.007113 | 0.762060211 | 0.835849448 |
| cg01351315 | HOXB-AS3 | N_Shore | TSS200 | 9.11815 | 0.000149 | 0.614287039 | 0.713299303 |
| cg01371072 | PITX2 | S_Shelf | Body | 8.89022 | 0.000324 | 0.283985433 | 0.34386531 |
| cg01402735 | ADGRL4 | S_Shore | TSS200 | 4.39356 | 0.009244 | 0.305126542 | 0.377621437 |
| cg01405040 | HOXD12 | S_Shore | TSS1500 | 8.74668 | 2.36E−08 | 0.201324534 | 0.359307049 |
| cg01405445 | HSPB6 | Island | 3UTR | 6.67282 | 1.03E−05 | 0.503580603 | 0.666384496 |
| cg01438365 | TBX2 | Island | Body | 7.73761 | 2.50E−05 | 0.511092655 | 0.631568949 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg01449663 | NTN1 | Island | Body | 77.0292 | 6.42E−14 | 0.308803 | 0.488207879 |
| cg01456368 | DNAH1 | | 5URT | 13.6129 | 7.24E−08 | 0.166824068 | 0.283797049 |
| cg01460436 | SLC12A5 | Island | 3UTR | 19.6905 | 1.16E−09 | 0.3067875 | 0.456929925 |
| cg01463565 | NTN1 | Island | Body | 15.8196 | 1.03E−10 | 0.089877795 | 0.227808991 |
| cg01467266 | JSRP1 | Island | Body | 7.80021 | 6.22E−06 | 0.363951202 | 0.491581073 |
| cg01484487 | LBX2 | Island | Body | 6.05421 | 0.000145 | 0.230136183 | 0.335505836 |
| cg01494454 | BCAT1 | N_Shore | 1stExon | 14.433 | 7.85E−08 | 0.202156688 | 0.319796983 |
| cg01499197 | CDX2 | Island | TSS1500 | 7.75673 | 5.51E−05 | 0.261030774 | 0.348812792 |
| cg01530101 | KCNQ1DN | Island | TSS200 | 6.74401 | 2.51E−06 | 0.268464648 | 0.401149077 |
| cg01533258 | GSC | N_Shelf | Body | 8.88002 | 1.32E−06 | 0.112399653 | 0.236846456 |
| cg01550148 | H2AFY | S_Shore | TSS1500 | 8.44036 | 0.000622 | 0.296437357 | 0.356835615 |
| cg01564135 | EVX1 | N_Shelf | TSS1500 | 6.00986 | 1.67E−05 | 0.446642618 | 0.594596172 |
| cg01587682 | PAX6 | Island | Body | 11.8454 | 9.96E−12 | 0.252639806 | 0.474091567 |
| cg01602621 | ACP5 | S_Shore | TSS1500 | 6.85593 | 4.00E−06 | 0.355163159 | 0.481147742 |
| cg01622304 | PDX1 | N_Shore | Body | 6.31336 | 0.000977 | 0.175900355 | 0.246920972 |
| cg01627823 | PAX9 | N_Shore | TSS1500 | 9.13267 | 6.10E−08 | 0.285641891 | 0.459152363 |
| cg01631162 | RNF39 | Island | 1stExon | 8.45506 | 3.54E−06 | 0.209455381 | 0.33377347 |
| cg01645998 | SDR42E1 | Island | TSS200 | 14.7948 | 2.63E−08 | 0.396627711 | 0.570259373 |
| cg01655831 | GREB1L | Island | 5URT | 8.18989 | 2.57E−06 | 0.174013931 | 0.291218337 |
| cg01658421 | EVX2 | N_Shelf | Body | 7.32668 | 2.44E−05 | 0.318822401 | 0.428823948 |
| cg01665555 | PAX6 | Island | 5URT | 3.52945 | 0.001039 | 0.324205235 | 0.424872836 |
| cg01673674 | GDF6 | N_Shelf | Body | 11.0363 | 1.65E−06 | 0.457229408 | 0.597537303 |
| cg01693350 | WT1 | Island | 1stExon | 8.16132 | 6.32E−07 | 0.425426445 | 0.59533214 |
| cg01708273 | HOXD11 | S_Shore | 3UTR | 4.45151 | 0.00056 | 0.240404204 | 0.349318532 |
| cg01713701 | DLX4 | S_Shelf | TSS1500 | 4.05267 | 0.005361 | 0.312889498 | 0.382019266 |
| cg01727145 | SPEG | Island | Body | 15.4128 | 5.56E−06 | 0.528836513 | 0.68062323 |
| cg01739725 | TTC6 | N_Shelf | 5URT | 8.02241 | 3.23E−07 | 0.120323456 | 0.24486317 |
| cg01789499 | PRDM8 | Island | 5URT | 8.77905 | 0.000104 | 0.598265837 | 0.688878343 |
| cg01803928 | DLEU1 | Island | Body | 5.43855 | 0.000248 | 0.369220664 | 0.468627013 |
| cg01811325 | EBF3 | Island | Body | 11.1627 | 7.47E−08 | 0.19962491 | 0.333947493 |
| cg01815671 | CCDC37 | Island | TSS200 | 8.24919 | 7.25E−08 | 0.101209463 | 0.236943776 |
| cg01819512 | HOXA10-AS | N_Shore | TSS1500 | 8.58434 | 0.000227 | 0.444329961 | 0.524834808 |
| cg01821018 | TACSTD2 | Island | TSS200 | 8.26762 | 0.000106 | 0.541982868 | 0.634825475 |
| cg01824969 | TCF24 | Island | TSS1500 | 6.80998 | 3.74E−05 | 0.153891159 | 0.24947656 |
| cg01832036 | DLX4 | Island | Body | 6.4572 | 8.90E−07 | 0.214231841 | 0.385945834 |
| cg01850449 | LYPD1 | Island | 5URT | 5.83717 | 0.004198 | 0.136623119 | 0.190500443 |
| cg01853561 | SIM2 | Island | 3UTR | 11.1775 | 3.88E−07 | 0.381472052 | 0.525188129 |
| cg01882880 | HOXB-AS1 | N_Shelf | Body | 6.34311 | 0.001074 | 0.645805907 | 0.722304869 |
| cg01896761 | FBLN2 | Island | TSS200 | 4.74647 | 2.44E−05 | 0.23701325 | 0.369284338 |
| cg01904410 | DKFZp686K1684 | Island | TSS1500 | 9.84664 | 2.50E−07 | 0.195901616 | 0.323569333 |
| cg01913455 | TBX2 | Island | Body | 26.8413 | 3.05E−06 | 0.430191978 | 0.541895 |
| cg01921432 | BARHL2 | Island | 1stExon | 16.8334 | 2.25E−10 | 0.123501363 | 0.246600247 |
| cg01926269 | POMC | Island | TSS200 | 7.22484 | 0.000243 | 0.289255916 | 0.386545049 |
| cg01934626 | SCGB3A1 | Island | TSS200 | 7.81221 | 1.42E−09 | 0.134863643 | 0.337329678 |
| cg01939477 | MIR129-2 | Island | TSS200 | 13.2881 | 4.20E−11 | 0.060656044 | 0.190832 |
| cg01942863 | GPC2 | Island | Body | 13.0308 | 2.08E−09 | 0.370223887 | 0.554347384 |
| cg01946451 | NBPF8 | S_Shore | Body | 11.1883 | 4.39E−08 | 0.250016988 | 0.374381152 |
| cg01961447 | GALR3 | Island | Body | 11.9563 | 7.75E−09 | 0.07429998 | 0.209523388 |
| cg01972418 | PAX9 | N_Shore | TSS1500 | 7.62618 | 9.23E−07 | 0.2821947 | 0.418507289 |
| cg02005600 | HOXA5 | Island | TSS1500 | 4.79515 | 0.003763 | 0.479041426 | 0.548242707 |
| cg02006615 | PTPRN2 | Island | Body | 5.48878 | 0.002594 | 0.498599567 | 0.569470677 |
| cg02022733 | PCDHGC4 | Island | TSS200 | 4.4107 | 6.00E−05 | 0.320379435 | 0.472483835 |
| cg02032558 | LRAT | S_Shore | 5URT | 6.45159 | 0.000284 | 0.561049896 | 0.686101545 |
| cg02037307 | PITX1 | Island | 3UTR | 9.79597 | 2.84E−08 | 0.383990581 | 0.581448187 |
| cg02051616 | NKX2-5 | Island | Body | 14.8523 | 1.46E−07 | 0.328432884 | 0.444282737 |
| cg02055963 | CDX2 | S_Shelf | TSS200 | 10.1156 | 5.47E−08 | 0.214485474 | 0.345188708 |
| cg02058624 | LINC00403 | N_Shore | Body | 6.21801 | 1.62E−05 | 0.254777874 | 0.380992929 |
| cg02069715 | GABRG3 | Island | TSS1500 | 7.85629 | 3.86E−05 | 0.346038304 | 0.467250822 |
| cg02086801 | OTP | N_Shelf | Body | 7.20521 | 5.78E−05 | 0.413101419 | 0.504017667 |
| cg02100373 | PITX1 | S_Shore | Body | 19.3543 | 6.29E−09 | 0.313121857 | 0.450246491 |
| cg02102424 | SYN2 | Island | Body | 5.43408 | 0.00318 | 0.298312453 | 0.361996214 |
| cg02108033 | FAM1848 | Island | TSS200 | 11.2464 | 3.04E−07 | 0.072428905 | 0.165648982 |
| cg02109484 | M1AP | Island | TSS200 | 5.75708 | 2.76E−05 | 0.235539929 | 0.337535602 |
| cg02115599 | HOTTIP | Island | Body | 4.94818 | 0.000277 | 0.136968084 | 0.224072282 |
| cg02120658 | PAX3 | Island | Body | 5.59853 | 0.00093 | 0.149631291 | 0.216708531 |
| cg02132714 | HOXB4 | S_Shelf | TSS1500 | 4.14182 | 0.000133 | 0.280682901 | 0.38808181 |
| cg02145932 | ISM1 | Island | TSS1500 | 9.45599 | 9.87E−08 | 0.10924131 | 0.229839915 |
| cg02150354 | NR2F1-AS1 | N_Shore | Body | 10.0314 | 7.00E−08 | 0.338864078 | 0.548808297 |
| cg02151625 | PRR18 | Island | TSS200 | 6.90138 | 2.79E−05 | 0.199344395 | 0.30192599 |
| cg02154252 | ADGRL4 | Island | TSS200 | 9.17623 | 0.000115 | 0.31824814 | 0.414856202 |
| cg02185185 | RNF39 | S_Shore | Body | 8.62369 | 0.001494 | 0.607472381 | 0.687571354 |
| cg02194789 | SIM2 | S_Shore | Body | 4.6577 | 0.000271 | 0.16482024 | 0.262396915 |
| cg02213684 | PITX1 | S_Shore | Body | 8.18273 | 1.42E−08 | 0.216359574 | 0.387903838 |
| cg02233197 | TNFAIP8L3 | S_Shelf | Body | 4.60211 | 0.006792 | 0.564692736 | 0.633177768 |
| cg02250594 | ONECUT2 | Island | 1stExon | 6.59273 | 2.28E−06 | 0.27143413 | 0.41810386 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg02281208 | GABRG3 | Island | TSS1500 | 21.2525 | 1.28E−10 | 0.180299421 | 0.334801792 |
| cg02283931 | SDR42E1 | N_Shore | 5URT | 7.32431 | 4.94E−05 | 0.512484868 | 0.627216747 |
| cg02285920 | JAK3 | S_Shore | TSS200 | 7.58997 | 0.000774 | 0.4946198 | 0.594739188 |
| cg02286091 | BHMT | | 5URT | 93.552 | 4.65E−09 | 0.604337512 | 0.734554 |
| cg02330683 | ITPKA | Island | Body | 13.2753 | 0.000165 | 0.62405414 | 0.736696455 |
| cg02335804 | HNF1B | S_Shore | TSS200 | 4.61338 | 0.001419 | 0.122732664 | 0.1975712921 |
| cg02346492 | NTN1 | Island | Body | 3.64372 | 0.002117 | 0.184303237 | 0.264962073 |
| cg02348751 | LOC90768 | Island | Body | 9.49702 | 3.01E−10 | 0.179731474 | 0.385594779 |
| cg02360980 | LTK | Island | Body | 6.66606 | 1.57E−05 | 0.079910642 | 0.171702881 |
| cg02364236 | SHISA3 | N_Shore | TSS1500 | 9.71748 | 1.15E−06 | 0.158354457 | 0.256364945 |
| cg02367696 | LBX1-AS1 | Island | Body | 10.49 | 1.72E−07 | 0.331959318 | 0.476934305 |
| cg02428056 | PAX9 | S_Shore | TSS1500 | 10.3887 | 3.07E−06 | 0.269526427 | 0.369440748 |
| cg02435495 | HNF1B | Island | Body | 3.25385 | 0.001407 | 0.201856548 | 0.314692642 |
| cg02439266 | HOXA3 | Island | Body | 6.91117 | 0.000324 | 0.575609287 | 0.660179293 |
| cg02458062 | HOXB3 | S_Shore | Body | 5.2714 | 0.000541 | 0.412196209 | 0.493733 |
| cg02468250 | PAX6 | Island | 5URT | 4.70147 | 0.000709 | 0.240163217 | 0.328508347 |
| cg02483701 | HOXA10-HOXA9 | N_Shelf | Body | 7.07197 | 0.000511 | 0.491468411 | 0.558451404 |
| cg02487130 | SPEG | Island | Body | 4.02835 | 0.002897 | 0.262993717 | 0.357651737 |
| cg02495310 | PITX1 | S_Shore | Body | 10.8464 | 1.72E−09 | 0.230644126 | 0.416737188 |
| cg02497558 | HOXB1 | S_Shore | TSS1500 | 4.06605 | 0.000314 | 0.469568077 | 0.598702245 |
| cg02511456 | MNX1 | Island | Body | 7.03104 | 2.97E−06 | 0.396138753 | 0.531196366 |
| cg02524946 | TBX20 | Island | TSS1500 | 14.2593 | 2.60E−08 | 0.185506974 | 0.301015227 |
| cg02530022 | DLX6-AS1 | N_Shelf | Body | 5.85943 | 1.71E−05 | 0.26657213 | 0.395653072 |
| cg02552311 | RNF39 | Island | Body | 6.81085 | 2.27E−06 | 0.082060426 | 0.196994138 |
| cg02553516 | SIM2 | N_Shore | Body | 9.30088 | 3.16E−07 | 0.202993038 | 0.33832287 |
| cg02569236 | ALDH1L1 | S_Shore | 1stExon | 6.96139 | 1.82E−05 | 0.153801595 | 0.254817317 |
| cg02585702 | BCAT1 | N_Shore | 1stExon | 9.25237 | 5.22E−06 | 0.241930915 | 0.355081176 |
| cg02595832 | FOXI2 | Island | 1stExon | 9.87276 | 1.44E−09 | 0.087475403 | 0.229388163 |
| cg02596153 | NR2E1 | Island | Body | 4.05372 | 0.008121 | 0.203314488 | 0.263205132 |
| cg02599464 | HIST1H2BK | N_Shore | 3UTR | 5.78193 | 4.37E−05 | 0.250990051 | 0.382206029 |
| cg02611848 | M1AP | Island | TSS1500 | 7.0688 | 6.38E−08 | 0.187664935 | 0.351330054 |
| cg02623050 | FAM84B | Island | Body | 12.6305 | 3.48E−09 | 0.157291424 | 0.293563177 |
| cg02624770 | TRIL | Island | Body | 10.4554 | 7.20E−08 | 0.326162386 | 0.4822965 |
| cg02628323 | MGAT4D | S_Shore | TSS200 | 5.79031 | 3.07E−05 | 0.277233507 | 0.385823818 |
| cg02633371 | LHX1 | Island | Body | 7.3666 | 0.000109 | 0.334927605 | 0.416747636 |
| cg02642123 | PAX6 | Island | 5URT | 6.76549 | 6.70E−07 | 0.204792677 | 0.347364243 |
| cg02642822 | HOXB-AS3 | N_Shelf | TSS1500 | 5.76502 | 0.000133 | 0.16358525 | 0.252092073 |
| cg02646491 | KCNQ1DN | Island | TSS1500 | 14.2004 | 1.60E−09 | 0.333097952 | 0.497769223 |
| cg02655630 | SLC12A5 | Island | Body | 9.23931 | 7.90E−06 | 0.324876543 | 0.42886099 |
| cg02660440 | MIR199A1 | | TSS200 | 26.1824 | 1.72E−06 | 0.670980946 | 0.799887747 |
| cg02688752 | F2RL1 | S_Shore | Body | 10.9516 | 7.79E−06 | 0.114254047 | 0.232900868 |
| cg02694427 | HOXD12 | S_Shelf | TSS200 | 10.9272 | 9.03E−11 | 0.240707797 | 0.427205006 |
| cg02700894 | SYN2 | N_Shore | TSS1500 | 3.45005 | 0.003266 | 0.183851555 | 0.301186263 |
| cg02701080 | SIM2 | N_Shore | Body | 7.26188 | 8.85E−05 | 0.295690425 | 0.385924016 |
| cg02703870 | SDR42E1 | Island | TSS200 | 10.0695 | 1.10E−06 | 0.269207568 | 0.401618841 |
| cg02741882 | SEZ6L2 | Island | Body | 23.1324 | 8.25E−07 | 0.378327236 | 0.513288477 |
| cg02760031 | TCF15 | Island | TSS1500 | 10.6295 | 9.06E−07 | 0.161988444 | 0.284281806 |
| cg02767242 | TBR1 | S_Shore | Body | 4.97074 | 0.000486 | 0.495354667 | 0.615470381 |
| cg02768694 | M1AP | Island | TSS1500 | 8.02086 | 0.000226 | 0.455294558 | 0.543964071 |
| cg02770983 | PAX6 | N_Shelf | Body | 17.2812 | 2.66E−08 | 0.491579357 | 0.646022615 |
| cg02771142 | PAX6 | N_Shore | Body | 18.0344 | 5.93E−11 | 0.305157093 | 0.484222313 |
| cg02781618 | BEND4 | Island | Body | 10.5191 | 4.97E−08 | 0.251525191 | 0.395463694 |
| cg02798576 | LINC01475 | Island | Body | 5.77888 | 7.61E−05 | 0.111466728 | 0.197559286 |
| cg02800607 | HPSE2 | N_Shore | Body | 4.90126 | 0.004655 | 0.149575929 | 0.220563177 |
| cg02803914 | APB81IP | Island | 5URT | 15.6982 | 4.20E−09 | 0.1684828 | 0.289341751 |
| cg02865068 | DKFZp686K1684 | S_Shore | Body | 6.01837 | 0.000616 | 0.514782295 | 0.607527608 |
| cg02873421 | HOXB3 | S_Shore | Body | 4.84173 | 0.003726 | 0.425897457 | 0.495652283 |
| cg02874942 | ACP5 | Island | 5URT | 8.81167 | 2.41E−08 | 0.13720768 | 0.273386218 |
| cg02878244 | DBX1 | Island | TSS200 | 8.67144 | 4.64E−07 | 0.123444715 | 0.231479873 |
| cg02885007 | HOXD9 | Island | 1stExon | 13.7751 | 1.01E−09 | 0.134741609 | 0.264423439 |
| cg02886033 | HOXA10-AS | N_Shore | TSS1500 | 5.04793 | 0.006094 | 0.593816062 | 0.674513212 |
| cg02906047 | SSPO | N_Shore | ExonBod | 47.4153 | 7.29E−08 | 0.701407643 | 0.856738889 |
| cg02907064 | MIR199A1 | | TSS200 | 11.5991 | 0.000343 | 0.656385047 | 0.755694485 |
| cg02916932 | PLLP | Island | TSS1500 | 5.35762 | 2.21E−05 | 0.150924617 | 0.282460365 |
| cg02948475 | GSC | Island | Body | 6.05619 | 1.39E−05 | 0.160540538 | 0.27277727 |
| cg02964031 | COL14A1 | Island | 5URT | 10.3867 | 1.92E−07 | 0.116243284 | 0.221621627 |
| cg02971322 | LBX1-AS1 | S_Shore | Body | 74.3183 | 7.86E−09 | 0.569535519 | 0.690219899 |
| cg03001942 | LINC01143 | S_Shore | Body | 5.66514 | 0.001736 | 0.173263916 | 0.229577945 |
| cg03011535 | TOX2 | Island | 1stExon | 5.98231 | 0.000339 | 0.078471913 | 0.160466429 |
| cg03020554 | STK3 | N_Shore | 5URT | 3.8879 | 0.00137 | 0.299884358 | 0.38961328 |
| cg03024760 | GABRG3 | Island | TSS1500 | 6.09499 | 5.71E−08 | 0.199487986 | 0.41034481 |
| cg03036592 | LINC01475 | Island | Body | 8.28478 | 8.82E−07 | 0.13420514 | 0.23278097 |
| cg03045635 | DRD5 | Island | TSS200 | 10.2921 | 2.00E−09 | 0.179558772 | 0.350196017 |
| cg03086235 | SOX7 | Island | Body | 9.36209 | 3.34E−05 | 0.473429494 | 0.594646455 |
| cg03091551 | OTX2 | Island | Body | 12.5473 | 6.20E−08 | 0.176764776 | 0.279247115 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg03099728 | ZNF274 | S_Shore | 5URT | 17.3353 | 0.000116 | 0.728492667 | 0.814833091 |
| cg03102494 | NBPF8 | | Body | 6.40069 | 1.40E−05 | 0.441430231 | 0.566673865 |
| cg03129884 | MAL | S_Shore | Body | 9.67144 | 2.87E−06 | 0.191864533 | 0.298059562 |
| cg03133868 | NKX2-2 | Island | 3UTR | 6.64641 | 2.67E−05 | 0.359596481 | 0.476189303 |
| cg03144922 | PITX2 | S_Shore | Body | 7.8105 | 3.87E−07 | 0.190462605 | 0.30788119 |
| cg03148184 | PITX2 | S_Shore | 5URT | 4.10567 | 0.00189 | 0.241987271 | 0.327200451 |
| cg03171465 | KIAA1211L | Island | TSS1500 | 15.9753 | 4.75E−07 | 0.447094099 | 0.586707677 |
| cg03177551 | ITPKA | Island | Body | 15.6101 | 2.77E−13 | 0.151671396 | 0.352050624 |
| cg03181248 | SP9 | Island | TSS200 | 26.0349 | 2.57E−09 | 0.150059892 | 0.26878377 |
| cg03219282 | RNF39 | Island | Body | 7.77047 | 2.52E−06 | 0.08418392 | 0.190425975 |
| cg03219968 | ESRRG | N_Shore | 5URT | 7.36827 | 8.61E−09 | 0.24347508 | 0.427494335 |
| cg03242698 | LBX1-AS1 | S_Shore | Body | 19.043 | 4.08E−11 | 0.394950794 | 0.601149701 |
| cg03276408 | LINC00403 | Island | Body | 8.99938 | 8.00E−08 | 0.094000168 | 0.222792543 |
| cg03293507 | RNF39 | N_Shelf | Body | 10.5225 | 3.39E−05 | 0.59442824 | 0.700764162 |
| cg03301582 | PON3 | Island | TSS1500 | 13.0758 | 8.95E−09 | 0.278756802 | 0.411526847 |
| cg03323462 | LHX1 | Island | 3UTR | 12.8563 | 4.64E−07 | 0.096686791 | 0.183477551 |
| cg03325664 | GATA4 | N_Shelf | TSS1500 | 5.27072 | 0.00869 | 0.274042393 | 0.363782997 |
| cg03343571 | RNF39 | Island | Body | 5.27825 | 2.50E−05 | 0.319013513 | 0.456539884 |
| cg03347590 | PITX1 | S_Shore | Body | 5.46476 | 1.87E−05 | 0.184870539 | 0.327529286 |
| cg03350299 | APOB | Island | TSS200 | 5.79666 | 0.000618 | 0.462482775 | 0.559319899 |
| cg03356900 | QRFPR | Island | TSS200 | 13.5323 | 1.26E−08 | 0.217274385 | 0.364720474 |
| cg03405909 | DKFZp686K1684 | N_Shore | Body | 10.7846 | 4.08E−12 | 0.298723347 | 0.535053654 |
| cg03405983 | LYNX1 | Island | 5URT | 5.73527 | 0.00163 | 0.416113124 | 0.500072263 |
| cg03431846 | REC8 | Island | TSS200 | 25.1931 | 4.38E−13 | 0.3025359 | 0.535462101 |
| cg03465861 | ISL2 | Island | Body | 13.5627 | 1.92E−07 | 0.33617466 | 0.472074649 |
| cg03491584 | JAK3 | S_Shore | TSS200 | 8.38591 | 0.000139 | 0.350502716 | 0.453809687 |
| cg03522132 | LBX2 | Island | 3UTR | 12.5129 | 1.85E−08 | 0.287045305 | 0.406859622 |
| cg03529432 | HOXA-AS3 | Island | Body | 10.1972 | 2.77E−06 | 0.176740755 | 0.306479652 |
| cg03562044 | EPHX3 | Island | Body | 14.6068 | 1.82E−12 | 0.098006067 | 0.267463674 |
| cg03572772 | PCDHB15 | S_Shelf | TSS200 | 4.87163 | 0.000123 | 0.118397759 | 0.206668348 |
| cg03583111 | DES | Island | 1stExon | 20.5343 | 3.94E−11 | 0.197015481 | 0.332682502 |
| cg03596280 | GAD2 | Island | Body | 4.20908 | 0.00444 | 0.12007581 | 0.178699508 |
| cg03609639 | LINC01475 | S_Shore | TSS1500 | 12.6355 | 6.78E−08 | 0.294703821 | 0.420858768 |
| cg03636532 | ONECUT2 | Island | Body | 8.77141 | 2.55E−06 | 0.222343911 | 0.326343228 |
| cg03637815 | LOC101927248 | Island | Body | 9.78757 | 3.72E−08 | 0.118046125 | 0.253463774 |
| cg03640756 | PCDHGC4 | Island | TSS200 | 6.27644 | 5.18E−06 | 0.231813034 | 0.362171047 |
| cg03650674 | GRHL2 | Island | Body | 18.1371 | 6.00E−16 | 0.144644841 | 0.367358931 |
| cg03655683 | OTX1 | S_Shore | Body | 17.4863 | 1.44E−11 | 0.261859764 | 0.446722446 |
| cg03656099 | TBX2 | N_Shelf | Body | 3.73222 | 0.000635 | 0.180804303 | 0.289345535 |
| cg03660500 | LHX9 | Island | Body | 5.775 | 0.000888 | 0.163508712 | 0.241639494 |
| cg03669298 | GATA3 | S_Shore | Body | 8.03398 | 0.000257 | 0.406613802 | 0.520518353 |
| cg03672342 | GATA3-AS1 | Island | Body | 3.32123 | 0.002435 | 0.212879417 | 0.317958259 |
| cg03692563 | DKFZp686K1684 | N_Shore | Body | 13.9572 | 8.98E−11 | 0.208013049 | 0.365422262 |
| cg03694713 | NKX2-6 | Island | TSS200 | 17.021 | 4.16E−08 | 0.129976099 | 0.232864124 |
| cg03695236 | PTPRN2 | Island | Body | 7.21056 | 0.00012 | 0.470650501 | 0.55757427 |
| cg03711485 | NKX2-3 | N_Shelf | 3UTR | 6.60456 | 9.83E−07 | 0.341733313 | 0.485493122 |
| cg03733219 | SPRED3 | Island | Body | 5.17645 | 0.001083 | 0.300898205 | 0.373052289 |
| cg03733760 | FGF19 | S_Shore | Body | 4.54743 | 0.000172 | 0.256462395 | 0.369348746 |
| cg03735496 | GREB1L | Island | 5URT | 8.25656 | 1.28E−07 | 0.079158539 | 0.197425684 |
| cg03744440 | MYO15B | Island | TSS200 | 18.6841 | 4.95E−19 | 0.140396231 | 0.337035329 |
| cg03744763 | HOXA5 | Island | TSS1500 | 10.5054 | 1.19E−06 | 0.237168054 | 0.327892148 |
| cg03771840 | TRIM15 | Island | 3UTR | 11.2579 | 0.002406 | 0.711416457 | 0.780360899 |
| cg03774463 | DLX6 | S_Shore | Body | 5.2222 | 0.000234 | 0.28273975 | 0.37267829 |
| cg03780851 | GRHL2 | Island | TSS200 | 10.2671 | 6.65E−08 | 0.270769599 | 0.44580223 |
| cg03826976 | CYB5R2 | Island | 5URT | 10.8637 | 1.95E−05 | 0.452616725 | 0.567828804 |
| cg03851159 | VAX1 | N_Shore | 3UTR | 7.04373 | 4.90E−05 | 0.142264788 | 0.241347655 |
| cg03854796 | PAX6 | N_Shore | Body | 16.0162 | 1.46E−07 | 0.395560566 | 0.517687525 |
| cg03867465 | LOC90768 | Island | Body | 9.10674 | 2.48E−06 | 0.479714023 | 0.651848155 |
| cg03885037 | ADAM8 | Island | Body | 5.28413 | 0.000205 | 0.236108988 | 0.343000682 |
| cg03905867 | PAX6 | Island | Body | 11.8021 | 1.15E−10 | 0.264501852 | 0.469462673 |
| cg03927133 | ITPKA | Island | Body | 23.3197 | 9.65E−11 | 0.262750464 | 0.416308498 |
| cg03945700 | PRR18 | Island | TSS200 | 6.96745 | 0.00022 | 0.217055362 | 0.305625355 |
| cg03947464 | UPK3A | Island | TSS200 | 10.5551 | 5.67E−08 | 0.112067382 | 0.228035911 |
| cg03951853 | NBPF8 | | Body | 7.06289 | 0.000235 | 0.445971867 | 0.501907495 |
| cg03958979 | NR2E1 | Island | TSS1500 | 9.33962 | 2.28E−05 | 0.376855736 | 0.475414889 |
| cg03959515 | FAM84B | Island | 5URT | 6.47902 | 2.88E−07 | 0.17301173 | 0.523691305 |
| cg03960072 | KAAG1 | Island | 1stExon | 36.9545 | 8.11E−10 | 0.314402351 | 0.439506303 |
| cg03964958 | HOXD12 | Island | 1stExon | 12.5171 | 5.30E−09 | 0.122362503 | 0.245863702 |
| cg03970615 | IRX3 | Island | Body | 7.28154 | 3.63E−05 | 0.308284913 | 0.426766852 |
| cg03975235 | GALR3 | Island | Body | 11.5382 | 0.000824 | 0.489935519 | 0.567151626 |
| cg03981954 | FEZF1 | N_Shore | 3UTR | 5.81951 | 1.31E−06 | 0.149783744 | 0.274631337 |
| cg03989480 | DMRTA2 | Island | Body | 5.66812 | 0.000182 | 0.335058427 | 0.428202706 |
| cg04022561 | LOC642366 | | Body | 11.2364 | 4.34E−08 | 0.114521412 | 0.231744442 |
| cg04025675 | GATM | Island | TSS200 | 3.55026 | 0.004476 | 0.220640217 | 0.307631915 |
| cg04046669 | HORMAD2 | Island | TSS1500 | 13.1346 | 1.15E−12 | 0.179208873 | 0.403051353 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg04047221 | SOX1 | Island | 3UTR | 12.2824 | 1.71E−08 | 0.146817957 | 0.273742583 |
| cg04052466 | AMH | Island | Body | 8.48992 | 2.13E−09 | 0.246444269 | 0.446683465 |
| cg04059568 | PTPRN2 | Island | Body | 8.56297 | 6.16E−07 | 0.154539162 | 0.268259715 |
| cg04065086 | SEMA6C | Island | 3UTR | 5.05 | 3.87E−05 | 0.383561956 | 0.528837553 |
| cg04079760 | ESRP2 | N_Shelf | Body | 23.3056 | 1.03E−09 | 0.451476727 | 0.628448162 |
| cg04080041 | PCDHGA12 | Island | 1stExon | 12.8918 | 8.72E−09 | 0.331931211 | 0.500179594 |
| cg04080282 | PON3 | Island | TSS1500 | 24.2223 | 7.66E−08 | 0.527982992 | 0.66176999 |
| cg04091063 | AKR7A3 | Island | TSS200 | 15.0349 | 1.51E−08 | 0.296122638 | 0.475935021 |
| cg04131898 | WT1-AS | Island | Body | 5.56518 | 0.001756 | 0.1314334 | 0.188783143 |
| cg04134048 | TNFRSF10D | S_Shore | TSS200 | 7.28106 | 7.85E−06 | 0.347644368 | 0.493013443 |
| cg04136369 | HNF1B | | Body | 27.3908 | 1.82E−05 | 0.687851837 | 0.796073717 |
| cg04142323 | LINC00461 | S_Shore | TSS1500 | 9.88372 | 5.47E−06 | 0.18544802 | 0.285239913 |
| cg04158367 | GFI1 | Island | TSS1500 | 8.70001 | 1.01E−06 | 0.301580489 | 0.452683437 |
| cg04178316 | TLX3 | N_Shelf | Body | 5.23369 | 0.001939 | 0.157414454 | 0.228749578 |
| cg04180086 | IRX4 | Island | Body | 8.87726 | 4.74E−06 | 0.145040065 | 0.239534967 |
| cg04193970 | TTC6 | Island | Body | 9.63885 | 2.56E−10 | 0.181277708 | 0.377229253 |
| cg04198914 | HNF1B | S_Shore | TSS1500 | 3.37251 | 0.005973 | 0.427471109 | 0.501742755 |
| cg04203646 | APC2 | Island | Body | 5.44756 | 0.000626 | 0.407663692 | 0.508755421 |
| cg04213746 | GATA3 | | Body | 7.14256 | 0.001142 | 0.721690977 | 0.808597889 |
| cg04236178 | ESRRG | N_Shore | 5URT | 10.3024 | 1.19E−08 | 0.329913803 | 0.490934079 |
| cg04251368 | KCNQ1DN | Island | TSS1500 | 7.1927 | 2.99E−07 | 0.195311103 | 0.343130074 |
| cg04255230 | LBX2 | Island | Body | 4.81047 | 4.45E−05 | 0.271341088 | 0.415139664 |
| cg04265576 | HOXA-AS3 | Island | Body | 7.48154 | 6.92E−05 | 0.133919803 | 0.206062225 |
| cg04290367 | D6X1 | Island | Body | 8.87731 | 1.90E−07 | 0.096948607 | 0.202125059 |
| cg04328477 | ESRP2 | Island | TSS200 | 4.10116 | 0.002371 | 0.372415165 | 0.462467043 |
| cg04342594 | LINC01391 | N_Shore | TSS200 | 9.22501 | 1.00E−05 | 0.415627669 | 0.527453626 |
| cg04360793 | ADGRL4 | Island | 1stExon | 5.17727 | 1.14E−06 | 0.34204361 | 0.537357309 |
| cg04366687 | OPLAH | Island | Body | 14.2546 | 1.96E−06 | 0.349784004 | 0.467116788 |
| cg04369341 | TOX2 | Island | Body | 4.74436 | 0.003488 | 0.215849031 | 0.288371991 |
| cg04378886 | RCN3 | S_Shore | 5URT | 10.0352 | 1.56E−07 | 0.27244142 | 0.423281952 |
| cg04403809 | SLC12A5 | Island | 3UTR | 27.1545 | 1.05E−07 | 0.28116814 | 0.374360717 |
| cg04407470 | NR2E1 | Island | Body | 5.06396 | 0.000235 | 0.060659067 | 0.135995183 |
| cg04415176 | HOXD13 | Island | 1stExon | 9.12268 | 3.49E−06 | 0.083375797 | 0.191715974 |
| cg04415798 | PAX9 | S_Shore | 5URT | 4.27388 | 4.18E−05 | 0.152159215 | 0.287995812 |
| cg04418091 | ATP5G2 | Island | TSS1500 | 3.59509 | 0.001164 | 0.14083792 | 0.24525896 |
| cg04446345 | UPK3A | Island | TSS200 | 8.81311 | 1.58E−05 | 0.208272716 | 0.312046441 |
| cg04450456 | FAM1843 | | Body | 17.4558 | 6.86E−08 | 0.557261791 | 0.687451505 |
| cg04456238 | WT1 | S_Shore | Body | 11.4207 | 3.82E−07 | 0.336912504 | 0.465736646 |
| cg04461228 | NR2F1-AS1 | Island | Body | 13.8976 | 2.55E−07 | 0.424953636 | 0.56465222 |
| cg04467589 | RNF35 | S_Shore | TSS1500 | 11.9626 | 0.000351 | 0.445556775 | 0.505938091 |
| cg04469219 | LINC00403 | Island | TSS1500 | 11.6448 | 2.27E−08 | 0.091970892 | 0.190622294 |
| cg04489012 | C2CD4D | S_Shore | 5URT | 12.3436 | 4.19E−06 | 0.456766573 | 0.598791373 |
| cg04504066 | PAX6 | S_Shore | 5URT | 20.5935 | 1.58E−11 | 0.180852284 | 0.338366544 |
| cg04513006 | ESRP2 | Island | TSS200 | 3.7056 | 0.004063 | 0.286814628 | 0.367666594 |
| cg04514123 | SYNGR8 | S_Shore | Body | 10.8376 | 7.89E−10 | 0.145936802 | 0.300849631 |
| cg04515001 | KAAG1 | Island | 1stExon | 6.55596 | 3.75E−08 | 0.186840236 | 0.354998889 |
| cg04521510 | HOTTIP | N_Shelf | Body | 5.00434 | 0.000169 | 0.123783385 | 0.221535142 |
| cg04543413 | BCAT1 | Island | TSS1500 | 16.1327 | 1.21E−09 | 0.184927666 | 0.317019285 |
| cg04552206 | TLX1 | Island | Body | 6.62135 | 0.000726 | 0.273026248 | 0.346458455 |
| cg04554928 | TRIM15 | Island | 3UTR | 6.35467 | 0.002373 | 0.478086349 | 0.564725768 |
| cg04558175 | RCN3 | S_Shore | 5URT | 11.7018 | 6.74E−05 | 0.628132868 | 0.743755818 |
| cg04566159 | ACPS | Island | 5URT | 11.3638 | 4.50E−05 | 0.402818565 | 0.536090131 |
| cg04574034 | PRAC2 | S_Shelf | TSS1500 | 4.51916 | 7.96E−05 | 0.291220253 | 0.419839379 |
| cg04586579 | SDR42E1 | Island | 5URT | 8.09315 | 5.29E−06 | 0.258890266 | 0.397663561 |
| cg04597433 | DRD5 | Island | TSS200 | 7.81426 | 1.40E−05 | 0.119448781 | 0.216242634 |
| cg04597449 | GPR150 | N_Shore | TSS1500 | 3.43764 | 0.008851 | 0.333395374 | 0.413057141 |
| cg04598774 | PAX6 | S_Shore | Body | 27.3606 | 8.60E−13 | 0.218210078 | 0.38766699 |
| cg04617948 | FOX12 | Island | TSS1500 | 31.6937 | 7.76E−10 | 0.43486481 | 0.6017015 |
| cg04623837 | HCG9 | N_Shore | Body | 7.98941 | 4.53E−07 | 0.298498815 | 0.480692037 |
| cg04630292 | PRRT1 | Island | 3UTR | 3.98086 | 0.006055 | 0.439294058 | 0.504842645 |
| cg04636269 | LHX1 | Island | 3UTR | 5.20672 | 0.001157 | 0.312285322 | 0.39083719 |
| cg04648480 | SIM2 | S_Shore | Body | 5.27688 | 0.000265 | 0.401238405 | 0.502791257 |
| cg04654580 | OTX1 | Island | Body | 9.48413 | 1.97E−10 | 0.275466332 | 0.475796179 |
| cg04673825 | ZNF518B | Island | TSS200 | 10.5496 | 1.76E−08 | 0.152019913 | 0.281781773 |
| cg04685170 | PON3 | Island | TSS200 | 5.98353 | 0.00024 | 0.309790053 | 0.387507674 |
| cg04688051 | LYNX1 | Island | 5URT | 6.72173 | 2.46E−07 | 0.142443015 | 0.285497693 |
| cg04728480 | APB81IP | N_Shore | TSS1500 | 3.59417 | 0.001725 | 0.236139391 | 0.337756086 |
| cg04729913 | GATA3-A51 | Island | Body | 12.3779 | 0.00013 | 0.465038411 | 0.556351222 |
| cg04730685 | LOC101927248 | S_Shelf | Body | 14.9126 | 1.28E−07 | 0.381336222 | 0.514076535 |
| cg04738888 | MYO15B | Island | TSS200 | 30.5143 | 1.18E−12 | 0.25561768 | 0.427184443 |
| cg04739647 | HOXD9 | Island | 5URT | 6.64276 | 2.96E−05 | 0.149606771 | 0.248272855 |
| cg04765277 | GATA3-AS1 | Island | Body | 4.89144 | 0.000146 | 0.292924856 | 0.419140007 |
| cg04775710 | IER3 | Island | Body | 12.7649 | 3.30E−09 | 0.214689078 | 0.389077326 |
| cg04787024 | KIAA1211L | Island | TSS1500 | 8.21827 | 5.20E−10 | 0.268113979 | 0.496846403 |
| cg04796181 | HIST1H3I | Island | 1stExon | 11.4896 | 1.19E−08 | 0.133404667 | 0.264818755 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg04809787 | CHRNB1 | Island | TSS200 | 10.9969 | 9.73E-07 | 0.249933354 | 0.371353219 |
| cg04821708 | SDR42E1 | Island | TSS200 | 12.5748 | 8.20E-07 | 0.333422556 | 0.467231894 |
| cg04850999 | C10orf11 | Island | Body | 7.87629 | 0.003061 | 0.713162171 | 0.801042697 |
| cg04854328 | NR2F1-AS1 | Island | Body | 6.47623 | 1.80E-05 | 0.140541447 | 0.259469238 |
| cg04856858 | AGAP1 | Island | TSS1500 | 8.55341 | 4.81E-08 | 0.25187456 | 0.42131318 |
| cg04864199 | SHF | S_Shelf | 5URT | 30.8243 | 5.11E-09 | 0.497527629 | 0.678207076 |
| cg04886060 | SDR42E1 | N_Shore | 5URT | 8.56277 | 8.41E-06 | 0.473221262 | 0.615325889 |
| cg04887494 | JSRP1 | Island | Body | 4.30211 | 3.51E-05 | 0.321180862 | 0.470707462 |
| cg04904318 | HOXB1 | Island | 1stExon | 4.05689 | 0.001389 | 0.517519174 | 0.612871879 |
| cg04916091 | JAK3 | Island | 5URT | 5.67689 | 4.51E-05 | 0.256277892 | 0.396706996 |
| cg04937416 | PTPRN2 | Island | Body | 3.3275 | 0.004443 | 0.442201133 | 0.532210548 |
| cg04938549 | PAX6 | N_Shore | 5URT | 10.3475 | 4.49E-13 | 0.220136969 | 0.468327634 |
| cg04956913 | IER3 | Island | TSS200 | 7.3777 | 1.30E-05 | 0.256258891 | 0.398895634 |
| cg04959815 | CYB5R2 | Island | 5URT | 7.36013 | 8.67E-06 | 0.11218199 | 0.210789062 |
| cg04972566 | FGF19 | N_Shore | Body | 5.93737 | 7.26E-06 | 0.185602878 | 0.302986239 |
| cg04972745 | LINC01475 | Island | Body | 4.01885 | 0.000676 | 0.313178154 | 0.415709533 |
| cg04996219 | CTNND2 | Island | 1stExon | 9.46443 | 4.89E-08 | 0.068156759 | 0.17834887 |
| cg05001964 | IRX3 | Island | Body | 4.25429 | 0.000137 | 0.158731104 | 0.285621993 |
| cg05009601 | FEZF1 | Island | 1stExon | 7.70169 | 4.62E-06 | 0.309059788 | 0.436804884 |
| cg05027336 | HOXA10-AS | Island | Body | 3.82266 | 0.008025 | 0.142675695 | 0.208360182 |
| cg05029822 | KCNQ1DN | Island | TSS200 | 14.6722 | 3.63E-05 | 0.318111847 | 0.390980719 |
| cg05031521 | LMF1 | Island | Body | 11.4525 | 9.96E-07 | 0.183132995 | 0.312258364 |
| cg05065507 | TACSTD2 | Island | 1stExon | 17.6008 | 1.21E-07 | 0.235009493 | 0.323873895 |
| cg05072100 | LYNX1 | Island | 5URT | 7.90314 | 1.16E-06 | 0.209027203 | 0.335639659 |
| cg05140806 | SHH | N_Shelf | Body | 5.19567 | 0.000604 | 0.177646875 | 0.266475565 |
| cg05142617 | MAL | N_Shore | TSS1500 | 9.20848 | 9.90E-07 | 0.393394839 | 0.541751609 |
| cg05142765 | GSC | Island | 3UTR | 4.85342 | 0.000325 | 0.288989178 | 0.395936251 |
| cg05158615 | NPY | Island | TSS1500 | 7.534 | 2.45E-07 | 0.293681987 | 0.447260552 |
| cg05165940 | SATB2 | Island | 1stExon | 11.2209 | 1.21E-06 | 0.28832389 | 0.382720922 |
| cg05167251 | HOXD9 | Island | 5URT | 7.55624 | 2.51E-06 | 0.198387284 | 0.309700661 |
| cg05180443 | CHAD | Island | TSS1500 | 3.91693 | 0.000389 | 0.22316233 | 0.34412746 |
| cg05193369 | CYP26C1 | N_Shelf | Body | 5.91729 | 0.000789 | 0.187634088 | 0.258500834 |
| cg05196969 | ISL2 | N_Shore | TSS1500 | 9.98068 | 4.12E-09 | 0.154595415 | 0.312671802 |
| cg05210501 | HOXA10-HOXA9 | Island | Body | 6.91782 | 0.000241 | 0.195591357 | 0.263659144 |
| cg05222924 | WT1 | N_Shore | Body | 6.44924 | 1.41E-05 | 0.088734745 | 0.185265833 |
| cg05236677 | STK3 | Island | 5URT | 8.32458 | 2.80E-06 | 0.224798536 | 0.358093791 |
| cg05256269 | HOXD13 | S_Shore | TSS1500 | 16.8971 | 3.28E-08 | 0.304113184 | 0.435109899 |
| cg05290058 | KCNQ1DN | Island | TSS1500 | 5.06864 | 1.37E-05 | 0.410864829 | 0.561331284 |
| cg05301866 | TBR1 | Island | Body | 22.5958 | 2.23E-08 | 0.410505628 | 0.518827919 |
| cg05317714 | KIFC2 | Island | Body | 57.2249 | 4.73E-14 | 0.295231785 | 0.529090365 |
| cg05345154 | AMH | Island | Body | 8.01784 | 1.36E-09 | 0.24790974 | 0.459142351 |
| cg05347898 | KAAG1 | Island | 1stExon | 6.90488 | 6.57E-08 | 0.096868476 | 0.2423145 |
| cg05351827 | SPEG | Island | Body | 14.5346 | 6.51E-05 | 0.533432313 | 0.643321309 |
| cg05368740 | HSPB6 | Island | Body | 4.28673 | 0.001806 | 0.328825281 | 0.420606382 |
| cg05376374 | MIR129-2 | Island | TSS200 | 15.6956 | 1.05E-12 | 0.059778181 | 0.203785349 |
| cg05377576 | SEZ6L2 | N_Shore | Body | 16.7414 | 6.58E-05 | 0.554689663 | 0.670872374 |
| cg05380821 | NR2E1 | Island | Body | 5.1387 | 0.000716 | 0.236612465 | 0.313793468 |
| cg05387167 | HOXB3 | S_Shore | Body | 8.21026 | 0.000217 | 0.456289597 | 0.529069051 |
| cg05408649 | HOXC4 | Island | 5URT | 4.35073 | 0.006926 | 0.738861209 | 0.785422273 |
| cg05449136 | PROB1 | Island | 1stExon | 11.3355 | 5.93E-10 | 0.146969409 | 0.313063182 |
| cg05457563 | APC2 | Island | Body | 6.97355 | 0.000893 | 0.376479927 | 0.462124805 |
| cg05470554 | WNT16 | N_Shore | Body | 8.54167 | 2.53E-09 | 0.235299112 | 0.437242342 |
| cg05475249 | APBB1IP | Island | 1stExon | 7.39348 | 4.52E-07 | 0.186522658 | 0.329101564 |
| cg05477444 | INPP5A | Island | Body | 11.215 | 0.000671 | 0.714821558 | 0.789695202 |
| cg05488632 | EPHX3 | Island | 1stExon | 85.8683 | 1.03E-12 | 0.390814822 | 0.559915343 |
| cg05490659 | HOXA10 | S_Shelf | Body | 4.21112 | 0.001722 | 0.245250948 | 0.335412057 |
| cg05498007 | KATNAL2 | N_Shore | TSS200 | 6.58294 | 8.12E-08 | 0.203589678 | 0.386896059 |
| cg05500840 | HOXD11 | Island | TSS200 | 12.527 | 1.38E-09 | 0.257812474 | 0.440698546 |
| cg05501996 | LOC642865 | | Body | 14.5033 | 6.77E-13 | 0.184712326 | 0.374705466 |
| cg05520409 | LMF1 | Island | Body | 11.1912 | 4.54E-06 | 0.358776165 | 0.505580327 |
| cg05522011 | PRDM8 | N_Shore | Body | 3.07765 | 0.006963 | 0.624171176 | 0.708011343 |
| cg05527530 | LHX9 | S_Shore | Body | 5.19536 | 0.002405 | 0.168759788 | 0.240135155 |
| cg05529506 | KATNAL2 | Island | 1stExon | 8.19031 | 1.18E-08 | 0.137086846 | 0.311434044 |
| cg05555207 | TBX5-AS1 | Island | Body | 5.48129 | 5.24E-05 | 0.148260033 | 0.232468557 |
| cg05578840 | OTP | N_Shore | Body | 6.42378 | 7.65E-06 | 0.353794321 | 0.498461196 |
| cg05592035 | CD300A | | Body | 9.31261 | 1.64E-07 | 0.308964828 | 0.486762432 |
| cg05603881 | SHISA3 | S_Shore | Body | 4.78043 | 0.000903 | 0.147096058 | 0.217968074 |
| cg05604079 | QRFPR | Island | TSS200 | 7.33625 | 2.96E-08 | 0.19745714 | 0.377169215 |
| cg05635754 | JAK3 | Island | 5URT | 5.76455 | 8.06E-05 | 0.372507206 | 0.501759223 |
| cg05639205 | SHH | Island | Body | 11.1548 | 1.36E-07 | 0.213370517 | 0.338072454 |
| cg05656180 | KCNQ1DN | N_Shore | TSS1500 | 4.38423 | 0.00978 | 0.329915253 | 0.397065605 |
| cg05658487 | IRX4 | Island | TSS1500 | 20.1532 | 1.34E-09 | 0.223245993 | 0.348368599 |
| cg05667348 | VAX1 | Island | Body | 5.18024 | 1.19E-05 | 0.180764685 | 0.304268554 |
| cg05678749 | GABRG3 | Island | Body | 5.68088 | 0.000174 | 0.136910791 | 0.228655153 |
| cg05690644 | GDF6 | Island | Body | 53.7262 | 1.18E-07 | 0.597656312 | 0.772548253 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg05697849 | ELAVL4 | Island | 5URT | 19.5073 | 1.52E−09 | 0.275810197 | 0.404820727 |
| cg05724997 | BCL2 | S_Shelf | TSS1500 | 6.69085 | 1.37E−05 | 0.252322091 | 0.373295122 |
| cg05736768 | DFYS | Island | 1stExon | 23.949 | 1.54E−12 | 0.187180757 | 0.340324042 |
| cg05744332 | MNX1 | N_Shore | Body | 22.6607 | 5.49E−05 | 0.602450375 | 0.69059104 |
| cg05766510 | PTPRN2 | Island | Body | 3.08886 | 0.007926 | 0.580438012 | 0.645238596 |
| cg05787556 | TLX3 | Island | TSS1500 | 20.4256 | 2.00E−10 | 0.217448751 | 0.345871152 |
| cg05818685 | CTNND2 | Island | Body | 10.1471 | 0.000186 | 0.459162729 | 0.55107703 |
| cg05822926 | ICA1 | Island | TSS1500 | 23.2354 | 1.64E−08 | 0.338808268 | 0.479127516 |
| cg05835105 | PITX2 | S_Shelf | Body | 9.07141 | 7.36E−12 | 0.203399107 | 0.452202498 |
| cg05839235 | NPR3 | Island | 1stExon | 15.1652 | 9.97E−13 | 0.143704891 | 0.326434855 |
| cg05853632 | RNF39 | Island | 1stExon | 6.44474 | 5.25E−06 | 0.218287822 | 0.352576493 |
| cg05890484 | BHMT | | TSS200 | 20.8374 | 1.03E−05 | 0.540446093 | 0.643199364 |
| cg05896902 | GATM | Island | TSS200 | 3.66491 | 0.004096 | 0.233615904 | 0.330899056 |
| cg05899618 | GDF7 | Island | TSS1500 | 13.4991 | 9.88E−09 | 0.205282742 | 0.35049826 |
| cg05905176 | TNFAIP8L3 | Island | Body | 5.19304 | 2.05E−07 | 0.239630407 | 0.440286099 |
| cg05915293 | SYNGR3 | S_Shore | Body | 5.921 | 2.27E−06 | 0.268004435 | 0.446662949 |
| cg05921905 | HOXA2 | N_Shelf | TSS200 | 4.78279 | 0.000329 | 0.134393118 | 0.224593638 |
| cg05922610 | NR2E1 | N_Shore | Body | 19.7272 | 1.15E−09 | 0.230347274 | 0.341964081 |
| cg05924583 | TP73 | Island | 5URT | 11.7884 | 4.17E−05 | 0.440948772 | 0.564297823 |
| cg05925327 | LOC101929076 | Island | Body | 4.32618 | 0.000161 | 0.256723886 | 0.380661308 |
| cg05928186 | HOXA-AS3 | Island | Body | 8.71673 | 0.000281 | 0.244843558 | 0.308103502 |
| cg05929882 | TBX5-AS1 | Island | Body | 8.41999 | 4.00E−06 | 0.097954926 | 0.181912476 |
| cg05937630 | AKR7A3 | Island | TSS1500 | 7.98694 | 1.72E−07 | 0.178576405 | 0.353656995 |
| cg05942128 | HOXD11 | Island | TSS200 | 20.671 | 7.31E−11 | 0.29540255 | 0.448715437 |
| cg05974274 | PRDM8 | N_Shore | Body | 8.18823 | 3.52E−07 | 0.197495261 | 0.330610299 |
| cg05975410 | LOC648987 | S_Shore | TSS1500 | 5.08264 | 0.001893 | 0.292908925 | 0.390920108 |
| cg05976500 | NTN1 | Island | Body | 27.781 | 1.80E−15 | 0.164488905 | 0.396399184 |
| cg05977669 | HOXA11-AS | Island | Body | 26.6529 | 1.39E−06 | 0.474222062 | 0.574849141 |
| cg05990544 | HIST1HB1 | S_Shore | TSS1500 | 10.5824 | 9.88E−11 | 0.135833619 | 0.297756112 |
| cg06005695 | HIST1HB1 | S_Shore | TSS1500 | 22.9412 | 9.73E−10 | 0.223187505 | 0.349656841 |
| cg06023345 | FAM84B | N_Shore | 3UTR | 7.26993 | 5.62E−05 | 0.359474053 | 0.492969881 |
| cg06049868 | LINC00403 | S_Shore | Body | 7.8033 | 0.000157 | 0.291233663 | 0.378114604 |
| cg06055873 | HOXA2 | N_Shelf | 1stExon | 16.631 | 1.01E−08 | 0.368848872 | 0.51710603 |
| cg06060135 | IRX1 | Island | Body | 6.39132 | 1.40E−06 | 0.106804028 | 0.224072525 |
| cg06102419 | LOC151174 | N_Shore | Body | 33.332 | 7.51E−06 | 0.579995612 | 0.675802646 |
| cg06133205 | DLEU1 | N_Shore | Body | 5.58808 | 4.03E−05 | 0.188124649 | 0.292899905 |
| cg06142537 | LINC01143 | Island | TSS1500 | 5.4592 | 0.000749 | 0.224659264 | 0.304354166 |
| cg06146234 | SHH | S_Shore | 5URT | 5.08883 | 3.27E−05 | 0.296388516 | 0.437446254 |
| cg06148812 | TBX1 | Island | 5URT | 23.1023 | 1.18E−05 | 0.579195643 | 0.692901162 |
| cg06150468 | BATF3 | S_Shore | TSS1500 | 8.86271 | 7.67E−08 | 0.106960341 | 0.253960487 |
| cg06157318 | APBB1IP | Island | TSS200 | 10.1179 | 1.04E−06 | 0.186548505 | 0.313333229 |
| cg06159394 | DMRTA2 | Island | 5URT | 5.49183 | 0.006272 | 0.526456171 | 0.576542889 |
| cg06166809 | GPR150 | Island | 1stExon | 23.9557 | 5.23E−10 | 0.152129994 | 0.279360984 |
| cg06178563 | NKX2-2 | Island | TSS200 | 11.9168 | 1.25E−06 | 0.196268349 | 0.300952132 |
| cg06198398 | KATNAL2 | N_Shore | TSS200 | 6.99904 | 8.61E−09 | 0.141469797 | 0.318931845 |
| cg06226156 | LBX2 | Island | 1stExon | 5.16483 | 0.000356 | 0.190362384 | 0.286278345 |
| cg06226630 | ZAR1 | Island | Body | 25.2837 | 1.57E−12 | 0.383122488 | 0.555957939 |
| cg06230848 | FAM84B | Island | Body | 10.5875 | 1.52E−07 | 0.240957931 | 0.385725809 |
| cg06238409 | MECOM | Island | TSS200 | 4.04426 | 0.004356 | 0.161929971 | 0.228024847 |
| cg06239355 | NPR3 | Island | Body | 9.85931 | 8.67E−09 | 0.183383193 | 0.346782453 |
| cg06249604 | RNF39 | Island | Body | 3.93003 | 4.25E−05 | 0.263301856 | 0.415649398 |
| cg06254440 | LHX2 | Island | Body | 3.93656 | 0.003764 | 0.211087295 | 0.287557315 |
| cg06255670 | DLEU1 | | Body | 6.07287 | 8.25E−06 | 0.339033453 | 0.527471672 |
| cg06262436 | ISM1 | Island | TSS1500 | 10.3694 | 2.52E−07 | 0.223783874 | 0.34915112 |
| cg06272038 | ASCL2 | Island | TSS1500 | 12.661 | 1.07E−07 | 0.05079888 | 0.148702194 |
| cg06274159 | ZFP42 | Island | TSS200 | 9.81907 | 3.55E−11 | 0.201375337 | 0.41292663 |
| cg06287951 | DLX4 | S_Shore | Body | 14.6705 | 2.10E−06 | 0.383364258 | 0.499547 |
| cg06303875 | CDX2 | S_Shelf | TSS200 | 11.0416 | 7.52E−08 | 0.182710151 | 0.295716758 |
| cg06312283 | PAX6 | S_Shore | TSS1500 | 19.2436 | 1.77E−12 | 0.137502719 | 0.270344635 |
| cg06323023 | HIST1H31 | S_Shore | TSS1500 | 10.6927 | 4.52E−08 | 0.167164061 | 0.311430898 |
| cg06367117 | ALDOC | | 5URT | 36.9295 | 3.47E−09 | 0.156168537 | 0.26086272 |
| cg06367311 | PLLP | Island | Body | 6.80999 | 3.61E−06 | 0.40393705 | 0.544994926 |
| cg06375967 | ISL2 | Island | Body | 6.26597 | 1.28E−05 | 0.19262367 | 0.282325826 |
| cg06376715 | TP73 | Island | Body | 20.1013 | 5.64E−06 | 0.601157636 | 0.716308788 |
| cg06382344 | TBR1 | Island | Body | 13.5958 | 3.72E−15 | 0.118598433 | 0.356284372 |
| cg06382559 | TLX1 | Island | Body | 3.45764 | 0.008023 | 0.261063491 | 0.314466023 |
| cg06386307 | SIM1 | Island | Body | 7.05704 | 4.02E−05 | 0.380077302 | 0.492924949 |
| cg06390536 | MYO15B | Island | TSS200 | 10.5771 | 2.08E−07 | 0.171430236 | 0.289146776 |
| cg06410191 | LVRN | Island | 1stExon | 15.9907 | 7.04E−08 | 0.227524578 | 0.34438589 |
| cg06410537 | TLX3 | Island | 1stExon | 16.4501 | 4.38E−09 | 0.155685643 | 0.29692154 |
| cg06428620 | PCDHGC4 | N_Shore | TSS1500 | 4.9205 | 5.88E−05 | 0.234660733 | 0.380898562 |
| cg06440348 | PRDM8 | S_Shore | 5URT | 11.1971 | 2.68E−05 | 0.632337047 | 0.71132196 |
| cg06451900 | LOC145845 | N_Shore | Body | 5.72026 | 0.00032 | 0.412754411 | 0.513207667 |
| cg06488443 | TBR1 | Island | Body | 30.0459 | 2.84E−11 | 0.253759163 | 0.384046656 |
| cg06490225 | LHX1 | Island | Body | 5.79275 | 0.00032 | 0.25866663 | 0.343269871 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg06497848 | VAX1 | Island | Body | 8.04193 | 0.000134 | 0.389835388 | 0.452445566 |
| cg06520675 | LBX1-AS1 | Island | Body | 7.94911 | 1.85E−05 | 0.166851953 | 0.330531853 |
| cg06585993 | APBB1IP | Island | TSS200 | 7.00562 | 1.95E−05 | 0.146532671 | 0.245046367 |
| cg06554090 | LOC101929076 | Island | Body | 8.21623 | 1.39E−06 | 0.28802705 | 0.423138456 |
| cg06571387 | HOXD12 | S_Shore | TSS1500 | 13.6857 | 1.20E−06 | 0.37625662 | 0.488498677 |
| cg06579271 | PLLP | Island | TSS1500 | 9.58144 | 3.05E−05 | 0.217283791 | 0.321234876 |
| cg06615152 | AMH | Island | Body | 11.8308 | 2.85E−05 | 0.510813961 | 0.631844475 |
| cg06626599 | KCNQ4 | Island | Body | 14.1385 | 1.53E−05 | 0.478628428 | 0.582496929 |
| cg06632207 | ATP5G2 | S_Shore | TSS1500 | 3.38557 | 0.008113 | 0.082155288 | 0.147204271 |
| cg06637517 | DNAH1 | | Body | 4.35003 | 2.91E−05 | 0.291351831 | 0.458736311 |
| cg06644373 | SATB2 | Island | 5URT | 3.49707 | 0.007679 | 0.28293666 | 0.364917126 |
| cg06666008 | PAX6 | N_Shore | Body | 12.1861 | 9.51E−13 | 0.205925812 | 0.446187038 |
| cg06667574 | IGLON5 | Island | Body | 8.20214 | 0.000784 | 0.63913838 | 0.745123697 |
| cg06702880 | LRAT | N_Shore | 5URT | 6.28077 | 6.33E−06 | 0.118959668 | 0.22326278 |
| cg06704518 | GATA4 | Island | 5URT | 4.59876 | 0.002197 | 0.207443826 | 0.28668601 |
| cg06705930 | PAX6 | N_Shelf | 5URT | 9.69726 | 0.000335 | 0.630173628 | 0.727324172 |
| cg06708634 | SIM1 | S_Shore | Body | 7.53796 | 1.93E−06 | 0.398221261 | 0.546436879 |
| cg06710082 | HCG9 | N_Shore | Body | 6.90499 | 8.02E−07 | 0.371448774 | 0.560210055 |
| cg06723863 | ESRP2 | Island | 1stExon | 6.99852 | 5.27E−05 | 0.065670505 | 0.134618864 |
| cg06724305 | DMRTA2 | Island | 5URT | 4.293 | 0.005039 | 0.29089591 | 0.363960642 |
| cg06732395 | SCGB3A1 | Island | TSS1500 | 22.6843 | 1.99E−10 | 0.27929364 | 0.426210253 |
| cg06754197 | MIR199A1 | | TSS200 | 35.3724 | 3.79E−06 | 0.614658202 | 0.719448232 |
| cg06765217 | TTC6 | Island | Body | 10.2106 | 3.67E−11 | 0.071472511 | 0.215188256 |
| cg06779449 | TOX2 | Island | Body | 10.7538 | 6.53E−07 | 0.080850172 | 0.185210946 |
| cg06804210 | CD8A | S_Shelf | TSS1500 | 14.3491 | 2.10E−07 | 0.33357462 | 0.45325798 |
| cg06813578 | TNFAIP8L3 | Island | Body | 5.89644 | 5.70E−06 | 0.173513354 | 0.31028461 |
| cg06818052 | NTN1 | Island | Body | 11.8809 | 4.34E−05 | 0.461386946 | 0.567006863 |
| cg06818777 | CHAD | Island | TSS1500 | 4.58976 | 0.000862 | 0.272921576 | 0.384367489 |
| cg06825142 | DRD4 | Island | TSS200 | 7.48677 | 5.40E−06 | 0.10020074 | 0.20381938 |
| cg06842954 | PITX2 | N_Shore | 5URT | 7.23515 | 4.42E−07 | 0.180063419 | 0.304475343 |
| cg06845853 | WT1-AS | S_Shore | Body | 10.6891 | 7.20E−12 | 0.149371217 | 0.322196318 |
| cg06854084 | NKX2-3 | N_Shore | TSS200 | 8.04535 | 0.000122 | 0.148501078 | 0.191719088 |
| cg06866686 | GSC | S_Shore | TSS1500 | 6.16697 | 0.001813 | 0.421445349 | 0.496426152 |
| cg06872257 | FGF20 | S_Shore | 1stExon | 25.2623 | 3.76E−08 | 0.467465767 | 0.609856904 |
| cg06911121 | TBX5-AS1 | Island | Body | 5.30745 | 0.000656 | 0.158440819 | 0.229145194 |
| cg06916239 | PAX3 | S_Shelf | Body | 6.62476 | 7.97E−06 | 0.243614275 | 0.364036427 |
| cg06942183 | HOXB-AS1 | S_Shore | Body | 4.34571 | 0.003037 | 0.284047372 | 0.364007342 |
| cg06942701 | TBR1 | Island | Body | 86.3924 | 9.76E−13 | 0.407200876 | 0.543208242 |
| cg06943420 | MMP23B | Island | TSS1500 | 8.07491 | 3.97E−10 | 0.2100618 | 0.424244613 |
| cg06962944 | TOX2 | Island | TSS200 | 7.04067 | 2.54E−06 | 0.082193076 | 0.212878265 |
| cg06966811 | OTX2 | N_Shore | Body | 16.9613 | 2.12E−10 | 0.31196753 | 0.492314091 |
| cg06975048 | KCNAB3 | Island | 3UTR | 9.91146 | 4.79E−06 | 0.199350688 | 0.304158052 |
| cg06991300 | QRFPR | Island | 1stExon | 13.819 | 7.38E−08 | 0.140336902 | 0.259937392 |
| cg06992285 | STK3 | Island | 5URT | 5.37559 | 8.80E−06 | 0.216394633 | 0.35785876 |
| cg07010088 | SKOR1 | Island | Body | 4.93113 | 0.003819 | 0.238633922 | 0.293784595 |
| cg07010228 | JSRP1 | Island | Body | 8.90391 | 0.000163 | 0.255354814 | 0.332621396 |
| cg07017875 | PCDHG86 | Island | 1stExon | 16.004 | 6.93E−07 | 0.479779496 | 0.598656949 |
| cg07020001 | KDM2B | S_Shore | TSS1500 | 4.86584 | 0.000879 | 0.143982427 | 0.239040424 |
| cg07021246 | UPK3A | Island | 5URT | 10.2246 | 4.18E−07 | 0.226893244 | 0.361062474 |
| cg07029873 | ESRRG | Island | 1stExon | 9.56191 | 3.69E−10 | 0.138112815 | 0.311573376 |
| cg07033624 | LINC00403 | N_Shelf | Body | 14.0182 | 2.87E−08 | 0.164622669 | 0.282675488 |
| cg07046818 | GDF6 | N_Shelf | Body | 6.04561 | 2.33E−05 | 0.348011051 | 0.463268873 |
| cg07050616 | LBX1-AS1 | Island | Body | 9.62885 | 1.58E−08 | 0.157130462 | 0.318356733 |
| cg07060233 | SLC12A5 | Island | 3UTR | 44.5703 | 1.38E−11 | 0.366929124 | 0.506961182 |
| cg07095230 | TBX2 | Island | Body | 4.03414 | 0.000182 | 0.383930524 | 0.512640611 |
| cg07104660 | TCF24 | Island | Body | 17.8474 | 2.87E−11 | 0.16164926 | 0.304270466 |
| cg07116997 | HOXA11-AS | S_Shore | Body | 8.44641 | 0.000108 | 0.183230529 | 0.255319415 |
| cg07121856 | PON3 | Island | TSS200 | 15.2066 | 6.30E−13 | 0.141504037 | 0.334556926 |
| cg07124117 | PAX6 | Island | Body | 12.8326 | 1.55E−09 | 0.219689223 | 0.382253517 |
| cg07135614 | LINC01391 | N_Shore | TSS1500 | 5.5274 | 9.57E−05 | 0.29196725 | 0.407797311 |
| cg07147475 | MGAT4D | S_Shore | TSS200 | 10.342 | 8.47E−06 | 0.395251711 | 0.518101239 |
| cg07155223 | ESRRG | N_Shore | 5URT | 5.78903 | 1.01E−06 | 0.09639401 | 0.199869088 |
| cg07160932 | SEZ6L2 | S_Shore | Body | 9.21759 | 2.14E−08 | 0.286851089 | 0.502690903 |
| cg07178825 | TP73 | Island | 3UTR | 49.6557 | 1.47E−13 | 0.440568326 | 0.619546192 |
| cg07195011 | CTNND2 | Island | 1stExon | 8.80107 | 1.39E−09 | 0.085908935 | 0.229889145 |
| cg07201017 | LBX1-AS1 | Island | Body | 12.5843 | 6.43E−08 | 0.325290793 | 0.46231202 |
| cg07211140 | WT1 | S_Shelf | Body | 8.22282 | 2.03E−07 | 0.168148605 | 0.307013632 |
| cg07247419 | NKX2-4 | Island | 3UTR | 12.7573 | 8.58E−07 | 0.315247287 | 0.434596404 |
| cg07274716 | PITX1 | Island | 3UTR | 10.7107 | 1.03E−11 | 0.248936197 | 0.470384833 |
| cg07281879 | WT1-AS | Island | Body | 11.8386 | 7.57E−08 | 0.137990289 | 0.255356689 |
| cg07300846 | SEZ6L2 | S_Shore | ExonBnd | 5.76948 | 1.47E−05 | 0.254227504 | 0.408846359 |
| cg07302910 | VAX1 | N_Shore | 3UTR | 4.40459 | 0.000651 | 0.265083289 | 0.35850637 |
| cg07311313 | CDX2 | S_Shelf | TSS200 | 8.12688 | 1.09E−08 | 0.094611722 | 0.226825864 |
| cg07322064 | PRR18 | Island | 3UTR | 11.0121 | 6.08E−05 | 0.466917442 | 0.549986838 |
| cg07323141 | LOC151174 | Island | Body | 4.91533 | 0.002033 | 0.208585111 | 0.295466371 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg07329360 | DKFZp686K1684 | Island | Body | 16.6189 | 3.27E-11 | 0.312894591 | 0.480329035 |
| cg07330230 | ALDH1L1 | S_Shore | 1stExon | 4.94285 | 3.63E-05 | 0.153605512 | 0.272795436 |
| cg07333715 | ASCL2 | Island | TSS1500 | 9.24636 | 3.62E-10 | 0.163841346 | 0.361614096 |
| cg07359633 | LTK | Island | Body | 6.68189 | 0.000291 | 0.290410173 | 0.36553503 |
| cg07367232 | KCNAB3 | Island | 3UTR | 7.44099 | 1.03E-05 | 0.105800144 | 0.202783451 |
| cg07371589 | SEMA6C | Island | 3UTR | 3.88852 | 0.000311 | 0.543665056 | 0.661379807 |
| cg07380026 | TERT | S_Shore | TSS1500 | 18.0107 | 9.53E-05 | 0.652038674 | 0.740083253 |
| cg07382347 | RNF39 | Island | Body | 6.98191 | 2.34E-06 | 0.406932169 | 0.5622676 |
| cg07382943 | IGLON5 | Island | Body | 5.36098 | 0.000192 | 0.432114708 | 0.564647343 |
| cg07303092 | NKX2-5 | S_Shelf | TSS1500 | 9.89379 | 6.50E-08 | 0.329076045 | 0.498830912 |
| cg07407736 | MGAT4D | | Body | 4.21075 | 0.003683 | 0.281324196 | 0.350332998 |
| cg07411620 | EVX2 | N_Shelf | TSS200 | 5.35624 | 1.24E-05 | 0.358021001 | 0.47450737 |
| cg07416664 | GALR3 | Island | 3UTR | 5.60422 | 0.001283 | 0.618287264 | 0.694581626 |
| cg07434271 | PAX6 | S_Shore | TSS1500 | 21.5421 | 6.22E-16 | 0.144036724 | 0.348245551 |
| cg07440414 | TCF7 | Island | TSS1500 | 17.4839 | 4.22E-11 | 0.158247908 | 0.317328809 |
| cg07440775 | GAD2 | Island | Body | 8.64491 | 2.01E-05 | 0.38701995 | 0.502670929 |
| cg07447773 | AKR7A3 | N_Shore | Body | 8.68543 | 0.005234 | 0.691376868 | 0.75700303 |
| cg07483304 | HOXA10 | S_Shelf | Body | 3.70733 | 0.008254 | 0.372224738 | 0.448420414 |
| cg07502389 | NEFM | Island | TSS1500 | 15.5495 | 2.62E-08 | 0.281389257 | 0.408542561 |
| cg07515422 | SPTBN4 | N_Shelf | Body | 24.6972 | 6.61E-09 | 0.514467633 | 0.716035075 |
| cg07516252 | REC8 | Island | TSS200 | 21.5435 | 8.49E-13 | 0.271671274 | 0.488728262 |
| cg07522913 | HOXA3 | S_Shelf | 5URT | 9.74608 | 0.000221 | 0.511928783 | 0.057686313 |
| cg07529210 | KDM2B | S_Shore | TSS1500 | 5.02938 | 0.002588 | 0.354769687 | 0.445178188 |
| cg07536110 | EVX2 | N_Shelf | 1stExon | 8.96009 | 1.74E-07 | 0.263254118 | 0.416078784 |
| cg07539798 | PCDHGA12 | Island | 1stExon | 17.5279 | 4.24E-06 | 0.595596938 | 0.719313131 |
| cg07541200 | LOC648987 | S_Shore | TSS1500 | 4.22398 | 0.007637 | 0.325952015 | 0.407391053 |
| cg07545037 | HOXC6 | S_Shore | 3UTR | 517.823 | 4.58E-08 | 0.711818597 | 0.826766354 |
| cg07552803 | NEFM | Island | TSS1500 | 18.6549 | 8.12E-11 | 0.169502645 | 0.291078075 |
| cg07578695 | SLC34A2 | Island | TSS1500 | 6.6203 | 7.80E-06 | 0.151460871 | 0.267796383 |
| cg07592963 | KCNQ1DN | Island | TSS1500 | 6.22493 | 1.62E-07 | 0.178661897 | 0.345640134 |
| cg07595776 | LOC101929154 | Island | TSS200 | 9.45963 | 6.84E-10 | 0.135370743 | 0.28342468 |
| cg07606384 | CYP26C1 | Island | Body | 6.68184 | 0.000374 | 0.441954225 | 0.533425283 |
| cg07615087 | SIM2 | N_Shelf | Body | 3.58602 | 0.0075 | 0.234275619 | 0.30896857 |
| cg07653946 | GREB1L | Island | 5URT | 10.8697 | 4.18E-08 | 0.259665205 | 0.411714958 |
| cg07660671 | SOX7 | S_Shore | Body | 15.7414 | 3.72E-08 | 0.431462163 | 0.582563717 |
| cg07696699 | FAM184B | Island | TSS1500 | 5.7036 | 5.98E-07 | 0.210884331 | 0.39049271 |
| cg07702750 | TRIL | Island | TSS200 | 9.16408 | 8.11E-08 | 0.128885084 | 0.271552312 |
| cg07703462 | SSPO | Island | Body | 13.3702 | 8.23E-13 | 0.266026535 | 0.580334178 |
| cg07778029 | HOXA9 | Island | 1stExon | 5.61277 | 0.000322 | 0.186206651 | 0.280611154 |
| cg07785447 | GSC | Island | Body | 9.13622 | 2.33E-08 | 0.154242667 | 0.304139342 |
| cg07788369 | DLX6-AS1 | | Body | 18.7668 | 3.09E-09 | 0.181249002 | 0.294584467 |
| cg07791578 | KAAG1 | Island | 1stExon | 11.9354 | 5.46E-10 | 0.171653952 | 0.312989076 |
| cg07793808 | KDM2B | S_Shore | TSS1500 | 4.66737 | 0.000325 | 0.153938716 | 0.268187382 |
| cg07802350 | HOXD13 | Island | TSS1500 | 8.17406 | 5.10E-10 | 0.177210008 | 0.36701786 |
| cg07838106 | AKR7A3 | Island | TSS200 | 49.5186 | 1.35E-08 | 0.472668295 | 0.602705594 |
| cg07855083 | SATB2 | Island | 5URT | 3.0641 | 0.003704 | 0.13304088 | 0.225666628 |
| cg07860213 | PRDM14 | Island | Body | 12.7997 | 1.90E-12 | 0.228971578 | 0.474873856 |
| cg07871947 | SLC12A5 | Island | TSS200 | 6.62281 | 0.000838 | 0.171775677 | 0.0249920988 |
| cg07877559 | CTNND2 | N_Shore | Body | 6.66442 | 7.54E-05 | 0.202223943 | 0.30331834 |
| cg07879739 | GALR3 | Island | Body | 9.06369 | 1.10E-08 | 0.174734818 | 0.336442663 |
| cg07881405 | IRX1 | Island | Body | 9.2586 | 7.53E-10 | 0.110754914 | 0.261654085 |
| cg07938743 | OTX1 | Island | Body | 5.73923 | 0.003255 | 0.631908295 | 0.702495333 |
| cg07939836 | EVX2 | Island | TSS1500 | 7.79595 | 3.58E-05 | 0.093124483 | 0.177740516 |
| cg07974511 | OTX1 | Island | Body | 10.2 | 5.33E-11 | 0.310228367 | 0.558914471 |
| cg07991112 | HIST1H31 | S_Shore | TSS1500 | 13.615 | 1.05E-12 | 0.124471345 | 0.295487683 |
| cg07996594 | RUNX3 | Island | TSS1500 | 3.2751 | 0.003527 | 0.569073647 | 0.659312249 |
| cg08022244 | PTPRN2 | Island | Body | 3.64082 | 0.000698 | 0.134820109 | 0.23204121 |
| cg08034867 | ABR | | Body | 12.7754 | 0.000397 | 0.679664279 | 0.765799727 |
| cg08066129 | SIM2 | N_Shelf | Body | 8.82211 | 3.91E-07 | 0.291328891 | 0.444891606 |
| cg08079908 | HOXD8 | S_Shore | 3UTR | 8.0269 | 7.71E-07 | 0.333793427 | 0.480905144 |
| cg08085357 | SOX2-OT | N_Shore | Body | 30.8979 | 7.23E-07 | 0.255685122 | 0.338520537 |
| cg08089301 | HOXB4 | Island | 1stExon | 7.18954 | 4.74E-07 | 0.114534278 | 0.256682763 |
| cg08116462 | PAX6 | N_Shelf | 5URT | 10.8785 | 1.31E-08 | 0.225803489 | 0.381389378 |
| cg08118159 | SPTBN4 | Island | Body | 3.49625 | 0.00305 | 0.34717212 | 0.435882779 |
| cg08126211 | KAAG1 | Island | 5URT | 16.5502 | 4.70E-10 | 0.29338811 | 0.452258586 |
| cg08138435 | BATF3 | S_Shore | TSS1500 | 7.03017 | 2.01E-05 | 0.200252405 | 0.377102944 |
| cg08163199 | HLA-1 | Island | Body | 5.49491 | 5.01E-05 | 0.100546598 | 0.199758134 |
| cg08182446 | GABRG3 | Island | TSS1500 | 21.2981 | 1.02E-12 | 0.130479117 | 0.313677633 |
| cg08196968 | PPP1R14A | Island | Body | 4.97821 | 2.24E-05 | 0.418621778 | 0.570853853 |
| cg08203260 | HOXA4 | S_Shore | TSS1500 | 12.7514 | 5.72E-06 | 0.60464538 | 0.720686343 |
| cg08206318 | PITX1 | Island | 3UTR | 15.014 | 2.56E-11 | 0.272170181 | 0.449239288 |
| cg08227526 | LRAT | N_Shore | 5URT | 8.03662 | 1.12E-05 | 0.182168624 | 0.267664288 |
| cg08231710 | MMP23B | Island | TSS1500 | 10.1429 | 1.83E-09 | 0.384275077 | 0.614727335 |
| cg08247587 | TTC6 | N_Shore | Body | 11.5921 | 1.72E-09 | 0.209435862 | 0.374884737 |
| cg08274589 | SHF | S_Shore | 5URT | 110.22 | 1.58E-09 | 0.447071526 | 0.586194528 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg08278487 | POU4F1 | N_Shelf | TSS200 | 12.474 | 1.30E−07 | 0.171151833 | 0.275588763 |
| cg08279075 | IRX3 | Island | Body | 3.4654 | 0.00012 | 0.18910068 | 0.339620705 |
| cg08305551 | MAST1 | Island | Body | 9.40142 | 6.52E−07 | 0.101244984 | 0.219732621 |
| cg08307030 | ISL2 | Island | 3UTR | 6.02195 | 0.000557 | 0.196708126 | 0.258678975 |
| cg08309809 | TNFRSF10C | Island | 5URT | 20.485 | 1.48E−11 | 0.274621861 | 0.454917212 |
| cg08318726 | TBX5 | N_Shore | 5URT | 6.32419 | 0.000935 | 0.117928388 | 0.179148543 |
| cg08325845 | HLA-J | Island | Body | 5.13258 | 3.62E−05 | 0.134642485 | 0.247463407 |
| cg08370178 | LOC648987 | N_Shelf | Body | 6.81612 | 0.00697 | 0.436645767 | 0.50275998 |
| cg08373003 | PITX1 | S_Shore | Body | 14.9597 | 8.89E−07 | 0.252567718 | 0.372093099 |
| cg08381274 | GDF6 | N_Shelf | Body | 15.4612 | 7.01E−08 | 0.492104844 | 0.665550433 |
| cg08431536 | PAX3 | Island | Body | 12.7624 | 1.03E−12 | 0.173996353 | 0.390700297 |
| cg08457898 | EPHX3 | S_Shore | 5URT | 22.7283 | 1.71E−11 | 0.204066523 | 0.344169793 |
| cg08465346 | HOXC4 | Island | 5URT | 3.81433 | 0.001851 | 0.483110791 | 0.577835322 |
| cg08473330 | OTX1 | Island | Body | 22.5708 | 5.38E−10 | 0.364137053 | 0.513038626 |
| cg08479590 | HOXA11-AS | S_Shore | TSS1500 | 5.00923 | 0.000587 | 0.167978388 | 0.244806283 |
| cg08480826 | LINC00461 | Island | TSS1500 | 7.05323 | 0.000223 | 0.121449564 | 0.200037248 |
| cg08481464 | C10orf11 | N_Shore | Body | 29.2066 | 9.33E−05 | 0.746482543 | 0.827638818 |
| cg08481491 | ALDH1L1 | S_Shore | TSS1500 | 6.29713 | 0.009152 | 0.658953767 | 0.720887737 |
| cg08492173 | IRX1 | Island | Body | 4.53866 | 0.000106 | 0.28864169 | 0.402412636 |
| cg08499046 | PAX6 | N_Shore | 5URT | 13.6643 | 1.56E−11 | 0.283545371 | 0.516088316 |
| cg08509840 | SLC41A3 | | TSS1500 | 7.52402 | 0.000205 | 0.412567802 | 0.491769202 |
| cg08511651 | HIST1H1A | N_Shelf | 1stExon | 6.76149 | 1.84E−05 | 0.477757163 | 0.610183281 |
| cg08547691 | NTN1 | Island | 3UTR | 4.67394 | 8.23E−05 | 0.139178866 | 0.256739873 |
| cg08555655 | LINC01391 | S_Shelf | Body | 6.86616 | 2.55E−05 | 0.34641655 | 0.452882498 |
| cg08575330 | SP9 | Island | 1stExon | 15.0931 | 1.87E−08 | 0.067789705 | 0.154136625 |
| cg08587845 | NEUROG1 | N_Shore | 3UTR | 8.01439 | 0.00019 | 0.271920348 | 0.354515533 |
| cg08598654 | DLX6-AS1 | Island | Body | 4.63629 | 0.000894 | 0.399000682 | 0.494693392 |
| cg08599448 | ACP5 | Island | 5URT | 8.81295 | 7.14E−08 | 0.165191883 | 0.297231146 |
| cg08613144 | LYPD1 | Island | 5URT | 2.97882 | 0.005611 | 0.435526818 | 0.529428249 |
| cg08622757 | MNX1 | Island | Body | 4.36751 | 0.002423 | 0.189796327 | 0.262379154 |
| cg08657492 | HOXA4 | S_Shore | TSS1500 | 7.25973 | 0.000893 | 0.38263386 | 0.450298616 |
| cg08680048 | ITPKA | Island | Body | 11.8852 | 1.23E−11 | 0.212373675 | 0.432674401 |
| cg08694969 | ESRP2 | Island | TSS200 | 4.42589 | 0.001632 | 0.389096586 | 0.484984749 |
| cg08702941 | BEND4 | S_Shore | TSS1500 | 10.107 | 0.001991 | 0.782138853 | 0.846029111 |
| cg08703872 | C2CD4D | Island | 5URT | 5.68938 | 0.000134 | 0.608515842 | 0.741496891 |
| cg08704562 | SPRED3 | S_Shore | Body | 6.33441 | 0.001281 | 0.443122363 | 0.529453613 |
| cg08712054 | HOXC4 | S_Shore | TSS1500 | 6.64908 | 0.000915 | 0.26592445 | 0.327364006 |
| cg08726248 | DRD4 | Island | TSS1500 | 35.9285 | 3.66E−11 | 0.20304968 | 0.354255703 |
| cg08745288 | DLX6 | S_Shelf | Body | 5.3534 | 0.007822 | 0.554399248 | 0.621538333 |
| cg08746900 | IRX1 | Island | Body | 7.98462 | 1.32E−07 | 0.235090226 | 0.376738594 |
| cg08784969 | CPM | S_Shore | TSS1500 | 5.21554 | 0.002184 | 0.542231605 | 0.61301798 |
| cg08781140 | MYO15B | Island | 1stExon | 9.68095 | 5.47E−13 | 0.15131809 | 0.404888232 |
| cg08784129 | PAX6 | S_Shore | Body | 15.8728 | 7.19E−10 | 0.351740274 | 0.547383227 |
| cg08787968 | WT1 | S_Shelf | Body | 7.20922 | 4.09E−05 | 0.498584981 | 0.620879737 |
| cg08793976 | LINC01143 | Island | Body | 9.28811 | 7.39E−09 | 0.149568198 | 0.307441445 |
| cg08813062 | SP9 | Island | TSS1500 | 12.8472 | 1.63E−06 | 0.168803022 | 0.266017165 |
| cg08825084 | EN1 | N_Shelf | Body | 9.86512 | 3.29E−05 | 0.207569934 | 0.27952679 |
| cg08828819 | PON3 | Island | TSS200 | 5.99266 | 5.99E−06 | 0.17246284 | 0.285199425 |
| cg08829841 | FOXI2 | Island | TSS200 | 8.19331 | 0.000157 | 0.319398318 | 0.409729222 |
| cg08858649 | TRIM15 | Island | Body | 3.20734 | 0.007901 | 0.192300553 | 0.279740069 |
| cg08865099 | EVX1 | S_Shelf | TSS1500 | 10.1282 | 1.16E−06 | 0.493333767 | 0.656054414 |
| cg08874512 | IGLON5 | S_Shore | Body | 10.9424 | 1.30E−09 | 0.242252623 | 0.428837938 |
| cg08879870 | HLA-J | Island | Body | 5.89136 | 1.03E−06 | 0.175856732 | 0.349495103 |
| cg08898155 | PON3 | Island | TSS1500 | 9.00469 | 1.21E−08 | 0.257349287 | 0.417773164 |
| cg08902977 | PLLP | Island | Body | 7.75936 | 9.17E−07 | 0.167494084 | 0.300486749 |
| cg08927006 | HPSE2 | S_Shore | Body | 6.56103 | 5.77E−05 | 0.114677434 | 0.218402813 |
| cg08938793 | HOXA10-AS | N_Shore | Body | 3.71061 | 0.000525 | 0.263115246 | 0.384330657 |
| cg08964780 | HOXA10-AS | Island | Body | 4.27115 | 0.007627 | 0.094318377 | 0.150416 |
| cg08965276 | LMF1 | Island | Body | 5.48137 | 0.000238 | 0.229057464 | 0.334592099 |
| cg08971771 | DLX4 | Island | Body | 5.07662 | 0.004108 | 0.321769942 | 0.385341372 |
| cg08973919 | SIM1 | Island | Body | 11.1061 | 2.49E−08 | 0.284362996 | 0.442438221 |
| cg08979895 | PITX2 | N_Shore | Body | 13.2288 | 4.10E−09 | 0.305618018 | 0.451036939 |
| cg08985979 | LOC90768 | S_Shore | Body | 8.5874 | 9.30E−05 | 0.539884202 | 0.661333212 |
| cg09010671 | POU4F1 | N_Shelf | TSS200 | 12.4516 | 2.04E−08 | 0.133113426 | 0.259183834 |
| cg09016822 | IER3 | Island | TSS200 | 8.29857 | 3.99E−07 | 0.202852156 | 0.352054082 |
| cg09041678 | PAX6 | S_Shore | TSS1500 | 27.2427 | 4.88E−09 | 0.280274694 | 0.41761796 |
| cg09042277 | TBX5 | Island | 5URT | 8.77965 | 2.57E−06 | 0.201589709 | 0.312155434 |
| cg09046055 | PRR18 | Island | 1stExon | 17.4382 | 1.20E−07 | 0.254259659 | 0.357762707 |
| cg09048251 | LOC101929154 | Island | TSS200 | 7.64012 | 3.67E−09 | 0.086145844 | 0.240297117 |
| cg09050331 | PRDM14 | S_Shore | Body | 17.9013 | 5.79E−05 | 0.547084194 | 0.646639717 |
| cg09064304 | MGAT4D | Island | Body | 6.26489 | 3.73E−05 | 0.087816312 | 0.198124567 |
| cg09071155 | EVX1 | N_Shelf | TSS1500 | 5.09354 | 0.000252 | 0.246011805 | 0.345445089 |
| cg09093485 | RNF39 | Island | 3UTR | 6.93844 | 0.006502 | 0.721870713 | 0.775979485 |
| cg09098195 | BEND4 | S_Shore | TSS1500 | 5.66929 | 3.02E−05 | 0.418619865 | 0.554878 |
| cg09105193 | CPM | Island | TSS1500 | 16.4916 | 9.13E−07 | 0.205222605 | 0.315143295 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg09127400 | IER3 | Island | TSS200 | 7.27736 | 1.71E−06 | 0.197831081 | 0.341743486 |
| cg09133092 | DRD4 | S_Shelf | Body | 10.0972 | 6.75E−05 | 0.434975977 | 0.542118756 |
| cg09135656 | PCDHB15 | N_Shore | 1stExon | 6.73573 | 6.78E−05 | 0.598642101 | 0.718853374 |
| cg09143801 | SEMA6C | Island | Body | 3.60127 | 0.001319 | 0.657554874 | 0.752062273 |
| cg09156097 | PROB1 | Island | 1stExon | 15.1972 | 4.05E−10 | 0.294551667 | 0.494254824 |
| cg09164580 | GDF6 | Island | Body | 5.38258 | 0.000306 | 0.261103078 | 0.371037677 |
| cg09180848 | BNC1 | Island | TSS1500 | 6.29981 | 0.00013 | 0.330962189 | 0.436571435 |
| cg09188099 | HOTTIP | S_Shore | Body | 7.55625 | 0.000148 | 0.264218328 | 0.350944839 |
| cg09194159 | HOXB4 | Island | 1stExon | 6.20174 | 0.000106 | 0.13279474 | 0.229663663 |
| cg09224689 | PAX6 | N_Shore | 5URT | 12.5203 | 2.34E−15 | 0.216375987 | 0.509931735 |
| cg09229918 | SYNGR3 | Island | Body | 8.11522 | 2.21E−08 | 0.263455755 | 0.441419542 |
| cg09233651 | TBX5 | Island | Body | 4.9558 | 6.34E−05 | 0.285938039 | 0.420097379 |
| cg09234518 | NEFM | Island | TSS1500 | 12.6959 | 5.11E−09 | 0.104511177 | 0.237903817 |
| cg09234616 | WT1 | Island | TSS1500 | 7.97392 | 1.38E−08 | 0.186676133 | 0.346339232 |
| cg09236434 | KIAA1211L | Island | TSS1500 | 8.66357 | 6.40E−08 | 0.289038912 | 0.464061653 |
| cg09238180 | HOXD8 | Island | TSS1500 | 11.5125 | 9.01E−08 | 0.075343361 | 0.173472059 |
| cg09252999 | DKFZp686K1684 | N_Shore | TSS1500 | 8.51775 | 4.21E−08 | 0.112451065 | 0.245507505 |
| cg09257796 | GABRG3 | Island | TSS1500 | 5.51368 | 0.000112 | 0.307840527 | 0.438485 |
| cg09257824 | WT1 | N_Shelf | Body | 9.47964 | 4.56E−08 | 0.155637375 | 0.288150506 |
| cg09279736 | RNF39 | Island | Body | 9.16597 | 4.96E−05 | 0.487407619 | 0.606497329 |
| cg09299055 | ITPKA | Island | Body | 15.9638 | 1.22E−07 | 0.445718078 | 0.595180545 |
| cg09313705 | HOXB-AS1 | S_Shore | Body | 5.64094 | 0.000228 | 0.321222067 | 0.423902202 |
| cg09359114 | DLX5 | S_Shelf | Body | 5.40576 | 1.85E−05 | 0.326755574 | 0.451554165 |
| cg09382096 | PAX6 | S_Shore | Body | 12.9358 | 4.94E−10 | 0.148697237 | 0.309017816 |
| cg09411999 | HOXA10 | Island | TSS1500 | 3.75679 | 0.006207 | 0.366743341 | 0.450001444 |
| cg09491991 | ISM1 | Island | TSS1500 | 8.09259 | 2.14E−08 | 0.131391309 | 0.292686298 |
| cg09498572 | LINC000403 | Island | Body | 6.2762 | 4.74E−06 | 0.199176674 | 0.328912662 |
| cg09500443 | SCGB3A1 | Island | 1stExon | 9.96248 | 2.04E−09 | 0.170769476 | 0.351729318 |
| cg09502866 | KCNQ1DN | Island | TSS1500 | 9.57298 | 0.00014 | 0.464518085 | 0.541069515 |
| cg09509183 | IRF6 | Island | TSS200 | 13.907 | 5.46E−08 | 0.140147101 | 0.267438327 |
| cg09515953 | PPP1R14A | Island | TSS200 | 30.9543 | 1.78E−08 | 0.504652565 | 0.651268467 |
| cg09537620 | PAX6 | Island | TSS1500 | 12.8597 | 1.91E−13 | 0.212198392 | 0.473850545 |
| cg09554509 | HOTTIP | Island | TSS1500 | 5.64974 | 0.000439 | 0.323328364 | 0.423086768 |
| cg09554951 | KCNQ1DN | Island | TSS1500 | 17.7183 | 1.58E−09 | 0.279655182 | 0.412002141 |
| cg09586183 | TLX1 | N_Shelf | TSS1500 | 7.88302 | 0.000194 | 0.41390511 | 0.509769172 |
| cg09591524 | HOXA3 | Island | Body | 6.04615 | 0.000798 | 0.515768388 | 0.592310485 |
| cg09595479 | PRPH | Island | 1stExon | 4.03112 | 0.004014 | 0.375467126 | 0.451033251 |
| cg09614415 | FOX12 | Island | TSS200 | 13.8358 | 3.85E−09 | 0.246993008 | 0.414592934 |
| cg09622982 | LYPD1 | Island | 5URT | 3.93256 | 0.002853 | 0.205485304 | 0.288362735 |
| cg09639151 | PCDHGA12 | Island | 1stExon | 9.28526 | 1.52E−08 | 0.303918526 | 0.510654158 |
| cg09656395 | PAX6 | Island | TSS1500 | 11.8739 | 8.85E−11 | 0.213471005 | 0.386318653 |
| cg09661370 | HOXA11-AS | Island | Body | 12.4182 | 3.76E−05 | 0.323703612 | 0.39229582 |
| cg09671258 | LHX4 | Island | Body | 8.45738 | 5.13E−11 | 0.115852118 | 0.288785625 |
| cg09672187 | IRX4 | Island | 5URT | 5.64327 | 0.000101 | 0.367022354 | 0.493542719 |
| cg09672383 | POMC | N_Shore | 5URT | 13.6288 | 1.19E−05 | 0.481664279 | 0.600165273 |
| cg09686443 | CCDC37 | Island | TSS200 | 9.79307 | 1.88E−07 | 0.104062729 | 0.221003128 |
| cg09695430 | WT1 | N_Shore | Body | 4.43415 | 0.005337 | 0.321396093 | 0.386171238 |
| cg09696159 | LINC01391 | S_Shore | Body | 4.2084 | 0.004215 | 0.417994752 | 0.492784343 |
| cg09704116 | HOXB-A33 | N_Shelf | TSS1500 | 6.37315 | 0.000436 | 0.221848094 | 0.293098957 |
| cg09706122 | ATP5G2 | Island | TSS1500 | 3.48179 | 0.002185 | 0.177490622 | 0.278877416 |
| cg09709472 | SOX7 | S_Shore | Body | 12.612 | 1.14E−05 | 0.41586096 | 0.520380899 |
| cg09731996 | IRX1 | Island | Body | 12.0422 | 4.61E−11 | 0.29624417 | 0.497267249 |
| cg09767822 | DBX1 | Island | Body | 26.5295 | 7.96E−13 | 0.188538735 | 0.35250637 |
| cg09792881 | DMRTA2 | Island | Body | 12.5702 | 3.85E−07 | 0.090862984 | 0.174475161 |
| cg09797337 | LINC00403 | S_Shore | Body | 11.745 | 2.46E−09 | 0.102274235 | 0.251774041 |
| cg09803262 | DLX6-AS1 | | Body | 9.16754 | 2.97E−07 | 0.243288226 | 0.357295923 |
| cg09826050 | EDRRG | N_Shore | 5URT | 7.92817 | 6.64E−06 | 0.509534119 | 0.648659923 |
| cg09854626 | LMF1 | Island | Body | 12.658 | 2.83E−07 | 0.191658395 | 0.330935962 |
| cg09857513 | WNT16 | N_Shore | Body | 9.36084 | 1.16E−05 | 0.438390302 | 0.568246424 |
| cg09866983 | PRAC2 | S_Shelf | TSS1500 | 5.39714 | 4.69E−05 | 0.196192305 | 0.313547852 |
| cg09868598 | LOC642366 | | Body | 6.27552 | 0.000105 | 0.223075509 | 0.309642361 |
| cg09888562 | IRX3 | S_Shelf | Body | 4.1908 | 0.001498 | 0.116633047 | 0.205114528 |
| cg09935588 | GFI1 | Island | Body | 4.33866 | 0.00487 | 0.423498543 | 0.494465208 |
| cg09936824 | HOXA-AS3 | S_Shelf | Body | 7.98742 | 8.15E−05 | 0.148676625 | 0.230635268 |
| cg09938227 | C1orf61 | N_Shore | 5URT | 7.66101 | 6.61E−06 | 0.395072548 | 0.54391396 |
| cg09983051 | MAL | Island | TSS200 | 4.59613 | 0.002886 | 0.174069019 | 0.243575552 |
| cg10004780 | ARHGEF4 | S_Shore | Body | 9.76679 | 1.26E−06 | 0.370631819 | 0.504917566 |
| cg10035294 | PAX3 | N_Shelf | TSS1500 | 5.33268 | 9.60E−05 | 0.120569757 | 0.226497141 |
| cg10060574 | IER3 | Island | TSS200 | 9.04605 | 1.85E−05 | 0.221470846 | 0.330330437 |
| cg10068417 | DLEU1 | N_Shore | Body | 15.9542 | 2.83E−07 | 0.534037612 | 0.674070495 |
| cg10074409 | IRF6 | Island | 1stExon | 20.5702 | 7.59E−13 | 0.22023883 | 0.384189096 |
| cg10084644 | GPC2 | Island | TSS1500 | 24.2026 | 2.84E−10 | 0.136373097 | 0.25506711 |
| cg10094489 | SHH | Island | Body | 17.2643 | 1.00E−10 | 0.276750212 | 0.468147141 |
| cg10114327 | QRFPR | Island | 1stExon | 8.3278 | 9.10E−05 | 0.217852681 | 0.29205139 |
| cg10122865 | OTX1 | Island | Body | 4.17075 | 6.58E−05 | 0.353863274 | 0.495327084 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg10131194 | GDF6 | Island | Body | 6.57385 | 0.000186 | 0.149709165 | 0.236587793 |
| cg10137231 | REC8 | N_Shore | TSS1500 | 56.1001 | 2.94E−11 | 0.468514256 | 0.620307525 |
| cg10146929 | HIST1H1A | N_Shelf | 1stExon | 6.20351 | 5.75E−06 | 0.391991233 | 0.538500289 |
| cg10147797 | SDR42E1 | Island | 1stExon | 9.04143 | 6.33E−10 | 0.228458416 | 0.445737993 |
| cg10169241 | APC2 | Island | Body | 5.01963 | 0.000348 | 0.383859226 | 0.495420326 |
| cg10172669 | BEND4 | Island | 5URT | 12.2644 | 7.66E−10 | 0.204238498 | 0.358497387 |
| cg10195901 | HORMAD2 | Island | TSS200 | 10.0352 | 7.47E−07 | 0.323685537 | 0.453139761 |
| cg10242160 | ZAR1 | Island | Body | 10.7264 | 3.07E−07 | 0.318371039 | 0.433800141 |
| cg10242602 | ZFP42 | Island | TSS200 | 11.1904 | 2.05E−08 | 0.337679466 | 0.517529672 |
| cg10245273 | SOX1 | S_Shelf | 3UTR | 4.67187 | 0.000924 | 0.242752784 | 0.324129913 |
| cg10245988 | SYN2 | Island | ExonBnd | 9.40017 | 4.09E−07 | 0.214975 | 0.348727117 |
| cg10288510 | PROX1-AS1 | Island | Body | 10.8597 | 8.31E−07 | 0.239522732 | 0.351650141 |
| cg10300188 | KCNQ1DN | Island | TSS1500 | 11.5991 | 0.000331 | 0.464158333 | 0.537704162 |
| cg10303487 | DPYS | Island | 1stExon | 6.041 | 6.26E−06 | 0.062408253 | 0.167982564 |
| cg10331779 | CTNND2 | S_Shore | TSS1500 | 48.0325 | 3.55E−10 | 0.177938553 | 0.272077057 |
| cg10334767 | ZNF518B | Island | TSS200 | 10.5729 | 6.73E−08 | 0.179857128 | 0.303992066 |
| cg10344832 | SKOR1 | Island | Body | 17.3533 | 2.39E−09 | 0.222910407 | 0.341060832 |
| cg10347335 | TACSTD2 | Island | 1stExon | 6.05381 | 0.000208 | 0.233464909 | 0.306597505 |
| cg10356613 | LHX1 | Island | TSS1500 | 6.94183 | 6.24E−06 | 0.081029232 | 0.175810062 |
| cg10357657 | JAK3 | Island | 5URT | 10.2996 | 1.32E−05 | 0.157145195 | 0.257115862 |
| cg10366797 | HOXC4 | Island | 5URT | 29.0514 | 9.48E−07 | 0.592405349 | 0.687697859 |
| cg10421979 | CHAD | Island | TSS200 | 3.92485 | 0.000329 | 0.227963574 | 0.363060729 |
| cg10439765 | SLC12A5 | Island | 5URT | 15.1335 | 1.07E−09 | 0.095726603 | 0.200327056 |
| cg10456990 | SIM2 | N_Shelf | Body | 3.71941 | 0.009115 | 0.198960606 | 0.265556813 |
| cg10475970 | PCDHGAB | Island | 1stExon | 33.2528 | 4.66E−12 | 0.329747031 | 0.482509091 |
| cg10479082 | TRIL | Island | Body | 16.1443 | 1.75E−11 | 0.171703895 | 0.337100062 |
| cg10500362 | SIM2 | S_Shore | Body | 16.8724 | 6.02E−06 | 0.529934031 | 0.635513283 |
| cg10508993 | SCGB3A1 | Island | TSS200 | 10.7966 | 5.93E−07 | 0.196189595 | 0.302974744 |
| cg10511988 | VAX1 | N_Shore | 3UTR | 5.62292 | 8.34E−05 | 0.269122054 | 0.407997249 |
| cg10526374 | ASCL2 | Island | TSS1500 | 11.4498 | 8.70E−08 | 0.05920574 | 0.168102887 |
| cg10532489 | SEZ6L2 | Island | Body | 5.81626 | 4.20E−05 | 0.331679242 | 0.474720293 |
| cg10536898 | LOC642366 | | Body | 20.1631 | 1.07E−11 | 0.358995713 | 0.536003475 |
| cg10537450 | NBPF8 | Island | Body | 22.1861 | 8.67E−06 | 0.438182062 | 0.506966818 |
| cg10588696 | ISL2 | S_Shelf | Body | 5.76378 | 5.41E−05 | 0.35049756 | 0.470118863 |
| cg10588962 | HOXB-A53 | N_Shore | TSS200 | 7.06082 | 9.94E−08 | 0.320369589 | 0.486445386 |
| cg10603004 | NKX2-6 | Island | TSS200 | 9.7666 | 2.77E−06 | 0.180637448 | 0.283563559 |
| cg10657141 | HOXA11-AS | N_Shore | Body | 13.2069 | 1.70E−06 | 0.276686925 | 0.372236899 |
| cg10659805 | DLX6-AS1 | N_Shelf | Body | 8.90601 | 4.90E−08 | 0.243029012 | 0.393836448 |
| cg10660256 | BHMT | | 5URT | 49.5233 | 5.34E−11 | 0.484227194 | 0.639939434 |
| cg10682560 | DKFZp686K1684 | N_Shore | Body | 12.4474 | 1.14E−06 | 0.480962716 | 0.620314452 |
| cg10689404 | LHX1 | Island | 3UTR | 11.2255 | 1.86E−06 | 0.242936302 | 0.355552665 |
| cg10689528 | GDF6 | Island | Body | 7.4001 | 1.39E−06 | 0.134920426 | 0.250564504 |
| cg10724867 | HOXA10-HOXA9 | N_Shore | Body | 17.0683 | 1.04E−06 | 0.58984669 | 0.695939616 |
| cg10741025 | PAX9 | Island | Body | 3.78791 | 0.000821 | 0.129727883 | 0.215902894 |
| cg10745499 | SIM1 | Island | Body | 3.33913 | 0.004526 | 0.350666025 | 0.429264566 |
| cg10757144 | PCDHB15 | S_Shelf | 1stExon | 4.25491 | 0.000808 | 0.177543849 | 0.267551624 |
| cg10767223 | TERT | Island | TSS1500 | 18.8804 | 4.84E−10 | 0.379046877 | 0.526890232 |
| cg10782668 | PDX1 | Island | Body | 5.30538 | 0.001217 | 0.140135129 | 0.205854312 |
| cg10798171 | ICA1 | S_Shore | TSS1500 | 7.14824 | 2.41E−06 | 0.201468657 | 0.350483933 |
| cg10798682 | SLC41A3 | | 1stExon | 36.4821 | 2.41E−07 | 0.607802984 | 0.730013788 |
| cg10825473 | ISL2 | Island | Body | 13.6547 | 2.23E−08 | 0.22424549 | 0.353090456 |
| cg10835584 | ONECUT2 | Island | Body | 10.3083 | 4.74E−07 | 0.057105257 | 0.144544992 |
| cg10850930 | SIM2 | N_Shore | Body | 6.86049 | 0.002203 | 0.613732798 | 0.687522869 |
| cg10859133 | OTX1 | Island | Body | 25.6545 | 4.87E−09 | 0.410904984 | 0.537526182 |
| cg10865856 | RNF39 | Island | 1stExon | 4.97877 | 0.000231 | 0.092297655 | 0.178510471 |
| cg10895452 | EN1 | N_Shelf | Body | 5.58778 | 5.78E−05 | 0.209537907 | 0.307907708 |
| cg10911990 | PAX9 | S_Shore | 5URT | 3.28841 | 0.008825 | 0.243159468 | 0.324198692 |
| cg10916998 | FLOT1 | Island | TSS1500 | 9.14504 | 3.44E−08 | 0.338997498 | 0.530957659 |
| cg10930308 | RNF39 | Island | Body | 5.74199 | 2.90E−05 | 0.459634134 | 0.602776067 |
| cg10938374 | IER3 | Island | Body | 10.6163 | 1.18E−11 | 0.150986656 | 0.377955083 |
| cg10940462 | NRXN2 | Island | Body | 3.8876 | 0.000247 | 0.250057522 | 0.387689454 |
| cg10945201 | C1orf61 | | TSS1500 | 4.11519 | 0.000722 | 0.329809047 | 0.447268753 |
| cg10953317 | CD300A | | TSS200 | 12.563 | 3.49E−05 | 0.371705338 | 0.471515062 |
| cg10954251 | TBR1 | S_Shore | TSS1500 | 5.1599 | 0.000199 | 0.147559542 | 0.245399118 |
| cg10954469 | LINC01143 | Island | Body | 9.36353 | 1.41E−07 | 0.134322719 | 0.2443784 |
| cg10957151 | HOXD9 | Island | TSS1500 | 4.61975 | 0.003628 | 0.281270691 | 0.345664464 |
| cg10964421 | TNFRSF10D | Island | Body | 11.951 | 1.78E−09 | 0.132322652 | 0.279382034 |
| cg10977770 | ESRRG | N_Shore | 5URT | 13.182 | 3.66E−09 | 0.286516086 | 0.429441477 |
| cg10979436 | HOTTIP | N_Shelf | Body | 5.04735 | 0.000134 | 0.095966249 | 0.188729396 |
| cg10983478 | TRIM58 | Island | TSS200 | 16.2842 | 5.57E−09 | 0.114201938 | 0.244806359 |
| cg10989897 | ELAVL4 | Island | TSS200 | 14.845 | 2.24E−10 | 0.108558528 | 0.224069455 |
| cg10997718 | TBR1 | S_Shore | Body | 12.5008 | 6.11E−09 | 0.273866972 | 0.431588697 |
| cg11015251 | HOXA4 | Island | TSS200 | 14.2562 | 1.24E−07 | 0.335861334 | 0.44644321 |
| cg11022432 | ALDH1L1 | S_Shore | 1stExon | 5.22667 | 1.07E−05 | 0.145257533 | 0.296916145 |
| cg11025705 | KIFC2 | Island | Body | 86.1394 | 2.95E−12 | 0.41849231 | 0.587120737 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg11060441 | SSPO | N_Shore | Body | 35.0177 | 1.07E−06 | 0.654628372 | 0.774756596 |
| cg11075029 | SHF | S_Shore | 5URT | 8.39843 | 1.37E−07 | 0.187656884 | 0.34894378 |
| cg11076994 | TCF15 | Island | TSS1500 | 20.3299 | 1.32E−08 | 0.139085556 | 0.234768108 |
| cg11080549 | NR2F1-AS1 | S_Shore | Body | 10.7771 | 2.27E−06 | 0.41834253 | 0.582599451 |
| cg11086764 | NR2E1 | Island | Body | 9.22958 | 4.32E−06 | 0.127293425 | 0.212657107 |
| cg11097541 | HOXA10-AS | N_Shore | TSS1500 | 11.2992 | 4.96E−06 | 0.244468791 | 0.333403646 |
| cg11101117 | LBX1-AS1 | S_Shore | Body | 7.64953 | 1.77E−07 | 0.275642303 | 0.466333029 |
| cg11111460 | LOC90768 | Island | Body | 11.2971 | 1.98E−06 | 0.574232802 | 0.711423401 |
| cg11128216 | PAX6 | Island | TSS200 | 11.5677 | 8.08E−10 | 0.350681107 | 0.554415187 |
| cg11162118 | DKFZp686K1684 | Island | TSS1500 | 6.58767 | 1.74E−07 | 0.335928761 | 0.510457651 |
| cg11168433 | KCNQ4 | Island | ExonBnd | 32.7561 | 4.98E−08 | 0.567723891 | 0.711173929 |
| cg11179081 | HIST1H23K | S_Shore | 3UTR | 3.89317 | 0.004639 | 0.494047639 | 0.582601063 |
| cg11196848 | FGF20 | S_Shore | TSS200 | 18.5709 | 0.00017 | 0.700089395 | 0.788481859 |
| cg11207534 | ANK1 | Island | Body | 12.9423 | 2.45E−05 | 0.147028214 | 0.22199097 |
| cg11229513 | PRDM14 | Island | TSS1500 | 8.03748 | 2.91E−05 | 0.212457433 | 0.296093825 |
| cg11229862 | CCDC37 | Island | TSS200 | 8.35884 | 3.06E−06 | 0.138860612 | 0.247322508 |
| cg11233384 | AKR7A3 | S_Shore | TSS1500 | 8.6911 | 6.36E−05 | 0.400233891 | 0.524285929 |
| cg11280525 | LINC00461 | Island | Body | 20.6051 | 1.66E−08 | 0.265839864 | 0.394563705 |
| cg11282676 | HISTIH1A | N_Shelf | 5URT | 9.90773 | 8.65E−06 | 0.365720756 | 0.482940576 |
| cg11301556 | SLC12A5 | Island | TSS200 | 6.41751 | 0.00015 | 0.157213418 | 0.249876458 |
| cg11320910 | GATA4 | Island | 5URT | 29.3702 | 7.88E−09 | 0.372212651 | 0.493148717 |
| cg11325997 | AMH | Island | Body | 30.2868 | 5.85E−10 | 0.271474938 | 0.414804552 |
| cg11330740 | NKX2-5 | Island | Body | 9.96574 | 0.000377 | 0.478069682 | 0.561559687 |
| cg11335335 | DRD4 | Island | Body | 10.1416 | 0.000131 | 0.592375979 | 0.708992825 |
| cg11359133 | EVX2 | N_Shelf | TSS200 | 7.39901 | 6.58E−07 | 0.331291113 | 0.461562689 |
| cg11368643 | PCDHB15 | S_Shelf | 5URT | 20.4105 | 2.74E−09 | 0.268315226 | 0.393278391 |
| cg11397370 | GRHL2 | Island | TSS200 | 20.5187 | 3.28E−09 | 0.214270804 | 0.349032242 |
| cg11418477 | SP9 | Island | TSS200 | 14.6008 | 4.47E−06 | 0.176523971 | 0.279260216 |
| cg11435506 | PON3 | Island | TSS1500 | 9.91863 | 3.12E−09 | 0.307274088 | 0.489407326 |
| cg11469061 | PAX6 | Island | TSS1500 | 16.0312 | 2.30E−14 | 0.154525969 | 0.363489059 |
| cg11469778 | ARHGEF4 | S_Shore | TSS1500 | 4.95756 | 0.003171 | 0.465942168 | 0.54295198 |
| cg11471772 | SIM1 | N_Shelf | TSS200 | 4.85052 | 5.35E−05 | 0.175868906 | 0.292676685 |
| cg11472521 | DLX4 | Island | Body | 4.2666 | 0.001663 | 0.431103093 | 0.531433207 |
| cg11475550 | NPY | Island | 5URT | 3.43701 | 0.008535 | 0.196253386 | 0.257823266 |
| cg11485451 | TCF7 | Island | TSS200 | 10.8092 | 8.03E−10 | 0.309068173 | 0.52311637 |
| cg11485595 | NPR3 | Island | Body | 8.48464 | 1.01E−07 | 0.112023276 | 0.24435177 |
| cg11500797 | DLX5 | Island | Body | 5.39912 | 0.000378 | 0.238454151 | 0.32557966 |
| cg11508828 | SSPO | Island | Body | 13.3887 | 2.12E−05 | 0.49084586 | 0.595345939 |
| cg11523020 | UPK3A | S_Shore | Body | 22.411 | 9.05E−08 | 0.382621393 | 0.507177212 |
| cg11529250 | LIPK3A | N_Shore | TSS1500 | 5.30122 | 4.82E−05 | 0.140324321 | 0.243332794 |
| cg11538631 | SIM1 | N_Shelf | Body | 4.98232 | 4.40E−05 | 0.292735853 | 0.412089714 |
| cg11540692 | SIM1 | Island | TSS1500 | 7.40857 | 8.76E−05 | 0.248331369 | 0.323636328 |
| cg11605835 | IRX1 | Island | Body | 8.95968 | 1.98E−08 | 0.294331442 | 0.469414206 |
| cg11616651 | AMH | Island | Body | 11.3565 | 1.60E−10 | 0.21201655 | 0.423223295 |
| cg11625005 | TERT | Island | TSS1500 | 4.72634 | 0.000161 | 0.374007884 | 0.490540023 |
| cg11638298 | ZFP42 | S_Shore | 5URT | 6.28575 | 0.000573 | 0.39812143 | 0.490456717 |
| cg11644479 | ASCL2 | Island | TSS1500 | 5.29529 | 0.005569 | 0.604096358 | 0.66798104 |
| cg11648594 | MMP23B | Island | TSS1500 | 6.11 | 2.27E−07 | 0.266911991 | 0.456886426 |
| cg11651285 | NKX2-2 | Island | TSS200 | 10.1528 | 1.59E−05 | 0.280996806 | 0.375315826 |
| cg11663667 | LRAT | S_Shore | 5URT | 6.74162 | 2.98E−05 | 0.436425109 | 0.579243388 |
| cg11667020 | NKX2-4 | Island | 1stExon | 10.333 | 3.17E−10 | 0.123798491 | 0.279686414 |
| cg11667086 | DKFZp686K1684 | Island | Body | 5.68763 | 0.0006 | 0.094874515 | 0.172254134 |
| cg11671598 | PITX2 | S_Shelf | 1stExon | 8.29026 | 6.90E−05 | 0.518653171 | 0.597968606 |
| cg11679455 | GATA3 | Island | Body | 6.6013 | 0.006322 | 0.798564597 | 0.858478778 |
| cg11700800 | NR2F1-AS1 | Island | Body | 5.23124 | 0.00204 | 0.814014127 | 0.396130636 |
| cg11724134 | RNF39 | S_Shore | TSS200 | 8.17163 | 3.71E−06 | 0.18787539 | 0.293942616 |
| cg11741189 | DKFZp686K1684 | N_Shelf | Body | 10.8418 | 1.22E−08 | 0.393777786 | 0.586224771 |
| cg11754318 | HOXD12 | S_Shelf | TSS200 | 11.5034 | 5.45E−07 | 0.367504876 | 0.487584232 |
| cg11770080 | BHMT | | Body | 4.91959 | 8.71E−06 | 0.22203796 | 0.407015969 |
| cg11772171 | ASCL2 | Island | TSS1500 | 7.59457 | 2.00E−06 | 0.125973509 | 0.235435424 |
| cg11789612 | ITPKA | Island | Body | 11.6606 | 1.86E−13 | 0.126004371 | 0.349646136 |
| cg11800620 | ESRRG | S_Shore | TSS1500 | 4.98139 | 2.44E−05 | 0.300581095 | 0.432389181 |
| cg11806672 | POU4F1 | Island | Body | 23.8502 | 2.27E−11 | 0.197183953 | 0.329205928 |
| cg11823511 | BARHL2 | Island | TSS1500 | 9.97971 | 2.33E−09 | 0.11159678 | 0.249968451 |
| cg11827910 | PAX6 | Island | 5URT | 13.9055 | 9.73E−10 | 0.417511434 | 0.624910141 |
| cg11853320 | PDX1 | S_Shore | TSS1500 | 10.4305 | 4.21E−07 | 0.281451814 | 0.405942482 |
| cg11853830 | NR2F1-AS1 | N_Shore | Body | 24.3189 | 1.59E−07 | 0.587821858 | 0.790941384 |
| cg11854154 | AMPD3 | Island | TSS200 | 5.02552 | 0.000692 | 0.191287998 | 0.280976332 |
| cg11866296 | HNF1B | | Body | 6.64005 | 0.000264 | 0.244260691 | 0.340077945 |
| cg11891393 | SIM1 | N_Shelf | Body | 9.2349 | 1.88E−06 | 0.204055279 | 0.31220807 |
| cg11904906 | LOC151174 | N_Shore | Body | 7.6273 | 7.44E−06 | 0.284219535 | 0.414818179 |
| cg11910375 | HOXA-AS3 | S_Shore | Body | 8.37918 | 0.000237 | 0.159098216 | 0.219262914 |
| cg11916729 | SCGB3A1 | Island | TSS200 | 10.1315 | 2.08E−10 | 0.119576398 | 0.310519186 |
| cg11930477 | DKFZp686K1684 | S_Shelf | Body | 15.1846 | 1.86E−09 | 0.159756347 | 0.274739177 |
| cg11931731 | KATNAL2 | Island | 5URT | 6.84976 | 8.22E−09 | 0.172180564 | 0.360768351 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg11945824 | PRRT1 | Island | 3UTR | 6.28934 | 0.000815 | 0.601914349 | 0.672759303 |
| cg11946503 | NEUROG1 | N_Shore | 3UTR | 5.33819 | 0.000437 | 0.30599935 | 0.410681973 |
| cg11947493 | TNFRSF10D | Island | 1stExon | 10.8915 | 1.17E-07 | 0.316887709 | 0.480101344 |
| cg11949335 | TTC22 | Island | Body | 9.29929 | 0.001219 | 0.669952473 | 0.723164626 |
| cg11965311 | LOC145845 | N_Shore | TSS200 | 4.46979 | 0.001685 | 0.377009324 | 0.447727247 |
| cg11969002 | IER3 | Island | 1stExon | 6.89251 | 9.82E-08 | 0.279592875 | 0.481414613 |
| cg12006284 | WT1 | Island | Body | 9.87543 | 5.83E-06 | 0.305079158 | 0.418529697 |
| cg12018098 | SPRED3 | Island | Body | 3.48044 | 0.002288 | 0.297320482 | 0.3862115 |
| cg12064276 | RNF219-AS1 | Island | Body | 4.74441 | 0.00234 | 0.330319326 | 0.400964939 |
| cg12065840 | COL14A1 | S_Shore | 5URT | 6.39092 | 8.92E-07 | 0.395051158 | 0.574608368 |
| cg12074182 | EVX2 | N_Shore | 1stExon | 11.7178 | 8.98E-06 | 0.26933362 | 0.353775192 |
| cg12090740 | BCL2 | S_Shelf | TSS1500 | 5.27945 | 0.00061 | 0.48011662 | 0.584088038 |
| cg12110087 | HOXA-AS3 | S_Shelf | Body | 6.39135 | 0.000677 | 0.187065374 | 0.247584496 |
| cg12118246 | CD300A | | TSS200 | 6.36681 | 0.00232 | 0.533286029 | 0.611540382 |
| cg12147489 | HOXA11-AS | S_Shelf | Body | 6.06786 | 9.09E-05 | 0.190073146 | 0.285341705 |
| cg12163132 | TBX2 | Island | TSS1500 | 12.6534 | 1.73E-05 | 0.483960977 | 0.585550949 |
| cg12164596 | MNX1 | Island | Body | 17.9593 | 1.30E-06 | 0.298142558 | 0.393756798 |
| cg12171183 | KATNAL2 | N_Shore | TSS200 | 8.60191 | 2.18E-10 | 0.114444297 | 0.296725188 |
| cg12184886 | MYO15B | Island | TSS200 | 13.5608 | 1.33E-10 | 0.301012481 | 0.493721663 |
| cg12198813 | KCNQ1DN | Island | TSS200 | 5.78783 | 0.000204 | 0.309642026 | 0.405539714 |
| cg12200038 | TTC6 | Island | Body | 11.4 | 3.49E-12 | 0.149643411 | 0.363821761 |
| cg12213062 | SPEG | Island | TSS200 | 6.12436 | 7.14E-05 | 0.231187526 | 0.353382628 |
| cg12224030 | DLX4 | S_Shore | Body | 8.66417 | 7.45E-05 | 0.397200455 | 0.494769683 |
| cg12233379 | C2CD4D | Island | 5URT | 8.51442 | 0.000122 | 0.464945373 | 0.577410727 |
| cg12248614 | SPTBN4 | Island | Body | 24.3699 | 7.82E-08 | 0.515782742 | 0.691723995 |
| cg12258785 | THRB-AS1 | Island | Body | 5.61478 | 0.001075 | 0.593633163 | 0.67060731 |
| cg12266953 | GDF7 | N_Shelf | TSS200 | 4.41543 | 0.000449 | 0.055960468 | 0.142934981 |
| cg12268637 | HOXD12 | S_Shelf | TSS200 | 12.5017 | 4.89E-06 | 0.299423647 | 0.419984697 |
| cg12278467 | LINC00461 | Island | Body | 14.2163 | 5.56E-07 | 0.213344535 | 0.29564764 |
| cg12305431 | HOXA3 | S_Shelf | 5URT | 4.98264 | 0.001665 | 0.468909969 | 0.546158152 |
| cg12308746 | DLX1 | S_Shore | Body | 4.84722 | 0.001336 | 0.291872237 | 0.356015548 |
| cg12309653 | LOC145845 | N_Shelf | Body | 3.78509 | 0.00671 | 0.265807289 | 0.345250709 |
| cg12331932 | CD300A | | 5URT | 8.82618 | 6.95E-07 | 0.282764705 | 0.437189669 |
| cg12338417 | TRIM71 | Island | 1stExon | 14.0698 | 3.35E-09 | 0.201685908 | 0.357514314 |
| cg12349884 | HIST1H2BK | N_Shore | 5URT | 5.70368 | 1.54E-05 | 0.328347509 | 0.468301584 |
| cg12374721 | PRAC2 | S_Shelf | TSS1500 | 7.78488 | 9.58E-12 | 0.189220395 | 0.449903944 |
| cg12377139 | SPAG6 | Island | TSS200 | 11.3726 | 7.04E-08 | 0.237886291 | 0.375570137 |
| cg12384236 | TMPRSS2 | S_Shore | TSS1500 | 5.66932 | 0.003553 | 0.426987391 | 0.498744822 |
| cg12386646 | ITPKA | Island | Body | 8.90491 | 2.18E-07 | 0.230532931 | 0.365584281 |
| cg12393318 | LINC00461 | Island | TSS1500 | 18.2579 | 4.22E-10 | 0.133958562 | 0.249547709 |
| cg12405139 | GATA3 | | Body | 6.84378 | 0.001064 | 0.671925047 | 0.756305313 |
| cg12434982 | LHX9 | Island | Body | 43.334 | 4.16E-09 | 0.489409488 | 0.611427414 |
| cg12473406 | GREB1L | Island | 5URT | 4.54793 | 2.48E-05 | 0.180743432 | 0.323613619 |
| cg12518146 | F2RL1 | Island | Body | 7.7045 | 1.93E-06 | 0.341290983 | 0.486734551 |
| cg12520549 | TBR1 | S_Shore | 3UTR | 8.69701 | 2.84E-05 | 0.13679993 | 0.233207703 |
| cg12566152 | LBX1-AS1 | S_Shore | Body | 15.3291 | 3.33E-08 | 0.382129616 | 0.554121897 |
| cg12588917 | HLA-F | Island | Body | 47.3415 | 3.89E-06 | 0.571920973 | 0.651341273 |
| cg12606911 | CD8A | Island | TSS1500 | 4.57938 | 0.000168 | 0.205685651 | 0.2938799 |
| cg12610471 | SPAG6 | Island | TSS200 | 22.5388 | 6.12E-11 | 0.219430396 | 0.365355393 |
| cg12614105 | NPY | Island | 5URT | 3.757 | 0.001888 | 0.191134272 | 0.271748995 |
| cg12633154 | RNF39 | Island | Body | 12.4791 | 0.000187 | 0.670813979 | 0.772309596 |
| cg12636169 | ESRRG | N_Shore | 5URT | 11.1901 | 4.79E-08 | 0.405921698 | 0.566064003 |
| cg12648074 | PCDHGC4 | N_Shore | TSS1500 | 5.09057 | 3.05E-05 | 0.29104175 | 0.438440579 |
| cg12670347 | TBX5-AS1 | Island | Body | 8.16219 | 1.16E-05 | 0.327880761 | 0.437967781 |
| cg12673103 | PITX1 | N_Shelf | Body | 11.4342 | 8.64E-10 | 0.272483705 | 0.466955393 |
| cg12676702 | DLX1 | S_Shore | 3UTR | 4.85295 | 0.000373 | 0.349360511 | 0.432568939 |
| cg12685539 | AMPD3 | Island | TSS1500 | 3.91597 | 0.006058 | 0.504952116 | 0.598179044 |
| cg12700904 | FBLN2 | Island | 5URT | 6.43555 | 8.55E-06 | 0.13515415 | 0.239085341 |
| cg12736877 | RNF39 | N_Shelf | Body | 9.75787 | 0.000194 | 0.702471574 | 0.805423626 |
| cg12782180 | LEP | Island | TSS1500 | 9.40214 | 1.65E-08 | 0.346491947 | 0.527324681 |
| cg12788467 | HNF1B | Island | TSS1500 | 4.16374 | 0.001219 | 0.312264142 | 0.401452574 |
| cg12798259 | PAX6 | N_Shelf | 5URT | 62.4417 | 3.06E-08 | 0.634593938 | 0.773373091 |
| cg12807794 | TCF15 | Island | TSS200 | 13.0461 | 1.61E-06 | 0.135929377 | 0.243012886 |
| cg12810523 | HOXA-AS3 | Island | Body | 8.95793 | 1.07E-05 | 0.121947364 | 0.201956428 |
| cg12821804 | KCNQ1DN | Island | TSS1500 | 6.47471 | 5.65E-07 | 0.317049374 | 0.458569091 |
| cg12876716 | GFI1 | Island | Body | 7.4366 | 4.33E-05 | 0.300802698 | 0.38211982 |
| cg12883523 | SOX17 | Island | Body | 9.11479 | 8.32E-05 | 0.293723913 | 0.384119535 |
| cg12883980 | DLEU1 | S_Shelf | Body | 8.01939 | 0.000172 | 0.47203124 | 0.55021399 |
| cg12902206 | DNAH1 | | 5URT | 6.51081 | 0.000144 | 0.543136877 | 0.674361414 |
| cg12910706 | ARHGEF4 | Island | TSS1500 | 6.43703 | 0.00039 | 0.232164343 | 0.314418186 |
| cg12928379 | DRD4 | Island | TSS200 | 5.45491 | 1.65E-05 | 0.078505244 | 0.187030821 |
| cg12945444 | GATA4 | Island | 5URT | 13.8458 | 5.92E-08 | 0.15996906 | 0.248073929 |
| cg12953669 | BCL2 | S_Shelf | TSS1500 | 9.37243 | 2.04E-05 | 0.386564078 | 0.466781778 |
| cg12967914 | RNF39 | Island | 1stExon | 4.47364 | 3.64E-06 | 0.132900042 | 0.283289125 |
| cg12969193 | HOXD9 | S_Shore | Body | 6.42672 | 1.88E-05 | 0.382825116 | 0.502787577 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg12973941 | NKX3-2 | Island | 1stExon | 13.6876 | 3.90E−11 | 0.173925328 | 0.320769502 |
| cg12982322 | WT1 | S_Shore | Body | 6.48468 | 0.000373 | 0.32771907 | 0.400272283 |
| cg12984729 | ISL2 | Island | Body | 6.43216 | 1.26E−05 | 0.263307585 | 0.391906917 |
| cg12997720 | HOXA11-AS | Island | Body | 7.58896 | 3.91E−05 | 0.368146048 | 0.497772888 |
| cg12999453 | TBX2 | Island | Body | 3.09508 | 0.005125 | 0.223975444 | 0.321880888 |
| cg13016408 | LYPD1 | N_Shore | 5URT | 19.2203 | 1.06E−08 | 0.194973351 | 0.309842982 |
| cg13023623 | OTX2 | Island | Body | 4.93906 | 0.000139 | 0.274117076 | 0.389552712 |
| cg13025668 | POMC | Island | TSS200 | 7.67935 | 1.08E−05 | 0.212290791 | 0.342869899 |
| cg13028700 | PAX6 | Island | 5URT | 10.5581 | 6.18E−09 | 0.127799755 | 0.278899162 |
| cg13046271 | TCF7 | Island | TSS200 | 24.9628 | 8.66E−10 | 0.310896534 | 0.460638793 |
| cg13073773 | GSC | Island | 3UTR | 4.92109 | 1.28E−05 | 0.331311017 | 0.491597126 |
| cg13112154 | LBX1-AS1 | Island | Body | 15.0407 | 4.04E−09 | 0.19466912 | 0.346043156 |
| cg13115683 | HCG9 | N_Shore | Body | 5.74997 | 1.67E−06 | 0.256322455 | 0.428518193 |
| cg13137376 | IER3 | Island | 1stExon | 8.18428 | 2.60E−06 | 0.173674205 | 0.282862882 |
| cg13147822 | MECOM | Island | 1stExon | 7.56712 | 3.91E−05 | 0.265840778 | 0.39770754 |
| cg13163521 | LTK | N_Shore | Body | 7.84086 | 0.00017 | 0.42313884 | 0.506217347 |
| cg13185413 | RNF39 | Island | Body | 5.80524 | 2.00E−06 | 0.326688836 | 0.485006807 |
| cg13193239 | PITX2 | Island | Body | 22.8617 | 5.86E−09 | 0.242846795 | 0.344768687 |
| cg13210467 | GPC2 | Island | TSS1500 | 25.1222 | 2.68E−07 | 0.496041186 | 0.606976192 |
| cg13211683 | GDF6 | Island | Body | 5.89754 | 0.00058 | 0.089594178 | 0.167606413 |
| cg13230606 | HNF1B | Island | TSS1500 | 4.02872 | 0.003296 | 0.210870806 | 0.284155771 |
| cg13245152 | PAX6 | N_Shelf | 5URT | 14.9118 | 8.73E−08 | 0.49202105 | 0.656317798 |
| cg13301003 | WT1 | Island | Body | 8.2718 | 6.41E−05 | 0.475607806 | 0.589881061 |
| cg13305657 | RUNX3 | Island | TSS200 | 8.90931 | 0.000552 | 0.494884519 | 0.559468263 |
| cg13331550 | SEMA6C | Island | 5URT | 6.80241 | 5.44E−06 | 0.221839788 | 0.377575976 |
| cg13338137 | RNF219-AS1 | N_Shore | Body | 9.04608 | 3.82E−06 | 0.141680975 | 0.225800909 |
| cg13365524 | SIM1 | N_Shelf | Body | 6.78962 | 2.12E−05 | 0.255778125 | 0.361656149 |
| cg13368756 | CTNND2 | Island | 1stExon | 7.62656 | 3.92E−08 | 0.096583321 | 0.219273855 |
| cg13378628 | OTP | Island | TSS200 | 8.35047 | 0.000147 | 0.122364769 | 0.199601241 |
| cg13381984 | LEP | Island | 1stExon | 11.1997 | 4.55E−06 | 0.290130926 | 0.03741142 |
| cg13401893 | RNF39 | Island | Body | 9.36716 | 0.000293 | 0.670615192 | 0.772663716 |
| cg13407335 | KCNAB3 | N_Shelf | TSS200 | 11.9979 | 2.66E−06 | 0.589493791 | 0.711425879 |
| cg13409449 | GATA3 | Island | 5URT | 5.72693 | 1.10E−05 | 0.229138767 | 0.372526068 |
| cg13426079 | KCNQ4 | Island | Body | 5.77062 | 0.000643 | 0.580478484 | 0.669677869 |
| cg13434842 | GATA4 | S_Shore | 5URT | 15.4966 | 5.33E−10 | 0.156796369 | 0.294757757 |
| cg13443627 | TACSTD2 | Island | 1stExon | 7.40151 | 1.12E−05 | 0.349093956 | 0.480213532 |
| cg13445199 | ZNF5185 | Island | TSS200 | 8.45915 | 2.21E−07 | 0.157318902 | 0.277190093 |
| cg13459498 | TOX2 | Island | 1stExon | 6.49721 | 0.000219 | 0.090607309 | 0.176815177 |
| cg13476950 | DNAH1 |  | 5URT | 10.0886 | 4.22E−05 | 0.409690799 | 0.529263172 |
| cg13492692 | LHX2 | Island | Body | 11.1308 | 3.73E−09 | 0.127132857 | 0.271664542 |
| cg13502125 | NBPF8 | Island | Body | 20.6193 | 2.35E−08 | 0.520453463 | 0.688828667 |
| cg13528935 | FAM84B | Island | 5URT | 7.88759 | 7.72E−07 | 0.136628803 | 0.255677428 |
| cg13530938 | LOC151174 | Island | Body | 6.38122 | 3.60E−06 | 0.297460414 | 0.460294263 |
| cg13535212 | FOXI3 | Island | TSS1500 | 6.29034 | 1.04E−05 | 0.249519568 | 0.379507738 |
| cg13540960 | WT1 | N_Shore | Body | 9.37513 | 5.68E−08 | 0.102176159 | 0.203781828 |
| cg13552869 | SEZ6L2 | N_Shore | Body | 8.84234 | 0.000167 | 0.397762271 | 0.489042505 |
| cg13564825 | PPP1R14A | Island | 1stExon | 7.72339 | 1.06E−10 | 0.213319879 | 0.462577083 |
| cg13567542 | TRIM15 | Island | Body | 4.55736 | 0.000962 | 0.17590263 | 0.275526075 |
| cg13570101 | NKX2-5 | Island | 1stExon | 9.3238 | 1.05E−05 | 0.120154288 | 0.221241881 |
| cg13570972 | PAX6 | Island | TSS200 | 4.35325 | 0.00365 | 0.247366536 | 0.320463685 |
| cg13596833 | PAX6 | Island | Body | 15.7471 | 1.16E−11 | 0.114125652 | 0.273743335 |
| cg13604794 | DLX4 | Island | Body | 9.63385 | 4.36E−05 | 0.220114995 | 0.304732653 |
| cg13605398 | KCNAB3 | Island | 3UTR | 6.14233 | 5.75E−06 | 0.175484885 | 0.298217873 |
| cg13614181 | RGCC | Island | TSS1500 | 13.6218 | 8.61E−06 | 0.463725287 | 0.557841444 |
| cg13617591 | LOC101929076 | Island | Body | 7.41402 | 4.59E−06 | 0.137950929 | 0.24213276 |
| cg13641903 | WT1 | Island | TSS1500 | 16.8045 | 7.98E−08 | 0.326631302 | 0.458745279 |
| cg13643914 | QRFPR | Island | TSS200 | 8.76058 | 3.83E−07 | 0.05682172 | 0.15469307 |
| cg13660279 | IRX3 | S_Shelf | Body | 3.78295 | 0.008062 | 0.321422494 | 0.390681475 |
| cg13691247 | ATP5G2 | Island | TSS1500 | 3.41473 | 0.00145 | 0.097549792 | 0.197930443 |
| cg13692446 | LINC00403 | Island | Body | 13.2831 | 1.13E−13 | 0.103096408 | 0.306827221 |
| cg13694576 | DKFZp686K1684 | Island | TSS200 | 6.81459 | 0.001594 | 0.20278612 | 0.268589346 |
| cg13703049 | HOXA10-HOXA9 | Island | Body | 19.7056 | 9.30E−12 | 0.102623495 | 0.249122317 |
| cg13715631 | PITX1 | S_Shore | Body | 7.72371 | 8.55E−06 | 0.339909099 | 0.477012534 |
| cg13726459 | HOXC4 | N_Shelf | TSS1500 | 3.85017 | 0.001381 | 0.379902319 | 0.471530557 |
| cg13735819 | JSRP1 | Island | Body | 5.42346 | 3.42E−05 | 0.242931318 | 0.357270722 |
| cg13742526 | JSRP1 | Island | Body | 6.15767 | 4.74E−08 | 0.2853683 | 0.500366463 |
| cg13752649 | HOXB1 | S_Shore | TSS1500 | 7.76946 | 4.54E−05 | 0.471201535 | 0.574165242 |
| cg13762320 | ASCL2 | Island | TSS1500 | 8.70708 | 0.00097 | 0.584702372 | 0.655773566 |
| cg13764778 | CHAD | Island | TSS1500 | 5.38447 | 0.001643 | 0.312652583 | 0.395833313 |
| cg13774342 | DLEU1 | S_Shore | Body | 5.37973 | 0.004414 | 0.738923549 | 0.790965848 |
| cg13784235 | NR2E1 | N_Shore | Body | 14.4471 | 3.48E−10 | 0.263442383 | 0.412421966 |
| cg13799941 | DLX6-AS1 | S_Shore | Body | 13.5242 | 7.92E−07 | 0.349515519 | 0.449267414 |
| cg13803976 | CDBA | Island | Body | 8.74282 | 1.01E−05 | 0.150053105 | 0.238986572 |
| cg13804182 | FLOT1 | Island | TSS1500 | 9.15684 | 6.72E−09 | 0.316988381 | 0.537997999 |
| cg13813366 | SHISA3 | N_Shore | TSS1500 | 5.87144 | 8.16E−05 | 0.491128384 | 0.614594949 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg13826247 | HOXC6 | S_Shore | 3UTR | 4.62181 | 0.000297 | 0.450008462 | 0.557003626 |
| cg13870866 | TBX20 | Island | 1stExon | 10.058 | 0.000166 | 0.271168256 | 0.331129807 |
| cg13885561 | KCNQ1DN | Island | TSS1500 | 4.06919 | 0.005038 | 0.455452411 | 0.522336063 |
| cg13885965 | IER3 | Island | TSS200 | 5.83537 | 2.10E-06 | 0.224712908 | 0.399499356 |
| cg13891220 | PITX2 | Island | Body | 5.71795 | 0.000655 | 0.292976251 | 0.373341366 |
| cg13891702 | PAX6 | N_Shore | 5URT | 14.3954 | 3.73E-10 | 0.216900514 | 0.388425891 |
| cg13918754 | RNF39 | Island | Body | 5.22055 | 7.35E-06 | 0.163281703 | 0.298564105 |
| cg13922021 | F2RL1 | Island | Body | 39.1967 | 3.80E-08 | 0.472491891 | 0.589959424 |
| cg13929328 | FOXI2 | Island | 1stExon | 11.3167 | 7.87E-07 | 0.402985542 | 0.536186531 |
| cg13965612 | MIR199A1 | | TSS1500 | 9.28343 | 0.000215 | 0.592721512 | 0.680766919 |
| cg13967702 | ESRRG | S_Shore | TSS1500 | 6.48984 | 1.40E-06 | 0.267616488 | 0.426707968 |
| cg13974394 | IRX4 | N_Shelf | Body | 13.8641 | 2.17E-06 | 0.247993919 | 0.34193616 |
| cg13982098 | LINC00461 | Island | Body | 17.3123 | 9.31E-09 | 0.33450089 | 0.470155949 |
| cg13990559 | ALDOC | | TSS200 | 40.7063 | 4.68E-10 | 0.24829618 | 0.387324587 |
| cg14010318 | RNF219-AS1 | S_Shore | Body | 3.5105 | 0.002612 | 0.313186698 | 0.402130192 |
| cg14013695 | HOXA5 | Island | TSS1500 | 7.95389 | 8.23E-06 | 0.410005482 | 0.529976602 |
| cg14015044 | TNFRSF10C | Island | 5URT | 15.8398 | 1.00E-11 | 0.11000692 | 0.278207112 |
| cg14015441 | DPYS | Island | TSS200 | 9.18155 | 8.54E-08 | 0.219530945 | 0.37461871 |
| cg14029489 | PRPH | Island | 1stExon | 4.74702 | 6.51E-06 | 0.217821895 | 0.377853606 |
| cg14034197 | GREB1L | Island | 5URT | 5.60749 | 3.88E-05 | 0.189781316 | 0.304136425 |
| cg14044640 | HOXA-AS3 | Island | Body | 12.6778 | 1.46E-11 | 0.079247903 | 0.241340992 |
| cg14069965 | KAAG1 | Island | 5URT | 9.40757 | 1.05E-06 | 0.318146075 | 0.447658818 |
| cg14084907 | TP73 | Island | Body | 5.19343 | 8.25E-05 | 0.311378356 | 0.434132145 |
| cg14085358 | EVX2 | N_Shelf | TSS1500 | 5.64153 | 0.000363 | 0.350296643 | 0.441828495 |
| cg14097304 | MNX1 | Island | Body | 6.78494 | 4.46E-06 | 0.221925273 | 0.341250906 |
| cg14159342 | TP73 | S_Shore | Body | 17.0189 | 3.24E-07 | 0.462922054 | 0.596208354 |
| cg14177914 | C1orf61 | | TSS1500 | 8.04093 | 3.67E-06 | 0.45098763 | 0.606254106 |
| cg14181940 | CD300A | | Body | 8.5887 | 4.75E-05 | 0.425904459 | 0.541955 |
| cg14189571 | ZFP42 | S_Shore | 1stExon | 16.7346 | 1.06E-06 | 0.565770085 | 0.717826798 |
| cg14210607 | LOC101929076 | Island | Body | 5.2511 | 0.000374 | 0.345443798 | 0.452102584 |
| cg14228238 | MECOM | Island | TSS200 | 8.4467 | 1.51E-05 | 0.268087512 | 0.395772773 |
| cg14230397 | PRAC2 | N_Shore | TSS1500 | 11.2333 | 1.25E-07 | 0.171094905 | 0.291555508 |
| cg14239515 | SPRED3 | Island | Body | 2.9586 | 0.008382 | 0.221098705 | 0.30374516 |
| cg14239592 | ZNF274 | Island | 5URT | 22.7894 | 1.47E-05 | 0.695853876 | 0.779981525 |
| cg14244013 | TBX2-AS1 | Island | Body | 43.4861 | 7.43E-09 | 0.56876283 | 0.743882747 |
| cg14301212 | HCG9 | N_Shore | Body | 6.46623 | 0.001447 | 0.386004459 | 0.478843487 |
| cg14314744 | SIM1 | Island | Body | 7.80829 | 1.84E-08 | 0.222133657 | 0.386512518 |
| cg14317513 | SIM2 | N_Shore | Body | 7.51912 | 0.004101 | 0.632752938 | 0.705865949 |
| cg14319235 | ADGRL4 | Island | Body | 8.37399 | 3.50E-07 | 0.296350767 | 0.449644854 |
| cg14327531 | GATA3 | Island | 5URT | 7.03233 | 8.83E-05 | 0.360955997 | 0.479615796 |
| cg14337027 | HOXB13 | N_Shore | 3UTR | 8.32211 | 4.12E-06 | 0.409713703 | 0.539429707 |
| cg14345497 | HOXB4 | Island | 1stExon | 8.04459 | 4.86E-06 | 0.13726798 | 0.232549221 |
| cg14353137 | TCF24 | Island | Body | 10.0356 | 3.12E-09 | 0.083449275 | 0.224472564 |
| cg14355911 | TBX2-AS1 | Island | Body | 13.1296 | 1.45E-06 | 0.201063822 | 0.283530198 |
| cg14375937 | CYP26C1 | Island | Body | 6.20711 | 3.62E-05 | 0.127658284 | 0.232282321 |
| cg14385245 | BNC1 | Island | TSS1500 | 9.02353 | 2.22E-05 | 0.325916711 | 0.414728026 |
| cg14410016 | HOXD9 | Island | TSS1500 | 15.4815 | 2.43E-06 | 0.278506601 | 0.371386909 |
| cg14416523 | TBR1 | S_Shore | Body | 8.82131 | 3.09E-07 | 0.230427969 | 0.357622117 |
| cg14425514 | LHX2 | | Body | 5.56984 | 0.000242 | 0.296992353 | 0.401853684 |
| cg14428146 | NKX2-6 | Island | 1stExon | 11.3326 | 1.16E-08 | 0.109763084 | 0.230381575 |
| cg14432269 | TCF24 | N_Shore | Body | 4.64716 | 0.000125 | 0.288134922 | 0.40335312 |
| cg14432910 | SKOR1 | Island | Body | 6.48624 | 0.000152 | 0.261442813 | 0.340986787 |
| cg14439629 | PAX6 | S_Shore | 5URT | 14.8568 | 1.24E-07 | 0.31751593 | 0.439166152 |
| cg14443953 | DKFZp686K1684 | Island | TSS1500 | 8.49247 | 6.63E-08 | 0.300990197 | 0.461779536 |
| cg14448169 | WNT16 | N_Shore | Body | 8.65511 | 7.11E-08 | 0.153698139 | 0.290554765 |
| cg14451926 | NKX2-6 | S_Shelf | Body | 5.98253 | 0.004013 | 0.173293454 | 0.221275318 |
| cg14458068 | PCDHGA8 | N_Shore | 5URT | 9.31697 | 1.05E-06 | 0.387253436 | 0.537260828 |
| cg14459130 | SP9 | Island | TSS200 | 15.2367 | 3.73E-07 | 0.185629605 | 0.300829668 |
| cg14461582 | TLX1 | N_Shelf | Body | 5.46293 | 0.000897 | 0.493007792 | 0.574722281 |
| cg14473102 | HOXD8 | Island | TSS200 | 11.5597 | 1.07E-09 | 0.094771569 | 0.22146963 |
| cg14487292 | HNF1B | Island | TSS1500 | 4.2018 | 0.000202 | 0.218627355 | 0.316154892 |
| cg14501061 | ALDOC | | TSS200 | 11.8971 | 1.49E-06 | 0.222735935 | 0.338701517 |
| cg14506196 | NKX2-3 | S_Shelf | Body | 9.22168 | 2.87E-06 | 0.153132387 | 0.265345336 |
| cg14509403 | HORMAD2 | Island | TSS200 | 9.75362 | 1.34E-09 | 0.203018926 | 0.356081221 |
| cg14531663 | PRRT1 | Island | 3UTR | 3.03181 | 0.002766 | 0.436650205 | 0.516781703 |
| cg14542583 | SPRED3 | S_Shore | Body | 4.6049 | 0.008916 | 0.379739144 | 0.444482608 |
| cg14556683 | EPHX3 | Island | Body | 266.124 | 3.34E-10 | 0.542474054 | 0.659224788 |
| cg14557487 | TBR1 | N_Shelf | Body | 3.66066 | 0.004468 | 0.457305126 | 0.532436533 |
| cg14559388 | APC2 | S_Shore | Body | 4.73699 | 3.24E-05 | 0.1719199 | 0.309330383 |
| cg14598764 | SLC41A3 | | TSS200 | 13.7772 | 3.87E-07 | 0.459080636 | 0.567217475 |
| cg14604681 | OTX1 | S_Shelf | Body | 10.2714 | 4.64E-05 | 0.436878349 | 0.533413081 |
| cg14615784 | GPR150 | Island | TSS1500 | 5.78258 | 0.000135 | 0.115498843 | 0.201100734 |
| cg14619949 | F2RL1 | S_Shore | Body | 27.5045 | 0.00059 | 0.743681217 | 0.817955687 |
| cg14626259 | SIM2 | N_Shore | Body | 5.72139 | 3.90E-05 | 0.360848806 | 0.481280386 |
| cg14636534 | LINC00461 | N_Shore | Body | 21.2142 | 2.84E-12 | 0.34872869 | 0.538823535 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg14649140 | HOXA10 | Island | TSS1500 | 5.69525 | 0.000747 | 0.117110933 | 0.174707987 |
| cg14652095 | HIST1H1A | N_Shelf | TSS200 | 13.8896 | 5.88E−05 | 0.658506031 | 0.769997808 |
| cg14657834 | TCF24 | Island | TSS1500 | 4.17424 | 0.004683 | 0.198247367 | 0.268053214 |
| cg14668747 | ALDOC |  | TSS200 | 12.9714 | 8.85E−11 | 0.125141129 | 0.294460972 |
| cg14678774 | MAST1 | Island | Body | 25.7432 | 2.08E−08 | 0.438695077 | 0.608658859 |
| cg14703002 | HIST1H1A | N_Shelf | TSS200 | 8.87712 | 2.30E−07 | 0.250115524 | 0.388893254 |
| cg14757311 | LMF1 | Island | Body | 14.425 | 6.57E−05 | 0.66691986 | 0.742698889 |
| cg14776998 | TRIM71 | S_Shelf | Body | 4.9534 | 0.008232 | 0.699798395 | 0.771137798 |
| cg14780466 | GDF7 | Island | Body | 21.1984 | 9.18E−08 | 0.583839523 | 0.721946727 |
| cg14781281 | HLA-1 | Island | Body | 5.9254 | 4.36E−05 | 0.076101431 | 0.17472572 |
| cg14817655 | ZFP42 | Island | TSS200 | 13.2241 | 6.13E−14 | 0.207407309 | 0.463723621 |
| cg14879760 | LOC642366 |  | Body | 7.17182 | 5.88E−05 | 0.160745512 | 0.25210968 |
| cg14889643 | BCL2 | Island | Body | 8.44331 | 4.40E−05 | 0.238736396 | 0.357541533 |
| cg14891209 | LOC145845 | N_Shelf | Body | 4.28391 | 0.000307 | 0.234486124 | 0.352183654 |
| cg14891410 | WT1-AS | N_Shore | Body | 8.98816 | 5.28E−06 | 0.384702219 | 0.513093687 |
| cg14928902 | PRDM14 | Island | 5URT | 10.97 | 1.91E−05 | 0.256452086 | 0.33280978 |
| cg14944647 | MIR129-2 | Island | TSS200 | 14.6789 | 9.34E−12 | 0.046661843 | 0.180557427 |
| cg14958635 | NEUROG1 | Island | 1stExon | 13.1422 | 1.69E−09 | 0.214316792 | 0.356502062 |
| cg14974749 | HOXA5 | N_Shore | Body | 5.75881 | 0.000274 | 0.500670429 | 0.575029566 |
| cg14982276 | TMPRSS2 | Island | TSS1500 | 3.63224 | 0.001124 | 0.404273458 | 0.519408513 |
| cg14989164 | LHX4 | S_Shore | Body | 6.64443 | 5.03E−05 | 0.189609384 | 0.282277793 |
| cg14991487 | HOXD9 | N_Shore | TSS200 | 9.55815 | 5.93E−05 | 0.146523925 | 0.216274712 |
| cg14993283 | SIM1 | Island | Body | 19.1015 | 8.99E−06 | 0.359395264 | 0.453991102 |
| cg14996783 | TRIL | Island | Body | 7.51146 | 1.56E−06 | 0.104599512 | 0.214741819 |
| cg15006175 | KIFC2 | Island | Body | 34.2854 | 1.21E−09 | 0.530633681 | 0.781325113 |
| cg15014975 | RUNX3 | Island | TSS1500 | 3.34261 | 0.001193 | 0.409863922 | 0.5101684 |
| cg15015639 | DES | N_Shore | TSS200 | 4.04377 | 0.000601 | 0.494292476 | 0.612912345 |
| cg15017067 | FAM1848 |  | Body | 20.5351 | 2.24E−08 | 0.52672407 | 0.653316202 |
| cg15084543 | ADGRL4 | Island | 1stExon | 6.65983 | 1.33E−08 | 0.307247153 | 0.516300318 |
| cg15105182 | QRFPR | S_Shore | TSS200 | 9.06698 | 2.09E−07 | 0.244594852 | 0.390081244 |
| cg15126179 | RNF219-AS1 | Island | ExonEnd | 7.13865 | 5.90E−05 | 0.278927226 | 0.372169088 |
| cg15133719 | PAX3 | Island | TSS200 | 5.33657 | 0.001289 | 0.274900928 | 0.358737758 |
| cg15137566 | NKX3-2 | Island | Body | 4.31047 | 0.005279 | 0.252297543 | 0.300551774 |
| cg15140703 | GPC2 | Island | TSS1500 | 8.71914 | 4.35E−08 | 0.103306797 | 0.239288291 |
| cg15196806 | HOXA4 | S_Shore | TSS1500 | 6.8427 | 0.000704 | 0.456529295 | 0.515956444 |
| cg15209808 | HORMAD2 | Island | TSS200 | 11.3629 | 2.80E−10 | 0.242211998 | 0.419844515 |
| cg15234492 | KDM2B | S_Shore | Body | 4.05281 | 0.000254 | 0.247401212 | 0.384253682 |
| cg15235798 | LINC00403 | S_Shelf | Body | 5.93752 | 1.24E−05 | 0.240463122 | 0.361136811 |
| cg15236866 | DLX1 | N_Shelf | TSS1500 | 3.77426 | 0.005309 | 0.366588379 | 0.44088801 |
| cg15244327 | TNFRSF10D | S_Shore | TSS200 | 8.05348 | 4.08E−05 | 0.466352657 | 0.606850213 |
| cg15255890 | HOXB3 | Island | 5URT | 5.17806 | 0.002093 | 0.362904302 | 0.420692273 |
| cg15267232 | GATA3 | Island | Body | 4.2943 | 9.88E−05 | 0.37801236 | 0.526824293 |
| cg15299388 | ZAR1 | N_Shore | TSS1500 | 11.3782 | 2.08E−05 | 0.387109348 | 0.486298743 |
| cg15315385 | WT1 | S_Shore | TSS1500 | 9.10918 | 8.72E−08 | 0.215972564 | 0.334855181 |
| cg15325875 | TLX1 | N_Shelf | Body | 15.7732 | 1.55E−08 | 0.388681812 | 0.55432886 |
| cg15331332 | HLA-F | S_Shore | Body | 14.9686 | 5.24E−06 | 0.526207264 | 0.641224131 |
| cg15377283 | SOX17 | Island | Body | 4.51036 | 0.001332 | 0.345685631 | 0.438315236 |
| cg15402095 | NR2F1-AS1 | N_Shore | Body | 18.7485 | 2.85E−08 | 0.435399508 | 0.635211902 |
| cg15440688 | GSC | Island | TSS1500 | 9.91801 | 1.06E−05 | 0.484183499 | 0.616027415 |
| cg15444947 | TRIL | Island | Body | 14.2423 | 1.87E−07 | 0.100575993 | 0.190176041 |
| cg15446391 | WT1 | Island | TSS200 | 27.3954 | 1.22E−08 | 0.474104171 | 0.60534503 |
| cg15460093 | ADAM8 | Island | 1stExon | 5.90921 | 4.22E−05 | 0.118319191 | 0.224861282 |
| cg15461888 | AMPD3 | Island | TSS200 | 3.85418 | 0.005203 | 0.13689457 | 0.206328338 |
| cg15475840 | LBX1-AS1 | N_Shore | Body | 3.85036 | 0.009791 | 0.583117317 | 0.664176111 |
| cg15491102 | DLEU1 |  | Body | 9.57168 | 1.43E−05 | 0.498687868 | 0.635026131 |
| cg15500865 | PON3 | Island | TSS1500 | 26.7927 | 7.70E−13 | 0.20211126 | 0.345445922 |
| cg15505412 | IRX1 | Island | Body | 3.3983 | 0.006498 | 0.236276122 | 0.321745448 |
| cg15506477 | LYPD1 | N_Shore | 5URT | 4.57141 | 0.001183 | 0.20120695 | 0.286227349 |
| cg15515258 | LINC00403 | S_Shore | Body | 7.89795 | 2.54E−08 | 0.220295024 | 0.382486422 |
| cg15552158 | DLX1 | S_Shore | 3UTR | 9.20575 | 5.55E−07 | 0.243382412 | 0.360838604 |
| cg15556502 | MIR129-2 | Island | TSS200 | 11.8391 | 4.81E−10 | 0.050271183 | 0.180005538 |
| cg15564098 | EVX1 | N_Shelf | TSS1500 | 6.12901 | 2.83E−07 | 0.206339087 | 0.359701272 |
| cg15572489 | PTPRN2 | Island | Body | 6.74166 | 5.35E−05 | 0.468346929 | 0.593494276 |
| cg15590989 | LOC90768 | Island | Body | 6.10684 | 1.44E−05 | 0.361369917 | 0.506138635 |
| cg15607672 | OTX2 | S_Shore | TSS200 | 3.99619 | 0.00059 | 0.373912443 | 0.476411263 |
| cg15611279 | LINC00461 | N_Shore | TSS1500 | 10.6388 | 8.21E−05 | 0.081964312 | 0.169218818 |
| cg15613420 | H2AFY | S_Shore | TSS1500 | 6.33831 | 1.80E−08 | 0.312646591 | 0.523206235 |
| cg15634877 | SPEG | Island | TSS200 | 5.96249 | 0.000472 | 0.175682636 | 0.271603799 |
| cg15645660 | TTC22 | Island | Body | 7.25636 | 0.000111 | 0.517995589 | 0.603291717 |
| cg15652723 | PITX2 | N_Shore | 5URT | 5.44024 | 0.000554 | 0.279235288 | 0.355374546 |
| cg15653173 | LINC00403 | Island | Body | 12.676 | 4.18E−07 | 0.149868743 | 0.244933183 |
| cg15660418 | HOXC4 | N_Shelf | TSS1500 | 3.11084 | 0.007086 | 0.395937178 | 0.486979967 |
| cg15665400 | LYPD1 | Island | 5URT | 3.42973 | 0.007836 | 0.283230039 | 0.356109207 |
| cg15665928 | LINC01391 | S_Shelf | Body | 7.62884 | 0.000159 | 0.365917357 | 0.467478253 |
| cg15706250 | ANK1 | Island | Body | 94.2096 | 1.34E−10 | 0.403852326 | 0.520685646 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg15710198 | SOX17 | Island | TSS200 | 6.19041 | 0.001184 | 0.205206583 | 0.260531234 |
| cg15718581 | ZFP42 | N_Shore | TSS1500 | 7.3251 | 2.19E-05 | 0.55978453 | 0.695412483 |
| cg15724256 | EN1 | N_Shelf | Body | 4.36895 | 2.69E-05 | 0.251691757 | 0.383584156 |
| cg15736169 | LINC00403 | Island | TSS1500 | 8.55048 | 1.52E-06 | 0.123484738 | 0.233093171 |
| cg15741433 | HIST1H1A | N_Shelf | TSS200 | 4.2225 | 0.002514 | 0.429481923 | 0.53057402 |
| cg15772924 | HOXC6 | S_Shore | 5URT | 4.56126 | 0.0031 | 0.550127569 | 0.629484141 |
| cg15778437 | PAX6 | Island | TSS200 | 6.13217 | 1.11E-05 | 0.062314925 | 0.16223128 |
| cg15792487 | CHRNB1 | Island | TSS200 | 6.78728 | 2.42E-05 | 0.225338558 | 0.334932777 |
| cg15798385 | EVX1 | S_Shelf | TSS1500 | 5.56661 | 0.000161 | 0.488128571 | 0.61789602 |
| cg15826897 | EPHX3 | S_Shore | 5URT | 15.976 | 1.23E-11 | 0.320768647 | 0.539226052 |
| cg15829969 | NBPFB |  | Body | 4.25776 | 0.007346 | 0.641966651 | 0.692504707 |
| cg15835620 | ALDOC |  | 5URT | 51.9507 | 1.34E-09 | 0.439888614 | 0.605879393 |
| cg15854847 | NKX2-6 | Island | 1stExon | 16.8258 | 9.97E-07 | 0.106743251 | 0.199138975 |
| cg15861585 | DRD4 | Island | TSS1500 | 21.3068 | 1.13E-09 | 0.28276645 | 0.451054231 |
| cg15873301 | SYN2 | N_Shore | TSS1500 | 4.54276 | 0.00062 | 0.20828984 | 0.324050357 |
| cg15877520 | RNF39 | Island | Body | 5.33163 | 4.87E-06 | 0.252887085 | 0.416379843 |
| cg15880760 | CHAD | Island | TSS200 | 5.20142 | 0.000481 | 0.301170185 | 0.421657018 |
| cg15911153 | PROB1 | Island | 1stExon | 20.8658 | 4.56E-06 | 0.602955 | 0.730096434 |
| cg15912800 | HOXA10-AS | Island | Body | 4.31912 | 0.000214 | 0.275835303 | 0.398816031 |
| cg15927196 | PON3 | Island | TSS1500 | 24.4511 | 2.54E-08 | 0.397064698 | 0.513895455 |
| cg15949044 | PCDHGC4 | Island | TSS200 | 4.16741 | 2.39E-05 | 0.285209646 | 0.452341863 |
| cg15951188 | KCNAB3 | N_Shelf | 1stExon | 12.4082 | 0.000496 | 0.723545721 | 0.793964232 |
| cg15959715 | GAD2 | Island | Body | 7.60668 | 2.64E-06 | 0.128268283 | 0.221494638 |
| cg15981851 | AGAP1 | Island | Body | 19.4333 | 1.49E-05 | 0.484684752 | 0.573708192 |
| cg15982700 | HOXA3 | S_Shore | 5URT | 4.62446 | 0.003081 | 0.342638162 | 0.392987474 |
| cg15985184 | IGLON5 | Island | Body | 14.7563 | 1.44E-07 | 0.438496219 | 0.596025991 |
| cg15985775 | DBX1 | N_Shore | TSS1500 | 4.44725 | 0.000598 | 0.32861342 | 0.430467044 |
| cg15990629 | BCAT1 | N_Shore | Body | 11.5349 | 0.001268 | 0.69204914 | 0.738727727 |
| cg16017144 | RBFOX3 | Island | Body | 12.6246 | 4.79E-05 | 0.557372422 | 0.677758596 |
| cg16021909 | TRIM58 | Island | Body | 24.1732 | 1.29E-10 | 0.091625971 | 0.19752998 |
| cg16030177 | IRF6 | N_Shore | 5URT | 22.1436 | 0.000129 | 0.65754907 | 0.733656909 |
| cg16041686 | PITX2 | N_Shore | 5URT | 7.11277 | 8.23E-06 | 0.160682173 | 0.266662949 |
| cg16043357 | VAX1 | N_Shore | TSS200 | 9.71721 | 1.54E-07 | 0.216716208 | 0.351398275 |
| cg16051228 | TERT | Island | Body | 7.07452 | 0.000551 | 0.363092129 | 0.432070229 |
| cg16078649 | RNF39 | Island | Body | 12.6216 | 1.84E-06 | 0.542516702 | 0.662611394 |
| cg16084872 | TMPRSS2 | Island | 5URT | 4.03062 | 0.002127 | 0.349815595 | 0.462338268 |
| cg16092078 | WT1 | N_Shelf | Body | 4.88907 | 0.000246 | 0.194023822 | 0.292825797 |
| cg16104915 | HOXA9 | Island | TSS200 | 7.23797 | 1.50E-06 | 0.110442312 | 0.224542836 |
| cg16113681 | TBX1 | Island | Body | 6.87756 | 0.000196 | 0.26590667 | 0.364432953 |
| cg16117799 | PRDM8 | N_Shelf | 5URT | 4.93767 | 0.000679 | 0.216674098 | 0.302150582 |
| cg16138458 | HIST1H3I | Island | TSS1500 | 24.3189 | 1.74E-11 | 0.235883152 | 0.401079916 |
| cg16180353 | PAX6 | N_Shore | Body | 24.1891 | 5.11E-09 | 0.478653853 | 0.63154397 |
| cg16184495 | EPHX3 | S_Shore | 5URT | 20.8256 | 1.50E-11 | 0.374622083 | 0.585299737 |
| cg16197925 | FEZF1 | Island | 1stExon | 7.93342 | 1.26E-07 | 0.175488396 | 0.305393535 |
| cg16243019 | DLX6 | S_Shore | Body | 8.47873 | 1.65E-05 | 0.379708156 | 0.479205829 |
| cg16246169 | SOX2-OT | N_Shore | Body | 11.1404 | 0.00043 | 0.651898698 | 0.735388485 |
| cg16246489 | H2AFY | S_Shore | TSS1500 | 5.22965 | 0.00075 | 0.522076207 | 0.620088596 |
| cg16264705 | ATP5G2 | Island | TSS1500 | 3.64373 | 0.00089 | 0.130249609 | 0.2355965 |
| cg16281276 | CYB5R2 | Island | TSS1500 | 6.16364 | 1.07E-06 | 0.195221381 | 0.339427944 |
| cg16297569 | GFI1 | Island | TSS1500 | 12.4415 | 7.13E-07 | 0.394518856 | 0.530127524 |
| cg16302441 | POMC | Island | TSS1500 | 16.1045 | 2.52E-06 | 0.58060109 | 0.712357444 |
| cg16306115 | KAAG1 | Island | 1stExon | 10.0876 | 4.04E-08 | 0.136958562 | 0.263514457 |
| cg16306978 | APOB | Island | TSS200 | 3.8232 | 0.001408 | 0.51776577 | 0.632776777 |
| cg16331823 | FLOT1 | Island | TSS1500 | 10.0525 | 1.01E-09 | 0.267179987 | 0.470606525 |
| cg16353006 | LHX9 | S_Shore | Body | 7.45714 | 1.50E-06 | 0.146044313 | 0.256929939 |
| cg16362592 | TBX20 | N_Shelf | ExonEnd | 3.9498 | 0.005237 | 0.248790402 | 0.32555874 |
| cg16368146 | HCG9 | N_Shore | Body | 13.533 | 2.03E-06 | 0.382086505 | 0.533255177 |
| cg16373229 | FEZF1 | N_Shore | Body | 15.2309 | 4.74E-06 | 0.24131424 | 0.325261333 |
| cg16374999 | PRPH | Island | 5URT | 4.34004 | 0.004208 | 0.642138028 | 0.738408418 |
| cg16379704 | ICA1 | Island | TSS1500 | 23.5199 | 2.37E-07 | 0.487858078 | 0.637063657 |
| cg16390060 | NKX2-2 | Island | 1stExon | 11.3063 | 1.17E-07 | 0.160368595 | 0.265710746 |
| cg16392213 | FEZF1 | Island | Body | 10.7743 | 3.20E-08 | 0.12859394 | 0.257871147 |
| cg16407471 | MIR129-2 | Island | TSS200 | 20.3473 | 6.36E-13 | 0.155351964 | 0.30999726 |
| cg16410706 | BATF3 | Island | TSS1500 | 6.92078 | 7.30E-08 | 0.14083286 | 0.321316707 |
| cg16419441 | DPYS | Island | Body | 14.7332 | 8.32E-11 | 0.285184412 | 0.463370934 |
| cg16435779 | GRHL2 | N_Shore | TSS1500 | 6.43869 | 4.13E-06 | 0.197280159 | 0.331604184 |
| cg16440561 | SPEG | Island | Body | 4.86042 | 0.000301 | 0.601825258 | 0.731216093 |
| cg16458436 | TBX5-AS1 | Island | Body | 8.91599 | 2.61E-06 | 0.137558991 | 0.219814876 |
| cg16459364 | NEFM | Island | TSS1500 | 16.3338 | 3.48E-12 | 0.148411597 | 0.3423751 |
| cg16463460 | WT1 | S_Shelf | Body | 8.13919 | 0.002365 | 0.599164116 | 0.660481455 |
| cg16473141 | REC8 | Island | 1stExon | 29.4907 | 3.98E-11 | 0.402290596 | 0.613716667 |
| cg16493531 | FLOT1 | Island | TSS1500 | 7.65465 | 6.22E-08 | 0.37106665 | 0.591498945 |
| cg16501028 | WT1 | S_Shore | Body | 10.6347 | 0.000218 | 0.412398791 | 0.482729667 |
| cg16513459 | KCNAB3 | N_Shelf | TSS200 | 11.2953 | 7.75E-06 | 0.643410566 | 0.764900253 |
| cg16524928 | NKX2-2 | Island | TSS200 | 24.504 | 1.93E-08 | 0.22039776 | 0.327503137 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg16529477 | PAX3 | N_Shelf | TSS1500 | 8.77119 | 4.75E−07 | 0.444271716 | 0.583110137 |
| cg16544169 | NKX2-6 | Island | TSS1500 | 26.0301 | 5.67E−08 | 0.356898705 | 0.468082323 |
| cg16546442 | PITX2 | Island | Body | 34.872 | 2.47E−12 | 0.227935612 | 0.354180323 |
| cg16555165 | SHF | S_Shore | 5URT | 14.2226 | 2.28E−09 | 0.098624138 | 0.238725518 |
| cg16557178 | HOXB13 | Island | Body | 8.46004 | 3.93E−07 | 0.253898867 | 0.393296651 |
| cg16568727 | TTBK1 | Island | Body | 5.02281 | 0.003662 | 0.38536414 | 0.471324777 |
| cg16574871 | GDF6 | N_Shelf | Body | 18.3817 | 6.91E−07 | 0.551820039 | 0.668923232 |
| cg16582419 | RNF39 | N_Shelf | Body | 23.8595 | 2.91E−07 | 0.577653147 | 0.692054202 |
| cg16604516 | FBLN2 | Island | TSS1500 | 5.64401 | 0.000377 | 0.25504052 | 0.338056863 |
| cg16615829 | HSPB6 | Island | 3UTR | 8.78791 | 3.92E−05 | 0.402149002 | 0.495262939 |
| cg16615954 | PAX6 | Island | Body | 16.8774 | 2.24E−09 | 0.246096425 | 0.395636425 |
| cg16620526 | LVBN | Island | TSS200 | 18.9668 | 3.52E−09 | 0.116536159 | 0.228274784 |
| cg16638920 | LINC00461 | Island | Body | 9.95991 | 2.58E−06 | 0.345610054 | 0.449626253 |
| cg16642284 | FOXI2 | Island | TSS200 | 4.94409 | 1.66E−06 | 0.159498339 | 0.335120386 |
| cg16651126 | HOXA4 | Island | TSS200 | 12.7467 | 1.77E−06 | 0.279815538 | 0.369348424 |
| cg16652651 | AMPD3 | Island | TSS200 | 4.27463 | 0.003605 | 0.119407053 | 0.186505427 |
| cg16670554 | SKOR1 | Island | Body | 6.2874 | 6.17E−05 | 0.187367455 | 0.272957847 |
| cg16686158 | HORMAD2 | Island | TSS1500 | 24.628 | 3.44E−10 | 0.426714084 | 0.587359606 |
| cg16688483 | GRHL2 | Island | Body | 9.96497 | 3.51E−06 | 0.328346919 | 0.455555121 |
| cg16699148 | TACSTD2 | Island | TSS200 | 10.1831 | 6.32E−07 | 0.404067054 | 0.532669444 |
| cg16705627 | LINC00403 | Island | Body | 15.4489 | 4.37E−10 | 0.288392853 | 0.465216825 |
| cg16723488 | APOB | Island | TSS200 | 5.45366 | 0.00029 | 0.394224983 | 0.506687579 |
| cg16742873 | NKX3-2 | N_Shelf | Body | 21.3459 | 0.0001 | 0.590751543 | 0.668214303 |
| cg16747564 | SOX1 | S_Shelf | TSS1500 | 6.46694 | 0.000228 | 0.180641206 | 0.265598232 |
| cg16748008 | HOXA3 | Island | 5URT | 6.83301 | 0.000649 | 0.329235195 | 0.399208373 |
| cg16758800 | DLX6-AS1 | S_Shore | Body | 20.0438 | 4.72E−10 | 0.31897493 | 0.43315604 |
| cg16763443 | TTC6 | Island | Body | 13.7099 | 1.27E−08 | 0.384153504 | 0.501827192 |
| cg16783744 | DPYS | Island | Body | 26.7207 | 1.00E−10 | 0.111274247 | 0.2171099 |
| cg16786703 | ADAM8 | Island | Body | 8.11996 | 1.26E−05 | 0.229733819 | 0.335198744 |
| cg16787431 | HOXB3 | S_Shore | Body | 5.75506 | 9.49E−05 | 0.457385318 | 0.569877566 |
| cg16793394 | OTX2 | S_Shore | TSS1500 | 5.84726 | 3.55E−05 | 0.205871502 | 0.307380709 |
| cg16809460 | DMRTA2 | Island | Body | 3.84469 | 0.001442 | 0.16366241 | 0.23535763 |
| cg16830930 | SOX17 | Island | Body | 4.80678 | 0.008074 | 0.434181574 | 0.500956856 |
| cg16851417 | SIM2 | N_Shelf | Body | 10.1622 | 1.80E−07 | 0.202218953 | 0.323891397 |
| cg16865446 | PAX6 | N_Shelf | Body | 9.78659 | 1.43E−10 | 0.360377724 | 0.587807573 |
| cg16868298 | WNT16 | N_Shore | Body | 14.9448 | 9.24E−09 | 0.345177309 | 0.503736758 |
| cg16891104 | UPK3A | Island | Body | 37.4026 | 9.71E−07 | 0.492674074 | 0.590980475 |
| cg16957769 | HOXC4 | N_Shelf | TSS1500 | 3.1423 | 0.004554 | 0.225776692 | 0.324842721 |
| cg16938805 | DBX1 | Island | TSS200 | 3.36172 | 0.009801 | 0.263865972 | 0.323280127 |
| cg16961816 | DLX6-AS1 | N_Shore | Body | 4.69147 | 0.003976 | 0.398740023 | 0.470510556 |
| cg16964025 | PTPRN2 | Island | Body | 8.76891 | 7.89E−09 | 0.198294818 | 0.380152949 |
| cg16964348 | NPY | Island | TSS200 | 11.7172 | 2.54E−10 | 0.115642753 | 0.252968067 |
| cg16991515 | HIST1H2BK | N_Shore | 3UTR | 4.243 | 0.001901 | 0.371044831 | 0.473967295 |
| cg17011709 | CYP26C1 | Island | Body | 7.17817 | 1.64E−05 | 0.250935577 | 0.368466905 |
| cg17019053 | M1AP | Island | TSS200 | 3.83161 | 0.001744 | 0.267440985 | 0.34726932 |
| cg17029062 | TRIM71 | Island | TSS200 | 14.4008 | 1.39E−07 | 0.116275753 | 0.214411303 |
| cg17029168 | NKX2-2 | Island | 1stExon | 8.1321 | 0.000164 | 0.127972987 | 0.19253687 |
| cg17067528 | IER3 | S_Shore | TSS200 | 7.5979 | 1.11E−05 | 0.29573945 | 0.444713377 |
| cg17083494 | DLX5 | S_Shelf | TSS1500 | 3.57615 | 0.008152 | 0.524175119 | 0.604749344 |
| cg17107156 | CHRNB1 | S_Shore | ExonBnd | 6.4386 | 0.000429 | 0.393853808 | 0.506406816 |
| cg17138769 | VAX1 | Island | Body | 7.47368 | 2.29E−08 | 0.14756008 | 0.286338362 |
| cg17153568 | SP9 | N_Shore | TSS1500 | 5.27972 | 0.001353 | 0.143906081 | 0.204401204 |
| cg17163168 | TP73 | | Body | 5.47612 | 0.000436 | 0.195054477 | 0.285020183 |
| cg17181022 | CYP26C1 | S_Shore | Body | 8.10163 | 0.000254 | 0.328567705 | 0.410208475 |
| cg17194154 | LOC101927248 | S_Shelf | Body | 8.0749 | 5.04E−07 | 0.088094332 | 0.191760647 |
| cg17204275 | SATB2 | Island | 5URT | 4.30077 | 0.002371 | 0.17408703 | 0.254568259 |
| cg17210938 | TACSTD2 | Island | TSS200 | 5.46161 | 0.001427 | 0.219481331 | 0.283830022 |
| cg17214381 | ZFP42 | Island | TSS1500 | 21.8832 | 9.43E−14 | 0.25236621 | 0.447477493 |
| cg17236169 | NRXN2 | Island | Body | 10.1161 | 1.91E−08 | 0.142049216 | 0.28691151 |
| cg17241310 | BARHL2 | Island | TSS200 | 12.9545 | 1.28E−08 | 0.364281279 | 0.518114808 |
| cg17242937 | PITX2 | S_Shore | 5URT | 3.06255 | 0.008912 | 0.292894278 | 0.346999056 |
| cg17280740 | PAX6 | S_Shore | TSS1500 | 23.5664 | 1.60E−10 | 0.319711791 | 0.464824888 |
| cg17298275 | ABR | S_Shore | Body | 4.53081 | 0.000533 | 0.590716659 | 0.697514669 |
| cg17301223 | OPLAH | Island | Body | 3.75423 | 8.37E−05 | 0.273986153 | 0.423266957 |
| cg17303540 | PCDHGA8 | S_Shore | Body | 3.91222 | 0.004776 | 0.591401333 | 0.661568626 |
| cg17338212 | LINC01891 | N_Shore | TSS200 | 26.7677 | 2.58E−08 | 0.312696 | 0.434859636 |
| cg17353412 | HOXA2 | N_Shore | 1stExon | 6.05398 | 3.95E−05 | 0.468990587 | 0.59963218 |
| cg17380661 | SIM1 | N_Shore | TSS1500 | 7.78889 | 1.27E−06 | 0.131196166 | 0.241811092 |
| cg17386213 | NR2E1 | Island | TSS1500 | 5.62434 | 2.46E−05 | 0.396139808 | 0.517192194 |
| cg17423207 | JAK3 | S_Shore | TSS200 | 7.48801 | 0.000997 | 0.303973091 | 0.388413281 |
| cg17452615 | KDM2B | S_Shore | TSS1500 | 8.0564 | 3.16E−05 | 0.169394278 | 0.276190045 |
| cg17462200 | TBX5 | N_Shelf | 5URT | 4.19652 | 0.001069 | 0.164499394 | 0.253568195 |
| cg17476026 | EPHX3 | S_Shore | 5URT | 24.1894 | 5.18E−13 | 0.230741959 | 0.440025603 |
| cg17486860 | WT1 | S_Shelf | Body | 7.33563 | 1.70E−06 | 0.322646384 | 0.474772945 |
| cg17487170 | TCF7 | Island | TSS200 | 18.4589 | 1.05E−06 | 0.523662938 | 0.62002597 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg17507671 | PITX2 | Island | Body | 10.5903 | 2.03E−06 | 0.221260498 | 0.323759115 |
| cg17526483 | EVX1 | N_Shelf | TSS1500 | 14.0833 | 1.08E−06 | 0.38908107 | 0.507617828 |
| cg17561417 | FBLN2 | Island | TSS200 | 6.21456 | 0.000107 | 0.195414183 | 0.284386715 |
| cg17576288 | POU4F1 | N_Shelf | TSS200 | 10.3282 | 7.05E−06 | 0.134618242 | 0.233541237 |
| cg17594860 | AKR7A3 | Island | TSS200 | 7.21362 | 1.80E−07 | 0.288662004 | 0.501674064 |
| cg17602451 | BCL2 | Island | Body | 4.98874 | 0.000692 | 0.264673189 | 0.387334022 |
| cg17611674 | GATA3-AS1 | Island | Body | 8.37078 | 3.09E−05 | 0.412713357 | 0.541990597 |
| cg17626405 | MAL | Island | Body | 19.9531 | 1.39E−11 | 0.13047924 | 0.272047534 |
| cg17630392 | NPR3 | Island | 1stExon | 21.7926 | 1.62E−13 | 0.257257505 | 0.481289699 |
| cg17632937 | HORMAD2 | Island | TSS200 | 13.9925 | 3.86E−08 | 0.305976708 | 0.445203051 |
| cg17652435 | HNF1B | Island | Body | 8.5397 | 1.27E−05 | 0.112947249 | 0.211580814 |
| cg17658976 | PTPRN2 | S_Shore | Body | 4.47817 | 0.004582 | 0.474659015 | 0.558749929 |
| cg17665193 | GAD2 | Island | Body | 4.07202 | 0.002739 | 0.196090298 | 0.267172685 |
| cg17674725 | LYPD1 | N_Shore | 5URT | 16.7602 | 5.93E−08 | 0.381969788 | 0.524156516 |
| cg17694795 | TCF24 | Island | 5URT | 19.5938 | 7.67E−09 | 0.298240317 | 0.442733149 |
| cg17696160 | PAX9 | Island | Body | 7.24563 | 6.94E−05 | 0.10366358 | 0.189356726 |
| cg17698295 | OPLAH | Island | Body | 4.00191 | 2.86E−05 | 0.295852409 | 0.464393024 |
| cg17727529 | C1orf61 | | TSS1500 | 6.75367 | 0.000475 | 0.253236421 | 0.331276952 |
| cg17737681 | DLX1 | S_Shelf | Body | 11.4466 | 1.97E−08 | 0.252875965 | 0.400162921 |
| cg17753347 | LHX9 | N_Shelf | Body | 6.79502 | 1.54E−05 | 0.362180884 | 0.48494603 |
| cg17768491 | SPTBN4 | Island | Body | 31.9516 | 2.57E−06 | 0.596831866 | 0.73167896 |
| cg17774559 | IRX4 | Island | Body | 7.63032 | 1.52E−07 | 0.147490686 | 0.26915986 |
| cg17799033 | PTPRN2 | N_Shore | Body | 16.5949 | 5.30E−05 | 0.598189566 | 0.680222495 |
| cg17805882 | FGF20 | S_Shore | TSS1500 | 11.3507 | 0.000247 | 0.517911349 | 0.592594455 |
| cg17820365 | GDF6 | Island | Body | 4.9872 | 9.34E−05 | 0.209944898 | 0.32733554 |
| cg17833476 | TLX3 | Island | TSS200 | 21.7231 | 1.78E−08 | 0.174424072 | 0.281603325 |
| cg17858328 | GFI1 | Island | TSS1500 | 7.47149 | 1.14E−06 | 0.337729562 | 0.50938223 |
| cg17883033 | LYNX1 | Island | 5URT | 11.9498 | 1.32E−05 | 0.38728876 | 0.488255848 |
| cg17890928 | CHAD | Island | 5URT | 12.0383 | 4.17E−08 | 0.187541424 | 0.317844423 |
| cg17894318 | SOX2-OT | N_Shelf | Body | 4.85505 | 0.006927 | 0.292918 | 0.351362838 |
| cg17911021 | SHF | S_Shelf | TSS200 | 47.9817 | 1.16E−09 | 0.466465321 | 0.645995889 |
| cg17953764 | ZAR1 | Island | 1stExon | 12.1779 | 4.46E−08 | 0.350699606 | 0.489734795 |
| cg17955729 | PRRT1 | Island | Body | 9.11046 | 0.002102 | 0.590286395 | 0.659701818 |
| cg17968795 | KIAA12110 | Island | TSS1500 | 12.1468 | 5.46E−10 | 0.340340157 | 0.546382612 |
| cg17985646 | TBX20 | Island | TSS200 | 19.8363 | 1.06E−14 | 0.105382315 | 0.285893297 |
| cg17999376 | GDF6 | N_Shore | Body | 7.17236 | 6.61E−07 | 0.080721496 | 0.194295983 |
| cg18002447 | TBX2 | N_Shelf | Body | 9.52169 | 2.55E−05 | 0.502601525 | 0.626567465 |
| cg18004701 | PTPRN2 | Island | Body | 60.3432 | 1.31E−05 | 0.314220947 | 0.456252525 |
| cg18008037 | PTPRN2 | | Body | 12.423 | 6.01E−05 | 0.515893961 | 0.601632879 |
| cg18009690 | EN1 | N_Shelf | Body | 3.62404 | 0.006173 | 0.408456667 | 0.488124994 |
| cg18020955 | NBPF6 | S_Shore | Body | 13.2146 | 9.68E−10 | 0.315350464 | 0.512824132 |
| cg18034737 | ZFP42 | Island | TSS200 | 13.1511 | 1.32E−11 | 0.298751812 | 0.528559364 |
| cg18058747 | BHMT | | Body | 6.54294 | 6.07E−05 | 0.310740581 | 0.419380118 |
| cg18063017 | LHX4 | Island | Body | 8.54376 | 2.43E−07 | 0.164405681 | 0.288955422 |
| cg18064631 | PDX1 | N_Shore | Body | 15.0093 | 1.43E−08 | 0.305634029 | 0.441545632 |
| cg18082638 | PAX6 | Island | Body | 12.9733 | 6.76E−11 | 0.232736846 | 0.404154903 |
| cg18087266 | RUNX3 | Island | TSS1500 | 8.07854 | 0.000874 | 0.427078248 | 0.498311343 |
| cg18097224 | TCF7 | Island | TSS200 | 11.7289 | 3.81E−09 | 0.297002078 | 0.489776421 |
| cg18106668 | NPY | N_Shore | TSS1500 | 6.60869 | 2.63E−05 | 0.208961779 | 0.315276483 |
| cg18128164 | JSRP1 | Island | Body | 6.93476 | 5.35E−06 | 0.242165326 | 0.370465384 |
| cg18144593 | LINC01143 | Island | Body | 5.24299 | 0.001173 | 0.291878907 | 0.365592041 |
| cg18181229 | PBX1 | Island | Body | 19.1988 | 1.66E−05 | 0.709799167 | 0.815114051 |
| cg18182148 | GFI1 | Island | TSS1500 | 24.0419 | 6.65E−06 | 0.439434636 | 0.532292707 |
| cg18182399 | DES | N_Shore | 5URT | 6.69962 | 1.42E−06 | 0.182051221 | 0.331384302 |
| cg18202449 | ELAVL4 | Island | TSS200 | 10.8587 | 5.65E−08 | 0.078857392 | 0.173124169 |
| cg18221467 | GFI1 | Island | 5URT | 3.32963 | 0.00269 | 0.098510456 | 0.181995669 |
| cg18229178 | HSPB6 | Island | 3UTR | 6.31466 | 5.39E−05 | 0.491426869 | 0.627269212 |
| cg18235100 | PRDM8 | Island | Body | 5.33123 | 9.01E−06 | 0.225875627 | 0.358635163 |
| cg18240703 | RBFOX3 | S_Shore | Body | 8.59428 | 0.000115 | 0.290458174 | 0.387115047 |
| cg18247055 | SPAG6 | Island | TSS200 | 19.3193 | 1.02E−14 | 0.124712281 | 0.338985005 |
| cg18267374 | NEFM | Island | TSS1500 | 13.4286 | 1.04E−08 | 0.20676212 | 0.333002336 |
| cg18304448 | LOC90768 | N_Shore | Body | 26.9983 | 0.000897 | 0.714294194 | 0.773667220 |
| cg18311537 | HOXA10-AS | Island | Body | 5.38304 | 0.002039 | 0.254178464 | 0.327363658 |
| cg18318878 | PROX1-AS1 | Island | Body | 13.299 | 9.34E−08 | 0.187029062 | 0.298427348 |
| cg18322569 | BARHL2 | Island | 1stExon | 6.29987 | 2.16E−08 | 0.197396521 | 0.383766007 |
| cg18327157 | PTPRN2 | Island | Body | 13.4436 | 4.96E−05 | 0.61934575 | 0.708686101 |
| cg18336674 | TLX3 | Island | TSS1500 | 9.73175 | 8.58E−07 | 0.298246398 | 0.407585068 |
| cg18342279 | ZAR1 | Island | 1stExon | 30.9613 | 5.63E−12 | 0.062975676 | 0.17502701 |
| cg18358723 | LINC00461 | N_Shore | Body | 26.2331 | 2.01E−13 | 0.360938969 | 0.556964263 |
| cg18362330 | NEUROG1 | S_Shore | TSS1500 | 4.73319 | 0.002724 | 0.352742707 | 0.415974497 |
| cg18366919 | EPHX3 | Island | TSS1500 | 59.53 | 2.32E−14 | 0.401490765 | 0.628729481 |
| cg18372607 | PAX6 | S_Shore | TSS1500 | 13.3926 | 1.60E−08 | 0.419495719 | 0.620407781 |
| cg18394340 | H2AFY | S_Shore | TSS1500 | 9.82185 | 7.07E−07 | 0.22672006 | 0.327011825 |
| cg18400845 | DKFZp686K1684 | Island | TSS200 | 7.81442 | 0.000245 | 0.160146836 | 0.239914486 |
| cg18405727 | TRIM71 | Island | 1stExon | 10.2963 | 3.19E−09 | 0.073522285 | 0.195180408 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg18406197 | FBLN2 | Island | TSS200 | 5.70911 | 0.000326 | 0.115995684 | 0.196359008 |
| cg18407955 | PTPRN2 | Island | Body | 4.19021 | 0.001203 | 0.250637437 | 0.349141454 |
| cg18416576 | HOXA10 | Island | TSS200 | 13.6841 | 9.58E-08 | 0.121160838 | 0.21969374 |
| cg18435852 | GATM | S_Shore | TSS200 | 4.08219 | 0.002803 | 0.472096821 | 0.568737838 |
| cg18447772 | HOXA9 | Island | TSS200 | 6.5081 | 9.51E-07 | 0.167529767 | 0.285976453 |
| cg18459489 | VAX1 | N_Shore | 3UTR | 7.67101 | 5.78E-05 | 0.248709798 | 0.352316234 |
| cg18495682 | RGCC | Island | Body | 10.0128 | 3.08E-10 | 0.253291282 | 0.38447752 |
| cg18501555 | PITX2 | Island | 5URT | 7.90439 | 4.41E-07 | 0.164471828 | 0.268454837 |
| cg18502142 | DLX6-AS1 | | Body | 8.81352 | 5.22E-09 | 0.356040295 | 0.528492931 |
| cg18507379 | FCDHGB6 | N_Shore | TSS1500 | 10.4468 | 9.88E-10 | 0.082228509 | 0.233778193 |
| cg18512948 | REC8 | Island | 5URT | 32.5159 | 2.72E-09 | 0.493475405 | 0.690941253 |
| cg18528367 | SIM1 | Island | TSS200 | 5.82481 | 0.00082 | 0.151508981 | 0.21753899 |
| cg18534491 | REC8 | Island | TSS200 | 24.0735 | 5.41E-12 | 0.305632671 | 0.502323024 |
| cg18539122 | RNF219-AS1 | N_Shore | Body | 19.1792 | 1.57E-10 | 0.206935236 | 0.335809997 |
| cg18544365 | MIR199A1 | | TSS200 | 28.236 | 2.54E-05 | 0.708369473 | 0.825552071 |
| cg18552861 | GDF7 | Island | TSS1500 | 7.40243 | 2.88E-08 | 0.232560626 | 0.42899634 |
| cg18556834 | REC8 | Island | TSS200 | 30.6884 | 3.98E-12 | 0.317846961 | 0.518107681 |
| cg18560204 | BNC1 | Island | TSS1500 | 16.7946 | 2.51E-05 | 0.396627543 | 0.478962343 |
| cg18569734 | NR2E1 | N_Shore | Body | 16.3179 | 3.93E-10 | 0.239844657 | 0.381504319 |
| cg18579879 | WNT16 | N_Shore | Body | 19.4183 | 5.84E-10 | 0.289589062 | 0.425330833 |
| cg18588323 | TNFAIP8L3 | Island | Body | 5.8607 | 6.37E-06 | 0.457123502 | 0.627573555 |
| cg18599069 | GATA3 | Island | 5URT | 5.18647 | 0.00034 | 0.318744713 | 0.418446436 |
| cg18601426 | PTPRN2 | Island | TSS1500 | 7.4007 | 0.000319 | 0.378384829 | 0.470086596 |
| cg18603228 | FBLN2 | Island | TSS200 | 4.1224 | 0.000785 | 0.175238153 | 0.269520406 |
| cg18609783 | SP9 | N_Shore | TSS1500 | 5.93052 | 9.08E-05 | 0.199823974 | 0.292209257 |
| cg18614735 | ANK1 | Island | Body | 5.56832 | 0.000796 | 0.549223589 | 0.636190121 |
| cg18617005 | PCDHGB6 | N_Shore | TSS1500 | 8.11405 | 2.83E-09 | 0.115357692 | 0.28455606 |
| cg18628371 | REC8 | Island | TSS200 | 26.4715 | 4.77E-14 | 0.247613071 | 0.447531304 |
| cg18650716 | FLOT1 | Island | TSS1500 | 13.1511 | 6.64E-11 | 0.167437264 | 0.36048667 |
| cg18664869 | PCDHB15 | S_Shelf | 5URT | 5.50884 | 3.78E-05 | 0.162265126 | 0.27620882 |
| cg18687675 | GSC | Island | Body | 15.3921 | 7.49E-10 | 0.291807365 | 0.470013512 |
| cg18691434 | GPC2 | Island | TSS1500 | 16.5553 | 3.08E-07 | 0.257974009 | 0.358204774 |
| cg18725076 | CTNND2 | S_Shore | TSS1500 | 23.1262 | 1.14E-08 | 0.118424491 | 0.193368514 |
| cg18736063 | NKX2-4 | S_Shore | TSS1500 | 5.0293 | 0.000205 | 0.182061271 | 0.282565111 |
| cg18790597 | FAM184B | Island | TSS200 | 9.11841 | 1.22E-09 | 0.070912743 | 0.237619076 |
| cg18795809 | ZNF518B | Island | 5URT | 8.36665 | 5.57E-07 | 0.129595157 | 0.240899469 |
| cg18796287 | PROB1 | Island | Body | 20.5923 | 1.29E-08 | 0.539499651 | 0.701972818 |
| cg18817990 | NKX3-2 | N_Shore | 3UTR | 5.31089 | 0.003429 | 0.568214085 | 0.636472949 |
| cg18867200 | LINC01143 | S_Shore | Body | 4.77564 | 0.006418 | 0.520552419 | 0.594372525 |
| cg18867923 | TBX1 | S_Shore | Body | 11.9792 | 6.97E-06 | 0.427810295 | 0.546285681 |
| cg18873386 | DLX5 | S_Shore | Body | 7.51178 | 4.30E-05 | 0.490907624 | 0.599955266 |
| cg18884137 | CHRNB1 | Island | 1stExon | 7.80404 | 1.06E-06 | 0.183831388 | 0.316830618 |
| cg18898125 | NEFM | N_Shore | TSS1500 | 9.61316 | 2.33E-06 | 0.437298423 | 0.598517638 |
| cg18948488 | LBX1-AS1 | S_Shore | Body | 16.5964 | 8.12E-10 | 0.37951718 | 0.591820949 |
| cg18950778 | WT1 | S_Shelf | Body | 15.1075 | 8.25E-09 | 0.237997974 | 0.364574508 |
| cg18952647 | BNC1 | Island | TSS1500 | 5.37601 | 9.25E-05 | 0.376393719 | 0.498551567 |
| cg18984724 | SPEG | Island | TSS200 | 4.16953 | 0.008523 | 0.421400391 | 0.489853415 |
| cg19006378 | PAX6 | S_Shelf | 5URT | 14.5359 | 4.86E-06 | 0.191494257 | 0.287171432 |
| cg19006429 | RNF39 | Island | 1stExon | 5.6169 | 9.01E-06 | 0.262171297 | 0.411383047 |
| cg19022697 | TTC22 | Island | Body | 12.4534 | 9.76E-06 | 0.376542029 | 0.461752303 |
| cg19043574 | KIAA1211L | Island | Body | 5.73261 | 1.33E-06 | 0.226254804 | 0.402278031 |
| cg19046826 | CHAD | Island | TSS200 | 4.13726 | 0.000578 | 0.27575857 | 0.410218347 |
| cg19092981 | TBX1 | Island | Body | 12.4816 | 0.000116 | 0.720006729 | 0.813349848 |
| cg19098763 | ELAVL4 | Island | TSS200 | 10.6067 | 7.11E-10 | 0.084956398 | 0.221883706 |
| cg19103219 | LINC01475 | N_Shore | Body | 4.12703 | 0.008364 | 0.26200805 | 0.310319771 |
| cg19113641 | GDF7 | N_Shelf | TSS200 | 4.52751 | 0.000657 | 0.055786843 | 0.132334285 |
| cg19127283 | TRIM71 | Island | TSS200 | 11.8664 | 1.03E-10 | 0.126788653 | 0.281658589 |
| cg19131476 | NRXN2 | | Body | 11.2077 | 1.69E-05 | 0.437986124 | 0.543260569 |
| cg19164987 | HOXC6 | Island | 5URT | 3.45532 | 0.00477 | 0.512598324 | 0.591719046 |
| cg19181162 | TTC6 | Island | Body | 21.4468 | 1.09E-10 | 0.294844788 | 0.448929216 |
| cg19183743 | HOXA-AS3 | S_Shore | Body | 5.58012 | 0.000166 | 0.382559529 | 0.493138218 |
| cg19211915 | WT1 | Island | TSS200 | 21.0418 | 2.34E-10 | 0.247232195 | 0.391269267 |
| cg19241327 | PTPRN2 | Island | Body | 8.50737 | 2.28E-06 | 0.329177162 | 0.452448658 |
| cg19247475 | PCDHGB6 | Island | 1stExon | 44.3066 | 8.64E-09 | 0.611487473 | 0.770575283 |
| cg19258034 | SPTBN4 | Island | Body | 4.99719 | 0.003627 | 0.522056947 | 0.594846242 |
| cg19270505 | RUNX3 | Island | 1stExon | 7.77555 | 8.12E-07 | 0.113755246 | 0.218348874 |
| cg19281363 | RGCC | Island | TSS1500 | 16.0748 | 2.15E-08 | 0.352716495 | 0.503901001 |
| cg19290410 | TBX5-AS1 | Island | Body | 7.32905 | 1.85E-06 | 0.147292054 | 0.253437205 |
| cg19305681 | CYP26C1 | N_Shelf | Body | 4.90628 | 0.000157 | 0.153316146 | 0.261350188 |
| cg19325985 | HOXD13 | S_Shore | TSS200 | 9.1827 | 1.87E-06 | 0.399982423 | 0.534120061 |
| cg19329160 | RNF219-AS1 | Island | Body | 8.60088 | 1.98E-06 | 0.164899784 | 0.267264503 |
| cg19334350 | PTPRN2 | S_Shore | Body | 9.22478 | 4.00E-06 | 0.314449187 | 0.444292523 |
| cg19363499 | PRDM14 | Island | 5URT | 11.6897 | 3.45E-06 | 0.142179275 | 0.226016956 |
| cg19378036 | HNF1B | Island | TSS1500 | 4.34373 | 7.99E-05 | 0.266627511 | 0.392619205 |
| cg19384289 | HOXD8 | Island | TSS200 | 6.01803 | 1.19E-05 | 0.099368389 | 0.2095155 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg19392656 | FBLN2 | Island | TSS1500 | 6.1189 | 9.12E−05 | 0.15974956 | 0.248074327 |
| cg19403029 | SOX7 | S_Shore | Body | 10.382 | 3.83E−07 | 0.453441831 | 0.625600202 |
| cg19403104 | RCN3 | Island | 1stExon | 6.43783 | 1.04E−05 | 0.10711464 | 0.214153279 |
| cg19407095 | SOX1 | Island | TSS200 | 15.6357 | 0.000136 | 0.215413566 | 0.282166094 |
| cg19410791 | CD8A | S_Shelf | TSS1500 | 6.76389 | 0.003426 | 0.659376085 | 0.735806919 |
| cg19416570 | ZNF274 | Island | 5URT | 18.2928 | 2.64E−08 | 0.311816852 | 0.411938929 |
| cg19497031 | POU4F1 | Island | Body | 20.3991 | 9.86E−13 | 0.08002373 | 0.204831693 |
| cg19498960 | SIM2 | N_Shelf | Body | 6.4801 | 0.000118 | 0.213305814 | 0.306683987 |
| cg19520234 | MGAT4D | | Body | 6.83852 | 0.000227 | 0.426039488 | 0.500163212 |
| cg19537719 | ANK1 | Island | Body | 7.12919 | 0.00015 | 0.622529761 | 0.752024889 |
| cg19544662 | FOXI3 | Island | TSS200 | 11.033 | 3.26E−10 | 0.221597176 | 0.399217105 |
| cg19578835 | TTC6 | Island | 5URT | 8.40703 | 7.02E−09 | 0.125352736 | 0.267933818 |
| cg19593490 | HCG9 | N_Shore | Body | 7.79059 | 0.000178 | 0.369764078 | 0.480599628 |
| cg19594666 | LEP | Island | TSS200 | 7.6217 | 3.16E−05 | 0.287823723 | 0.391379455 |
| cg19616230 | SLC34A2 | Island | TSS1500 | 6.6873 | 7.48E−05 | 0.301621481 | 0.40064544 |
| cg19617672 | WNT16 | N_Shore | Body | 8.89686 | 1.27E−05 | 0.132662698 | 0.22709548 |
| cg19628148 | CCDC37 | Island | 5URT | 4.79364 | 0.000186 | 0.159824364 | 0.261712756 |
| cg19689322 | KCNQ4 | S_Shore | Body | 8.22529 | 6.89E−06 | 0.360362426 | 0.487983049 |
| cg19711783 | NTN1 | Island | Body | 12.3025 | 5.86E−14 | 0.15382545 | 0.417709614 |
| cg19718882 | WT1-AS | N_Shore | Body | 5.72747 | 4.87E−05 | 0.212520009 | 0.325131867 |
| cg19725343 | IGLON5 | Island | Body | 5.59984 | 1.08E−06 | 0.289951525 | 0.475914244 |
| cg19733042 | NBPF8 | | Body | 6.81366 | 0.005675 | 0.701039426 | 0.761447444 |
| cg19741645 | EBF3 | N_Shore | Body | 16.5096 | 0.000135 | 0.736955496 | 0.797555616 |
| cg19741945 | TRIM71 | Island | 1stExon | 16.574 | 2.43E−10 | 0.071768964 | 0.179200876 |
| cg19759671 | LOC90768 | Island | Body | 7.87859 | 0.000347 | 0.594065672 | 0.714661078 |
| cg19760241 | LHX1 | Island | Body | 12.3234 | 2.83E−08 | 0.215127779 | 0.338894894 |
| cg19761110 | AGAP1 | Island | Body | 12.8399 | 2.15E−06 | 0.459220209 | 0.582516 |
| cg19762657 | MAL | S_Shore | Body | 5.40415 | 0.00039 | 0.188733259 | 0.274674552 |
| cg19766441 | SLC34A2 | Island | TSS1500 | 7.50814 | 2.64E−07 | 0.176200335 | 0.330598912 |
| cg19767800 | NR2F1-AS1 | N_Shore | Body | 26.8457 | 2.91E−08 | 0.547704163 | 0.74524497 |
| cg19770541 | ZAR1 | N_Shore | TSS1500 | 8.06612 | 0.000348 | 0.318610147 | 0.381747705 |
| cg19792544 | KIFC2 | N_Shelf | 5UTR | 15.4103 | 7.71E−07 | 0.298568269 | 0.443074728 |
| cg19802138 | LINC00403 | Island | Body | 29.1631 | 9.82E−11 | 0.344062543 | 0.496177364 |
| cg19808978 | RCN3 | Island | 1stExon | 6.34664 | 9.10E−07 | 0.087848633 | 0.221149819 |
| cg19816811 | HOXA-AS3 | N_Shore | Body | 3.84325 | 0.002921 | 0.49767724 | 0.589245283 |
| cg19842809 | PAX9 | S_Shore | TSS1500 | 5.90394 | 0.000151 | 0.236785631 | 0.324544787 |
| cg19844326 | ANK1 | S_Shore | TSS1500 | 10.6964 | 1.36E−06 | 0.208115856 | 0.319461275 |
| cg19844653 | TCF7 | S_Shore | TSS200 | 11.7742 | 0.000104 | 0.420360022 | 0.504726748 |
| cg19852958 | NKX3-2 | Island | 1stExon | 11.0387 | 3.63E−10 | 0.213761278 | 0.390592106 |
| cg19876672 | VAX1 | N_Shore | 5UTR | 5.92833 | 1.02E−05 | 0.267581817 | 0.408519767 |
| cg19884262 | FOXI2 | Island | 1stExon | 12.2074 | 4.67E−08 | 0.253363243 | 0.405949632 |
| cg19909239 | PITX2 | Island | 5URT | 14.0877 | 2.05E−07 | 0.190493558 | 0.281078255 |
| cg19923650 | NKX2-5 | N_Shelf | 5UTR | 7.36311 | 1.63E−07 | 0.120904266 | 0.256820906 |
| cg19961043 | CHAD | Island | TSS1500 | 5.85916 | 8.87E−05 | 0.198159036 | 0.311028029 |
| cg19962750 | DLX5 | S_Shelf | TSS1500 | 22.7974 | 2.38E−05 | 0.636280651 | 0.722495444 |
| cg19980151 | NR2F1-AS1 | N_Shore | Body | 9.97179 | 3.06E−08 | 0.351144177 | 0.577298493 |
| cg19989295 | REC8 | Island | TSS200 | 22.0461 | 9.87E−14 | 0.285248684 | 0.530623958 |
| cg20003638 | SLC12A5 | S_Shore | 5UTR | 100.175 | 4.98E−08 | 0.724658581 | 0.847930172 |
| cg20014398 | PAX6 | Island | TSS200 | 19.3007 | 8.68E−14 | 0.36145828 | 0.620588756 |
| cg20014822 | FGF19 | N_Shore | Body | 4.61986 | 0.000787 | 0.211106193 | 0.296092176 |
| cg20027296 | TLX3 | Island | ExonBnd | 15.8661 | 6.96E−07 | 0.420871829 | 0.542703212 |
| cg20049415 | NKX2-4 | Island | 1stExon | 35.0598 | 3.29E−12 | 0.15292705 | 0.283244542 |
| cg20065463 | DES | N_Shore | 5URT | 7.10268 | 1.30E−07 | 0.272935362 | 0.451054271 |
| cg20073553 | NKX3-2 | Island | Body | 3.77127 | 0.004533 | 0.424616469 | 0.512879401 |
| cg20080624 | DLX5 | Island | Body | 4.99817 | 0.000339 | 0.43875945 | 0.533856923 |
| cg20094830 | PRAC2 | N_Shore | TSS1500 | 8.91098 | 9.65E−07 | 0.200785164 | 0.317781466 |
| cg20099830 | TBX5 | N_Shelf | 5URT | 10.081 | 6.28E−08 | 0.310201287 | 0.458847958 |
| cg20120208 | TLX1 | S_Shore | 3UTR | 3.81635 | 0.002147 | 0.301842871 | 0.376603662 |
| cg20125091 | GFI1 | S_Shore | TSS1500 | 29.536 | 2.12E−06 | 0.542301519 | 0.643652556 |
| cg20146541 | TRIM58 | Island | 1stExon | 21.9197 | 4.81E−17 | 0.110349952 | 0.363890803 |
| cg20177385 | SLC41A3 | | TSS200 | 10.8829 | 2.00E−06 | 0.350382508 | 0.45587501 |
| cg20204986 | WT1 | N_Shore | Body | 6.5651 | 0.000519 | 0.403866388 | 0.474765061 |
| cg20232102 | FPP1R14A | Island | 1stExon | 12.0711 | 1.60E−10 | 0.175226145 | 0.362609666 |
| cg20248516 | EN1 | N_Shelf | Body | 5.52909 | 7.46E−05 | 0.292354778 | 0.391684679 |
| cg20249327 | RNF39 | Island | Body | 7.57819 | 4.08E−06 | 0.286282178 | 0.423838529 |
| cg20250981 | KCNQ1DN | Island | TSS1500 | 4.28637 | 0.001209 | 0.349317588 | 0.439709273 |
| cg20262306 | SHH | S_Shore | 5URT | 13.0136 | 8.04E−07 | 0.509360164 | 0.655855596 |
| cg20264732 | ESRP2 | N_Shelf | 1stExon | 22.8949 | 3.08E−08 | 0.449200194 | 0.583696576 |
| cg20272979 | ITPKA | Island | Body | 10.8937 | 1.43E−06 | 0.546541036 | 0.736952009 |
| cg20293942 | DLEU1 | Island | Body | 23.9208 | 2.79E−06 | 0.621626008 | 0.719852111 |
| cg20311863 | BARHL2 | Island | TSS1500 | 14.0963 | 1.83E−08 | 0.094841735 | 0.200530401 |
| cg20312228 | CCDC37 | Island | TSS200 | 12.8881 | 2.06E−07 | 0.141265823 | 0.24330336 |
| cg20322977 | CYP26C1 | Island | 1stExon | 6.50117 | 0.003475 | 0.417134062 | 0.481221879 |
| cg20342079 | BCAT1 | N_Shore | TSS200 | 7.3502 | 1.03E−06 | 0.234865636 | 0.387089444 |
| cg20359285 | EN1 | S_Shelf | 1stExon | 7.63444 | 0.000115 | 0.06692167 | 0.142306297 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg20371765 | ICA1 | S_Shore | TSS1500 | 10.2615 | 9.41E-09 | 0.269309276 | 0.442337595 |
| cg20377305 | DLX5 | Island | Body | 8.39082 | 2.67E-07 | 0.150803543 | 0.264619552 |
| cg20381115 | GATM | S_Shore | TSS200 | 4.21907 | 0.004171 | 0.385953412 | 0.476913108 |
| cg20387815 | POMC | Island | TSS200 | 6.15625 | 2.36E-05 | 0.328587554 | 0.475714212 |
| cg20399462 | LINC00403 | Island | Body | 4.98615 | 0.004884 | 0.246342644 | 0.299333357 |
| cg20399871 | HOXA9 | Island | 1stExon | 3.72556 | 0.007223 | 0.204600263 | 0.269153764 |
| cg20403557 | LVRN | Island | Body | 4.40426 | 0.000455 | 0.228286075 | 0.329090854 |
| cg20429172 | TRIM58 | Island | TSS200 | 16.8021 | 1.21E-11 | 0.20154422 | 0.366979731 |
| cg20434586 | TTBK1 | Island | Body | 5.32912 | 0.000785 | 0.197843039 | 0.277545371 |
| cg20467957 | DKFZp686K1684 | N_Shore | Body | 73.2361 | 3.31E-11 | 0.430357829 | 0.581849596 |
| cg20469799 | KATNAL2 | N_Shore | TSS200 | 7.23421 | 1.08E-08 | 0.120873816 | 0.286978555 |
| cg20512711 | DKFZp686K1684 | Island | Body | 15.5295 | 5.50E-14 | 0.173467838 | 0.379902061 |
| cg20521696 | SHH | S_shore | 5URT | 19.7989 | 4.30E-06 | 0.598288736 | 0.710110727 |
| cg20528093 | DKFZp686K1684 | Island | TSS1500 | 4.83392 | 0.001201 | 0.479566101 | 0.581024374 |
| cg20529344 | DLEU1 | S_Shelf | Body | 10.5902 | 6.25E-05 | 0.546257504 | 0.633352505 |
| cg20540209 | ISL2 | Island | Body | 5.18123 | 0.000136 | 0.12172766 | 0.199163155 |
| cg20541178 | LYNX1 | Island | 5URT | 7.57694 | 0.0002 | 0.195868433 | 0.275332524 |
| cg20572816 | TLX1 | N_Shelf | Body | 3.475 | 0.00267 | 0.23055551 | 0.314436154 |
| cg20574490 | GRHL2 | Island | TSS200 | 18.0176 | 3.25E-11 | 0.299093352 | 0.48818099 |
| cg20582655 | C1orf61 | N_Shore | 5URT | 6.1528 | 9.44E-05 | 0.261635712 | 0.347146778 |
| cg20615879 | TLX1 | N_Shelf | Body | 5.41754 | 2.17E-05 | 0.241452736 | 0.359267755 |
| cg20650802 | IER3 | Island | 1stExib | 5.49153 | 2.84E-07 | 0.309682419 | 0.520558419 |
| cg20672981 | HOTTIP | N_Shelf | Body | 26.5811 | 2.13E-07 | 0.487395504 | 0.597795364 |
| cg20682146 | PBX1 | Island | Body | 31.5081 | 1.51E-07 | 0.490240953 | 0.589135818 |
| cg20688917 | HOXA3 | N_Shore | TSS1500 | 7.1669 | 0.004168 | 0.729594217 | 0.808881212 |
| cg20705938 | PITX2 | N_Shore | 5URT | 5.48117 | 0.002748 | 0.156584745 | 0.207863097 |
| cg20710709 | PAX9 | Island | ExonBnd | 5.02087 | 0.000623 | 0.365077084 | 0.456764364 |
| cg20725253 | HOXA-AS3 | S_Shore | Body | 6.70603 | 0.000115 | 0.130638186 | 0.223778848 |
| cg20731469 | NR2E1 | N_Shore | Body | 9.86331 | 3.60E-06 | 0.42968854 | 0.563242816 |
| cg20739435 | LOC648987 | S_Shore | TSS1500 | 3.80035 | 0.00209 | 0.21265756 | 0.308835924 |
| cg20747380 | HOXA2 | N_Shelf | 1stExon | 17.7323 | 4.10E-06 | 0.496721643 | 0.594180293 |
| cg20755721 | SIM2 | Island | TSS1500 | 5.34343 | 0.004409 | 0.221784242 | 0.291734221 |
| cg20785796 | SATB2 | Island | 5URT | 9.01048 | 1.70E-06 | 0.381194418 | 0.497477384 |
| cg20800022 | GDF6 | Island | Body | 10.9567 | 2.06E-07 | 0.159999612 | 0.280002285 |
| cg20801476 | EVX1 | N_Shore | TSS1500 | 7.87768 | 2.65E-05 | 0.328250073 | 0.440481091 |
| cg20817131 | HOXA5 | Island | TSS1500 | 4.13629 | 0.002962 | 0.421847659 | 0.502763475 |
| cg20871902 | PRDM8 | Island | Body | 6.34751 | 7.24E-06 | 0.097698513 | 0.204762599 |
| cg20884887 | HOXA10-AS | N_Shore | TSS1500 | 4.75543 | 3.31E-06 | 0.233650447 | 0.374850679 |
| cg20892260 | NKX2-6 | Island | 1stExon | 20.4729 | 4.78E-07 | 0.145169532 | 0.232744898 |
| cg20927242 | HLA-F | Island | Body | 9.88346 | 4.65E-08 | 0.18031307 | 0.335948479 |
| cg20931042 | DRD4 | Island | TSS200 | 8.4648 | 2.41E-06 | 0.09253981 | 0.191767053 |
| cg20941110 | BNC1 | Island | TSS1500 | 3.96019 | 0.006217 | 0.502587245 | 0.575406453 |
| cg20956738 | ONECUT2 | Island | Body | 7.64958 | 5.00E-05 | 0.162875956 | 0.248824632 |
| cg20959460 | LOC101929154 | N_Shore | TSS1500 | 16.1241 | 1.71E-11 | 0.314473133 | 0.492731738 |
| cg20974609 | HOXA5 | N_Shore | Body | 4.33753 | 0.001555 | 0.428540455 | 0.504480212 |
| cg20977170 | ICA1 | Island | TSS1500 | 12.7054 | 1.57E-08 | 0.092850781 | 0.227330971 |
| cg20988073 | ALDH1L1 | S_Shore | TSS1500 | 7.76164 | 0.000203 | 0.413372124 | 0.514290566 |
| cg20992114 | PITX2 | S_Shelf | Body | 8.59712 | 0.000777 | 0.339611031 | 0.414515455 |
| cg20994253 | HOXA11-AS | S_Shelf | Body | 3.25154 | 0.005737 | 0.227420309 | 0.293249725 |
| cg20994660 | TBR1 | S_Shore | TSS1500 | 4.37658 | 0.000809 | 0.40604368 | 0.507094444 |
| cg21010475 | SHISA3 | S_Shore | Body | 8.41646 | 2.86E-05 | 0.262301313 | 0.357312472 |
| cg21011139 | CYB5R2 | Island | 5URT | 8.97949 | 1.34E-06 | 0.397531471 | 0.567621456 |
| cg21016589 | PAX6 | N_Shore | Body | 12.1428 | 4.73E-12 | 0.224624653 | 0.455485739 |
| cg21017569 | KCNAB3 | N_Shelf | TSS200 | 12.4852 | 0.001121 | 0.800880837 | 0.878251333 |
| cg21052682 | FGF19 | S_Shore | Body | 7.86271 | 1.99E-06 | 0.073381482 | 0.164926489 |
| cg21063282 | GSC | N_Shelf | Body | 8.0954 | 1.61E-05 | 0.120703974 | 0.207035663 |
| cg21063716 | ASCL2 | Island | TSS1500 | 12.9965 | 2.31E-06 | 0.29074841 | 0.394816487 |
| cg21073927 | GATA4 | Island | 5URT | 10.4951 | 5.61E-07 | 0.227256102 | 0.34987529 |
| cg21073930 | MAST1 | Island | Body | 4.26334 | 0.005436 | 0.718901295 | 0.795161434 |
| cg21101465 | PDX1 | S_Shore | TSS1500 | 5.35582 | 0.000317 | 0.339050261 | 0.434711273 |
| cg21113740 | ADGRL4 | Island | 1stExon | 9.1566 | 1.91E-08 | 0.282772483 | 0.44115039 |
| cg21117330 | PCDHGA8 | N_Shore | 5URT | 5.08556 | 0.00041 | 0.476529093 | 0.580492727 |
| cg21124497 | TRIM71 | Island | TSS200 | 12.8291 | 7.26E-09 | 0.136333319 | 0.248641648 |
| cg21128569 | HOXD13 | S_Shelf | TSS1500 | 8.68744 | 6.63E-06 | 0.459708043 | 0.604441172 |
| cg21132352 | CHRNB1 | S_Shore | Body | 11.1103 | 8.30E-05 | 0.564250713 | 0.690790717 |
| cg21134232 | HOXA3 | S_Shore | 5URT | 4.19316 | 0.002936 | 0.490188502 | 0.552001929 |
| cg21146503 | DBX1 | Island | Body | 9.4313 | 0.000103 | 0.227824808 | 0.322576416 |
| cg21165027 | NKX2-3 | Island | TSS1500 | 13.0488 | 2.30E-06 | 0.29774207 | 0.392608063 |
| cg21172322 | BCAT1 | N_Shore | 2stExon | 8.12604 | 9.53E-06 | 0.345576027 | 0.478118571 |
| cg21172377 | HOXA10-HOXA9 | Island | Body | 8.81032 | 4.60E-06 | 0.219481758 | 0.322923671 |
| cg21174746 | CTNND2 | N_Shore | Body | 8.03986 | 1.87E-06 | 0.176832071 | 0.292922422 |
| cg21195468 | LHX2 | S_Shore | TSS1500 | 7.65383 | 3.16E-05 | 0.222284622 | 0.322005837 |
| cg21200656 | NKX2-5 | Island | TSS200 | 15.2788 | 2.42E-08 | 0.168404029 | 0.289018852 |
| cg21200703 | SLC34A2 | S_Shore | 5URT | 8.28113 | 5.52E-05 | 0.461891595 | 0.567723828 |
| cg21201099 | TBX2 | Island | Body | 4.36298 | 0.001954 | 0.247275088 | 0.329164387 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg21211357 | CPM | Island | TSS1500 | 12.8348 | 6.19E−06 | 0.341610504 | 0.445220364 |
| cg21242356 | HOXB-AS3 | N_Shore | TSS200 | 8.29475 | 1.39E−05 | 0.334272388 | 0.44093593 |
| cg21245652 | MAL | Island | TSS1500 | 19.5844 | 2.22E−07 | 0.307562458 | 0.416126319 |
| cg21249371 | KDM28 | S_Shore | TSS1500 | 3.36862 | 0.002204 | 0.315109408 | 0.443699404 |
| cg21266502 | LRAT | N_Shore | 5URT | 6.17457 | 2.45E−07 | 0.167118575 | 0.323547329 |
| cg21269897 | HIST1H2BK | N_Shore | 3UTR | 5.45511 | 0.000419 | 0.279402227 | 0.379044661 |
| cg21279601 | DRD5 | N_Shore | TSS1500 | 6.97504 | 0.00063 | 0.543905783 | 0.634019293 |
| cg21303011 | THRB-AS1 | Island | Body | 4.024 | 0.000615 | 0.308635694 | 0.414030698 |
| cg21429745 | LBX2 | Island | Body | 8.97637 | 1.13E−06 | 0.096486193 | 0.201153287 |
| cg21460081 | HOXB4 | S_Shore | TSS1500 | 11.8038 | 2.44E−09 | 0.084045451 | 0.199574331 |
| cg21463349 | EN1 | N_Shore | Body | 11.865 | 5.99E−07 | 0.078455924 | 0.163290233 |
| cg21472506 | OTX1 | N_Shore | Body | 5.45161 | 5.21E−05 | 0.210010069 | 0.419778793 |
| cg21174786 | HOXB3 | Island | 5URT | 5.25595 | 0.007164 | 0.424891899 | 0.480124343 |
| cg21484228 | TRIM71 | Island | TSS200 | 13.2 | 7.02E−11 | 0.128590807 | 0.281500941 |
| cg21485895 | SATB2 | Island | 5URT | 4.42512 | 0.000713 | 0.132985433 | 0.218265706 |
| cg21561970 | ISM1 | Island | TSS1500 | 8.86787 | 2.83E−08 | 0.120169877 | 0.263760053 |
| cg21595709 | EPHX3 | Island | TSS1500 | 81.9004 | 2.02E−15 | 0.303608994 | 0.497211734 |
| cg21601837 | ALDH1L1 | S_Shore | TSS1500 | 5.3971 | 0.000174 | 0.375285658 | 0.495886224 |
| cg21606115 | PTPRN2 | Island | Body | 3.8577 | 0.000691 | 0.14111287 | 0.234996 |
| cg21614303 | PITX1 | S_Shore | Body | 8.03165 | 9.19E−05 | 0.425736203 | 0.543282747 |
| cg21652531 | DLX6 | S_Shore | Body | 4.31227 | 0.008678 | 0.250049617 | 0.312964366 |
| cg21684012 | SIM1 | Island | TSS1500 | 17.9987 | 1.26E−09 | 0.083035309 | 0.18335952 |
| cg21697851 | SIM2 | N_Shelf | Body | 9.37866 | 2.25E−09 | 0.17714261 | 0.344302642 |
| cg21711132 | GABRG3 | Island | TSS1500 | 8.00195 | 9.13E−06 | 0.323187644 | 0.458412327 |
| cg21713473 | LRAT | N_Shore | 5URT | 5.75518 | 3.99E−05 | 0.218598381 | 0.327787801 |
| cg21726372 | PITX2 | S_Shore | Body | 5.04614 | 2.13E−05 | 0.146965164 | 0.252853967 |
| cg21753226 | KCNQ1DN | Island | TSS1500 | 5.29155 | 4.53E−05 | 0.360042953 | 0.503972436 |
| cg21762523 | NR2E1 | Island | Exon8nd | 4.27447 | 0.002898 | 0.103195074 | 0.161328936 |
| cg21769619 | WT1 | S_Shelf | Body | 12.9888 | 7.56E−05 | 0.46072276 | 0.560838152 |
| cg21774338 | DMRTA2 | Island | 3UTR | 8.93362 | 9.80E−06 | 0.279551432 | 0.385666273 |
| cg21784383 | ESRRG | Island | TSS200 | 12.0597 | 3.92E−09 | 0.224802477 | 0.356644404 |
| cg21791017 | LTK | Island | Body | 21.3453 | 7.70E−07 | 0.44291415 | 0.556013485 |
| cg21793948 | BCL2 | S_Shelf | TSS1500 | 5.82334 | 2.97E−05 | 0.17768038 | 0.285786712 |
| cg21811143 | EN1 | Island | 3UTR | 2.95187 | 0.004889 | 0.198834755 | 0.294231757 |
| cg21843594 | HORMAD2 | Island | TSS200 | 13.3142 | 1.29E−09 | 0.314167553 | 0.483250241 |
| cg21865150 | HOXB13 | Island | Body | 4.96682 | 2.03E−05 | 0.313784264 | 0.441979663 |
| cg21890667 | HORMAD2 | Island | TSS1500 | 26.5912 | 4.98E−12 | 0.424362917 | 0.587528212 |
| cg21912060 | LINC01391 | N_Shore | TSS200 | 6.30522 | 3.31E−06 | 0.376253791 | 0.529332661 |
| cg21915313 | PCDHGAB | Island | 1stExon | 24.5935 | 4.37E−09 | 0.566020798 | 0.735252939 |
| cg21932368 | SHF | S_Shore | 5URT | 37.997 | 7.77E−10 | 0.463776553 | 0.640867477 |
| cg21945930 | DLX6-AS1 | N_Shelf | Body | 5.13758 | 0.000253 | 0.339683889 | 0.428517229 |
| cg21949512 | TBR1 | Island | Body | 5.75984 | 1.41E−05 | 0.099245161 | 0.19930497 |
| cg21951975 | IRF6 | S_Shore | TSS1500 | 20.498 | 3.69E−08 | 0.299056932 | 0.431778556 |
| cg21971285 | DKFZp686K1684 | S_Shelf | Body | 21.6561 | 2.00E−10 | 0.28271755 | 0.421670949 |
| cg22010052 | LVRN | Island | 1stExon | 15.6049 | 3.14E−10 | 0.194089848 | 0.347209183 |
| cg22038124 | TNFAIP8L3 | | Body | 3.62007 | 0.00944 | 0.395430767 | 0.454771545 |
| cg22039909 | TP73 | Island | Body | 12.1417 | 0.001467 | 0.760562326 | 0.83305797 |
| cg22044002 | CYP26C1 | Island | Body | 5.90795 | 3.77E−05 | 0.384815199 | 0.538603907 |
| cg22056595 | PTPRN2 | | Body | 6.13129 | 0.007287 | 0.333674517 | 0.398391444 |
| cg22084642 | DNAH1 | | 5URT | 6.65081 | 5.29E−06 | 0.418105356 | 0.562459404 |
| cg22097249 | BEND4 | | Body | 5.54496 | 0.000239 | 0.43385394 | 0.534596382 |
| cg22105332 | RNF39 | Island | 1stExon | 5.08268 | 7.14E−07 | 0.241261662 | 0.425499092 |
| cg22118240 | ESRRG | Island | TSS1500 | 11.5249 | 2.64E−08 | 0.120001963 | 0.229305397 |
| cg22120446 | LINC01391 | N_Shore | Body | 9.3174 | 0.000149 | 0.48362631 | 0.579314172 |
| cg22125838 | WNT10A | Island | Body | 7.22989 | 0.000129 | 0.260322178 | 0.365792475 |
| cg22132508 | LINC01391 | S_Shelf | Body | 4.12412 | 0.0032 | 0.259183763 | 0.332735863 |
| cg22149137 | HOXB13 | Island | Body | 7.48842 | 1.25E−06 | 0.247579345 | 0.381321621 |
| cg22204479 | NKX2-4 | Island | TSS200 | 6.01779 | 5.77E−06 | 0.122060921 | 0.238212891 |
| cg22241820 | SKOR1 | N_Shelf | Body | 11.6758 | 0.000752 | 0.660270558 | 0.735255717 |
| cg22249789 | OTX1 | S_Shore | Body | 8.56642 | 1.78E−09 | 0.173777343 | 0.353262294 |
| cg22265644 | NKX2-2 | Island | TSS200 | 12.7748 | 8.71E−07 | 0.257804912 | 0.355724495 |
| cg22268510 | PRRT1 | Island | Body | 4.56532 | 0.003525 | 0.573836291 | 0.655524081 |
| cg22272282 | HIST1H2BK | S_Shore | 3UTR | 5.48686 | 0.001937 | 0.561603825 | 0.656952361 |
| cg22283925 | ZFP42 | S_Shore | 5URT | 11.1438 | 1.37E−06 | 0.433798837 | 0.552435273 |
| cg22287064 | MYO15B | Island | TSS200 | 7.13041 | 4.13E−07 | 0.110727003 | 0.241164653 |
| cg22289831 | SIM2 | N_Shelf | Body | 3.4192 | 0.008976 | 0.232055198 | 0.313108439 |
| cg22303418 | OTX1 | S_Shore | Body | 26.3038 | 6.03E−06 | 0.600733333 | 0.701248919 |
| cg22341104 | GFI1 | Island | 5URT | 3.88568 | 0.000398 | 0.215481322 | 0.300320506 |
| cg22345692 | NPR3 | Island | Body | 12.1034 | 1.10E−07 | 0.09600835 | 0.198956753 |
| cg22436336 | LHX4 | S_Shore | Body | 6.16602 | 9.09E−06 | 0.311893325 | 0.42341982 |
| cg22442454 | IRF6 | Island | 1stExon | 6.34926 | 1.63E−06 | 0.099544043 | 0.22580171 |
| cg22459630 | SKOR1 | Island | Body | 5.80606 | 0.000303 | 0.191352767 | 0.274424614 |
| cg22463553 | PCDHGB6 | N_Shore | 1stExon | 14.249 | 4.73E−06 | 0.606110295 | 0.720875717 |
| cg22469274 | HOXA-AS3 | Island | Body | 17.2804 | 6.47E−10 | 0.057619553 | 0.172769822 |
| cg22474464 | NKX2-2 | Island | Body | 8.64867 | 1.14E−10 | 0.082635274 | 0.237251752 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg22496377 | SHF | S_Shore | 5URT | 39.0186 | 6.25E-10 | 0.453229504 | 0.598199089 |
| cg22498143 | SPTBN4 | N_Shore | Body | 21.069 | 4.21E-06 | 0.640750977 | 0.792903022 |
| cg22505086 | DLX6 | S_Shelf | 3UTR | 5.8833 | 0.000848 | 0.286864372 | 0.345839043 |
| cg22511262 | WT1 | S_Shelf | Body | 9.41329 | 3.62E-07 | 0.159214555 | 0.274852851 |
| cg22531668 | VAX1 | N_Shore | 3UTR | 14.584 | 6.99E-08 | 0.453199062 | 0.611862071 |
| cg22533573 | WT1 | S_Shore | TSS1500 | 13.7978 | 5.67E-08 | 0.14795094 | 0.250127828 |
| cg22557091 | PAX6 | Island | Body | 14.6401 | 1.10E-09 | 0.158600792 | 0.309527235 |
| cg22557662 | PPP1R14A | Island | TSS200 | 19.236 | 1.08E-07 | 0.547188083 | 0.714845321 |
| cg22559034 | NR2F1-AS1 | S_Shore | Body | 7.71168 | 1.24E-05 | 0.46278823 | 0.635338986 |
| cg22560193 | APC2 | Island | Body | 10.4725 | 0.000598 | 0.399053443 | 0.474002812 |
| cg22571664 | NPR3 | Island | Body | 9.92306 | 1.76E-09 | 0.21545106 | 0.423046241 |
| cg22572908 | ARHGEF4 | S_Shore | Body | 6.76475 | 0.000913 | 0.280091768 | 0.362902791 |
| cg22614142 | KIFC2 | Island | Body | 30.5204 | 4.24E-11 | 0.352119809 | 0.613047689 |
| cg22616881 | DLX6-AS1 | N_Shelf | Body | 5.09098 | 0.001228 | 0.114079502 | 0.170060134 |
| cg22623223 | PTPRN2 | Island | Body | 4.68816 | 0.000587 | 0.256707027 | 0.347335654 |
| cg22637538 | CHRNB1 | Island | TSS200 | 6.58602 | 4.36E-07 | 0.276723921 | 0.441389322 |
| cg22660933 | HOXB1 | Island | TSS200 | 5.04489 | 0.000478 | 0.55730887 | 0.635605899 |
| cg22666373 | OTX1 | S_Shore | Body | 15.3527 | 3.38E-08 | 0.42074545 | 0.566590677 |
| cg22674699 | HOXD9 | Island | 1stExon | 10.242 | 7.95E-06 | 0.059148891 | 0.124531201 |
| cg22711111 | TRIM15 | Island | Body | 5.38684 | 9.93E-05 | 0.265351435 | 0.388795697 |
| cg22720790 | ZNF274 | Island | 5URT | 9.41078 | 3.44E-05 | 0.562506674 | 0.667911899 |
| cg22730140 | NKX2-5 | Island | Body | 10.0985 | 1.45E-06 | 0.124523364 | 0.213164766 |
| cg22730464 | GPR150 | Island | TSS200 | 10.7352 | 3.01E-07 | 0.258252384 | 0.403291076 |
| cg22740492 | PAX6 | Island | Body | 17.759 | 1.59E-12 | 0.149710173 | 0.326517684 |
| cg22770911 | GATA3 | S_Shore | Body | 13.7179 | 0.000541 | 0.577785783 | 0.665098929 |
| cg22774088 | JSRP1 | Island | Body | 4.25009 | 1.37E-05 | 0.197505494 | 0.35245203 |
| cg22777724 | HOXB-AS1 | S_Shore | Body | 3.53866 | 0.00072 | 0.357495003 | 0.467293199 |
| cg22778788 | NKX2-3 | N_Shelf | Body | 6.64241 | 7.81E-05 | 0.342002399 | 0.435237929 |
| cg22783363 | TNFRSF10D | Island | TSS200 | 9.70479 | 3.00E-07 | 0.243123222 | 0.396629565 |
| cg22799963 | GATA4 | Island | 5URT | 17.5528 | 6.93E-06 | 0.47390493 | 0.578669384 |
| cg22807449 | HOXB-AS1 | S_Shore | Body | 4.52324 | 2.35E-05 | 0.320011555 | 0.455339277 |
| cg22814261 | BCAT1 | N_Shore | TSS200 | 14.4296 | 4.07E-08 | 0.158362062 | 0.280640049 |
| cg22827250 | PITX1 | Island | 3UTR | 12.7205 | 2.34E-08 | 0.281253935 | 0.442493603 |
| cg22839075 | SYN2 | N_Shore | TSS1500 | 7.59931 | 0.000275 | 0.128141188 | 0.213019953 |
| cg22840219 | RCN3 | Island | ExonBnd | 11.8477 | 1.42E-07 | 0.323252038 | 0.475138543 |
| cg22849665 | PRRT1 | Island | Body | 9.19065 | 0.002107 | 0.703011247 | 0.776908717 |
| cg22859061 | SCGB3A1 | Island | TSS200 | 5.59467 | 7.02E-05 | 0.122888481 | 0.280112138 |
| cg22859289 | LOC101927248 | S_Shore | Body | 4.75129 | 0.000621 | 0.276602955 | 0.360681745 |
| cg22876812 | LINC01143 | Island | Body | 5.57666 | 1.47E-07 | 0.186988353 | 0.351329937 |
| cg22878622 | TCF24 | Island | Body | 13.8512 | 1.43E-09 | 0.144264364 | 0.270933809 |
| cg22882523 | OPLAH | Island | Body | 11.8791 | 6.70E-06 | 0.448850134 | 0.569208691 |
| cg22888055 | ITPKA | S_Shore | 3UTR | 24.6165 | 7.52E-10 | 0.436490881 | 0.606547041 |
| cg22897615 | PRRT1 | Island | Body | 3.84647 | 0.006841 | 0.619061517 | 0.697345682 |
| cg22900229 | POMC | Island | TSS1500 | 5.33411 | 0.000301 | 0.333085078 | 0.442527124 |
| cg22902505 | PRDM8 | S_Shore | 5URT | 3.54023 | 0.000843 | 0.276370197 | 0.349599736 |
| cg22937649 | NTN1 | Island | Body | 13.5905 | 1.68E-14 | 0.106284316 | 0.368860752 |
| cg22951509 | GPR150 | Island | TSS200 | 10.0424 | 1.67E-05 | 0.181613438 | 0.2762579 |
| cg22973789 | SATB2 | Island | 5URT | 3.48414 | 0.00446 | 0.114521178 | 0.191994366 |
| cg22975961 | WT1-AS | N_Shelf | Body | 3.80356 | 0.001312 | 0.351106634 | 0.452161401 |
| cg22976224 | SIM2 | Island | TSS1500 | 8.46301 | 7.98E-07 | 0.077895895 | 0.174327331 |
| cg22982368 | PAX6 | Island | TSS200 | 11.8471 | 1.29E-13 | 0.197057369 | 0.432168778 |
| cg22997113 | HOXA4 | Island | 1stExon | 5.18912 | 0.006029 | 0.431223853 | 0.457729909 |
| cg23016129 | SPAG6 | Island | TSS200 | 21.0506 | 1.72E-12 | 0.178919671 | 0.364979752 |
| cg23027574 | RNF39 | Island | 1stExon | 5.29116 | 5.34E-05 | 0.251970986 | 0.374812267 |
| cg23042510 | EBF3 | Island | Body | 10.6104 | 5.61E-07 | 0.122017123 | 0.231835397 |
| cg23044079 | FOXI3 | Island | 1stExon | 6.03851 | 0.000399 | 0.202877564 | 0.267768172 |
| cg23051664 | TNFRSF10D | N_Shore | Body | 7.86272 | 8.87E-06 | 0.118847589 | 0.213830427 |
| cg23054289 | TRIM58 | Island | 1stExon | 15.2492 | 5.38E-14 | 0.188259264 | 0.43685849 |
| cg23064601 | PITX1 | Island | Body | 21.1745 | 3.31E-07 | 0.411121927 | 0.531312982 |
| cg23068797 | MIR199A1 | | TSS1500 | 20.7834 | 2.47E-06 | 0.671865202 | 0.797639919 |
| cg23082339 | PCDHGA12 | S_Shelf | TSS200 | 4.03889 | 0.002182 | 0.102695718 | 0.181629681 |
| cg23097402 | DMRTA2 | Island | 3UTR | 5.48978 | 8.48E-05 | 0.216296137 | 0.327091954 |
| cg23100152 | AMPD3 | Island | TSS200 | 3.34808 | 0.00484 | 0.131480948 | 0.211547722 |
| cg23104954 | DLEU1 | Island | Body | 5.41075 | 0.000286 | 0.42306875 | 0.522236282 |
| cg23125492 | PAX6 | Island | Body | 15.9741 | 6.30E-11 | 0.251836022 | 0.429903922 |
| cg23129270 | HOXA-AS3 | Island | Body | 17.4303 | 1.45E-07 | 0.338158326 | 0.437141859 |
| cg23130254 | HOXD12 | Island | 1stExon | 13.3545 | 6.87E-08 | 0.124428058 | 0.22551666 |
| cg23158731 | COL14A1 | Island | 5URT | 6.63561 | 1.36E-07 | 0.140430404 | 0.289315465 |
| cg23165310 | SOX2-OT | | Body | 6.02918 | 2.83E-05 | 0.298211924 | 0.403143336 |
| cg23167906 | FGF19 | S_Shore | Body | 3.50823 | 0.001774 | 0.188961676 | 0.262867646 |
| cg23196831 | COL14A1 | Island | 1stExon | 11.5137 | 9.36E-08 | 0.181447871 | 0.320937438 |
| cg23218559 | AMH | Island | Body | 12.4766 | 2.66E-09 | 0.232576255 | 0.406197975 |
| cg23229261 | OTX1 | Island | Body | 7.10692 | 2.56E-09 | 0.165176781 | 0.353178044 |
| cg23244790 | PCDHGA12 | Island | 1stExon | 8.30347 | 7.70E-10 | 0.231109879 | 0.45777318 |
| cg23244913 | HCG9 | N_Shore | Body | 7.48065 | 2.46E-06 | 0.365494322 | 0.54155302 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg23268208 | HORMAD2 | Island | TSS200 | 13.7572 | 2.32E−08 | 0.252420597 | 0.360956081 |
| cg23278196 | ATP5G2 | Island | TSS1500 | 3.87564 | 0.000705 | 0.088454962 | 0.186450567 |
| cg23286646 | SIM2 | Island | Body | 4.86857 | 1.18E−05 | 0.219794027 | 0.354247731 |
| cg23290344 | NEFM | Island | TSS1500 | 12.4376 | 2.03E−14 | 0.139231716 | 0.372266651 |
| cg23345004 | KATNAL2 | N_Shore | TSS1500 | 7.96059 | 1.53E−05 | 0.500575095 | 0.659920881 |
| cg23357257 | SEZ6L2 | Island | Body | 12.3914 | 2.73E−06 | 0.365022309 | 0.494450385 |
| cg23442209 | LBX1-AS1 | N_Shore | Body | 6.5594 | 1.28E−05 | 0.196035255 | 0.324344519 |
| cg23445461 | PCDHGC4 | Island | TSS200 | 4.8621 | 2.15E−06 | 0.303451733 | 0.502209951 |
| cg23483840 | HLA-J | Island | Body | 5.8642 | 4.60E−05 | 0.120279602 | 0.230990284 |
| cg23497383 | LOC151174 | Island | Body | 6.4894 | 7.37E−06 | 0.341004812 | 0.497464532 |
| cg23500724 | RNF39 | Island | 1stExon | 4.68294 | 0.000778 | 0.058372736 | 0.134162122 |
| cg23501406 | DRD4 | Island | TSS1500 | 26.0624 | 8.99E−11 | 0.245814062 | 0.417622791 |
| cg23503176 | LBX1-AS1 | S_Shore | Body | 8.70704 | 5.13E−06 | 0.186153121 | 0.282366413 |
| cg23511613 | FOXI3 | Island | TSS1500 | 6.41775 | 3.90E−07 | 0.075169072 | 0.195152508 |
| cg23513966 | ISL2 | Island | Body | 8.89981 | 0.000268 | 0.284522008 | 0.344287657 |
| cg23514619 | TTBK1 | Island | Body | 4.02301 | 0.000856 | 0.125150023 | 0.205127556 |
| cg23528400 | TRIM71 | Island | TSS200 | 13.7847 | 7.19E−09 | 0.093515739 | 0.204913171 |
| cg23530553 | HOXB-AS1 | S_Shore | Body | 4.96747 | 0.001176 | 0.470218775 | 0.559645081 |
| cg23546474 | PAX3 | Island | Body | 5.39576 | 0.000368 | 0.463882674 | 0.552153538 |
| cg23586322 | COL14A1 | S_Shelf | 5URT | 7.07347 | 1.43E−06 | 0.46711853 | 0.62595027 |
| cg23587449 | LRAT | N_Shore | 5URT | 10.7775 | 2.50E−05 | 0.130083934 | 0.205671265 |
| cg23598080 | LHX4 | Island | Body | 7.49566 | 0.000239 | 0.143535736 | 0.205230488 |
| cg23619365 | LINC00403 | Island | Body | 8.63652 | 1.15E−07 | 0.103818198 | 0.221808533 |
| cg23619399 | RNF219-AS1 | N_Shore | Body | 8.88908 | 1.65E−06 | 0.261460278 | 0.331275873 |
| cg23623622 | TRIM15 | Island | Body | 4.46835 | 0.008133 | 0.151855743 | 0.217229153 |
| cg23634124 | DLX4 | Island | Body | 4.92389 | 0.000471 | 0.257215491 | 0.350835693 |
| cg23637494 | LINC01391 | N_Shore | TSS1500 | 6.25304 | 4.67E−05 | 0.292638345 | 0.385950087 |
| cg23655970 | PAX9 | S_Shore | TSS200 | 4.41708 | 0.00161 | 0.163220498 | 0.231557932 |
| cg23663774 | PITX2 | Island | 5URT | 9.30858 | 2.94E−08 | 0.067928751 | 0.164025673 |
| cg23676151 | NR2E1 | Island | Body | 9.91886 | 1.13E−06 | 0.449251457 | 0.598177879 |
| cg23683588 | PAX9 | Island | Body | 8.08678 | 7.29E−08 | 0.120659357 | 0.262138377 |
| cg23695707 | GSC | Island | 3UTR | 4.62315 | 0.000142 | 0.168637961 | 0.281846693 |
| cg23697546 | HOXC6 | S_Shore | 3UTR | 4.82912 | 0.000101 | 0.186174868 | 0.286545028 |
| cg23707289 | BLC2 | S_Shelf | TSS1500 | 8.45746 | 1.37E−05 | 0.218283002 | 0.319906794 |
| cg23712018 | RNF39 | Island | Body | 10.1331 | 2.67E−07 | 0.140609447 | 0.257377802 |
| cg23724641 | LYPD1 | Island | 5URT | 7.61781 | 0.000192 | 0.145698396 | 0.210488969 |
| cg23740652 | PTPRN2 | S_Shore | Body | 7.13035 | 0.00589 | 0.803957612 | 0.859832646 |
| cg23767994 | DLX6-AS1 | | Body | 7.80921 | 2.51E−06 | 0.331337767 | 0.448147069 |
| cg23792314 | BCAT1 | Island | TSS1500 | 12.6155 | 4.56E−08 | 0.140783788 | 0.253710807 |
| cg23829024 | HIST1H1A | N_Shelf | TSS200 | 7.68857 | 2.27E−07 | 0.229658204 | 0.380509071 |
| cg23831143 | TNFRSF10C | Island | 5URT | 55.4052 | 8.36E−10 | 0.489023538 | 0.663491341 |
| cg23847722 | DRD5 | Island | TSS200 | 6.90811 | 1.47E−06 | 0.155066689 | 0.291915593 |
| cg23874561 | PRDM8 | Island | Body | 9.87044 | 6.78E−10 | 0.111619412 | 0.280528361 |
| cg23880589 | KCNAB3 | S_Shore | Body | 29.753 | 1.05E−08 | 0.398107899 | 0.513836758 |
| cg23896126 | SIM2 | Island | 3UTR | 21.0144 | 3.52E−06 | 0.510540417 | 0.613669129 |
| cg23907108 | NRXN2 | N_Shelf | Body | 13.9937 | 1.03E−06 | 0.426980853 | 0.554542384 |
| cg23917057 | FOXI3 | Island | TSS1500 | 11.6 | 4.79E−09 | 0.220920102 | 0.373813957 |
| cg23933618 | DKFZp686K1684 | Island | TSS1500 | 6.36392 | 4.12E−07 | 0.167953229 | 0.303772567 |
| cg23937893 | WNT10A | Island | Body | 6.23231 | 0.001129 | 0.264951309 | 0.353386735 |
| cg23939808 | RNF39 | Island | 1stExon | 4.668 | 9.13E−05 | 0.091813884 | 0.198822377 |
| cg23941075 | PCDHB15 | S_Shelf | 5URT | 9.35336 | 5.43E−06 | 0.203467116 | 0.309065099 |
| cg23965061 | TNFRSF10C | Island | 5URT | 12.1175 | 5.39E−08 | 0.178507434 | 0.318997626 |
| cg23971069 | PROX1-AS1 | N_Shelf | 5URT | 19.3112 | 1.20E−07 | 0.267771527 | 0.36612499 |
| cg23973429 | GRHL2 | Island | 5URT | 85.3366 | 7.33E−09 | 0.407950783 | 0.566660424 |
| cg23974473 | PCDHB15 | N_Shore | 1stExon | 10.4647 | 5.39E−05 | 0.617862039 | 0.727866848 |
| cg23979631 | HOXA2 | N_Shelf | TSS200 | 7.47665 | 1.10E−05 | 0.173805747 | 0.272675545 |
| cg23994043 | SATB2 | Island | 5URT | 4.47791 | 0.000233 | 0.273602127 | 0.361899128 |
| cg24001710 | EN1 | Island | TSS1500 | 5.04029 | 0.000374 | 0.175106502 | 0.246951919 |
| cg24005685 | PITX2 | Island | Body | 14.273 | 3.52E−10 | 0.157821613 | 0.272118806 |
| cg24008908 | AKR7A3 | Island | TSS200 | 12.6395 | 3.09E−08 | 0.366760932 | 0.568326313 |
| cg24016627 | RNF39 | Island | 1stExon | 4.3238 | 6.15E−05 | 0.081081917 | 0.194659067 |
| cg24030449 | FGF20 | S_Shore | 1stExon | 5.23328 | 0.000118 | 0.412238089 | 0.552448481 |
| cg24039697 | GATA3-AS1 | Island | Body | 3.43044 | 0.000236 | 0.245337404 | 0.409261579 |
| cg24051554 | C2CD4D | Island | 5URT | 7.34684 | 4.93E−07 | 0.285531122 | 0.447180062 |
| cg24080247 | SIM2 | S_Shore | Body | 6.72944 | 6.81E−07 | 0.161306786 | 0.293104493 |
| cg24157892 | TBX2-AS1 | Island | Body | 5.88056 | 3.92E−06 | 0.119243805 | 0.23065081 |
| cg24169669 | TTC6 | Island | Body | 8.14047 | 7.17E−11 | 0.219806976 | 0.452180468 |
| cg24228707 | DLX1 | S_Shelf | TSS1500 | 5.68754 | 3.79E−05 | 0.2319201 | 0.330308325 |
| cg24241823 | HOXB3 | S_Shelf | 5URT | 3.53374 | 0.009604 | 0.590567566 | 0.659156768 |
| cg24280832 | C10orf11 | N_Shore | Body | 9.31918 | 0.001074 | 0.76451676 | 0.854504778 |
| cg24309555 | APOB | Island | TSS200 | 6.81403 | 0.000727 | 0.47869114 | 0.574216768 |
| cg24328539 | GATM | Island | TSS200 | 3.46508 | 0.007076 | 0.240330661 | 0.331177869 |
| cg24330456 | RNF39 | N_Shelf | Body | 10.5698 | 1.53E−05 | 0.662954644 | 0.801047505 |
| cg24351901 | HLA-F | Island | Body | 31.2632 | 1.57E−07 | 0.466853688 | 0.583886788 |
| cg24354581 | SIM2 | N_Shore | Body | 4.58415 | 0.000412 | 0.213289015 | 0.305992435 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg24370475 | FGF19 | S_Shore | Body | 5.74453 | 1.92E−05 | 0.142829115 | 0.244095591 |
| cg24375215 | CD300A | | 5URT | 8.45314 | 8.18E−07 | 0.314102137 | 0.464290485 |
| cg24382527 | ADAM8 | Island | 1stExon | 4.31291 | 0.000739 | 0.124411883 | 0.214731954 |
| cg24425021 | POU4F1 | N_Shelf | 1stExon | 13.3206 | 8.50E−09 | 0.05114992 | 0.159439107 |
| cg24425171 | POMC | Island | TSS200 | 5.51594 | 0.000316 | 0.458558334 | 0.585620717 |
| cg24425838 | C2CD4D | Island | 5URT | 8.04978 | 4.06E−05 | 0.577504616 | 0.716433145 |
| cg24426072 | TRIL | Island | Body | 9.10441 | 3.87E−07 | 0.096674815 | 0.19428478 |
| cg24430580 | PITX2 | Island | 1stExon | 18.593 | 2.33E−10 | 0.200261234 | 0.335632042 |
| cg24446586 | HOXA11-AS | Island | Body | 18.7192 | 8.44E−07 | 0.419317947 | 0.538348879 |
| cg24453580 | PRPH | Island | Body | 4.08088 | 0.000156 | 0.1640223 | 0.272120074 |
| cg24479590 | CHRNB1 | Island | TSS200 | 6.48528 | 7.18E−07 | 0.243173068 | 0.400215708 |
| cg24524285 | NRXN2 | N_Shore | Body | 12.672 | 8.09E−07 | 0.479458597 | 0.602308889 |
| cg24535439 | MMP23B | Island | TSS1500 | 16.759 | 3.48E−12 | 0.268441284 | 0.480289835 |
| cg24550149 | TTC22 | Island | Body | 8.97432 | 1.94E−05 | 0.563631047 | 0.674299828 |
| cg24565496 | LMF1 | Island | TSS1500 | 53.2216 | 3.20E−12 | 0.327989706 | 0.491670521 |
| cg24575083 | CYB5R2 | Island | TSS1500 | 6.53952 | 1.27E−05 | 0.332238009 | 0.473399612 |
| cg24582934 | RGCC | S_Shore | Body | 6.77881 | 3.71E−05 | 0.23754295 | 0.358488555 |
| cg24592027 | DBX1 | N_Shore | TSS1500 | 5.67804 | 0.001973 | 0.140878014 | 0.197944163 |
| cg24628744 | H2AFY | S_Shore | TSS1500 | 7.57965 | 4.39E−07 | 0.298722368 | 0.438587136 |
| cg24630419 | ESRRG | Island | TSS1500 | 9.71741 | 1.23E−06 | 0.225442794 | 0.340091548 |
| cg24633978 | HOXD11 | S_Shore | 1stExon | 14.6389 | 7.33E−10 | 0.13621414 | 0.286895208 |
| cg24646414 | GATA4 | Island | 5URT | 8.6012 | 8.40E−07 | 0.274792632 | 0.414211108 |
| cg24657817 | BEND4 | Island | Body | 11.7396 | 2.54E−11 | 0.13015339 | 0.29672914 |
| cg24663845 | SLC4A13 | | TSS200 | 22.9315 | 4.13E−08 | 0.491411442 | 0.628085667 |
| cg24683414 | GFI1 | Island | TSS1500 | 14.7337 | 7.29E−05 | 0.504974193 | 0.597381483 |
| cg24697184 | TTC22 | Island | 1stExon | 12.7557 | 5.48E−07 | 0.329935798 | 0.458033191 |
| cg24701575 | DKFZp686K1684 | N_Shore | Body | 10.6083 | 1.58E−08 | 0.349888943 | 0.532783919 |
| cg24721899 | NKX3-2 | Island | Body | 12.1962 | 9.34E−12 | 0.151703874 | 0.33521706 |
| cg24725574 | HLA-J | Island | Body | 5.07393 | 0.000682 | 0.07796217 | 0.154549086 |
| cg24727399 | QRFPR | Island | TSS200 | 7.65875 | 3.66E−08 | 0.113600428 | 0.272340194 |
| cg24745495 | EPHX3 | Island | TSS1500 | 71.2682 | 6.88E−15 | 0.293213641 | 0.468886086 |
| cg24747764 | LINC00403 | S_Shore | TSS1500 | 9.47399 | 9.84E−04 | 0.155334642 | 0.264396424 |
| cg24787138 | TTBK1 | Island | Body | 11.0163 | 1.06E−05 | 0.44878814 | 0.567278929 |
| cg24796272 | STK3 | N_Shore | 1stExon | 4.51356 | 0.005053 | 0.364208086 | 0.433055798 |
| cg24797840 | GATA3-AS1 | Island | Body | 3.08176 | 0.006193 | 0.244332112 | 0.33097299 |
| cg24804179 | PRPH | Island | Body | 3.92504 | 0.008539 | 0.186555185 | 0.251161329 |
| cg24880701 | SKOR1 | Island | Body | 12.0383 | 1.40E−09 | 0.18221125 | 0.363152841 |
| cg24896649 | ZFP42 | Island | TS200 | 12.5101 | 1.40E−13 | 0.162287041 | 0.392712148 |
| cg24901042 | TMPRSS2 | Island | TSS1500 | 3.83391 | 0.009399 | 0.290989035 | 0.359391135 |
| cg24913868 | NKX2-3 | N_Shelf | 5UTR | 10.0149 | 1.10E−06 | 0.314263032 | 0.412929301 |
| cg24914355 | HOXD13 | S_Shelf | Body | 11.7194 | 1.64E−09 | 0.204600198 | 0.380260256 |
| cg24927800 | DES | Island | 1stExon | 10.5912 | 1.35E−10 | 0.140562602 | 0.326382139 |
| cg24928391 | SOX17 | Island | TSS200 | 5.23559 | 0.000496 | 0.081429571 | 0.16216134 |
| cg24933173 | SHF | S_Shore | 5URT | 7.38014 | 7.66E−06 | 0.094971677 | 0.19938698 |
| cg24951286 | PCDHB15 | S_Shelf | 5URT | 7.74918 | 4.36E−05 | 0.290059291 | 0.37683902 |
| cg24953321 | TRIM71 | S_Shore | Body | 4.69296 | 0.00569 | 0.381839648 | 0.456402129 |
| cg24988255 | HOXA11-AS | Island | Body | 5.53106 | 0.000533 | 0.265744748 | 0.340130847 |
| cg25008858 | SPEG | Island | Body | 21.5039 | 3.99E−06 | 0.504573092 | 0.624879778 |
| cg25032094 | MYO15B | Island | TSS1500 | 15.331 | 1.08E−07 | 0.456609021 | 0.620584928 |
| cg25034395 | HPSE2 | S_Shelf | TSS1500 | 5.09092 | 0.000662 | 0.402043378 | 0.514921873 |
| cg25035485 | APOB | N_Shore | Body | 3.34154 | 0.005895 | 0.477120519 | 0.586136599 |
| cg25044651 | LVRN | Island | 1stExon | 12.6662 | 2.05E−07 | 0.209436771 | 0.332881008 |
| cg25051331 | LOC101929154 | Island | TSS1500 | 7.32715 | 0.000242 | 0.177458389 | 0.243695189 |
| cg25062797 | VAX1 | Island | Body | 3.51017 | 0.003409 | 0.18238856 | 0.272392099 |
| cg25071744 | APOB | S_Shore | TSS200 | 8.99596 | 0.001005 | 0.560700209 | 0.637106313 |
| cg25083618 | CYP26C1 | Island | TSS200 | 7.0896 | 0.001695 | 0.609983659 | 0.685111354 |
| cg25112312 | ZNF518B | Island | TSS1500 | 14.871 | 4.15E−07 | 0.283440614 | 0.395711422 |
| cg25125060 | NR2E1 | Island | TSS1500 | 7.42331 | 0.001244 | 0.482871279 | 0.552940444 |
| cg25160978 | GDF7 | N_Shelf | TSS1500 | 7.65188 | 9.43E−07 | 0.10427144 | 0.231791465 |
| cg25161512 | PON3 | Island | TSS1500 | 11.1007 | 1.25E−06 | 0.261804003 | 0.375530995 |
| cg25188395 | HOXA9 | Island | Body | 4.37431 | 0.000316 | 0.171249677 | 0.259552867 |
| cg25192855 | IRF6 | N_Shore | 5URT | 16.6074 | 2.95E−09 | 0.421099306 | 0.6404799 |
| cg25196158 | PROX1-AS1 | N_Shelf | Body | 4.87306 | 0.000105 | 0.250761262 | 0.35518823 |
| cg25200152 | NBPF8 | S_Shore | Body | 6.97059 | 3.27E−07 | 0.233071439 | 0.378369403 |
| cg25203481 | KCNQ1DN | Island | TSS200 | 5.19083 | 8.70E−05 | 0.260605263 | 0.378628758 |
| cg25212190 | LHX9 | S_Shore | Body | 7.49612 | 7.25E−06 | 0.167839743 | 0.254862429 |
| cg25247290 | WT1-AS | S_Shore | Body | 16.7301 | 1.58E−13 | 0.196596173 | 0.372124214 |
| cg25258843 | SOX7 | Island | Body | 6.04651 | 0.000114 | 0.363064993 | 0.479177466 |
| cg25307665 | HOXA5 | Island | TSS1500 | 5.93145 | 4.11E−05 | 0.324350438 | 0.42384864 |
| cg25318809 | HLA-J | Island | Body | 5.64026 | 2.09E−05 | 0.113565088 | 0.227900399 |
| cg25330243 | GRHL2 | Island | TSS200 | 8.01586 | 8.42E−09 | 0.189124865 | 0.373253666 |
| cg25336332 | THRB-AS1 | Island | Body | 4.89357 | 0.000386 | 0.556842095 | 0.67117136 |
| cg25342207 | EBF3 | | Body | 13.1495 | 0.001497 | 0.747840395 | 0.810068869 |
| cg25371919 | OTX1 | S_Shore | Body | 10.513 | 4.56E−07 | 0.488625012 | 0.634837316 |
| cg25377206 | TBX20 | Island | TSS1500 | 14.328 | 9.57E−09 | 0.413568473 | 0.549091909 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg25382400 | SOX2-OT | S_Shore | Body | 7.50343 | 1.84E−05 | 0.269019012 | 0.387940161 |
| cg25390165 | HOXA5 | Island | TSS1500 | 11.6613 | 0.000146 | 0.397156682 | 0.458243424 |
| cg25412546 | OTP | Island | 3UTR | 9.62002 | 1.94E−06 | 0.168593483 | 0.261996869 |
| cg25437411 | HPSE2 | S_Shelf | TSS1500 | 3.27338 | 0.007114 | 0.153940144 | 0.230454038 |
| cg25442600 | IRX4 | S_Shore | TSS1500 | 3.7993 | 0.001734 | 0.412884144 | 0.512836301 |
| cg25471923 | HOTTIP | N_Shelf | Body | 8.16751 | 6.87E−05 | 0.304269897 | 0.406051929 |
| cg25478600 | KCNQ1DN | Island | TSS1500 | 4.29621 | 0.000306 | 0.222243894 | 0.328805502 |
| cg25479916 | HIST1H31 | S_Shore | TSS1500 | 7.44871 | 8.35E−08 | 0.223387767 | 0.373628442 |
| cg25485294 | HIST1H31 | S_Shore | TSS1500 | 8.39854 | 6.04E−09 | 0.20296936 | 0.388257668 |
| cg25506432 | HOXA5 | Island | TSS1500 | 10.37 | 0.000356 | 0.671558364 | 0.751274333 |
| cg25527090 | VAX1 | Island | Body | 4.75398 | 0.000603 | 0.22171125 | 0.315296307 |
| cg25536137 | GATA3-AS1 | Island | Body | 5.69024 | 0.000979 | 0.140877152 | 0.222272837 |
| cg25539045 | FOXI2 | Island | TSS1500 | 11.2076 | 2.42E−07 | 0.435622679 | 0.617786807 |
| cg25547580 | ONECUT2 | Island | 1stExon | 8.44103 | 1.03E−09 | 0.124406002 | 0.291231792 |
| cg25576011 | FOXI2 | Island | TSS200 | 7.79966 | 1.66E−07 | 0.173596996 | 0.332067053 |
| cg25586361 | WT1 | N_Shelf | Body | 5.1979 | 0.001054 | 0.34646815 | 0.431798869 |
| cg25593794 | TP73 | | 5URT | 9.26225 | 0.003298 | 0.659005729 | 0.706849687 |
| cg25608490 | WNT16 | N_Shore | Body | 9.8664 | 1.54E−06 | 0.320328894 | 0.451435535 |
| cg25622366 | OTX1 | Island | Body | 13.1368 | 3.37E−15 | 0.153557254 | 0.408855264 |
| cg25639415 | GRHL2 | Island | TSS200 | 8.46181 | 2.24E−07 | 0.226757884 | 0.390591678 |
| cg25678088 | DLX6-AS1 | S_Shore | Body | 15.713 | 1.70E−07 | 0.307650186 | 0.414402939 |
| cg25685262 | PDX1 | S_Shore | TSS1500 | 17.3908 | 3.58E−07 | 0.19105396 | 0.280696763 |
| cg25702780 | MECOM | N_Shelf | 5URT | 7.75589 | 0.000101 | 0.099598867 | 0.180158912 |
| cg25720804 | TLX3 | Island | 1stExon | 11.22 | 2.70E−10 | 0.114630116 | 0.265155621 |
| cg25746778 | EBF3 | Island | Body | 3.84577 | 8.24E−05 | 0.390170692 | 0.561990607 |
| cg25755575 | ESRRG | Island | TSS1500 | 10.5222 | 9.44E−09 | 0.186347842 | 0.333320779 |
| cg25756435 | MAST1 | Island | Body | 14.1342 | 1.12E−10 | 0.056817843 | 0.193368065 |
| cg25775494 | NR2E1 | S_Shore | Body | 12.4111 | 1.04E−06 | 0.192080868 | 0.315540502 |
| cg25782229 | WT1 | N_Shore | Body | 5.08188 | 5.53E−05 | 0.291332308 | 0.426482596 |
| cg25802093 | SPAG6 | Island | TSS1500 | 12.0008 | 4.58E−07 | 0.261892001 | 0.382851879 |
| cg25835733 | GAD2 | S_Shelf | TSS1500 | 16.7435 | 3.21E−06 | 0.40886986 | 0.51689504 |
| cg25845597 | HIST1H3I | Island | TSS1500 | 22.2672 | 1.37E−11 | 0.102347663 | 0.228474179 |
| cg25845985 | PRRT1 | Island | Body | 7.58847 | 0.00111 | 0.398367349 | 0.479750485 |
| cg25851789 | ESRRG | N_Shore | 5URT | 7.55386 | 1.18E−07 | 0.238601846 | 0.39876221 |
| cg25884711 | NPY | Island | 1stExon | 6.57281 | 6.22E−07 | 0.067096877 | 0.173597491 |
| cg25887069 | GALR3 | Island | Body | 8.14393 | 7.99E−06 | 0.074521401 | 0.17966753 |
| cg25903779 | LOC101929076 | Island | Body | 4.43091 | 2.06E−05 | 0.239431807 | 0.387931609 |
| cg25903783 | TBX2-AS1 | Island | Body | 7.76112 | 0.000577 | 0.412828961 | 0.489642374 |
| cg25916711 | NKX2-5 | Island | 3UTR | 11.4637 | 4.57E−09 | 0.108888036 | 0.242450121 |
| cg25923240 | SOX17 | S_Shore | 3UTR | 4.88709 | 0.004845 | 0.511143581 | 0.588707525 |
| cg25930229 | LBX1-AS1 | S_Shore | Body | 13.9234 | 8.77E−07 | 0.451616922 | 0.625450517 |
| cg25939676 | SHISA3 | N_Shore | TSS1500 | 7.39638 | 9.41E−06 | 0.117279008 | 0.207519362 |
| cg25942450 | TLX3 | Island | TSS200 | 10.9743 | 1.08E−06 | 0.324578629 | 0.460319566 |
| cg25960038 | HOXB-AS3 | N_Shore | Body | 9.70669 | 1.87E−07 | 0.410568783 | 0.561982182 |
| cg25965471 | TTBK1 | Island | 1stExon | 5.93549 | 1.40E−05 | 0.326181665 | 0.468041207 |
| cg25984671 | TCF15 | Island | TSS200 | 8.43721 | 2.22E−08 | 0.134977915 | 0.289996672 |
| cg25988034 | GATA3-AS1 | Island | ExonBnd | 4.38813 | 0.000249 | 0.192513788 | 0.306488474 |
| cg26000619 | AMH | Island | Body | 7.39291 | 4.48E−08 | 0.348938581 | 0.543758393 |
| cg26006870 | GATA4 | S_Shore | 5URT | 6.81839 | 0.000134 | 0.42045824 | 0.520033808 |
| cg26006951 | TERT | S_Shore | TSS1500 | 13.8185 | 8.42E−06 | 0.331547036 | 0.423735485 |
| cg26019112 | PAX6 | Island | Body | 21.2925 | 2.34E−12 | 0.188893009 | 0.358015893 |
| cg26057751 | CD8A | Island | Body | 8.88691 | 2.27E−07 | 0.292058771 | 0.445982855 |
| cg26058074 | MECOM | Island | TSS200 | 7.91242 | 0.000188 | 0.172968013 | 0.26075307 |
| cg26060971 | DNAH1 | | Body | 14.689 | 0.000424 | 0.599878248 | 0.686936646 |
| cg26067760 | HPSE2 | S_Shelf | TSS1500 | 7.38632 | 5.07E−07 | 0.375213837 | 0.525892972 |
| cg26069745 | HOXA2 | N_Shelf | 1stExon | 13.0658 | 3.34E−06 | 0.351834764 | 0.44697104 |
| cg26072906 | BATF3 | S_Shore | TSS1500 | 6.68444 | 1.06E−07 | 0.17365335 | 0.362048732 |
| cg26094599 | WNT10A | Island | Body | 76.9534 | 2.04E−07 | 0.581748767 | 0.700005727 |
| cg26094789 | PAX9 | Island | Body | 5.64759 | 0.000592 | 0.435690047 | 0.544594788 |
| cg26099134 | SIM1 | Island | ExonBnd | 7.58624 | 7.43E−06 | 0.268121495 | 0.371403074 |
| cg26115633 | FOXI2 | Island | 1stExon | 8.05555 | 8.71E−08 | 0.38540356 | 0.558311436 |
| cg26144458 | SIM2 | Island | TSS1500 | 8.72753 | 5.94E−05 | 0.261333946 | 0.351203622 |
| cg26149275 | EVX2 | Island | TSS1500 | 7.15986 | 4.85E−07 | 0.236275136 | 0.399529956 |
| cg26151467 | SOX1 | S_Shore | 3UTR | 4.33594 | 0.000215 | 0.241894916 | 0.357166732 |
| cg26160218 | THRB-AS1 | S_Shore | Body | 4.27155 | 0.00289 | 0.569530752 | 0.670255192 |
| cg26176204 | AGAP1 | N_Shore | TSS1500 | 13.713 | 8.15E−05 | 0.326480151 | 0.483341919 |
| cg26190890 | HIST1H2BK | S_Shore | 3UTR | 5.04842 | 0.000278 | 0.484847692 | 0.604845826 |
| cg26195178 | IRX4 | Island | 5URT | 4.08092 | 0.000317 | 0.134972206 | 0.235857774 |
| cg26199906 | OPLAH | Island | Body | 6.909 | 3.37E−05 | 0.297374112 | 0.412710604 |
| cg26206948 | NKX2-5 | Island | TSS1500 | 26.0679 | 2.13E−09 | 0.385637357 | 0.527252323 |
| cg26212180 | VAX1 | S_Shore | TSS1500 | 8.46876 | 1.54E−06 | 0.151713372 | 0.255673904 |
| cg26214742 | H2AFY | S_Shore | TSS1500 | 16.5714 | 6.16E−08 | 0.467164116 | 0.586909495 |
| cg26224060 | GPR150 | Island | 1stExon | 17.5302 | 1.80E−08 | 0.302262295 | 0.422238172 |
| cg26241806 | APBB1IP | Island | TSS200 | 9.77631 | 2.78E−07 | 0.099475271 | 0.205115261 |
| cg26248075 | SIM1 | S_Shore | Body | 6.28913 | 4.92E−05 | 0.365692 | 0.4846957 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg26254045 | SPRED3 | S_Shore | Body | 7.04283 | 0.002009 | 0.52900457 | 0.601639822 |
| cg26256263 | RUNX3 | Island | TSS1500 | 3.70081 | 0.00062 | 0.348527662 | 0.449295081 |
| cg26259537 | HOXA10-AS | | Body | 6.73686 | 3.23E-05 | 0.155708133 | 0.254192375 |
| cg26261502 | DKFZp686K1684 | N_Shore | Body | 8.75406 | 8.13E-06 | 0.184531733 | 0.26259027 |
| cg26263263 | VAX1 | S_Shore | Body | 6.72144 | 0.000285 | 0.304858898 | 0.383230222 |
| cg26277730 | BCL2 | S_Shelf | TSS1500 | 4.63522 | 7.95E-05 | 0.191322874 | 0.308971636 |
| cg26277754 | LOC642366 | | Body | 11.6333 | 2.75E-09 | 0.183016824 | 0.333665734 |
| cg26295921 | PTPRN2 | N_Shore | Body | 11.7045 | 0.000133 | 0.538315244 | 0.631481646 |
| cg26296488 | DRD5 | Island | TSS200 | 4.13921 | 6.41E-05 | 0.149136715 | 0.281469118 |
| cg26299169 | PDX1 | Island | 3UTR | 4.77207 | 9.52E-05 | 0.114245238 | 0.216815945 |
| cg26309194 | TMPRSS2 | Island | TSS1500 | 4.33724 | 0.001059 | 0.384399108 | 0.483950244 |
| cg26322248 | ISM1 | Island | TSS1500 | 12.7477 | 1.43E-08 | 0.078599664 | 0.20826524 |
| cg26327071 | HOXB4 | S_Shore | TSS200 | 9.37065 | 5.56E-07 | 0.109497328 | 0.198771454 |
| cg26330518 | NEFM | N_Shore | TSS1500 | 17.2163 | 5.80E-10 | 0.307635028 | 0.508179908 |
| cg26331172 | SEMA6C | Island | 5URT | 5.11016 | 1.93E-05 | 0.349950231 | 0.518152009 |
| cg26365545 | OTP | N_Shelf | Body | 7.9715 | 5.46E-07 | 0.301894073 | 0.447436076 |
| cg26370729 | F2RL1 | Island | Body | 6.90473 | 1.85E-07 | 0.139148714 | 0.296043 |
| cg26371731 | C1orf61 | N_Shore | 5URT | 6.76108 | 2.40E-07 | 0.216201957 | 0.365090893 |
| cg26376168 | IER3 | Island | TSS200 | 5.00339 | 7.94E-04 | 0.22004826 | 0.36022581 |
| cg26380443 | PCDHB15 | S_Shelf | 1stExon | 3.80615 | 0.003727 | 0.142221797 | 0.213678939 |
| cg26388730 | NRXN2 | Island | Body | 7.24742 | 0.003485 | 0.533759465 | 0.600493909 |
| cg26410483 | LHX4 | Island | Body | 5.44455 | 0.000262 | 0.074242948 | 0.14889501 |
| cg26413174 | TTC22 | Island | 1stExon | 6.65187 | 6.30E-05 | 0.185177553 | 0.268575959 |
| cg26421310 | RUNX3 | Island | TSS1500 | 4.47804 | 0.0004434 | 0.137657345 | 0.20383534 |
| cg26422458 | ADGRL4 | Island | 1stExon | 8.0834 | 3.99E-08 | 0.211370453 | 0.383782913 |
| cg26429925 | BNC1 | Island | TSS1500 | 5.1253 | 0.0009 | 0.498803319 | 0.603335596 |
| cg26437825 | LOC648987 | S_Shore | TSS1500 | 6.81687 | 2.85E-06 | 0.206528777 | 0.351434737 |
| cg26446499 | LOC101929154 | N_Shore | TSS1500 | 12.0122 | 2.98E-12 | 0.239723033 | 0.455434442 |
| cg26457809 | KCNQ1DN | Island | TSS1500 | 5.69033 | 0.000164 | 0.36545956 | 0.485924214 |
| cg26476852 | HOXA8 | Island | 1stExon | 13.5927 | 3.67E-07 | 0.176670594 | 0.270323785 |
| cg26506288 | HOXB13 | S_Shelf | 3UTR | 5.19516 | 8.18E-05 | 0.217533988 | 0.331205621 |
| cg26517171 | TLX3 | Island | TSS1500 | 8.87894 | 2.60E-07 | 0.210043847 | 0.324803151 |
| cg26517714 | TLX3 | Island | TSS200 | 16.0372 | 5.44E-09 | 0.186080333 | 0.302858773 |
| cg26521404 | HOXA9 | Island | 1stExon | 11.9081 | 2.05E-08 | 0.066737467 | 0.172729722 |
| cg26551975 | HOXA10 | N_Shelf | Body | 4.10625 | 0.000433 | 0.159896935 | 0.259631492 |
| cg26559315 | LYNX1 | Island | 5URT | 4.97513 | 5.20E-06 | 0.160019299 | 0.295721502 |
| cg26560222 | DMRTA2 | Island | 1stExon | 8.18758 | 5.07E-07 | 0.224504707 | 0.332990389 |
| cg26585452 | DLEU1 | S_Shore | Body | 8.03656 | 0.000822 | 0.707903992 | 0.773862505 |
| cg26589785 | ITPKA | Island | Body | 18.5156 | 1.43E-08 | 0.366107466 | 0.529862714 |
| cg26601317 | KCNQ1DN | Island | TSS1500 | 4.74595 | 0.001343 | 0.278451437 | 0.359453891 |
| cg26618965 | TCF24 | Island | 5URT | 14.0539 | 1.56E-08 | 0.087905065 | 0.196064312 |
| cg26659805 | AMH | Island | Body | 13.4807 | 8.84E-09 | 0.279336936 | 0.457531811 |
| cg26660800 | TBX2 | Island | Body | 5.76442 | 0.001106 | 0.488101093 | 0.582014141 |
| cg26673012 | TBX20 | Island | TSS200 | 33.7769 | 8.01E-13 | 0.070220453 | 0.192037793 |
| cg26674479 | EVX1 | N_Shore | TSS1500 | 8.43421 | 0.000201 | 0.421966543 | 0.515589576 |
| cg26674943 | ISL2 | N_Shore | TSS1500 | 6.40645 | 0.003825 | 0.12725121 | 0.178737921 |
| cg26687072 | HOXB1 | Island | TSS200 | 5.97237 | 0.000281 | 0.429621984 | 0.514800384 |
| cg26690075 | WNT16 | N_Shore | Body | 11.7612 | 3.25E-09 | 0.338750395 | 0.508539336 |
| cg26698450 | ZNF274 | Island | 5URT | 9.32518 | 0.000139 | 0.56225555 | 0.640660171 |
| cg26701242 | SIM2 | N_Shore | Body | 7.02496 | 3.72E-05 | 0.213306933 | 0.295784498 |
| cg26702958 | LBX1-AS1 | Island | Body | 10.6897 | 6.32E-09 | 0.240206662 | 0.414780264 |
| cg26708319 | PITX2 | N_Shore | Body | 7.25131 | 1.99E-08 | 0.128863698 | 0.30390463 |
| cg26751356 | LINC00403 | Island | Body | 10.4959 | 1.57E-09 | 0.153902633 | 0.295522499 |
| cg26755097 | FLOT1 | Island | TSS1500 | 10.3497 | 5.14E-10 | 0.210337051 | 0.39845602 |
| cg26783057 | VAX1 | N_Shore | 3UTR | 7.50764 | 4.30E-08 | 0.200365347 | 0.352008325 |
| cg26796135 | GATM | Island | TSS200 | 3.97259 | 0.007881 | 0.195812144 | 0.277825016 |
| cg26811372 | PCDHGA8 | N_Shore | 5URT | 4.94074 | 0.000438 | 0.427603122 | 0.519320922 |
| cg26814075 | LEP | Island | TSS200 | 39.8104 | 6.47E-11 | 0.304399043 | 0.422158867 |
| cg26816907 | LHX9 | Island | Body | 11.7079 | 2.94E-07 | 0.34004184 | 0.474208497 |
| cg26844246 | TLX3 | Island | TSS200 | 14.7228 | 6.07E-10 | 0.236601845 | 0.401345928 |
| cg26848718 | WT1 | S_Shelf | Body | 25.0638 | 6.59E-15 | 0.170313747 | 0.372272164 |
| cg26870224 | MAST1 | S_Shore | ExonEnd | 9.22225 | 1.80E-08 | 0.162565004 | 0.318644265 |
| cg26879945 | PLLP | Island | TSS1500 | 8.54738 | 8.00E-05 | 0.253532887 | 0.36326841 |
| cg26890354 | PCDHGCA | N_Shore | TSS1500 | 6.04397 | 1.47E-05 | 0.228546397 | 0.341574774 |
| cg26951440 | LINC01475 | S_Shore | TSS1500 | 8.08893 | 1.62E-05 | 0.21718056 | 0.31402834 |
| cg26990102 | EN1 | Island | TSS1500 | 5.70395 | 1.34E-06 | 0.1999158 | 0.317105949 |
| cg26993537 | OTX2 | S_Shore | TSS200 | 3.54397 | 0.002488 | 0.315328522 | 0.398058144 |
| cg27009703 | HOXA8 | N_Shelf | 1stExon | 6.46776 | 0.000188 | 0.278100441 | 0.374885937 |
| cg27011060 | PAX6 | N_Shore | 5URT | 17.5783 | 2.29E-09 | 0.313376714 | 0.498753046 |
| cg27029217 | PRDM14 | Island | TSS200 | 14.4148 | 1.42E-05 | 0.32864667 | 0.418247576 |
| cg27032146 | DLX5 | Island | Body | 3.82544 | 0.002069 | 0.264300564 | 0.361466154 |
| cg27035251 | JAK3 | S_Shore | 1stExon | 11.6696 | 0.000134 | 0.332023276 | 0.423832606 |
| cg27076669 | CPM | Island | TSS1500 | 12.291 | 2.98E-07 | 0.225567823 | 0.32843323 |
| cg27090216 | TNFRSF10C | Island | 5URT | 45.8607 | 3.07E-11 | 0.366740871 | 0.533705566 |
| cg27100227 | EVX1 | S_Shelf | TSS1500 | 3.80347 | 0.000844 | 0.257902582 | 0.360956638 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg27110277 | FGF20 | S_Shore | TSS1500 | 14.9939 | 0.000127 | 0.660840682 | 0.758241394 |
| cg27111250 | PRDM8 | S_Shore | 5URT | 5.12804 | 0.002436 | 0.384845171 | 0.44477299 |
| cg27111463 | FOXI3 | Island | Body | 13.1549 | 2.17E-10 | 0.073416725 | 0.221830714 |
| cg27125849 | TBX2-AS1 | Island | Body | 6.58446 | 6.62E-05 | 0.130957402 | 0.227827024 |
| cg27151303 | HOXA-AS3 | Island | Body | 4.91726 | 0.001416 | 0.332094093 | 0.426663074 |
| cg27157482 | HOXA10-HOXA9 | N_Shelf | Body | 7.84846 | 4.90E-05 | 0.494402574 | 0.586097909 |
| cg27162435 | KCNAB3 | N_Shelf | TSS1500 | 12.5188 | 6.88E-05 | 0.640068473 | 0.731904596 |
| cg27183188 | ALDOC | | TSS200 | 12.1761 | 3.00E-08 | 0.272570781 | 0.459714938 |
| cg27190967 | SYNGR3 | N_Shore | TSS1500 | 6.01313 | 0.000219 | 0.422827019 | 0.531480815 |
| cg27234067 | WT1-AS | Island | Body | 7.93853 | 1.09E-05 | 0.260355707 | 0.362303911 |
| cg27252696 | SIM1 | Island | TSS1500 | 9.00942 | 7.13E-09 | 0.112319336 | 0.253240779 |
| cg27267227 | SEZ6L2 | Island | Body | 5.83417 | 6.05E-06 | 0.303641627 | 0.459877785 |
| cg27304406 | BNC1 | Island | TSS1500 | 8.36286 | 7.73E-05 | 0.324330193 | 0.416052447 |
| cg27309110 | JAK3 | Island | ExonEnd | 4.78704 | 0.0095 | 0.526012488 | 0.564634414 |
| cg27312652 | SIM2 | Island | Body | 10.2251 | 3.32E-05 | 0.176516904 | 0.235390672 |
| cg27363141 | RNF39 | N_Shelf | Body | 66.564 | 0.000183 | 0.840916341 | 0.915282121 |
| cg27364741 | OTX1 | Island | Body | 9.5317 | 3.67E-10 | 0.261176026 | 0.453886912 |
| cg27398720 | PITX2 | S_Shore | Body | 8.55604 | 0.000522 | 0.375857775 | 0.442852053 |
| cg27448110 | PTPRN2 | Island | Body | 20.5199 | 3.77E-07 | 0.354946636 | 0.465087303 |
| cg27449191 | IER3 | Island | Body | 11.9179 | 1.24E-11 | 0.161100357 | 0.371042507 |
| cg27493649 | RNF39 | Island | Body | 5.51227 | 0.000122 | 0.207871899 | 0.311842277 |
| cg27513574 | SLC34A2 | Island | 1stExon | 5.86041 | 1.43E-06 | 0.180614395 | 0.323174817 |
| cg27520776 | ESRRG | S_Shore | TSS1500 | 4.69708 | 6.98E-06 | 0.195413895 | 0.328023662 |
| cg27521974 | TLX1 | Island | Body | 4.31476 | 0.000348 | 0.339844224 | 0.451746313 |
| cg27526665 | THRB-AS1 | Island | Body | 6.427 | 1.03E-05 | 0.233645664 | 0.347253078 |
| cg27532187 | RNF39 | Island | 1stExon | 6.99188 | 2.17E-05 | 0.303351074 | 0.432222583 |
| cg27539480 | HOXA3 | S_Shore | 3UTR | 7.1808 | 0.003141 | 0.746917287 | 0.812943434 |
| cg27542551 | ACP5 | Island | 5URT | 10.5057 | 1.35E-05 | 0.176023701 | 0.266421349 |
| cg27583307 | SATB2 | Island | Body | 4.24446 | 0.000343 | 0.453051023 | 0.596273901 |
| cg27616661 | SYNGR3 | S_shore | Body | 4.50082 | 0.002228 | 0.070545111 | 0.14231126 |
| cg27622506 | THRB-AS1 | Island | Body | 4.16577 | 0.000678 | 0.271323889 | 0.367695458 |
| cg27639457 | CTNND2 | Island | Body | 13.7883 | 3.50E-05 | 0.344498339 | 0.426716335 |
| cg27639662 | PRDM8 | S_Shore | 5URT | 12.1934 | 1.67E-05 | 0.378570512 | 0.451179465 |
| cg27650870 | ANK1 | Island | Body | 5.20913 | 0.004457 | 0.40599055 | 0.469508333 |
| cg27656658 | HOXB-AS1 | N_Shelf | Body | 3.97558 | 0.009116 | 0.418402057 | 0.460684586 |
| cg27661315 | BEND4 | | Body | 6.36107 | 9.38E-05 | 0.449504772 | 0.552114101 |
| cg12627726 | KCNQ4 | | Body | 0.020674 | 1.92E-09 | 0.689301388 | 0.583260727 |
| cg06749480 | PBX1 | | Body | 0.104414 | 5.90E-06 | 0.779912519 | 0.689612949 |
| cg07152605 | PBX1 | | 3UTR | 0.077624 | 2.88E-07 | 0.709354581 | 0.607090081 |
| cg12689805 | TRIM58 | | 3UTR | 0.106512 | 2.16E-05 | 0.833637194 | 0.745223758 |
| cg22029075 | AGAP1 | S_Shore | Body | 0.48733 | 1.84E-17 | 0.907829836 | 0.70669701 |
| cg10186395 | AGAP1 | S_Shore | Body | 0.017036 | 1.31E-17 | 0.883728558 | 0.751125212 |
| cg02406098 | TRIM71 | | Body | 0.092085 | 5.08E-07 | 0.856285419 | 0.760925616 |
| cg20789595 | ADCY5 | | Body | 0.052227 | 4.57E-10 | 0.737646535 | 0.628378657 |
| cg19008133 | ADCY5 | | Body | 0.072667 | 7.89E-05 | 0.59904531 | 0.540487677 |
| cg07366462 | ADCY5 | N_Shelf | Body | 0.042033 | 5.68E-08 | 0.763565481 | 0.680088404 |
| cg01246398 | ADCY5 | N_Shore | Body | 0.008935 | 1.48E-07 | 0.40769562 | 0.313433704 |
| cg08598988 | ADCY5 | Island | 1stExon | 0.031784 | 5.19E-11 | 0.705115085 | 0.531770202 |
| cg25661931 | ADCY5 | Island | 1stExon | 0.099426 | 4.44E-10 | 0.788356822 | 0.587644677 |
| cg22989209 | TERT | N_Shelf | Body | 0.058527 | 4.58E-07 | 0.727614891 | 0.630747152 |
| cg04830757 | LINC00461 | | Body | 0.131857 | 7.67E-05 | 0.717647845 | 0.635406434 |
| cg26863842 | DDX39B | N_Shelf | Body | 0.134966 | 0.002986 | 0.717371922 | 0.673810131 |
| cg26177760 | DDX39B | N_Shore | Body | 0.154181 | 0.003356 | 0.552406372 | 0.499392 |
| cg24124954 | DDX39B | N_Shore | ExonEnd | 0.085151 | 5.67E-05 | 0.537161775 | 0.459137566 |
| cg24332685 | DDX39B | N_Shore | Body | 0.155806 | 0.000119 | 0.518894326 | 0.428966466 |
| cg21179831 | DDX39B | N_Shore | Body | 0.098026 | 9.45E-05 | 0.528587674 | 0.459850232 |
| cg21079591 | DDX39B | S_Shore | TSS1500 | 0.029469 | 6.20E-11 | 0.5503733 | 0.371283727 |
| cg25711558 | CUX1 | | Body | 0.13343 | 2.39E-05 | 0.64200962 | 0.54130583 |
| cg03787603 | CUX1 | | Body | 0.107143 | 1.32E-08 | 0.897665512 | 0.776925732 |
| cg11911769 | CUX1 | | Body | 0.06142 | 1.45E-09 | 0.740554333 | 0.621220253 |
| cg09244071 | CUX1 | | Body | 0.068613 | 3.76E-08 | 0.712450031 | 0.605724939 |
| cg15755348 | CUX1 | | Body | 0.140885 | 7.81E-06 | 0.801085449 | 0.697959239 |
| cg26651148 | PTPRN2 | | Body | 0.176769 | 8.00E-05 | 0.817612767 | 0.721452768 |
| cg14759472 | PTPRN2 | | Body | 0.155188 | 1.63E-06 | 0.907684791 | 0.792914495 |
| cg26170014 | PTPRN2 | | Body | 0.129983 | 1.45E-06 | 0.826677845 | 0.710134414 |
| cg10473311 | PTPRN2 | | Body | 0.082167 | 4.32E-06 | 0.593989473 | 0.485019758 |
| cg21584493 | PTPRN2 | Island | Body | 0.046209 | 7.20E-08 | 0.641590783 | 0.553388717 |
| cg26793019 | CSMD1 | | 3UTR | 0.044095 | 1.01E-10 | 0.875629806 | 0.769001051 |
| cg02563011 | CSMD1 | | Body | 0.121439 | 1.57E-05 | 0.754183341 | 0.659321232 |
| cg02616558 | CSMD1 | | Body | 0.077825 | 2.84E-06 | 0.694586605 | 0.604867343 |
| cg22663467 | CSMD1 | | Body | 0.098811 | 0.000222 | 0.825373853 | 0.769627687 |
| cg26837853 | CSMD1 | | Body | 0.072424 | 1.00E-08 | 0.777059845 | 0.647961384 |
| cg12269374 | CSMD1 | | Body | 0.057368 | 3.18E-09 | 0.725910907 | 0.600711755 |
| cg08236285 | CSMD1 | | Body | 0.03072 | 4.35E-11 | 0.74507245 | 0.606898727 |
| cg12042060 | CSMD1 | N_Shelf | Body | 0.050705 | 5.30E-11 | 0.772679473 | 0.634973586 |

TABLE 9-continued

| Source | Gene Symbol | Relation to UC5C CpG Island | UC5C RefGene Group | Univariate COX HR | P-value COX | Average Bvalue NotRecurrent | Average Bvalue Recurrent |
|---|---|---|---|---|---|---|---|
| cg14207539 | C10orf11 | | Body | 0.056835 | 7.73E-12 | 0.750300574 | 0.544735707 |
| cg23264016 | C10orf11 | | Body | 0.032029 | 1.94E-11 | 0.672926256 | 0.480734505 |
| cg26193427 | INPPSA | N_Shore | Body | 0.262155 | 0.003355 | 0.457120976 | 0.370231695 |
| cg12507869 | INPPSA | N_Shore | Body | 0.17177 | 0.001573 | 0.420868341 | 0.338358101 |
| cg05714496 | INPPSA | N_Shore | Body | 0.199485 | 0.000125 | 0.687561442 | 0.549142131 |
| cg22900057 | INPPSA | S_Shelf | Body | 0.138777 | 6.81E-07 | 0.864730078 | 0.761965776 |
| cg09746086 | INPPSA | | Body | 0.028091 | 1.28E-13 | 0.825529953 | 0.712523697 |
| cg00221747 | IGF2 | N_Shore | 3UTR | 0.091459 | 7.06E-05 | 0.911026109 | 0.85081403 |
| cg05384664 | IGF2 | S_Shore | Body | 0.207634 | 0.009981 | 0.730679938 | 0.700431899 |
| cg06029905 | IGF2 | N_Shelf | Body | 0.065236 | 4.00E-07 | 0.742719512 | 0.656060717 |
| cg02808220 | IGF2 | N_Shelf | Body | 0.080443 | 3.05E-05 | 0.781334566 | 0.719292525 |
| cg24183187 | IGF2 | S_Shelf | Body | 0.12449 | 0.000146 | 0.760037225 | 0.68759202 |
| cg22932993 | IGF2 | S_Shelf | Body | 0.061998 | 7.37E-07 | 0.838422411 | 0.764560616 |
| cg21728792 | IGF2 | S_Shelf | Body | 0.089482 | 1.05E-05 | 0.806911209 | 0.723529788 |
| cg14890224 | IGF2 | S_Shelf | Body | 0.061468 | 1.65E-06 | 0.604576372 | 0.516556263 |
| cg01668279 | IGF2 | S_Shelf | Body | 0.098835 | 3.93E-06 | 0.799120667 | 0.710386727 |
| cg16794682 | CCND1 | S_Shelf | Body | 0.024588 | 1.54E-12 | 0.789872977 | 0.666508788 |
| cg12266049 | CCND1 | Island | Body | 0.058848 | 3.06E-11 | 0.913315481 | 0.77688797 |
| cg15974867 | CCND1 | S_Shelf | Body | 0.11123 | 1.46E-10 | 0.833008631 | 0.651952645 |
| cg04717045 | CCND1 | N_Shore | 3UTR | 0.018865 | 5.31E-12 | 0.688396899 | 0.546288869 |
| cg12263469 | CCND1 | Ialand | 3UTR | 0.016578 | 5.73E-11 | 0.744055566 | 0.634779485 |
| cg06868955 | ATP5G2 | N_Shore | Body | 0.126603 | 8.60E-05 | 0.478414854 | 0.374700999 |
| cg26013733 | ABR | S_Shelf | Body | 0.054933 | 1.22E-08 | 0.744664636 | 0.634846232 |
| cg13876604 | ABR | N_Shelf | Body | 0.122084 | 5.85E-07 | 0.739549372 | 0.615556828 |
| cg08458121 | ABR | Island | Body | 0.20146 | 0.001866 | 0.862431147 | 0.803541707 |
| cg02060732 | RBFOX3 | | 5URT | 0.04139 | 2.10E-09 | 0.833731442 | 0.714392323 |
| cg05604487 | RBFOX3 | | 5URT | 0.077287 | 1.80E-06 | 0.657583581 | 0.545713354 |
| cg04115702 | RBFOX3 | | 5URT | 0.102341 | 3.31E-05 | 0.610661302 | 0.534299768 |
| cg07490808 | GREB1L | | Body | 0.03196 | 1.00E-08 | 0.503961326 | 0.368909526 |

TABLE 10

Gene expression analysis using publicly available data of Homeobox family of genes and Tbox genes for which methylation data was also available for in our data set. Although these tumors were relatively hypermethylated at various sites in recurrent tumors versus non-recurrent tumors, they were either upregulated or non-differentially expressed in recurrent tumors.

| Column ID | p-value (1 vs. 0) | FoldChange (1 vs. 0) | FoldChange (1 vs. 0) (Description) |
|---|---|---|---|
| HOXD13 | 0.000114061 | 2.06041 | 1 up vs 0 |
| HOXA7 | 0.000172107 | 1.54672 | 1 up vs 0 |
| HOXB13 | 0.000356608 | 1.23524 | 1 up vs 0 |
| PITX1 | 0.000571527 | 3.42517 | 1 up vs 0 |
| HOXA5 | 0.000649674 | 1.56914 | 1 up vs 0 |
| HOXA1 | 0.00152652 | 1.66169 | 1 up vs 0 |
| HOXD12 | 0.00329604 | 1.18036 | 1 up vs 0 |
| PAX6 | 0.00709951 | 1.90785 | 1 up vs 0 |
| PAX9 | 0.0174741 | 1.12557 | 1 up vs 0 |
| HOXA10 | 0.0179756 | 1.23869 | 1 up vs 0 |
| POU4F1 | 0.0416546 | 1.05959 | 1 up vs 0 |
| HOXC10 | 0.0477096 | 1.40787 | 1 up vs 0 |
| HOXA3 | 0.0608012 | 1.18098 | 1 up vs 0 |
| HOXB3 | 0.0613335 | 2.05141 | 1 up vs 0 |
| FOXA2 | 0.0674789 | 1.07005 | 1 up vs 0 |
| TBX3 | 0.0701179 | 1.06385 | 1 up vs 0 |
| HOXC11 | 0.0971162 | 1.10363 | 1 up vs 0 |
| NKX2-3 | 0.106482 | 1.04019 | 1 up vs 0 |
| HOXB5 | 0.107014 | 1.06562 | 1 up vs 0 |
| HOXB4 | 0.11069 | 1.09051 | 1 up vs 0 |
| IRX3 | 0.120743 | -1.79627 | 1 down vs 0 |
| HOXC9 | 0.133088 | 1.52349 | 1 up vs 0 |
| HOXD10 | 0.134932 | 1.07023 | 1 up vs 0 |
| HOXD9 | 0.153315 | 1.06508 | 1 up vs 0 |
| PAX2 | 0.156918 | -1.22567 | 1 down vs 0 |
| HOXB7 | 0.159887 | 1.10388 | 1 up vs 0 |
| HOXA4 | 0.160191 | 1.06741 | 1 up vs 0 |
| HOXB6 | 0.166413 | 1.06457 | 1 up vs 0 |
| NKX2-8 | 0.245824 | -1.05089 | 1 down vs 0 |
| HOXC6 | 0.259377 | 1.4128 | 1 up vs 0 |
| HOXA13 | 0.279626 | 1.06615 | 1 up vs 0 |
| NKX2-5 | 0.281508 | 1.03816 | 1 up vs 0 |
| OTX2 | 0.286161 | 1.02241 | 1 up vs 0 |
| PBX1 | 0.293154 | -1.09442 | 1 down vs 0 |
| TBX2 | 0.31776 | -1.11363 | 1 down vs 0 |
| OTX1 | 0.350332 | 1.04444 | 1 up vs 0 |
| PITX2 | 0.379015 | 1.0237 | 1 up vs 0 |
| POU4F2 | 0.411171 | 1.03497 | 1 up vs 0 |
| NKX6-2 | 0.411643 | 1.03463 | 1 up vs 0 |
| DLX5 | 0.422143 | -1.07733 | 1 down vs 0 |
| HOXD8 | 0.433142 | -1.06484 | 1 down vs 0 |
| HOXD1 | 0.435759 | 1.03981 | 1 up vs 0 |
| PAX1 | 0.463461 | 1.02538 | 1 up vs 0 |
| HOXA2 | 0.468008 | 1.05235 | 1 up vs 0 |
| HOXD1 | 0.479934 | -1.01955 | 1 down vs 0 |
| NKX6-1 | 0.544333 | 1.03998 | 1 up vs 0 |
| HOXD11 | 0.581698 | 1.0156 | 1 up vs 0 |
| HOXA6 | 0.655808 | 1.02198 | 1 up vs 0 |
| HOXB8 | 0.664046 | 1.01057 | 1 up vs 0 |
| HOXC8 | 0.668768 | 1.02739 | 1 up vs 0 |
| DLX6 | 0.680374 | 1.01573 | 1 up vs 0 |
| TBX1 | 0.693979 | 1.01974 | 1 up vs 0 |
| IRX4 | 0.694484 | -1.07894 | 1 down vs 0 |
| HOXB1 | 0.703823 | 1.01884 | 1 up vs 0 |
| HOXC5 | 0.767971 | -1.03447 | 1 down vs 0 |
| HOXD3 | 0.835941 | -1.01269 | 1 down vs 0 |
| PAX3 | 0.843197 | -1.00904 | 1 down vs 0 |
| NKX2-1 | 0.865339 | 1.00688 | 1 up vs 0 |

TABLE 10-continued

Gene expression analysis using publicly available data of Homeobox family of genes and Tbox genes for which methylation data was also available for in our data set. Although these tumors were relatively hypermethylated at various sites in recurrent tumors versus non-recurrent tumors, they were either upregulated or non-differentially expressed in recurrent tumors.

| Column ID | p-value (1 vs. 0) | FoldChange (1 vs. 0) | FoldChange (1 vs. 0) (Description) |
|---|---|---|---|
| HOXC4 | 0.868251 | 1.0286 | 1 up vs 0 |
| PAX7 | 0.877734 | −1.00675 | 1 down vs 0 |
| MNX1 | 0.88141 | 1.00704 | 1 up vs 0 |
| HOXC12 | 0.897218 | −1.0118 | 1 down vs 0 |
| FOXB1 | 0.913163 | 1.00606 | 1 up vs 0 |
| PAX5 | 0.940595 | −1.00921 | 1 down vs 0 |
| IRX5 | 0.993078 | 1.00224 | 1 up vs 0 |

Annotation:
1 = recurrent,
0 = non-recurrent

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST

1. Ostrom Q T, Gittleman H, Xu J, et al. CBTRUS statistical report: Primary brain and other central nervous system tumors diagnosed in the United States in 2009-2013. *Neuro Oncol.* 2016; 18(suppl_5):v1-v75. doi:10.1093/neuonc/nov189.
2. Melamed S, Sahar A, Beller A J. The recurrence of intracranial meningiomas. *Neurochirurgia (Stuttg).* 1979; 22(2):47-51. doi:10.1055/s-0028-1090287.
3. Weber D C, Ares C, Villa S, et al. Adjuvant postoperative high-dose radiotherapy for atypical and malignant meningioma: A phase-II parallel non-randomized and observation study (EORTC 22042-26042). *Radiother Oncol.* 2018; 128(2):260-265. doi:10.1016/j.radonc.2018.06.018.
4. Rogers L, Zhang P, Vogelbaum M A, et al. Intermediate-risk meningioma: initial outcomes from NRG Oncology RTOG 0539. *J Neurosurg.* 2018; 129(1):35-47. doi:10.3171/2016.11.JNS161170.
5. Rogers L, Barani I, Chamberlain M, et al. Meningiomas: knowledge base, treatment outcomes, and uncertainties. A RANO review. *J Neurosurg.* 2015; 122(1):4-23. doi:10.3171/2014.7.JNS131644.
6. Toro-Moreno A C, Serna-Velez L, Gallego-González D, Jaramillo-Jaramillo L I, Martinez-Sánchez L M, Álvarez-Hernández L F. Tumores de sistema nervioso central en pediatria: Presente y futuro del abordaje diagnóstico. *Rev Ecuatoriana Neurol.* 2017; 26(3):283-288. doi:10.1007/s00401-016-1545-1.
7. Brastianos P K, Horowitz P M, Santagata S, et al. Genomic sequencing of meningiomas identifies oncogenic SMO and AKT1 mutations. *Nat Genet.* 2013; 45(3):285-289. doi:10.1038/ng.2526.
8. Clark V E, Erson-Omay E Z, Serin A, et al. Genomic analysis of non-NF2 meningiomas reveals mutations in TRAF7, KLF4, AKT1, and SMO. *Science (80-).* 2013; 339(6123):1077-1080. doi:10.1126/science.1233009.
9. Clark V E, Harmancl A S, Bai H, et al. Recurrent somatic mutations in POLR2A define a distinct subset of meningiomas. *Nat Genet.* 2016; 48(10):1253-1259. doi:10.1038/ng.3651.
10. Sahm F, Schrimpf D, Olar A, et al. TERT Promoter Mutations and Risk of Recurrence in Meningioma. *J Natl Cancer Inst.* 2016; 108(5):djv377. doi:10.1093/jnci/djv377.
11. Sahm F, Schrimpf D, Stichel D, et al. DNA methylation-based classification and grading system for meningioma: a multicentre, retrospective analysis. *Lancet Oncol.* 2017; 18(5):682-694. doi:10.1016/S1470-2045(17)30155-9.
12. Olar A, Wani K M, Wilson C D, et al. Global epigenetic profiling identifies methylation subgroups associated with recurrence-free survival in meningioma. *Acta Neuropathol.* 2017; 133(3):431-444. doi:10.1007/s00401-017-1678-x.
13. Reuss D E, Piro R M, Jones D T W, et al. Secretory meningiomas are defined by combined KLF4 K409Q and TRAF7 mutations. *Acta Neuropathol.* 2013; 125(3):351-358. doi:10.1007/500401-013-1093-x.
14. Lee Y, Liu J, Patel S, et al. Genomic landscape of meningiomas. *Brain Pathol.* 2010; 20(4):751-762. doi:10.1111/j.1750-3639.2009.00356.x.
15. Claus E B, Park P J, Carroll R, Chan J, Black P M. Specific genes expressed in association with progesterone receptors in meningioma. *Cancer Res.* 2008; 68(1):314-322. doi:10.1158/0008-5472.CAN-07-1796.
16. Hovestadt V, Zapatka M. conumee: Enhanced copy-number variation analysis using Illumina 450 k methylation arrays. R package version 0.99. *R Packag.* 2015.
17. Aizer A A, Abedalthagafi M, Linda Bi W, et al. A prognostic cytogenetic scoring system to guide the adjuvant management of patients with atypical meningioma. *Neuro Oncol.* 2016; 18(2):269-274. doi:10.1093/neuonc/nov177.
18. Heagerty P J, Lumley T, Pepe M S. Time-dependent ROC curves for censored survival data and a diagnostic marker. *Biometrics.* 2000; 56(2):337-344. doi:10.1111/j.0006-341X.2000.00337.x.
19. Huang D W, Sherman B T, Tan Q, et al. The DAVID Gene Functional Classification Tool: A novel biological module-centric algorithm to functionally analyze large gene lists. *Genome Biol.* 2007; 8(9):R183. doi:10.1186/gb-2007-8-9-r183.
20. Chambless L E, Diao G. Estimation of time-dependent area under the ROC curve for long-term risk prediction. *Stat Med.* 2006; 25(20):3474-3486. doi:10.1002/sim.2299.
21. Grambsch P M, Therneau T M. Proportional Hazards Tests and Diagnostics Based on Weighted Residuals Published by: Biometrika Trust Stable URL: http://www.jstor.org/stable/2337123. *Biometrika.* 2008; 81(3):515-526.
22. Harmancl A S, Youngblood M W, Clark V E, et al. Integrated genomic analyses of de novo pathways underlying atypical meningiomas. *Nat Commun.* 2017; 8:14433. doi:10.1038/ncomms14433.
23. Balachandran V P, Gonen M, Smith J J, DeMatteo R P. Nomograms in oncology: more than meets the eye. *Lancet Oncol.* 2015; 16(4):e173-80. doi:10.1016/S1470-2045(14)71116-7.
24. McShane L M, Cavenagh M M, Lively T G, et al. Criteria for the use of omics-based predictors in clinical trials. *Nature.* 2013; 502(7471):317-320. doi:10.1038/nature12564.

25. Sproul D, Meehan R R. Genomic insights into cancer-associated aberrant CpG island hypermethylation. *Brief Funct Genomics.* 2013; 12(3):174-190. doi:10.1093/bfgp/els063.
26. Huang R Y, Bi W L, Weller M, et al. Proposed Response Assessment and Endpoints for Meningioma Clinical Trials: Report from the Response Assessment in Neuro-Oncology (RANO) Working Group. *Neuro Oncol.* August 2018. doi:10.1093/neuonc/noy137.
27. Fortin J P, Triche T J, Hansen K D. Preprocessing, normalization and integration of the Illumina HumanMethylationEPIC array with minfi. *Bioinformatics.* 2017; 33(4):558-560. doi:10.1093/bioinformatics/btw691.
28. Morris T J, Beck S. Analysis pipelines and packages for Infinium HumanMethylation450 BeadChip (450 k) data. *Methods.* 2015; 72(C):3-8. doi:10.1016/j.ymeth.2014.08.011.
29. Hovestadt V, Zapatka M. conumee: Enhanced copy-number variation analysis using Illumina 450 k methylation arrays. R package version 0.99. *R Packag.* 2015.
30. Aizer A A, Abedalthagafi M, Linda Bi W, et al. A prognostic cytogenetic scoring system to guide the adjuvant management of patients with atypical meningioma. *Neuro Oncol.* 2016; 18(2):269-274. doi:10.1093/neuonc/nov177.
31. Sahm F, Schrimpf D, Stichel D, et al. DNA methylation-based classification and grading system for meningioma: a multicentre, retrospective analysis. *Lancet Oncol.* 2017; 18(5):682-694. doi:10.1016/S1470-2045(17)30155-9.
32. De Jay N, Papillon-Cavanagh S, Olsen C, El-Hachem N, Bontempi G, Haibe-Kains B. MRMRe: An R package for parallelized mRMR ensemble feature selection. *Bioinformatics.* 2013; 29(18):2365-2368. doi:10.1093/bioinformatics/btt383.
33. Huang D W, Sherman B T, Tan Q, et al. The DAVID Gene Functional Classification Tool: A novel biological module-centric algorithm to functionally analyze large gene lists. *Genome Biol.* 2007; 8(9):R183. doi:10.1186/gb-2007-8-9-r183.
34. Lee Y, Liu J, Patel S, et al. Genomic landscape of meningiomas. *Brain Pathol.* 2010; 20(4):751-762. doi:10.1111/j.1750-3639.2009.00356.x.
35. Claus E B, Park P J, Carroll R, Chan J, Black P M. Specific genes expressed in association with progesterone receptors in meningioma. *Cancer Res.* 2008; 68(1):314-322. doi:10.1158/0008-5472.CAN-07-1796.
36. Heagerty P J, Lumley T, Pepe M S. Time-dependent ROC curves for censored survival data and a diagnostic marker. *Biometrics.* 2000; 56(2):337-344. doi:10.1111/j.0006-341X.2000.00337.x.
37. Chambless L E, Diao G. Estimation of time-dependent area under the ROC curve for long-term risk prediction. *Stat Med.* 2006; 25(20):3474-3486. doi:10.1002/sim.2299.
38. Grambsch P M, Therneau T M. Proportional Hazards Tests and Diagnostics Based on Weighted Residuals Published by: Biometrika Trust Stable URL: http://www.jstor.org/stable/2337123. *Biometrika.* 2008; 81(3):515-526.

The invention claimed is:
1. An array consisting of probes for detecting CpG methylation at all 2332 loci represented by the following 2332 probes:

cg00015770, cg00018128, cg00025981, cg00028678, cg00035316, cg00036347, cg00048759, cg00055679, cg00060304, cg00063471, cg00073003, cg00099393, cg00117172, cg00123478, cg00130808, cg00143249, cg00155423, cg00155526, cg00158122, cg00168835, cg00182639, cg00184452, cg00204465, cg00204782, cg00222472, cg00237475, cg00247571, cg00254681, cg00255368, cg00262621, cg00286125, cg00298065, cg00299047, cg00299972, cg00306311, cg00323305, cg00337466, cg00360794, cg00384539, cg00407546, cg00418216, cg00425918, cg00431187, cg00434010, cg00435063, cg00445405, cg00463767, cg00487737, cg00490421, cg00495775, cg00499700, cg00503840, cg00504902, cg00505979, cg00506343, cg00507727, cg00513205, cg00553149, cg00556112, cg00567703, cg00574563, cg00585714, cg00599564, cg00616687, cg00629427, cg00663077, cg00667789, cg00673290, cg00674304, cg00687252, cg00714725, cg00716277, cg00733728, cg00756451, cg00762160, cg00767496, cg00779924, cg00790395, cg00795248, cg00806704, cg00838919, cg00840332, cg00864474, cg00867835, cg00877329, cg00882235, cg00887814, cg00905524, cg00913949, cg00926215, cg00928397, cg00947782, cg00949753, cg00963169, cg00970313, cg00982919, cg00982984, cg00983437, cg00985729, cg00989853, cg01003803, cg01031400, cg01040654, cg01054755, cg01078824, cg01141459, cg01156550, cg01163842, cg01172183, cg01174140, cg01177854, cg01182865, cg01229452, cg01243879, cg01258751, cg01277331, cg01277372, cg01285501, cg01286685, cg01287476, cg01295203, cg01323777, cg01351315, cg01371072, cg01402735, cg01405040, cg01405445, cg01438365, cg01449663, cg01456368, cg01460436, cg01463565, cg01467266, cg01484487, cg01494454, cg01499197, cg01530101, cg01533258, cg01550148, cg01564135, cg01587682, cg01602621, cg01622304, cg01627823, cg01631162, cg01645998, cg01655831, cg01658421, cg01665555, cg01673674, cg01693350, cg01708273, cg01713701, cg01727145, cg01739725, cg01789499, cg01803928, cg01811325, cg01815671, cg01819512, cg01821018, cg01824969, cg01832036, cg01850449, cg01853561, cg01882880, cg01896761, cg01904410, cg01913455, cg01921432, cg01926269, cg01934626, cg01939477, cg01942863, cg01946451, cg01961447, cg01972418, cg02005600, cg02006615, cg02022733, cg02032558, cg02037307, cg02051616, cg02055963, cg02058624, cg02069715, cg02086801, cg02100373, cg02102424, cg02108033, cg02109484, cg02115599, cg02120658, cg02132714, cg02145932, cg02150354, cg02151625, cg02154252, cg02188185, cg02194789, cg02213684, cg02233197, cg02250594, cg02281208, cg02283931, cg02285920, cg02286091, cg02330683, cg02335804, cg02346492, cg02348751, cg02360980, cg02364236, cg02367696, cg02428056, cg02435495, cg02439266, cg02458062, cg02468250, cg02483701, cg02487130, cg02495310, cg02497558, cg02511456, cg02524946, cg02530022, cg02552311, cg02553516, cg02569236, cg02585702, cg02595832, cg02596153, cg02599464, cg02611848, cg02623050, cg02624770, cg02628823, cg02633371, cg02642123, cg02642822, cg02646491, cg02655630, cg02660440, cg02688752, cg02694427, cg02700894, cg02701080, cg02703870, cg02741882, cg02760031, cg02767242, cg02768694, cg02770983, cg02771142, cg02781618, cg02798576, cg02800607, cg02803914, cg02865068, cg02873421, cg02874942, cg02878244, cg02885007, cg02886033, cg02906407, cg02907064, cg02916932, cg02948476, cg02964031, cg02971322, cg03001942, cg03011535, cg03020554, cg03024760, cg03036592, cg03045635, cg03086235, cg03091551, cg03099728, cg03102494, cg03129884, cg03133868, cg03144922, cg03148184, cg03171465, cg03177551, cg03181248, cg03219282, cg03219968, cg03242698, cg03276408, cg03293507, cg03301582, cg03323462, cg03325664, cg03343571, cg03347590, cg03350299, cg03356900, cg03405909, cg03405983, cg03431846, cg03465861, cg03491584, cg03522132, cg03529432, cg03562044, cg03572772, cg03583111, cg03596280, cg03609639, cg03636532, cg03637815, cg03640756, cg03650674, cg03655683, cg03656099, cg03660500, cg03669298, cg03672342, cg03692563, cg03694713, cg03695236, cg03711485, cg03733219, cg03733760, cg03735496, cg03744440, cg03744763, cg03771840, cg03774463, cg03780851, cg03826976, cg03851159, cg03854796, cg03867465, cg03885037, cg03905867, cg03927133, cg03945700, cg03947464, cg03951833, cg03958979, cg03959515, cg03960072, cg03964958, cg03970615, cg03975235, cg03981954, cg03989480, cg04022561, cg04025675, cg04046669, cg04047221, cg04052466, cg04059568, cg04065086, cg04079760, cg04080041, cg04080282, cg04091063, cg04131898, cg04134048, cg04136369, cg04142323, cg04158367, cg04178316, cg04180086, cg04193970, cg04198914, cg04203646, cg04213746, cg04236178, cg04251368, cg04255230, cg04265576, cg04290346, cg04328477, cg04342294, cg04360790, cg04366687, cg04369341, cg04378886, cg04403809, cg04407470, cg04415176, cg04415798, cg04418091, cg04446345, cg04450456, cg04456238, cg04461228, cg04467589, cg04469219, cg04489012, cg04504066, cg04513006, cg04514123, cg04515001, cg04521510, cg04543413, cg04552206, cg04554928, cg04558175, cg04566159, cg04574034, cg04586579, cg04597433, cg04597449, cg04598774, cg04617948, cg04623837, cg04630292, cg04636269, cg04648480, cg04654530, cg04673825, cg04685170, cg04688051, cg04728480, cg04729913, cg04730685, cg04738888, cg04739647, cg04765277, cg04775710, cg04787024, cg04796181, cg04809787, cg04821708, cg04850999, cg04854328, cg04856858, cg04864199, cg04886060, cg04887494, cg04904318, cg04916091, cg04937416, cg04938549, cg04956913, cg04959815, cg04972566, cg04972745, cg04996219, cg05001964, cg05009601, cg05027336, cg05029822, cg05031521, cg05065507, cg05072100, cg05140806, cg05142617, cg05142765, cg05158615, cg05165940, cg05167251, cg05180443, cg05193369, cg05196969, cg05210501, cg05222924, cg05236677, cg05256269, cg05290058, cg05301866, cg05317714, cg05345154, cg05347898, cg05351827, cg05368740, cg05376374, cg05377576, cg05380821, cg05387167, cg05408649, cg05449136, cg05457563, cg05470554, cg05475934, cg05477444, cg05488632, cg05490659, cg05498007, cg05500840, cg05501996, cg05520409, cg05522011, cg05527530, cg05529506, cg05555207, cg05578840, cg05592035, cg05603881, cg05604079, cg05635754, cg05639205, cg05656180, cg05658487, cg05667348, cg05678749, cg05690644, cg05697849, cg05724997, cg05736768, cg05744332, cg05766510, cg05787556, cg05818685, cg05822926, cg05835105, cg05839235, cg05853632, cg05890484, cg05896902, cg05899618, cg05905176, cg05915293, cg05921905, cg05922610, cg05924583, cg05925327, cg05928186, cg05929882, cg05937630, cg05942128, cg05974274, cg05975410, cg05976500, cg05977669, cg05990544, cg06005695, cg06023345, cg06049868, cg06055873, cg06060135, cg06102419, cg06133205, cg06142537, cg06146234, cg06148812, cg06150468, cg06157318, cg06159394, cg06166809, cg06178563, cg06198398, cg06226156, cg06226630, cg06230848, cg06238409, cg06239355, cg06249604, cg06254440, cg06255601, cg06262436, cg06272038, cg06274159, cg06287951, cg06303875, cg06312283, cg06323023, cg06367117, cg06367311, cg06375967, cg06376715, cg06382344, cg06382559, cg06386307, cg06390536, cg06410191, cg06410537, cg06428620, cg06440348, cg06451900, cg06488443, cg06490225, cg06497848, cg06520675, cg06535993, cg06554090, cg06571387, cg06579271, cg06615152, cg06626599, cg06632207, cg06637517, cg06644373, cg06666008, cg06667574, cg06702880, cg06704518, cg06705930, cg06708634, cg06710082, cg06723863, cg06724305, cg06732395, cg06754197, cg06765217, cg06779449, cg06804210, cg06813578, cg06818052, cg06818777, cg06825142, cg06842954, cg06845853, cg06854084, cg06866686, cg06872257, cg06911121, cg06916239, cg06942183, cg06942701, cg06943420, cg06962944, cg06966811, cg06975048, cg06991300, cg06992285, cg07010088, cg07010228, cg07017875, cg07020001, cg07021644, cg07029873, cg07033624, cg07046818, cg07050616, cg07060233, cg07095230, cg07104660, cg07116997, cg07121856, cg07124117, cg07135614, cg07147475, cg07155223, cg07160932, cg07178825, cg07195011, cg07201017, cg07211140, cg07247419, cg07274716, cg07281879, cg07300846, cg07302910, cg07311313, cg07322064, cg07323141, cg07329360, cg07330230, cg07333715, cg07359633, cg07367232, cg07371589, cg07380026, cg07382347, cg07382943, cg07383092, cg07407736, cg07411620, cg07416664, cg07434271, cg07440414, cg07440775, cg07447773, cg07483304, cg07502389, cg07515422, cg07516252, cg07522913, cg07529210, cg07536910, cg07539798, cg07541200, cg07545037, cg07552803, cg07578695, cg07592963, cg07595776, cg07606384, cg07615087, cg07653946, cg07660671, cg07696699, cg07702750, cg07703462, cg07778029, cg07785447, cg07788369, cg07791578, cg07793808, cg07802350, cg07838106, cg07855083, cg07860213, cg07871947, cg07877559, cg07879739, cg07881405, cg07938743, cg07939836, cg07974511, cg07991112, cg07996594, cg08022244, cg08034867, cg08066129, cg08079908, cg08085357, cg08089301, cg08116462, cg08118159, cg08126211, cg08138435, cg08163199, cg08182446, cg08196968, cg08203284, cg08206318, cg08227526, cg08231710, cg08247587, cg08274589, cg08278487, cg08279075, cg08305551, cg08307030, cg08309809, cg08318726, cg08325845, cg08370178, cg08373003, cg08381274, cg08431536, cg08457898, cg08465346, cg08473330, cg08479590, cg08480826, cg08481464, cg08481491, cg08492173, cg08499046, cg08509840, cg08511651, cg08547691, cg08555653, cg08575330, cg08587845, cg08598654, cg08599448, cg08613144, cg08622757, cg08657492, cg08680048, cg08694699, cg08702941, cg08703872, cg08704562, cg08712054, cg08726248, cg08745288, cg08746900, cg08748969, cg08781140, cg08784129, cg08787968, cg08793877, cg08813062, cg08825084, cg08828819, cg08829841, cg08858649, cg08865099, cg08874512, cg08879910, cg08898155, cg08902977, cg08927006, cg08938793, cg08964780, cg08965276, cg08971771, cg08979319, cg08979895, cg08985979, cg09010671, cg09016822, cg09041678, cg09042277, cg09046055, cg09048251, cg09050331, cg09064304, cg09071155, cg09093485, cg09098195, cg09105193, cg09127400, cg09133032, cg09135656, cg09143801, cg09156097, cg09164580, cg09180848, cg09188099, cg09194159, cg09224689, cg09229918, cg09233651, cg09234518, cg09234616, cg09236434, cg09238180, cg09252999, cg09257796, cg09257824, cg09279736, cg09299055,
cg09313705, cg09359114, cg09382096, cg09411999,
cg09491991, cg09498572, cg09500443, cg09502866,
cg09509183, cg09515953, cg09537620, cg09554509,
cg09554951, cg09586183, cg09591524, cg09595479,
cg09614415, cg09622982, cg09639151, cg09656389,
cg09661370, cg09671258, cg09672187, cg09672383,
cg09686443, cg09695430, cg09696159, cg09704116,
cg09706122, cg09709472, cg09731996, cg09767822,
cg09792881, cg09797337, cg09803262, cg09826050,
cg09854626, cg09857513, cg09866983, cg09868598,
cg09888562, cg09935388, cg09936824, cg09938227,
cg09983051, cg10004780, cg10035294, cg10060574,
cg10068417, cg10074409, cg10084644, cg10094489,
cg10114327, cg10122865, cg10131194, cg10137231,
cg10146929, cg10147797, cg10169241, cg10172669,
cg10195901, cg10242160, cg10242602, cg10245273,
cg10245988, cg10288510, cg10300188, cg10303487,
cg10331779, cg10334767, cg10344832, cg10347335,
cg10356613, cg10357657, cg10366797, cg10421979,
cg10439765, cg10456990, cg10475970, cg10479082,
cg10500362, cg10508993, cg10511988, cg10526374,
cg10532489, cg10536898, cg10537450, cg10588696,
cg10588962, cg10603004, cg10657141, cg10659805,
cg10660256, cg10682560, cg10689404, cg10689528,
cg10724867, cg10741025, cg10745499, cg10757144,
cg10767223, cg10782668, cg10798171, cg10798682,
cg10823473, cg10835584, cg10850930, cg10859133,
cg10865856, cg10895452, cg10911990, cg10916998,
cg10930308, cg10938374, cg10940462, cg10945917,
cg10953317, cg10954251, cg10954469, cg10957151,
cg10964421, cg10977770, cg10979436, cg10983544,
cg10989897, cg10997718, cg11015251, cg11022432,
cg11025705, cg11060441, cg11075029, cg11076994,
cg11080549, cg11086764, cg11097541, cg11101117,
cg11111460, cg11128216, cg11162118, cg11168433,
cg11179081, cg11196848, cg11207534, cg11229513,
cg11229862, cg11233384, cg11280525, cg11282676,
cg11301556, cg11320910, cg11325997, cg11330740,
cg11335335, cg11359133, cg11368643, cg11397370,
cg11418477, cg11435506, cg11469061, cg11469778,
cg11471772, cg11472521, cg11475550, cg11485451,
cg11485595, cg11500797, cg11508828, cg11523020,
cg11529250, cg11538641, cg11540692, cg11605835,
cg11616651, cg11625005, cg11638298, cg11644479,
cg11648594, cg11651285, cg11663667, cg11667020,
cg11667086, cg11671598, cg11679455, cg11700800,
cg11724134, cg11741189, cg11754318, cg11770080,
cg11772171, cg11789612, cg11800620, cg11806672,
cg11823511, cg11827910, cg11853320, cg11853830,
cg11854154, cg11866296, cg11891393, cg11904906,
cg11910375, cg11916729, cg11930477, cg11931731,
cg11945824, cg11946503, cg11947493, cg11949335,
cg11965311, cg11969002, cg12006284, cg12018098,
cg12064276, cg12065840, cg12074182, cg12090740,
cg12110087, cg12118246, cg12147489, cg12163132,
cg12164596, cg12171183, cg12184886, cg12198813,
cg12200038, cg12213062, cg12224030, cg12233379,
cg12248614, cg12258785, cg12266953, cg12268637,
cg12278467, cg12305431, cg12308746, cg12309653,
cg12331932, cg12338417, cg12349884, cg12374721,
cg12377139, cg12384236, cg12386646, cg12393318,
cg12405139, cg12434982, cg12473406, cg12518146,
cg12520549, cg12566152, cg12588917, cg12606911,
cg12610471, cg12614105, cg12633154, cg12636169,
cg12648074, cg12670347, cg12673103, cg12676702,
cg12685539, cg12700904, cg12736877, cg12782180,
cg12788467, cg12798259, cg12807794, cg12810523,
cg12821804, cg12876356, cg12883523, cg12883980,
cg12902206, cg12910906, cg12928379, cg12945444,
cg12953669, cg12967914, cg12969193, cg12973941,
cg12982322, cg12984729, cg12997720, cg12999453,
cg13016408, cg13023623, cg13025668, cg13028700,
cg13046271, cg13073773, cg13112154, cg13115683,
cg13137376, cg13147822, cg13163521, cg13185413,
cg13193239, cg13210467, cg13211683, cg13230606,
cg13245152, cg13301003, cg13305657, cg13331550,
cg13338137, cg13365524, cg13368756, cg13378628,
cg13381984, cg13401893, cg13407335, cg13409449,
cg13426079, cg13434842, cg13443627, cg13445199,
cg13459498, cg13476950, cg13492692, cg13502125,
cg13528935, cg13530938, cg13535212, cg13540960,
cg13552869, cg13564825, cg13567542, cg13570101,
cg13570972, cg13596833, cg13604794, cg13605398,
cg13614181, cg13617591, cg13641903, cg13643914,
cg13660279, cg13691247, cg13692446, cg13694576,
cg13703049, cg13715631, cg13726459, cg13735819,
cg13742526, cg13752649, cg13762320, cg13764778,
cg13774342, cg13784235, cg13799941, cg13803976,
cg13804182, cg13813366, cg13826247, cg13870866,
cg13885561, cg13885965, cg13891220, cg13891702,
cg13918754, cg13922021, cg13929328, cg13965612,
cg13967702, cg13974394, cg13982098, cg13990559,
cg14010318, cg14013695, cg14015044, cg14015441,
cg14029489, cg14034197, cg14044640, cg14069965,
cg14084907, cg14085358, cg14097304, cg14159342,
cg14177914, cg14181940, cg14189571, cg14210607,
cg14228238, cg14230397, cg14239515, cg14239592,
cg14244013, cg14301212, cg14314744, cg14317513,
cg14319235, cg14327531, cg14337027, cg14345497,
cg14353137, cg14355911, cg14375937, cg14385245,
cg14410016, cg14416523, cg14425564, cg14428146,
cg14432269, cg14432910, cg14439629, cg14443953,
cg14448169, cg14451926, cg14458068, cg14459130,
cg14461582, cg14473102, cg14487292, cg14501061,
cg14506196, cg14509403, cg14531663, cg14542583,
cg14556683, cg14557487, cg14559388, cg14598764,
cg14604681, cg14615784, cg14619949, cg14626259,
cg14636534, cg14649140, cg14652095, cg14657834,
cg14668747, cg14678774, cg14703002, cg14757311,
cg14776998, cg14780466, cg14781281, cg14817655,
cg14879760, cg14889643, cg14891209, cg14891410,
cg14928902, cg14944647, cg14958635, cg14974749,
cg14982276, cg14989164, cg14991487, cg14993283,
cg14996783, cg15006175, cg15014975, cg15015639,
cg15017067, cg15084543, cg15105182, cg15126179,
cg15133719, cg15137566, cg15140703, cg15196806,
cg15209808, cg15234492, cg15235798, cg15236866,
cg15244327, cg15255390, cg15267232, cg15299388,
cg15315385, cg15325875, cg15331332, cg15377283,
cg15402095, cg15440688, cg15444947, cg15446391,
cg15460093, cg15461888, cg15475840, cg15491102,
cg15500865, cg15505412, cg15506477, cg15515258,
cg15552158, cg15556502, cg15564098, cg15572489,
cg15590989, cg15607672, cg15611279, cg15613420,
cg15634877, cg15645660, cg15652723, cg15653173,
cg15660418, cg15665400, cg15665928, cg15706250,
cg15710198, cg15718581, cg15724256, cg15736169,
cg15741433, cg15772924, cg15778437, cg15792487,
cg15798385, cg15826897, cg15829969, cg15835620,
cg15854847, cg15861585, cg15873301, cg15877520,
cg15880760, cg15911153, cg15912800, cg15927196,
cg15949044, cg15951188, cg15959715, cg15981851,
cg15982700, cg15985184, cg15985775, cg15990629, cg16017144, cg16021909, cg16030177, cg16041686, cg16043357, cg16051228, cg16078649, cg16084872, cg16092786, cg16104915, cg16113681, cg16117799, cg16138458, cg16180353, cg16184495, cg16197925, cg16243019, cg16246169, cg16246489, cg16264705, cg16281276, cg16297569, cg16302441, cg16306115, cg16306978, cg16331823, cg16353006, cg16362592, cg16368146, cg16373229, cg16374999, cg16379704, cg16390060, cg16392213, cg16407471, cg16410706, cg16419441, cg16435779, cg16440561, cg16458436, cg16459364, cg16463460, cg16473141, cg16493531, cg16501028, cg16513459, cg16524928, cg16529477, cg16544169, cg16546442, cg16555165, cg16557178, cg16568727, cg16574871, cg16582419, cg16604516, cg16615829, cg16615954, cg16620526, cg16638920, cg16642284, cg16651126, cg16652651, cg16670554, cg16686158, cg16688483, cg16699148, cg16705627, cg16723488, cg16742873, cg16747564, cg16748008, cg16758800, cg16763443, cg16783744, cg16786703, cg16787431, cg16793394, cg16809460, cg16830930, cg16851417, cg16865446, cg16868298, cg16891104, cg16937769, cg16938805, cg16961816, cg16964025, cg16964348, cg16991515, cg17011709, cg17019053, cg17029062, cg17029168, cg17067528, cg17083494, cg17107156, cg17138769, cg17153568, cg17163168, cg17181022, cg17194154, cg17204275, cg17210938, cg17214381, cg17236169, cg17241310, cg17242937, cg17280740, cg17298275, cg17301223, cg17303540, cg17338212, cg17353412, cg17380661, cg17386213, cg17423207, cg17452615, cg17462200, cg17476026, cg17486860, cg17487170, cg17507671, cg17526483, cg17561417, cg17576288, cg17594860, cg17602451, cg17611674, cg17626405, cg17630392, cg17632937, cg17652435, cg17658976, cg17665193, cg17674725, cg17694795, cg17696160, cg17698295, cg17727529, cg17737681, cg17753347, cg17768491, cg17774559, cg17799033, cg17808882, cg17820365, cg17833476, cg17858328, cg17888033, cg17890928, cg17894318, cg17911021, cg17953764, cg17955729, cg17968795, cg17985646, cg17999376, cg18002447, cg18004701, cg18008037, cg18009690, cg18020955, cg18034737, cg18058747, cg18063017, cg18064631, cg18082638, cg18087266, cg18097224, cg18106668, cg18128164, cg18144593, cg18181229, cg18182148, cg18182399, cg18202449, cg18221467, cg18229178, cg18235100, cg18240703, cg18247055, cg18267374, cg18304448, cg18311537, cg18318878, cg18322569, cg18327157, cg18336674, cg18342279, cg18358723, cg18362330, cg18366919, cg18372607, cg18394340, cg18400845, cg18405727, cg18406197, cg18407955, cg18416576, cg18435832, cg18447772, cg18459489, cg18495682, cg18501555, cg18502142, cg18507379, cg18512948, cg18528367, cg18534491, cg18539122, cg18544365, cg18552861, cg18556834, cg18560204, cg18569734, cg18579879, cg18588323, cg18599069, cg18601426, cg18603228, cg18609783, cg18614735, cg18617005, cg18628371, cg18650716, cg18664869, cg18687675, cg18691434, cg18725076, cg18736063, cg18790597, cg18795809, cg18796287, cg18817990, cg18867200, cg18867923, cg18873386, cg18884137, cg18898125, cg18948488, cg18950778, cg18952647, cg18984724, cg19006378, cg19006429, cg19022697, cg19043574, cg19046826, cg19092981, cg19098763, cg19103219, cg19113641, cg19127283, cg19131476, cg19164987, cg19181162, cg19183743, cg19211915, cg19241327, cg19247475, cg19258034, cg19270505, cg19281363, cg19290410, cg19305681, cg19325985, cg19329160, cg19334350, cg19363499, cg19378036, cg19384289, cg19392656, cg19403029, cg19403104, cg19407095, cg19410791, cg19416570, cg19497031, cg19498960, cg19520234, cg19537719, cg19544662, cg19578835, cg19593490, cg19594666, cg19616230, cg19617672, cg19628148, cg19689322, cg19711783, cg19718882, cg19725343, cg19733042, cg19741645, cg19741945, cg19759671, cg19760241, cg19761110, cg19762657, cg19766441, cg19767800, cg19770541, cg19792544, cg19802138, cg19808978, cg19816811, cg19842809, cg19844326, cg19844653, cg19852958, cg19876672, cg19884262, cg19909239, cg19923650, cg19961043, cg19962750, cg19980151, cg19989295, cg20003638, cg20014398, cg20014822, cg20027296, cg20049415, cg20065463, cg20073553, cg20080624, cg20094830, cg20099830, cg20120208, cg20125091, cg20146541, cg20177385, cg20204986, cg20232102, cg20248516, cg20249327, cg20250981, cg20262306, cg20264732, cg20272979, cg20293942, cg20311863, cg20312228, cg20322977, cg20342079, cg20359285, cg20371765, cg20377305, cg20381115, cg20387815, cg20399462, cg20399871, cg20403557, cg20429172, cg20434586, cg20467957, cg20469799, cg20512711, cg20521696, cg20528093, cg20529344, cg20540209, cg20541178, cg20572816, cg20574490, cg20582655, cg20615879, cg20650802, cg20672981, cg20682146, cg20688917, cg20705938, cg20710709, cg20725013, cg20731469, cg20739435, cg20747380, cg20755721, cg20785796, cg20800022, cg20801476, cg20817131, cg20817902, cg20884887, cg20892260, cg20927242, cg20931042, cg20941110, cg20956738, cg20959460, cg20974609, cg20977170, cg20988073, cg20992114, cg20994254, cg20994660, cg21010475, cg21011139, cg21016855, cg21017569, cg21052682, cg21063282, cg21063716, cg21073927, cg21073930, cg21101465, cg21113740, cg21117330, cg21124497, cg21128569, cg21132352, cg21134232, cg21146503, cg21165027, cg21172322, cg21172377, cg21174746, cg21195468, cg21200656, cg21200703, cg21201099, cg21211357, cg21242356, cg21245652, cg21249371, cg21266502, cg21269897, cg21279601, cg21303011, cg21429745, cg21460081, cg21463349, cg21472506, cg21474786, cg21484228, cg21485895, cg21561970, cg21595709, cg21601837, cg21606115, cg21614303, cg21652531, cg21684012, cg21697851, cg21711132, cg21713473, cg21726372, cg21753226, cg21762523, cg21769619, cg21774338, cg21784383, cg21791017, cg21793948, cg21811143, cg21843594, cg21865150, cg21890667, cg21912060, cg21915313, cg21932368, cg21945930, cg21949512, cg21951975, cg21971285, cg22010052, cg22038124, cg22039909, cg22044002, cg22056595, cg22084642, cg22097249, cg22105332, cg22118524, cg22120446, cg22125838, cg22132508, cg22149137, cg22204479, cg22241820, cg22249789, cg22265644, cg22268510, cg22272282, cg22283925, cg22287064, cg22289831, cg22303418, cg22341104, cg22345692, cg22436336, cg22442454, cg22459630, cg22463553, cg22469274, cg22474464, cg22496377, cg22498143, cg22505086, cg22511262, cg22531668, cg22533573, cg22557091, cg22557662, cg22559034, cg22560193, cg22571664, cg22572908, cg22614142, cg22616881, cg22623223, cg22637538, cg22660933, cg22666373, cg22674699, cg22711111, cg22720790, cg22730140, cg22730464, cg22740492, cg22770911, cg22774088, cg22777724, cg22778788, cg22783363, cg22799963, cg22807449, cg22814146, cg22827250, cg22839075, cg22840219, cg22849665, cg22859061, cg22859289, cg22876812, cg22878622, cg22882523, cg22888055, cg22897615, cg22900229, cg22902505, cg22937649, cg22951509, cg22973789, cg22975913, cg22976224, cg22982368, cg22997113, cg23016129, cg23027574, cg23042510, cg23044079, cg23051664, cg23054189, cg23064601, cg23068797, cg23082339, cg23097402, cg23100152, cg23104954, cg23125492, cg23129930, cg23130254, cg23158731, cg23165310, cg23167906, cg23196831, cg23218559, cg23229261, cg23244790, cg23244913, cg23268208, cg23278196, cg23286646, cg23290344, cg23345004, cg23357257, cg23442209, cg23445461, cg23483840, cg23497383, cg23500724, cg23501406, cg23503176, cg23511613, cg23513966, cg23514619, cg23528400, cg23530553, cg23546474, cg23586322, cg23587449, cg23598080, cg23619365, cg23619399, cg23623622, cg23634124, cg23637494, cg23655970, cg23663774, cg23676151, cg23683588, cg23695707, cg23697546, cg23707289, cg23712018, cg23724641, cg23740652, cg23767994, cg23792314, cg23829024, cg23831143, cg23847712, cg23874561, cg23880589, cg23896164, cg23907108, cg23917057, cg23933618, cg23937893, cg23939808, cg23941075, cg23965061, cg23971069, cg23973429, cg23974473, cg23979631, cg23994043, cg24001710, cg24005685, cg24008908, cg24016627, cg24030449, cg24039697, cg24051554, cg24080247, cg24157892, cg24169669, cg24228707, cg24241823, cg24280832, cg24309555, cg24328539, cg24330456, cg24351901, cg24354581, cg24370475, cg24375215, cg24382527, cg24425021, cg24425171, cg24425838, cg24426072, cg24430580, cg24446586, cg24453580, cg24479590, cg24524285, cg24535439, cg24550149, cg24565496, cg24575083, cg24582934, cg24592027, cg24628744, cg24630419, cg24633978, cg24646414, cg24657817, cg24663845, cg24683414, cg24697184, cg24701575, cg24721899, cg24725574, cg24727399, cg24745495, cg24747764, cg24787138, cg24796272, cg24797840, cg24804179, cg24880701, cg24896649, cg24901042, cg24913868, cg24914355, cg24927800, cg24928391, cg24933173, cg24951286, cg24953321, cg24988255, cg25008858, cg25032094, cg25034395, cg25035485, cg25044651, cg25051331, cg25062797, cg25071744, cg25083618, cg25112312, cg25125060, cg25160978, cg25161512, cg25188395, cg25192855, cg25196158, cg25200152, cg25203481, cg25212090, cg25247290, cg25258843, cg25307665, cg25318809, cg25330243, cg25336332, cg25342207, cg25371919, cg25377206, cg25382400, cg25390165, cg25412546, cg25437411, cg25442600, cg25471923, cg25478600, cg25479916, cg25485294, cg25506432, cg25527090, cg25536137, cg25539045, cg25547580, cg25576011, cg25586361, cg25593794, cg25608490, cg25622366, cg25639415, cg25678088, cg25685262, cg25702780, cg25720804, cg25746778, cg25755575, cg25756435, cg25775494, cg25782229, cg25802093, cg25835733, cg25845597, cg25845985, cg25851789, cg25884711, cg25887069, cg25903779, cg25903783, cg25916711, cg25923240, cg25930229, cg25939676, cg25942450, cg25960038, cg25965471, cg25984671, cg25988034, cg26000619, cg26006870, cg26006951, cg26019112, cg26057751, cg26058714, cg26060971, cg26067760, cg26069745, cg26072906, cg26094599, cg26094789, cg26099134, cg26115633, cg26144458, cg26149275, cg26151467, cg26160218, cg26176204, cg26190890, cg26195178, cg26199906, cg26206948, cg26212180, cg26214742, cg26224060, cg26241806, cg26248075, cg26254045, cg26256263, cg26259537, cg26261502, cg26263263, cg26277730, cg26277754, cg26295921, cg26296488, cg26299169, cg26309194, cg26322248, cg26327071, cg26330518, cg26331172, cg26365545, cg26370729, cg26371731, cg26376168, cg26380443, cg26388730, cg26410483, cg26413174, cg26421310, cg26422458, cg26429925, cg26437825, cg26446499, cg26457809, cg26476852, cg26506288, cg26517171, cg26517714, cg26521404, cg26551975, cg26559315, cg26560222, cg26585452, cg26589785, cg26601317, cg26618965, cg26659805, cg26660800, cg26673012, cg26674479, cg26674943, cg26687072, cg26690075, cg26698460, cg26701242, cg26702958, cg26708319, cg26751356, cg26755097, cg26783057, cg26796135, cg26811372, cg26814075, cg26816907, cg26844246, cg26848718, cg26870725, cg26879945, cg26890354, cg26951440, cg26990102, cg26998537, cg27009703, cg27011060, cg27029821, cg27032146, cg27035251, cg27076669, cg27090216, cg27100227, cg27110277, cg27111250, cg27111463, cg27125849, cg27151303, cg27157482, cg27162435, cg27183188, cg27190967, cg27234067, cg27252696, cg27267227, cg27304406, cg27309110, cg27312652, cg27363141, cg27364741, cg27398720, cg27448110, cg27449131, cg27493649, cg27513574, cg27520776, cg27521476, cg27526665, cg27532187, cg27539480, cg27542552, cg27583307, cg27616661, cg27622506, cg27639457, cg27639662, cg27650870, cg27656658, cg27661315, cg12627726, cg06749480, cg07152605, cg12689806, cg22029015, cg10186395, cg02406098, cg20789595, cg19008133, cg07366462, cg01246398, cg08598988, cg25661931, cg22989209, cg04830757, cg26863842, cg26177760, cg24124954, cg24332685, cg21179831, cg21079591, cg25711558, cg03787603, cg11911769, cg09244071, cg15755348, cg26651148, cg14759472, cg26170014, cg10473311, cg21584493, cg26793019, cg02563011, cg02616558, cg22663467, cg26837853, cg12269374, cg08236285, cg12042060, cg14207539, cg23264016, cg26193427, cg12507869, cg05714496, cg22900057, cg09746086, cg00221747, cg05384664, cg06029905, cg02808220, cg24183187, cg22932993, cg21728792, cg14890224, cg01668279, cg16794682, cg12266049, cg15974867, cg04717045, cg12263469, cg06868955, cg26013733, cg13876604, cg08458121, cg02060732, cg05604487, cg04115702, and cg07490808.

2. The array of claim 1 consisting of the 2332 probes.

3. A method of predicting recurrence free survival in a patient with meningioma comprising:
(a) determining a tumor DNA methylation profile of a meningioma sample from the patient using the array of claim 1, wherein the tumor DNA methylation profile consists of the methylation status of the 2332 loci detected by the array of claim 1; and
(b) calculating a risk of meningioma recurrence by comparing the tumor DNA methylation profile with a reference methylation profile comprising the extent to which the methylation status of the 2332 loci is associated with the risk of recurrence.

4. The method of claim 3, wherein the calculating the risk is based further on at least one of the WHO grading and Simpson grading of the tumor.

5. The method of claim 3, further comprising calculating a predicted number of years of recurrence free survival (RFS Score).

6. The method of claim 5, further comprising stratifying the patient into a high, a medium or a low risk category based on said RFS Score compared to known reference patients.

7. The method of claim 6, further comprising treating the patient with adjuvant therapy if the patient is in the high or medium risk category.

8. The method of claim 7, wherein the adjuvant therapy comprises chemotherapy or radiotherapy.

* * * * *